(12) United States Patent
Wu et al.

(10) Patent No.: US 9,949,976 B2
(45) Date of Patent: *Apr. 24, 2018

(54) KINASE INHIBITOR AND USE THEREOF

(71) Applicants: Sihuan Pharmaceutical Holdings Group Ltd., West Balizhuang, Chaoyang District (CN); Xuanzhu Pharma Co., Ltd., Jinan (CN)

(72) Inventors: Frank Wu, Jinan (CN); Bo Chen, Jinan (CN)

(73) Assignees: XUANZHU PHARMA CO., LTD., Jinan, Shandong (CN); SIHUAN PHARMACEUTICAL HOLDINGS GROUP LTD., West Balizhuang, Chaoyang District (CN)

(*) Notice: Subject to any disclaimer, the term of this patent is extended or adjusted under 35 U.S.C. 154(b) by 0 days.

This patent is subject to a terminal disclaimer.

(21) Appl. No.: 15/704,542

(22) Filed: Sep. 14, 2017

(65) Prior Publication Data

US 2018/0000819 A1 Jan. 4, 2018

Related U.S. Application Data

(63) Continuation-in-part of application No. 15/108,903, filed as application No. PCT/CN2014/095615 on Dec. 30, 2014, now Pat. No. 9,796,701.

(30) Foreign Application Priority Data

Dec. 31, 2013 (CN) .......................... 2013 1 0749417

(51) Int. Cl.
*A61K 31/506* (2006.01)
*A61K 31/5377* (2006.01)
*A61K 31/5383* (2006.01)
*A61K 31/5386* (2006.01)

(52) U.S. Cl.
CPC ........ *A61K 31/506* (2013.01); *A61K 31/5377* (2013.01); *A61K 31/5383* (2013.01); *A61K 31/5386* (2013.01)

(58) Field of Classification Search
CPC .. C07D 401/14; C07D 471/10; C07D 487/04; C07D 487/10; A61K 31/496; A61K 31/506; A61K 31/5377; A61K 31/5383; A61K 31/5386
USPC .............. 544/105, 122, 295, 331; 514/230.5, 514/235.8, 252.18, 275
See application file for complete search history.

(56) References Cited

U.S. PATENT DOCUMENTS 7,456,168 B2 11/2008 Barvian et al.
7,855,211 B2 12/2010 Coates et al.
8,962,630 B2 2/2015 Brain et al.
9,796,701 B2 10/2017 Wu et al.
2010/0048597 A1 2/2010 Beckwith et al.

FOREIGN PATENT DOCUMENTS

| CN | 101001857 A | 7/2007 |
|---|---|---|
| CN | 101568529 A | 10/2009 |
| CN | 102186856 A | 9/2011 |
| CN | 102264725 A | 11/2011 |
| WO | 03070236 A2 | 8/2003 |

OTHER PUBLICATIONS

Schulz, Molecular Biology of Human Cancers: Chapter 1, Springer, pp. 1-23 (2007).*
Simone, Oncology: Introduction, Cecil Textbook of Medicine, 20th Edition, vol. 1, pp. 1004-1101 O, 1996.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
O'Leary et al., Treating cancer with selective CDK4/6 inhibitors, Nature Reviews: Clinical Oncology, vol. 13, pp. 417-430 (2016).*
International Search Report for Application No. PCT/CN2014/095615 dated Feb. 17, 2015, 8 pages.
English language abstract for CN 101001857 extracted from espacenet.com database on Jul. 7, 2016, 2 pages.
English language abstract for CN 102186856 extracted from espacenet.com database on Jul. 7, 2016, 2 pages.
English language abstract for CN 102264725 extracted from espacenet.com database on Jul. 7, 2016, 2 pages.
English language abstract for CN 101568529 extracted from espacenet.com database on Apr. 12, 2017, 1 page.
Gura, "Systems for identifying New Drugs Are Often Faulty", Cancer Models, Science, vol. 278, No. 5340, Nov. 1997, pp. 1041-1042.
Johnson et al., "Relationships between drug activity in NCI preclinical in vitro and in vivo models and early clinical trials", British Journal of Cancer 64(10), 2001, pp. 1424-1431.
Malumbres, Marcos et al., "Cell Cycle, CDKs and Cancer: A Changing Paradigm", Nature Reviews—Cancer, vol. 9, Mar. 2009, pp. 153-167.
O'Leary et al., "Treating cancer with selective CDK4/6 inhibitors", Nature Reviews: Clinical Oncology, vol. 13, 2016, pp. 417-430.
Pearce et al., "Failure modes in anticancer drug discovery and development", Cancer Drug Design and Discovery Edited by Stephen Neidle, Chapter 18, 2008, pp. 424-435.

(Continued)

*Primary Examiner* — Deepak R Rao
(74) *Attorney, Agent, or Firm* — Howard & Howard Attorneys PLLC

(57) ABSTRACT

The invention relates to a CDK4/6 kinase inhibitor, or a pharmaceutically acceptable salt, ester, or solvate thereof, or their isomers; a pharmaceutical formulation, pharmaceutical composition and kit comprising said CDK4/6 kinase inhibitor, or a pharmaceutically acceptable salt, ester, or solvate thereof, or their isomers, and use of said CDK4/6 kinase inhibitor, or a pharmaceutically acceptable salt, ester, or solvate thereof, or their isomers. For example, the compounds of the invention are useful for reducing or inhibiting the activity of CDK4/6 kinase in a cell, and/or treating and/or preventing a cancer-related disease mediated by CDK4/6 kinase.

22 Claims, No Drawings

(56) References Cited

OTHER PUBLICATIONS

Schulz, "Molecular Biology of Human Cancers: Chapter 1", Springer, 2007, pp. 1-23.
Shapiro, Geoffrey et al., "Cyclin-Dependent Kinase Pathways as Targets for Cancer Treatment", Journal of Clinical Oncology, vol. 24, No. 11, Apr. 10, 2006, pp. 1770-1783.
Simone, "Oncology: Introduction, Cecil Textbook of Medicine," 20th Edition, vol. 1, pp. 1004-1101, 1996.

* cited by examiner

KINASE INHIBITOR AND USE THEREOF

RELATED APPLICATIONS

This application is a continuation-in-part of U.S. patent application Ser. No. 15/108,903, filed on Jun. 29, 2016, which is the National Stage of International Patent Application No. PCT/CN2014/095615, filed on Dec. 30, 2014, which claims priority to and all the advantages of Chinese Patent Application No. 201310749417.3, filed on Dec. 31, 2013, the content of which is incorporated herein by reference.

TECHNICAL FIELD

The invention belongs to the technical field of medicines. Particularly, the invention relates to a CDK4/6 kinase inhibitor, or a pharmaceutically acceptable salt, ester, or solvate thereof, or their stereoisomers; a pharmaceutical formulation, a pharmaceutical composition and a kit comprising said CDK4/6 kinase inhibitor, or a pharmaceutically acceptable salt, ester, or solvate thereof, or their stereoisomers; and use of said CDK4/6 kinase inhibitor, and a pharmaceutically acceptable salt, ester, or solvate thereof, or their stereoisomers. For example, the compounds of the invention are useful for reducing or inhibiting the activity of CDK4/6 kinase in a cell, and/or treating and/or preventing a cancer-related disease mediated by CDK4/6 kinase.

BACKGROUND ART

Tumorigenesis is associated with the disbalance of oncogenes and antioncogenes. For almost all of the oncogenes or antioncogenes, their functions and effects are finally converged to cell cycle. Therefore, tumor can be taken as a cell cycle disease (CCD), and it is one of the routes for treating tumor by regulating or blocking cell cycle. In current, it is found that there are a lot of molecules associated with cell cycle regulation, among which Cyclin-Dependent-Kinases (CDKs) are core molecules of cell cycle regulatory network. CDKs, as catalytic subunits, are a class of Ser/Thr kinases, which participate in different stages of cell cycle as important signaling molecules in cells. Studies show that in a cell cycle regulatory network with CDKs as core, any abnormity would result in abnormal cell cycle and finally result in tumorigenesis. CDK family now has 21 isoforms, which work by binding to their regulatory subunit cyclins. In addition to the role in regulating the cell cycle, CDK isoforms are also involved in regulating transcription, DNA repair, differentiation and programmed cell death. Based on the key role of CDKs in regulating proliferation and death of tumor cells, the family of CDKs provides a chance and a new field for the discovery and development of anti-tumor drugs.

In the development of drugs, the first generation of CDK inhibitors, represented by flavopiridol, UCN-01 and the like, are designated as "pan-CDK" inhibitors, which block all the isoforms of CDK family equivalently and exhibit a relatively high toxicity in clinical trial, and some of them cannot be administered in a therapeutically effective amount. Therefore, human begins to develop selective CDK inhibitors to enhance the selectivity of the therapy and prevent normal cells from injury by some side effects.

Among the CDK isoforms involved in cell cycle, CDK4/6 plays an unreplaceable role. Cancer-associated cell cycle mutations are mainly present in G1 phase and G1/S transition. The complex formed by CDK4/6 and Cyclin D releases the bound transcriptional factor E2F by phosphorylation (pRb) of the antioncogene product Rb, and triggers transcription of genes associated with S phase, thereby promoting cells to pass the checkpoint and to transit from G1 phase to S phase. About 80% of human tumors are abnormal in cyclin D-CDK4/6-INK4-Rb pathway. Due to the alteration of the pathway, the G1 phase is accelerated so that tumor cells have the proliferation sped up and thus acquire survival advantage. Therefore, the interference of the pathway has become a strategy of treatment, and CDK4/6 has become a new anti-tumor target. CDK4/6 as anti-tumor target has the following advantages: (1) for most of proliferative cells, their proliferation is CDK2 or CDK4/6-dependent, however, CDK4/6 inhibitors do not exhibit the cytotoxicity of "pan-CDK inhibitors", such as bone marrow depression and intestinal reaction; and (2) preclinical tests show that if cyclin D level is increased or P16INK4a is inactivated in cells, the sensitivity of cells to drugs can be increased; since tumor cells have said phenomena relative to normal cells, the targeting property of drugs is increased to some extent.

So far, no CDK inhibitor drugs are approved for commercial marketing. A series of CDK4/6 inhibitors with good selectivity, which have been reported by some pharmaceutical companies including Pfizer, Eli Lilly and Novartis, are in clinical trials. Among them, of particular concern are PD0332991 (palbociclib) developed by Pfizer, LY2835219 (Phase III) developed by Eli Lilly and LEE-011 (Phase III) developed by Novartis

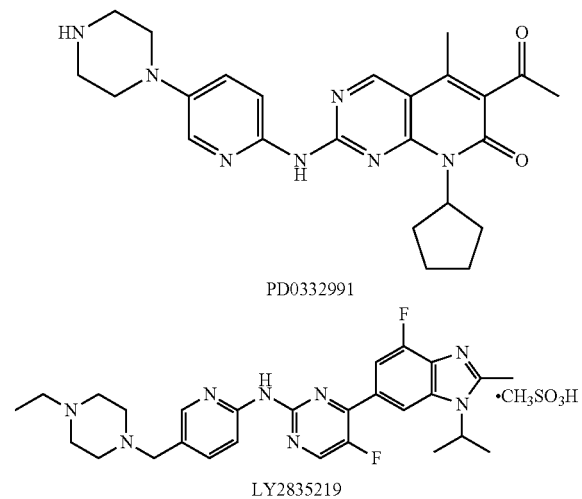

In April, 2013, Pfizer's PD0332991 received Breakthrough Therapy Designation from Food And Drug Administration (FDA); and in August, 2014, Pfizer submitted with FDA a New Drug Application (NDA) intended for approval of PD0332991 (palbociclib) in combination with letrozole as treatment of post-menopausal women with locally advanced or metastatic breast cancer, who are estrogen receptor-positive (ER+) and human epidermal growth factor 2 negative (HER2−), and did not received systemic treatment previously. It has very positive effect on the development of CDK4/6 inhibitors.

In order to achieve a better therapeutic effect for tumor and to better meet the market demand, the inventors hope to develop a new generation of CDK4/6 inhibitors with high efficacy and low toxicity. The invention provides selective CDK4/6 inhibitors with a new structure, and finds that the compounds with such a structure have good efficacy, and can effectively pass through the blood brain barrier, which makes CDK inhibitors as therapy for brain cancer possible.

CONTENTS OF INVENTION

In an aspect, the invention relates to an inhibitor/compound targeting CDK4/6 kinase. Particularly, the exemplified technical solutions of the invention are as follows:

1. A compound of Formula (I'), or a pharmaceutically acceptable salt, ester, or solvate thereof, or their stereoisomers,

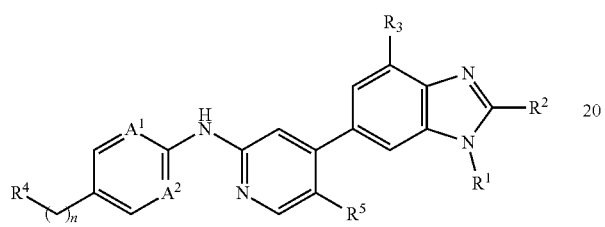

(I')

wherein:

$A^1$ and $A^2$ each are independently selected from nitrogen;

$R^1$ is selected from $C_{1-6}$alkyl, $C_{1-6}$alkoxy or 3-8 membered cycloalkyl optionally substituted by $Q^1$, wherein $Q^1$ is selected from $C_{1-6}$alkyl or $C_{1-6}$alkoxy;

$R^2$ is selected from $C_{1-6}$alkyl, $C_{1-6}$alkoxy, cyano, carbamoyl or $C_{1-6}$alkylcarbonylamino;

$R^3$ and $R^5$ each are independently selected from halogen or hydrogen, and at least one of $R^3$ and $R^5$ is halogen;

$R^4$ is selected from 3-8 membered heterocyclyl, 6-14 membered fused heterocyclyl, 5-8 membered heteroaryl, 6-14 membered fused heteroaryl, phenyl, naphthyl, 6-12 membered bridged heterocyclyl or 6-12 membered spiroheterocyclyl, each of which is optionally substituted by $Q^2$;

$Q^2$ is selected from amino, hydroxyl, halogen, trifluoromethyl, cyano, $C_{1-6}$alkoxy, $C_{1-6}$alkylsulfonyl, $C_{1-6}$alkylsulfonylamino, or di-$C_{1-6}$alkylamino; or $C_{1-6}$alkyl, 3-8 membered cycloalkyl, 3-8 membered heterocyclyl or 6-9 membered bridged heterocyclyl, each optionally substituted by a substituent, wherein the substituent is selected from amino, hydroxyl, halogen, trifluoromethyl, cyano, $C_{1-6}$alkyl, $C_{1-6}$alkoxy, $C_{1-6}$alkyl amino, di-$C_{1-6}$alkyl amino, $C_{1-6}$alkylsulfonyl, 3-8 membered heterocyclyl or 3-8 membered cycloalkyl;

n is selected from 0, 1, 2, 3, 4 or 5.

2. The compound, or a pharmaceutically acceptable salt, ester, or solvate thereof, or their stereoisomers according to Solution 1, wherein $A^1$ and $A^2$ each are independently selected from nitrogen;

$R^1$ is selected from $C_{1-4}$alkyl or $C_{1-4}$alkoxy;

$R^2$ is selected from $C_{1-4}$alkyl, $C_{1-4}$alkoxy, cyano, carbamoyl or $C_{1-4}$alkylcarbonylamino;

$R^3$ and $R^5$ each are independently selected from halogen;

$R^4$ is selected from a nitrogen-containing 5-6 membered heterocyclyl optionally substituted by $Q^2$; wherein the "nitrogen-containing 5-6 membered heterocyclyl" is preferably "a nitrogen-containing 6 membered heterocyclyl";

$Q^2$ is selected from amino, hydroxyl, halogen, trifluoromethyl, cyano, $C_{1-4}$alkoxy, or di-$C_{1-4}$alkylamino; or $C_{1-4}$alkyl, 3-6 membered cycloalkyl or 3-6 membered heterocyclyl, each optionally substituted by a substituent, wherein the substituent is selected from amino, hydroxyl, halogen, trifluoromethyl, $C_{1-4}$alkyl, $C_{1-4}$alkoxy, $C_{1-4}$alkylamino, di-$C_{1-4}$ alkylamino, or 3-6 membered cycloalkyl;

n is selected from 0.

3. The compound, or a pharmaceutically acceptable salt, ester, or solvate thereof, or their stereoisomers according to Solution 2, wherein the compound is selected from:

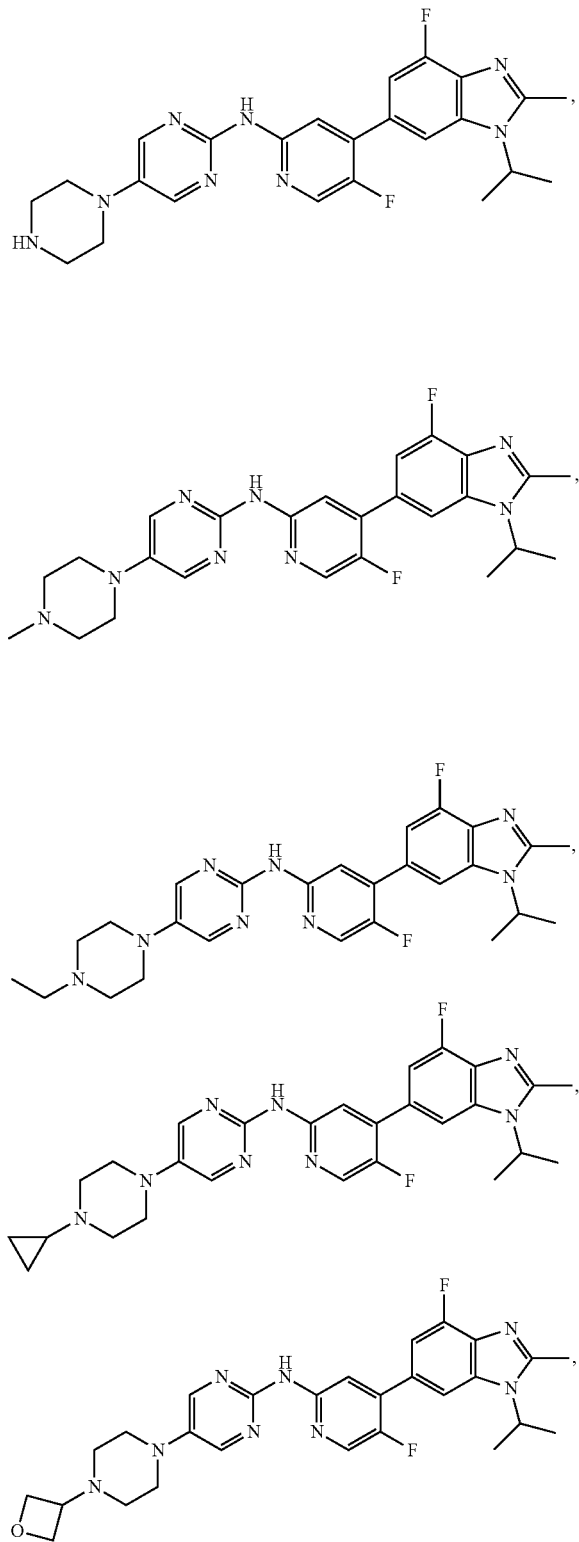

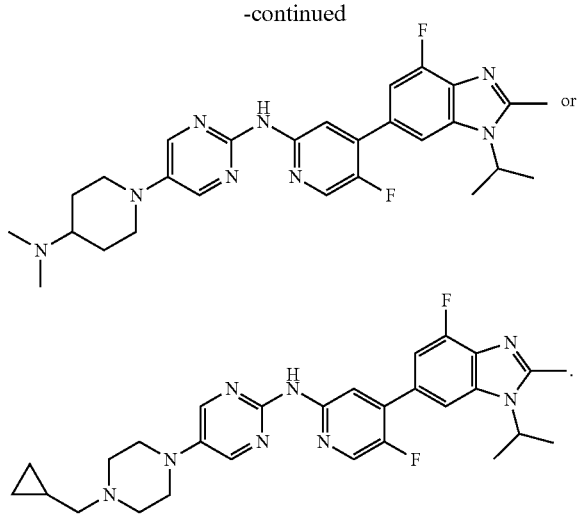

4. The compound, or a pharmaceutically acceptable salt, ester, or solvate thereof, or their stereoisomers according to Solution 1, wherein the compound has the structure of Formula (I),

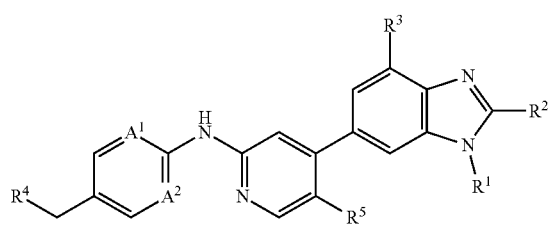

wherein:
A¹ and A² each are independently selected from nitrogen;
R¹ is selected from C₁₋₆alkyl, C₁₋₆alkoxy or 3-8 membered cycloalkyl optionally substituted by Q¹, wherein Q¹ is selected from C₁₋₆alkyl or C₁₋₆alkoxy;
R² is selected from C₁₋₆alkyl, C₁₋₆alkoxy, cyano, carbamoyl or C₁₋₆alkylcarbonylamino;
R³ and R⁵ each are independently selected from halogen or hydrogen, and at least one of R³ and R⁵ is halogen;
R⁴ is selected from 3-8 membered heterocyclyl, 6-14 membered fused heterocyclyl, 5-8 membered heteroaryl, 6-14 membered fused heteroaryl, phenyl, naphthyl, 6-12 membered bridged heterocyclyl or 6-12 membered spiroheterocyclyl, each optionally substituted by Q²; wherein Q² is selected from amino, hydroxyl, halogen, trifluoromethyl, cyano, C₁₋₆alkyl, C₁₋₆alkoxy, 3-8 membered heterocyclyl or 6-9 membered bridged heterocyclyl.

5. The compound, or a pharmaceutically acceptable salt, ester, or solvate thereof, or their stereoisomers according to Solution 4, wherein
A¹ and A² each are independently selected from nitrogen;
R¹ is selected from C₁₋₄alkyl or C₁₋₄alkoxy;
R² is selected from C₁₋₄alkyl, C₁₋₄alkoxy, cyano, carbamoyl or C₁₋₄alkylcarbonylamino;
R³ and R⁵ each are independently selected from halogen;
R⁴ is selected from 5-7 membered heterocyclyl, 6-11 membered fused heterocyclyl, 6-11 membered bridged heterocyclyl or 6-11 membered spiroheterocyclyl, each optionally substituted by Q²; wherein Q² is selected from amino, hydroxyl, trifluoromethyl, cyano, C₁₋₄alkyl, C₁₋₄alkoxy, 5-6 membered heterocyclyl or 7-9 membered bridged heterocyclyl.

6. The compound, or a pharmaceutically acceptable salt, ester, or solvate thereof, or their stereoisomers according to Solution 5, wherein
A¹ and A² each are independently selected from nitrogen;
R¹ is isopropyl;
R² is selected from methyl, methoxy, cyano, carbamoyl, or acetylamino;
R³ and R⁵ each are independently F;
R⁴ is selected from 5-6 membered heterocyclyl optionally substituted by Q²; wherein Q² is selected from amino, hydroxyl, trifluoromethyl, cyano, C₁₋₄alkyl, C₁₋₄alkoxy, 6 membered heterocyclyl or 8 membered bridged heterocyclyl.

7. The compound, or a pharmaceutically acceptable salt, ester, or solvate thereof, or their stereoisomers according to Solution 6, wherein
R² is methyl;
R⁴ is selected from a nitrogen-containing 5-6 membered heterocyclyl optionally substituted by Q²; wherein the nitrogen-containing 5-6 membered heterocyclyl is linked to the methylene of Formula (I) via a nitrogen atom, wherein Q² is selected from amino, hydroxyl, trifluoromethyl, cyano, C₁₋₄alkyl, C₁₋₄alkoxy, or a nitrogen-containing 8 membered bridged heterocyclyl;
wherein the nitrogen-containing 5-6 membered heterocyclyl is preferably a nitrogen-containing 5-6 membered heterocyclyl containing 1 to 2 nitrogen atoms;

8. The compound, or a pharmaceutically acceptable salt, ester, or solvate thereof, or their stereoisomers according to Solution 7, wherein
R⁴ is selected from

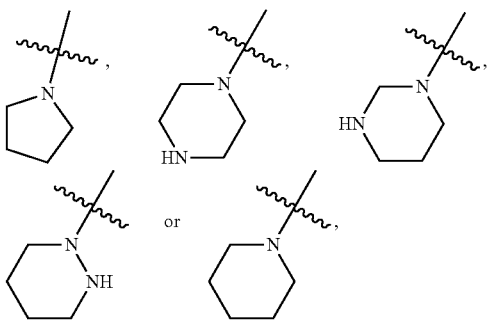

each optionally substituted by Q², wherein Q² is selected from C₁₋₄alkyl or a nitrogen-containing 8 membered bridged heterocyclyl.

9. The compound, or a pharmaceutically acceptable salt, ester, or solvate thereof, or their stereoisomers according to Solution 5, wherein
A¹ and A² each are independently selected from nitrogen;
R¹ is isopropyl;
R² is selected from methyl, methoxy, cyano, carbamoyl, or acetylamino;
R³ and R⁵ each are independently F;
R⁴ is selected from 7-9 membered bridged heterocyclyl optionally substituted by Q²; wherein Q² is selected from amino, hydroxyl, trifluoromethyl, cyano, C₁₋₄alkyl, 6 membered heterocyclyl or 8 membered bridged heterocyclyl.

10. The compound, or a pharmaceutically acceptable salt, ester, or solvate thereof, or their stereoisomers according to Solution 9, wherein $R^2$ is methyl;

$R^4$ is selected from a nitrogen-containing 7-9 membered bridged heterocyclyl optionally substituted by $Q^2$; wherein the nitrogen-containing 7-9 membered bridged heterocyclyl is linked to the methylene of Formula (I) via a nitrogen atom, wherein $Q^2$ is selected from amino, hydroxyl, trifluoromethyl, cyano, $C_{1-4}$alkyl, or a nitrogen-containing 6 membered heterocyclyl;

wherein the nitrogen-containing 7-9 membered bridged heterocyclyl is preferably a nitrogen-containing 7-9 membered bridged heterocyclyl containing 1 to 2 nitrogen atoms.

11. The compound, or a pharmaceutically acceptable salt, ester, or solvate thereof, or their stereoisomers according to Solution 10, wherein $R^4$ is selected from

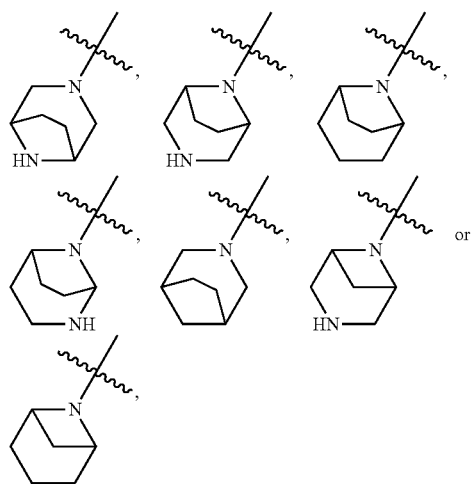

each optionally substituted by $Q^2$, wherein $Q^2$ is selected from $C_{1-4}$alkyl or a nitrogen-containing 6 membered heterocyclyl.

12. The compound, or a pharmaceutically acceptable salt, ester, or solvate thereof, or their stereoisomers according to Solution 5, wherein $A^1$ and $A^2$ each are independently selected from nitrogen;

$R^1$ is isopropyl;

$R^2$ is selected from methyl, methoxy, cyano, carbamoyl, or acetylamino;

$R^3$ and $R^5$ each are F;

$R^4$ is selected from 6-10 membered fused heterocyclyl optionally substituted by $Q^2$; wherein $Q^2$ is selected from amino, hydroxyl, trifluoromethyl, cyano, $C_{1-4}$alkyl, 6 membered heterocyclyl or 8 membered bridged heterocyclyl.

13. The compound, or a pharmaceutically acceptable salt, ester, or solvate thereof, or their stereoisomers according to Solution 12, wherein $R^2$ is methyl;

$R^4$ is selected from a nitrogen-containing 6-10 membered fused heterocyclyl that contains 1, 2 or 3 identical or different heteroatoms and is optionally substituted by $Q^2$; wherein the heteroatoms are preferably selected from nitrogen atom and oxygen atom, and contain at least one nitrogen atom, and the 6-10 membered fused heterocyclyl is linked to the methylene of Formula (I) via a nitrogen atom, wherein $Q^2$ is selected from amino, hydroxyl, trifluoromethyl, cyano, or $C_{1-4}$alkyl.

14. The compound, or a pharmaceutically acceptable salt, ester, or solvate thereof, or their stereoisomers according to Solution 13, wherein $R^4$ is selected from

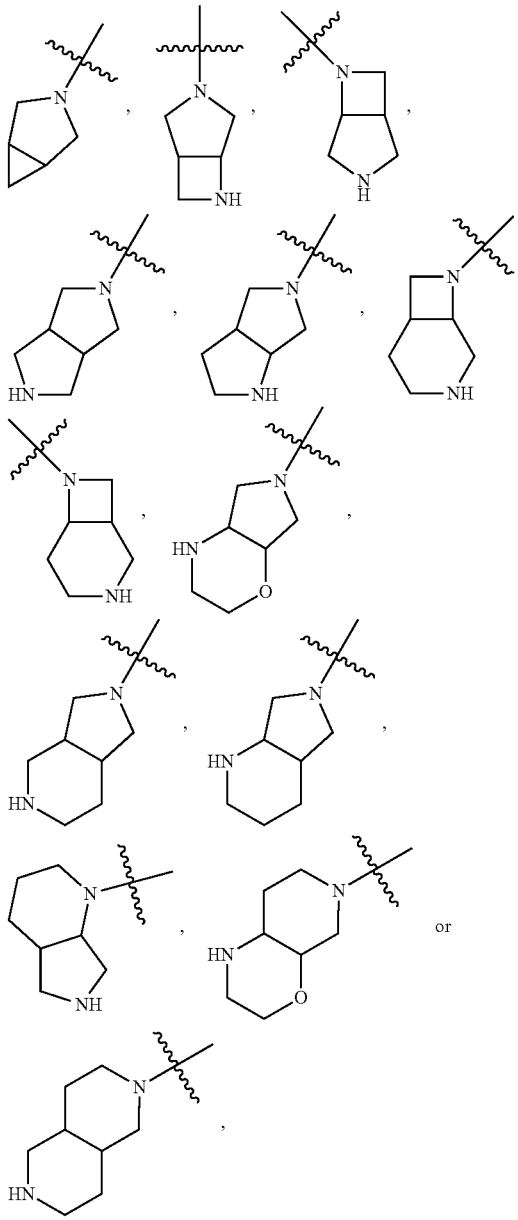

each optionally substituted by $Q^2$, wherein $Q^2$ is selected from amino or $C_{1-4}$alkyl.

15. The compound, or a pharmaceutically acceptable salt, ester, or solvate thereof, or their stereoisomers according to Solution 5, wherein $A^1$ and $A^2$ each are independently selected from nitrogen;

$R^1$ is isopropyl;

$R^2$ is selected from methyl, methoxy, cyano, carbamoyl, or acetylamino;

$R^3$ and $R^5$ each are F;

$R^4$ is selected from 7-11 membered spiroheterocyclyl optionally substituted by $Q^2$; wherein $Q^2$ is selected from amino, hydroxyl, trifluoromethyl, cyano, $C_{1-4}$alkyl, 6 membered heterocyclyl or 8 membered bridged heterocyclyl.

16. The compound, or a pharmaceutically acceptable salt, ester, or solvate thereof, or their stereoisomers according to Solution 15, wherein $R^2$ is selected from methyl;

$R^4$ is selected from a nitrogen-containing 7-11 membered spiroheterocyclyl optionally substituted by $Q^2$; wherein the nitrogen-containing 7-11 membered spiroheterocyclyl is linked to the methylene of Formula (I) via a nitrogen atom, wherein $Q^2$ is selected from amino, hydroxyl, trifluoromethyl, cyano, of $C_{1-4}$alkyl;

wherein the nitrogen-containing 7-11 membered spiroheterocyclyl is preferably a nitrogen-containing 7-11 membered spiroheterocyclyl containing 1 to 2 nitrogen atoms.

17. The compound, or a pharmaceutically acceptable salt, ester, or solvate thereof, or their stereoisomers according to Solution 16, wherein $R^4$ is selected from

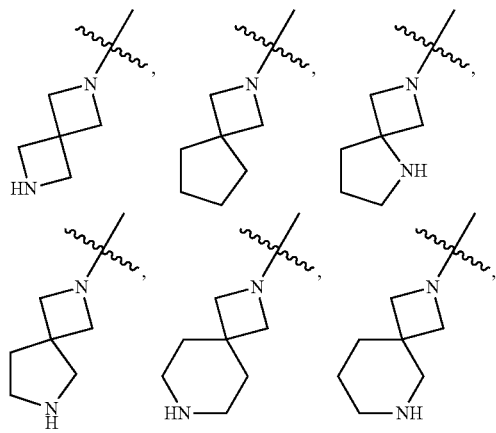

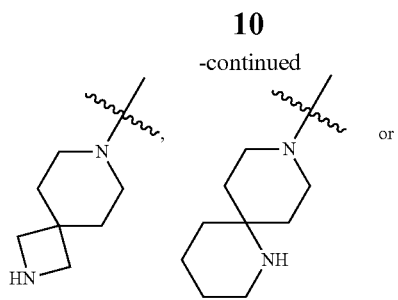

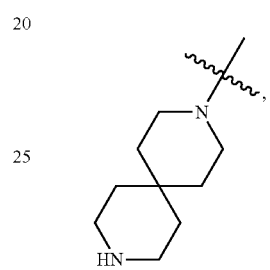

each optionally substituted by $Q^2$, wherein $Q^2$ is selected from $C_{1-4}$alkyl.

18. The compound, or a pharmaceutically acceptable salt, ester, or solvate thereof, or their stereoisomers according to Solution 1, wherein the compound is selected from the compounds shown in Table A.

TABLE A

A part of compounds of the invention

| No. | Formula |
|---|---|
| 1 | 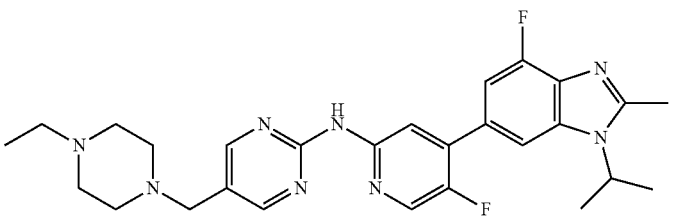 [SMILES: CCN1CCN(Cc2cnc(Nc3cc(-c4cc(F)c5nc(C)n(C(C)C)c5c4)c(F)cn3)nc2)CC1] |
| 2 | 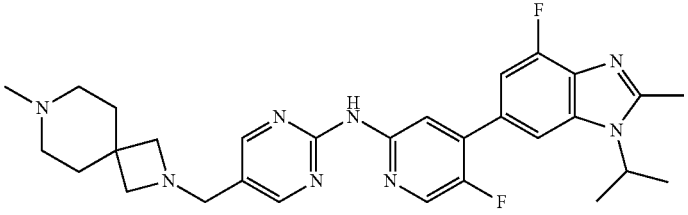 |

TABLE A-continued

A part of compounds of the invention

| No. | Formula |
|---|---|
| 3 | |
| 4 | |
| 5 | |
| 6 | |
| 6-1 | |
| 24-1 | |
| 6-2 | |

TABLE A-continued

A part of compounds of the invention

| No. | Formula |
|---|---|
| 6-2-1 | |
| 7 | |
| 7-1 | |
| 8 | |
| 8-1 | |
| 9 | |

TABLE A-continued

A part of compounds of the invention

| No. | Formula |
|-----|---------|
| 9-1 | |
| 10 | |
| 30-1 | |
| 11 | |
| 12 | |
| 13 | |

TABLE A-continued

A part of compounds of the invention

| No. | Formula |
|---|---|
| 32-1 | |
| 14 | |
| 15 | |
| 16 | |
| 17 | |
| 18 | |

TABLE A-continued
A part of compounds of the invention
| No. | Formula |
|---|---|
| 19 | 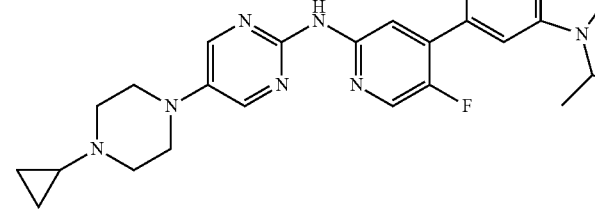 |
| 20 | 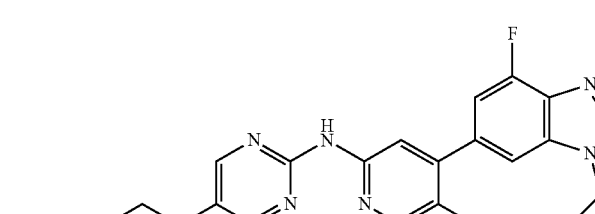 |
| 21 | 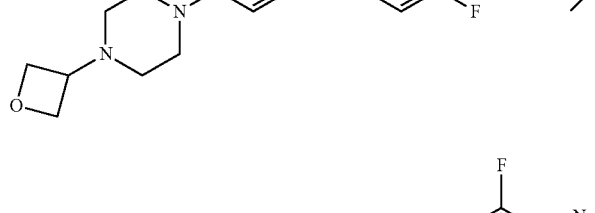 |
| 22 | 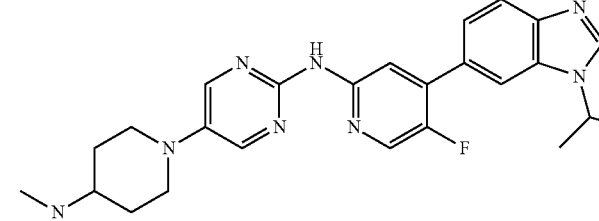 |
| 23 | 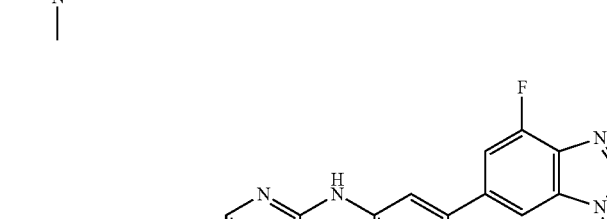 |

TABLE A-continued

A part of compounds of the invention

| No. | Formula |
|---|---|
| 23-1 | |
| 24 | |
| 25 | |
| 25-1 | |
| 26 | |
| 26-1 | |

TABLE A-continued

A part of compounds of the invention

| No. | Formula |
|---|---|
| 27 | |
| 27-1 | |
| 28 | |
| 29 | |
| 30 | |
| 31-1 | |

TABLE A-continued

A part of compounds of the invention

| No. | Formula |
|---|---|
| 31 | |
| 32 | |
| 33-1 | |
| 33 | |
| 34 | |
| 35 | |

The invention also relates to uses of the disclosed compounds. Therefore, the invention also relates to the following exemplified technical solutions:

19. A pharmaceutical composition comprising the compound, or a pharmaceutically acceptable salt, ester, or solvate thereof, or their stereoisomers according to any one of Solutions 1-18, and optionally one or more pharmaceutically acceptable carriers.

20. The pharmaceutical composition according to Solution 19, further comprising one or more additional anti-tumor agents and/or immunosuppressors.

21. The pharmaceutical composition according to Solution 20, wherein the additional anti-tumor agents and/or immunosuppressors are selected from one or more of: methotrexate, capecitabine, gemcitabine, doxifluridine, pemetrexed disodium, pazopanib, imatinib, erlotinib, lapatinib, gefitinib, vandetanib, herceptin, bevacizumab, rituximab, trastuzumab, paclitaxel, vinorelbine, docetaxel, doxorubicin, hydroxycamptothecine, mitomycin, epirubicin, pirarubicin, bleomycin, letrozole, tamoxifen, fulvestrant, triptorelin, flutamide, leuprorelin, anastrozole, ifosfamide, busulfan, cyclophosphamide, carmustine, nimustine, semustine, mechlorethamine, melphalan, chlorambucil, carboplatin, cisplatin, oxaliplatin, lobaplatin, topotecan, camptothecin, topotecan, everolimus, sirolimus, temsirolimus, 6-mercaptopurine, 6-thioguanine, azathioprine, Actinomycin D, daunorubicin, adriamycin, mitoxantrone, bleomycin, mithramycin and aminoglutethimide.

22. Use of the compound, or a pharmaceutically acceptable salt, ester, or solvate thereof, or their stereoisomers according to any one of Solutions 1-18, in the manufacture of a medicament for treating and/or preventing a cancer-related disease mediated by CDK4/6 kinase in a subject.

23. The use according to Solution 22, wherein the cancer-related disease is selected from brain tumor, lung cancer, squamous carcinoma, bladder carcinoma, gastric cancer, ovarian cancer, peritoneal carcinoma, pancreatic carcinoma, breast cancer, head and neck cancer, cervical cancer, endometrial cancer, rectal cancer, liver cancer, renal carcinoma, esophageal adenocarcinoma, esophageal squamous cancer, prostatic cancer, female reproductive duct cancer, cancer in situ, lymphoma, neurofibromas, thyroid carcinoma, osteocarcinoma, skin cancer, brain cancer, colon cancer, testiculus cancer, gastrointestinal stromal tumor, prostate neoplasms, mast cell tumor, multiple myeloma, melanoma, glioma, sarcoma, esophageal cancer, acute leukemia, malignant neoplasm of female genital organs, myeloma, teratoma, neuroblastoma, rhabdomyosarcoma, meningioma, colorectal cancer, cholangiocarcinoma, medulloepithelioma, anaplastic astrocytoma, malignant mesothelioma, malignant peripheral nerve sheath tumor, undifferentiated (embryonal) sarcoma, myelofibrosis, liposarcoma, dedifferentiated liposarcoma, soft-tissue sarcoma, ewing sarcoma, angiosarcoma, epithelioid sarcoma, fibrosarcoma, leiomyosarcoma, synovial sarcoma or myxofibrosarcoma;

preferably, said malignant neoplasm of female genital organs is selected from ovarian cancer, cervical cancer, endometrial cancer or carcinoma of fallopian tube;
preferably, said myeloma is multiple myeloma;
preferably, said lung cancer is non-small cell lung cancer;
preferably, said acute leukemia is selected from acute myeloid leukemia or acute lymphoblastic leukemia;
preferably, said lymphoma is mantle cell lymphoma.

24. The use according to Solution 22 or 23, wherein the subject is mammal, such as bovine, equine, caprid, suidae, canine, feline, rodent, and primate; wherein the particularly preferred subject is human.

25. The use according to any one of Solutions 22-24, wherein the medicament further comprises one or more additional anti-tumor agents and/or immunosuppressors; preferably, the additional anti-tumor agents and/or immunosuppressors are selected from one or more of: methotrexate, capecitabine, gemcitabine, doxifluridine, pemetrexed disodium, pazopanib, imatinib, erlotinib, lapatinib, gefitinib, vandetanib, herceptin, bevacizumab, rituximab, trastuzumab, paclitaxel, vinorelbine, docetaxel, doxorubicin, hydroxycamptothecine, mitomycin, epirubicin, pirarubicin, bleomycin, letrozole, tamoxifen, fulvestrant, triptorelin, flutamide, leuprorelin, anastrozole, ifosfamide, busulfan, cyclophosphamide, carmustine, nimustine, semustine, mechlorethamine, melphalan, chlorambucil, carboplatin, cisplatin, oxaliplatin, lobaplatin, topotecan, camptothecin, topotecan, everolimus, sirolimus, temsirolimus, 6-mercaptopurine, 6-thioguanine, azathioprine, Actinomycin D, daunorubicin, adriamycin, mitoxantrone, bleomycin, mithramycin and aminoglutethimide.

26. A method for treating and/or preventing a cancer-related disease mediated by CDK4/6 kinase, comprising administering to a subject in need thereof a therapeutically and/or prophylactically effective amount of the compound, or a pharmaceutically acceptable salt, ester, or solvate thereof, or their stereoisomers according to any one of Solutions 1-18 or the pharmaceutical composition according to any one of Solutions 19-21.

27. The method according to Solution 26, wherein the cancer-related disease is selected from brain tumor, lung cancer, squamous carcinoma, bladder carcinoma, gastric cancer, ovarian cancer, peritoneal carcinoma, pancreatic carcinoma, breast cancer, head and neck cancer, cervical cancer, endometrial cancer, rectal cancer, liver cancer, renal carcinoma, esophageal adenocarcinoma, esophageal squamous cancer, prostatic cancer, female reproductive duct cancer, cancer in situ, lymphoma, neurofibromas, thyroid carcinoma, osteocarcinoma, skin cancer, brain cancer, colon cancer, testiculus cancer, gastrointestinal stromal tumor, prostate neoplasms, mast cell tumor, multiple myeloma, melanoma, glioma, sarcoma, esophageal cancer, acute leukemia, malignant neoplasm of female genital organs, myeloma, teratoma, neuroblastoma, rhabdomyosarcoma, meningioma, colorectal cancer, cholangiocarcinoma, medulloepithelioma, anaplastic astrocytoma, malignant mesothelioma, malignant peripheral nerve sheath tumor, undifferentiated (embryonal) sarcoma, myelofibrosis, liposarcoma, dedifferentiated liposarcoma, soft-tissue sarcoma, ewing sarcoma, angiosarcoma, epithelioid sarcoma, fibrosarcoma, leiomyosarcoma, synovial sarcoma or myxofibrosarcoma;

preferably, said malignant neoplasm of female genital organs is selected from ovarian cancer, cervical cancer, endometrial cancer or carcinoma of fallopian tube;
preferably, said myeloma is multiple myeloma;
preferably, said lung cancer is non-small cell lung cancer;
preferably, said acute leukemia is selected from acute myeloid leukemia or acute lymphoblastic leukemia;
preferably, said lymphoma is mantle cell lymphoma.

28. The method according to Solution 26 or 27, wherein the subject is mammal, such as bovine, equine, caprid, suidae, canine, feline, rodent, and primate; wherein the particularly preferred subject is human.

29. The method according to any one of Solutions 25-28, wherein the method further comprises administering to the subject one or more additional anti-tumor agents and/or immunosuppressors; preferably the additional anti-tumor agents and/or immunosuppressors are selected from one or more of: methotrexate, capecitabine, gemcitabine, doxifluridine, pemetrexed disodium, pazopanib, imatinib, erlotinib, lapatinib, gefitinib, vandetanib, herceptin, bevacizumab, rituximab, trastuzumab, paclitaxel, vinorelbine, docetaxel, doxorubicin, hydroxycamptothecine, mitomycin, epirubicin, pirarubicin, bleomycin, letrozole, tamoxifen, fulvestrant, triptorelin, flutamide, leuprorelin, anastrozole, ifosfamide, busulfan, cyclophosphamide, carmustine, nimustine, semustine, mechlorethamine, melphalan, chlorambucil, carboplatin, cisplatin, oxaliplatin, lobaplatin, topotecan, camptothecin, topotecan, everolimus, sirolimus, temsirolimus, 6-mercaptopurine, 6-thioguanine, azathioprine, Actinomycin D, daunorubicin, adriamycin, mitoxantrone, bleomycin, mithramycin and aminoglutethimide.

30. The compound, or a pharmaceutically acceptable salt, ester, or solvate thereof, or their stereoisomers according to any one of Solutions 1-18, for use in the treatment and/or prevention of a cancer-related disease mediated by CDK4/6 kinase in a subject.

31. The compound, or a pharmaceutically acceptable salt, ester, or solvate thereof, or their stereoisomers according to Solution 30, wherein the cancer-related disease is selected from brain tumor, lung cancer, squamous carcinoma, bladder carcinoma, gastric cancer, ovarian cancer, peritoneal carcinoma, pancreatic carcinoma, breast cancer, head and neck cancer, cervical cancer, endometrial cancer, rectal cancer, liver cancer, renal carcinoma, esophageal adenocarcinoma, esophageal squamous cancer, prostatic cancer, female reproductive duct cancer, cancer in situ, lymphoma, neurofibromas, thyroid carcinoma, osteocarcinoma, skin cancer, brain cancer, colon cancer, testiculus cancer, gastrointestinal stromal tumor, prostate neoplasms, mast cell tumor, multiple myeloma, melanoma, glioma, sarcoma, esophageal cancer, acute leukemia, malignant neoplasm of female genital organs, myeloma, teratoma, neuroblastoma, rhabdomyosarcoma, meningioma, colorectal cancer, cholangiocarcinoma, medulloepithelioma, anaplastic astrocytoma, malignant mesothelioma, malignant peripheral nerve sheath tumor, undifferentiated (embryonal) sarcoma, myelofibrosis, liposarcoma, dedifferentiated liposarcoma, soft-tissue sarcoma, ewing sarcoma, angiosarcoma, epithelioid sarcoma, fibrosarcoma, leiomyosarcoma, synovial sarcoma or myxofibrosarcoma;

preferably, said malignant neoplasm of female genital organs is selected from ovarian cancer, cervical cancer, endometrial cancer or carcinoma of fallopian tube;

preferably, said myeloma is multiple myeloma;

preferably, said lung cancer is non-small cell lung cancer;

preferably, said acute leukemia is selected from acute myeloid leukemia or acute lymphoblastic leukemia;

preferably, said lymphoma is mantle cell lymphoma.

32. The compound, or a pharmaceutically acceptable salt, ester, or solvate thereof, or their stereoisomers according to Solution 30 or 31, wherein the subject is mammal, such as bovine, equine, caprid, suidae, canine, feline, rodent, and primate; wherein the particularly preferred subject is human.

33. The compound, or a pharmaceutically acceptable salt, ester, or solvate thereof, or their stereoisomers according to any one of Solutions 30-32, which is used in combination with one or more additional anti-tumor agents and/or immunosuppressors; preferably the additional anti-tumor agents and/or immunosuppressors are selected from one or more of: methotrexate, capecitabine, gemcitabine, doxifluridine, pemetrexed disodium, pazopanib, imatinib, erlotinib, lapatinib, gefitinib, vandetanib, herceptin, bevacizumab, rituximab, trastuzumab, paclitaxel, vinorelbine, docetaxel, doxorubicin, hydroxycamptothecine, mitomycin, epirubicin, pirarubicin, bleomycin, letrozole, tamoxifen, fulvestrant, triptorelin, flutamide, leuprorelin, anastrozole, ifosfamide, busulfan, cyclophosphamide, carmustine, nimustine, semustine, mechlorethamine, melphalan, chlorambucil, carboplatin, cisplatin, oxaliplatin, lobaplatin, topotecan, camptothecin, topotecan, everolimus, sirolimus, temsirolimus, 6-mercaptopurine, 6-thioguanine, azathioprine, Actinomycin D, daunorubicin, adriamycin, mitoxantrone, bleomycin, mithramycin and aminoglutethimide.

34. Use of the compound, or a pharmaceutically acceptable salt, ester, or solvate thereof, or their stereoisomers according to any one of Solutions 1-18, in the manufacture of a formulation for reducing and/or inhibiting CDK4 and/or CDK6 kinase activity in a cell.

35. The use according to Solution 34, wherein the formulation is administered in vivo or in vitro; for example, the formulation is administered to a subject (e.g., mammal, such as bovine, equine, caprid, suidae, canine, feline, rodent, and primate; e.g., human), to reduce or inhibit CDK4 and/or CDK6 kinase activity in a cell of the subject; or the formulation is administered to an in vitro cell (e.g., a cell line or a cell from a subject such as a cancer cell), to reduce or inhibit CDK4 and/or CDK6 kinase activity in the in vitro cell.

36. The use of Solution 34 or 35, wherein the cell is selected from brain tumor cells, lung cancer cells, squamous carcinoma cells, bladder carcinoma cells, gastric cancer cells, ovarian cancer cells, peritoneal carcinoma cells, pancreatic carcinoma cells, breast cancer cells, head and neck cancer cells, cervical cancer cells, endometrial cancer cells, rectal cancer cells, liver cancer cells, renal carcinoma cells, esophageal adenocarcinoma cells, esophageal squamous cancer cells, prostatic cancer cells, female reproductive duct cancer cells, cancer in situ cells, lymphoma cells, neurofibromas cells, thyroid carcinoma cells, osteocarcinoma cells, skin cancer cells, brain cancer cells, colon cancer cells, testiculus cancer cells, gastrointestinal stromal tumor cells, prostate neoplasms cells, mast cell tumor cells, multiple myeloma cells, melanoma cells, glioma cells, sarcoma cells, esophageal cancer cells, acute leukemia cells, malignant neoplasm cells of female genital organs, myeloma cells, teratoma cells, neuroblastoma cells, rhabdomyosarcoma cells, meningioma cells, colorectal cancer cells, cholangiocarcinoma cells, medulloepithelioma cells, anaplastic astrocytoma cells, malignant mesothelioma cells, malignant peripheral nerve sheath tumor cells, undifferentiated (embryonal) sarcoma cells, myelofibrosis cells, liposarcoma cells, dedifferentiated liposarcoma cells, soft-tissue sarcoma cells, ewing sarcoma cells, angiosarcoma cells, epithelioid sarcoma cells, fibrosarcoma cells, leiomyosarcoma cells, synovial sarcoma cells or myxofibrosarcoma cells;

preferably, said malignant neoplasm cells of female genital organs are selected from ovarian cancer cells, cervical cancer cells, endometrial cancer cells or carcinoma cells of fallopian tube;

preferably, said myeloma cells are multiple myeloma cells;

preferably, said lung cancer cells are non-small cell lung cancer cells;

preferably, said acute leukemia cells are selected from acute myeloid leukemia cells or acute lymphoblastic leukemia cells;

preferably, said lymphoma cells are mantle cell lymphoma cells.

37. A method for reducing or inhibiting CDK4 and/or CDK6 kinase activity in a cell, comprising administering to the cell an effective amount of the compound, or a pharmaceutically acceptable salt, ester, or solvate thereof, or their stereoisomers according to any one of Solutions 1-18.

38. The method according to Solution 37, wherein the method is performed in vivo, for example, the cell is a cell in a subject (e.g., mammal, such as bovine, equine, caprid, suidae, canine, feline, rodent, and primate; e.g., human); or the method is performed in vitro, for example, the cell is an in vitro cell (e.g., a cell line or a cell from a subject such as a cancer cell).

39. The method of Solution 37 or 38, wherein the cell is selected from brain tumor cells, lung cancer cells, squamous carcinoma cells, bladder carcinoma cells, gastric cancer cells, ovarian cancer cells, peritoneal carcinoma cells, pancreatic carcinoma cells, breast cancer cells, head and neck cancer cells, cervical cancer cells, endometrial cancer cells, rectal cancer cells, liver cancer cells, renal carcinoma cells, esophageal adenocarcinoma cells, esophageal squamous cancer cells, prostatic cancer cells, female reproductive duct cancer cells, cancer in situ cells, lymphoma cells, neurofibromas cells, thyroid carcinoma cells, osteocarcinoma cells, skin cancer cells, brain cancer cells, colon cancer cells, testiculus cancer cells, gastrointestinal stromal tumor cells, prostate neoplasms cells, mast cell tumor cells, multiple myeloma cells, melanoma cells, glioma cells, sarcoma cells, esophageal cancer cells, acute leukemia cells, malignant neoplasm cells of female genital organs, myeloma cells, teratoma cells, neuroblastoma cells, rhabdomyosarcoma cells, meningioma cells, colorectal cancer cells, cholangiocarcinoma cells, medulloepithelioma cells, anaplastic astrocytoma cells, malignant mesothelioma cells, malignant peripheral nerve sheath tumor cells, undifferentiated (embryonal) sarcoma cells, myelofibrosis cells, liposarcoma cells, dedifferentiated liposarcoma cells, soft-tissue sarcoma cells, ewing sarcoma cells, angiosarcoma cells, epithelioid sarcoma cells, fibrosarcoma cells, leiomyosarcoma cells, synovial sarcoma cells or myxofibrosarcoma cells;

preferably, said malignant neoplasm cells of female genital organs are selected from ovarian cancer cells, cervical cancer cells, endometrial cancer cells or carcinoma cells of fallopian tube;

preferably, said myeloma cells are multiple myeloma cells;

preferably, said lung cancer cells are non-small cell lung cancer cells;

preferably, said acute leukemia cells are selected from acute myeloid leukemia cells or acute lymphoblastic leukemia cells;

preferably, said lymphoma cells are mantle cell lymphoma cells.

40. The compound, or a pharmaceutically acceptable salt, ester, or solvate thereof, or their stereoisomers according to any one of Solution 1-18, for use in reduction or inhibition of CDK4 and/or CDK6 kinase activity in a cell.

41. The compound, or a pharmaceutically acceptable salt, ester, solvate or isomer thereof according to Solution 40, which is used for in vivo or in vitro administration; for example, the formulation is administered to a subject (e.g., mammal, such as bovine, equine, caprid, suidae, canine, feline, rodent, and primate; e.g., human), to reduce or inhibit CDK4 and/or CDK6 kinase activity in a cell of the subject; or the formulation is administered to an in vitro cell (e.g., a cell line or a cell from a subject such as a cancer cell), to reduce or inhibit CDK4 and/or CDK6 kinase activity in the in vitro cell.

42. The compound, or a pharmaceutically acceptable salt, ester, or solvate thereof, or their stereoisomers according to Solution 40 or 41, wherein the cell is selected from brain tumor cells, lung cancer cells, squamous carcinoma cells, bladder carcinoma cells, gastric cancer cells, ovarian cancer cells, peritoneal carcinoma cells, pancreatic carcinoma cells, breast cancer cells, head and neck cancer cells, cervical cancer cells, endometrial cancer cells, rectal cancer cells, liver cancer cells, renal carcinoma cells, esophageal adenocarcinoma cells, esophageal squamous cancer cells, prostatic cancer cells, female reproductive duct cancer cells, cancer in situ cells, lymphoma cells, neurofibromas cells, thyroid carcinoma cells, osteocarcinoma cells, skin cancer cells, brain cancer cells, colon cancer cells, testiculus cancer cells, gastrointestinal stromal tumor cells, prostate neoplasms cells, mast cell tumor cells, multiple myeloma cells, melanoma cells, glioma cells, sarcoma cells, esophageal cancer cells, acute leukemia cells, malignant neoplasm cells of female genital organs, myeloma cells, teratoma cells, neuroblastoma cells, rhabdomyosarcoma cells, meningioma cells, colorectal cancer cells, cholangiocarcinoma cells, medulloepithelioma cells, anaplastic astrocytoma cells, malignant mesothelioma cells, malignant peripheral nerve sheath tumor cells, undifferentiated (embryonal) sarcoma cells, myelofibrosis cells, liposarcoma cells, dedifferentiated liposarcoma cells, soft-tissue sarcoma cells, ewing sarcoma cells, angiosarcoma cells, epithelioid sarcoma cells, fibrosarcoma cells, leiomyosarcoma cells, synovial sarcoma cells or myxofibrosarcoma cells;

preferably, said malignant neoplasm cells of female genital organs are selected from ovarian cancer cells, cervical cancer cells, endometrial cancer cells or carcinoma cells of fallopian tube;

preferably, said myeloma cells are multiple myeloma cells;

preferably, said lung cancer cells are non-small cell lung cancer cells;

preferably, said acute leukemia cells are selected from acute myeloid leukemia cells or acute lymphoblastic leukemia cells;

preferably, said lymphoma cells are mantle cell lymphoma cells.

43. A kit for reducing or inhibiting CDK4 and/or CDK6 kinase activity in a cell, comprising the compound, or a pharmaceutically acceptable salt, ester, or solvate thereof, or their stereoisomers according to any one of Solutions 1-18, and optionally an instruction.

DETAILED CONTENTS OF INVENTION

In the description and claims of the present application, the compounds are named according to their formulae, and if the name and the formula for the same compound are not consistent with each other, the formula shall prevail.

In the present application, unless otherwise specified, the scientific and technical terms used herein have the meanings as generally understood by a person skilled in the art. However, in order to understand the invention better, definitions and explanations are provided for a part of terms. In addition, if the definitions and explanations of the terms provided in the present application are different from the meanings generally understood by a person skilled in the art, the definitions and explanations of the terms provided in the present application shall prevail.

The term "Me" used herein is methyl.

In the invention, the waveline "⌇" in a substituent means that the radical of the substituent is linked to the radical of a backbone (such as a phenyl ring) via a chemical bond at the position of the waveline.

The term "halogen" used herein refers to F, Cl, Br and I atom.

The term "$C_{1-6}$alkyl" used herein refers to linear or branched alkyl, including "$C_{1-4}$alkyl", "$C_{1-3}$alkyl" and the like, wherein its examples include, but are not limited to methyl, ethyl, n-propyl, isopropyl, n-butyl, 2-methylpropyl, 1-methylpropyl, 1,1-dimethylethyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, 1,2-dimethylpropyl, etc.

The terms "$C_{1-6}$alkoxy, $C_{1-6}$alkyl carbonyl amino, $C_{1-6}$alkylsulfonyl, $C_{1-6}$alkyl sulfonyl amino, $C_{1-6}$alkylamino, di-$C_{1-6}$alkylamino" used herein refer to groups formed in the form of C$_{1-6}$alkyl-O—, C$_{1-6}$alkyl-C(O)NH—, C$_{1-6}$alkyl-SO$_2$—, C$_{1-6}$alkyl-SO$_2$NH—, C$_{1-6}$alkyl-NH—, (C$_{1-6}$alkyl)$_2$-N—, wherein the term "C$_{1-6}$alkyl" has the same meanings as defined above.

The terms "C$_{1-4}$alkoxy, C$_{1-4}$alkyl carbonyl amino, C$_{1-4}$alkyl sulfonyl, C$_{1-4}$alkyl sulfonyl amino, C$_{1-4}$alkylamino, di-C$_{1-4}$alkylamino" used herein refer to groups formed in the form of C$_{1-4}$alkyl-O—, C$_{1-4}$alkyl-C(O)NH—, C$_{1-4}$alkyl-SO$_2$—, C$_{1-4}$alkyl-SO$_2$NH—, C$_{1-4}$alkyl-NH—, (C$_{1-4}$alkyl)$_2$-N—, wherein the term "C$_{1-4}$alkyl" has the same meanings as defined above.

The term "3-8 membered cycloalkyl" used herein refers to a cycloalkyl derived from removal of one hydrogen from a cycloalkane having 3-8 carbon atoms, including, e.g., "3-6 membered cycloalkyl" and "4-6 membered cycloalkyl", etc. Its examples include, but are not limited to: cyclopropyl, cyclobutyl, cyclopentyl and cyclohexyl, cycloheptyl, cyclooctyl, etc.

The term "3-8 membered heterocyclyl" used herein includes e.g. "3-7 membered heterocyclyl", "3-6 membered heterocyclyl", "4-7 membered heterocyclyl", "4-6 membered heterocyclyl", "5-7 membered heterocyclyl", "5-6 membered heterocyclyl", "5-6 membered nitrogen-containing heterocyclyl", "6 membered heterocyclyl", "6 membered nitrogen-containing heterocyclyl", etc. Its examples include, but are not limited to: aziridinyl, 2H-aziridinyl, diazacyclopropyl, 3H-diazacyclopropenyl, azetidinyl, 1,4-dioxanyl, 1,3-dioxanyl, 1,3-dioxacyclopentyl, 1,4-dioxa-cyclohexadienyl, tetrahydrofuryl, dihydropyrrolyl, pyrrolidinylyl, imidazolidinyl, 4,5-dihydroimidazolyl, pyrazolidinyl, 4,5-dihydropyrazolyl, 2,5-dihydrothienyl, tetrahydrothienyl, 4,5-dihydrothiazolyl, piperidyl, piperazinyl, morpholinyl, hexahydropyrimidinyl, hexahydropyridazinyl, 4,5-dihydrooxazolyl, 4,5-dihydroisoxazolyl, 2,3-dihydroisoxazolyl, 2H-1,2-oxazinyl, 6H-1,3-oxazinyl, 4H-1,3-thiazinyl, 6H-1,3-thiazinyl, 2H-pyranyl, 2H-pyran-2-one, 3,4-dihydro-2H-pyranyl, etc., preferably "5-6 membered nitrogen-containing heterocyclyl".

The term "linked to the methylene of Formula (I) via a nitrogen atom" used herein refers to a nitrogen-containing group (e.g., a nitrogen-containing heterocyclyl, such as "5-6 membered nitrogen-containing heterocyclyl" or "6 membered nitrogen-containing heterocyclyl"; a nitrogen-containing fused heterocyclyl, such as "6-10 membered nitrogen-containing fused heterocyclyl"; a nitrogen-containing bridged heterocyclyl, such as "7-9 membered nitrogen-containing bridged heterocyclyl" or "8 membered nitrogen-containing bridged heterocyclyl"; a nitrogen-containing spiroheterocyclyl, such as "7-11 membered nitrogen-containing spiroheterocyclyl") linked to the methylene of Formula (I) via a nitrogen atom.

According to IUPAC nomenclature rules, the fused ring of the invention refers to a fused ring structure formed by two or more ring structures that share two adjacent atoms (i.e., share one bond). The bridged ring of the invention refers to a bridged ring structure formed by two or more ring structures that share two non-adjacent carbon atoms. The spiroring of the invention refers to a spiroring structure formed by two or more ring structures that share one carbon atom.

The term "6-14 membered fused heterocyclyl" used herein refers to a 6-14 membered fused ring structure containing at least one heteroatom, formed by two or more ring structures that share two adjacent atoms (i.e., share one bond), including, e.g., "6-11 membered fused heterocyclyl", "6-10 membered fused heterocyclyl", "7-10 membered fused heterocyclyl", "9-10 membered fused heterocyclyl", "6-10 membered nitrogen-containing fused heterocyclyl" etc. Its examples include, but are not limited to: 3-azabicyclo[3.1.0]hexane, 3,6-diazabicyclo[3.2.0]heptane, 3,8-diazabicyclo[4.2.0]octane, 3,7-diazabicyclo[4.2.0]octane, octahydropyrrolo[3,4-c]pyrrole, octahydropyrrolo[3,4-b]pyrrole, octahydropyrrolo[3,4-b][1,4]oxazine, octahydro-1H-pyrrolo[3,4-c]pyridine, octahydro-1H-pyrrolo[3,4-b]pyridine, octahydro-1H-pyrido[3,4-b][1,4]oxazine, decahydro-2,6-naphthalene, tetrahydroimidazo[4,5-c]pyridinyl, 3,4-dihydroquinazolinyl, 1,2-dihydroquinoxalinyl, benzo[d][1,3]dioxacyclopentenyl, 1,3-dihydroisobenzofuryl, 2H-chromenyl, 2H-chromen-2-one, 4H-chromenyl, 4H-chromen-4-one, chromanyl, 4H-1,3-benzoxazinyl, 4,6-dihydro-1H-furo[3,4-d]imidazolyl, 3a,4,6,6a-tetrahydro-1H-furo[3,4-d]imidazolyl, 4,6-dihydro-1H-thieno[3,4-d]imidazolyl, 4,6-dihydro-1H-pyrrolo[3,4-d]imidazolyl, 4,5,6,7-tetrahydro-1H-benzo[d]imidazolyl, etc.

The term "5-8 membered heteroaryl" used herein, includes, e.g., "5-7 membered heteroaryl", "5-6 membered heteroaryl" etc. Its examples include, but are not limited to: furyl, thienyl, pyrrolyl, thiazolyl, isothiazolyl, thiadiazolyl, oxazolyl, isoxazolyl, oxadiazolyl, imidazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, 2-pyridone, 4-pyridone, pyrimidinyl, 1,4-dioxocyclohexadienyl, 2H-1,2-oxazinyl, 4H-1,2-oxazinyl, 6H-1,2-oxazinyl, 4H-1,3-oxazinyl, 6H-1,3-oxazinyl, 4H-1,4-oxazinyl, pyridazinyl, pyrazinyl, 1,2,3-triazinyl, 1,3,5-triazinyl, 1,2,4,5-tetrazinyl, azepinyl, 1,3-diazepinyl, azocinyl, etc., preferably "5~6 membered heteroaryl".

The term "6-14 membered fused heteroaryl" used herein refers to an aromatic 6-14 membered fused ring structure containing at least one heteroatom, formed by two or more ring structures that share two adjacent atoms (i.e., share one bond), including, e.g., "6-10 membered fused heteroaryl", "7-10 membered fused heteroaryl", "9-10 membered fused heteroaryl" etc. Its examples include, but are not limited to: benzofuranyl, isobenzofuranyl, benzothienyl, indolyl, isoindolyl, benzoxazolyl, benzoimidazolyl, indazolyl, benzotriazolyl, quinolinyl, quinolin-2-one, quinolin-4-one, isoquinolin-1-one, isoquinolinyl, acridinyl, phenanthridinyl, benzopyridazinyl, phthalazinyl, quinazolinyl, quinoxalinyl, phenazinyl, pteridinyl, purinyl, naphthyridinyl, phenazine, phenothiazine, etc.

The term "6-12 membered bridged heterocyclyl" used herein refers to a 6-12 membered bridged ring structure containing at least one heteroatom, formed by any two rings that share two non-adjacent atoms, wherein the heteroatom is selected from N, S, O, CO, SO and/or SO$_2$, etc. It includes, e.g., "6-11 membered bridged heterocyclyl", "6-9 membered bridged heterocyclyl", "7-10 membered bridged heterocyclyl", "7-9 membered bridged heterocyclyl", "7-9 membered nitrogen-containing bridged heterocyclyl", "7-8 membered bridged heterocyclyl", "8 membered bridged heterocyclyl", "8 membered nitrogen-containing bridged heterocyclyl" etc. Its examples include, but are not limited to

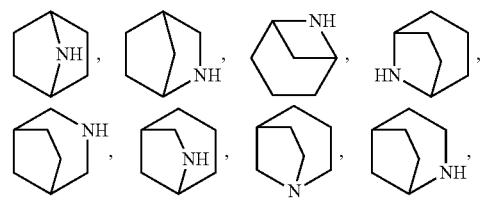

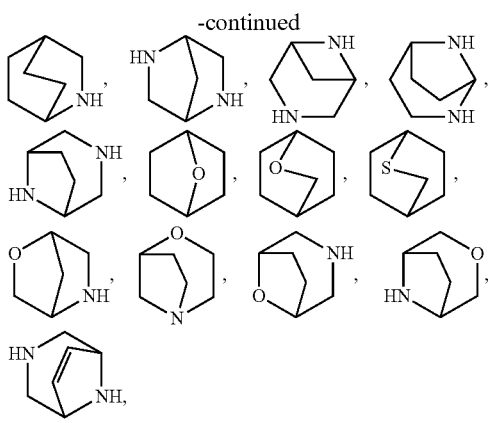

etc.

The term "6-12 membered spiroheterocyclyl" used herein refers to a 6-12 membered spiroring structure containing at least one heteroatom, formed by at least two rings that share one atom, wherein the heteroatom is selected from N, S, O, CO, SO and/or $SO_2$ etc. It includes, e.g., "6-11 membered spiroheterocyclyl", "7-11 membered spiroheterocyclyl", "7-11 membered nitrogen-containing spiroheterocyclyl", "7-10 membered spiroheterocyclyl", "7-9 membered spiroheterocyclyl", "7-8 membered spiroheterocyclyl" etc. Its examples include, but are not limited to:

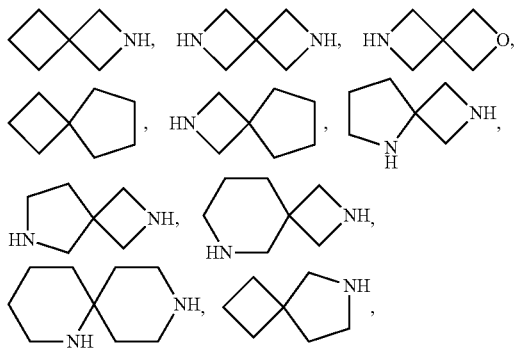

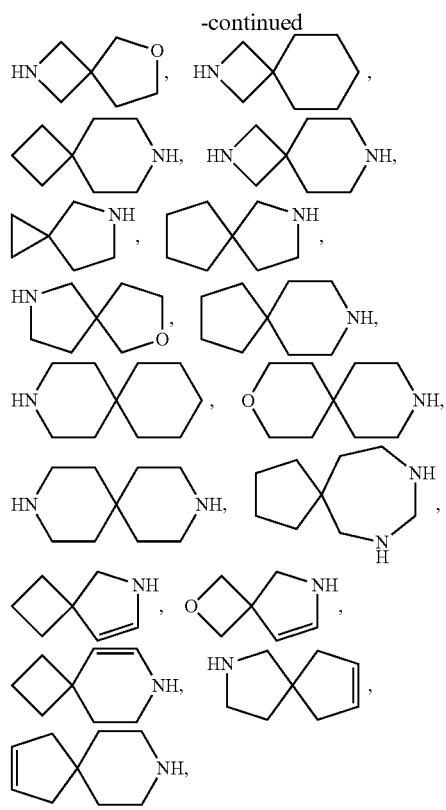

etc.

The invention also provides a method for preparing the compound of Formula (I'), including, but not limited to the following scheme (wherein the meanings of the abbreviations are described as follows: DCM: dichloromethane; DIPEA: N,N-diisopropylethylamine; DMF: N,N-dimethylformamide; DMSO: dimethyl sulfoxide; EA: ethyl acetate; HATU: 2-(7-azabenzotriazol-1-yl)-N,N,N',N'-tetramethyluronium hexafluorophosphate; MeOH: methanol; NBS: N-bromobutanimide; PE: petroleum ether; THF: tetrahydrofuran; Xant-phos: 4, 5-bis(diphenylphosphino)-9,9-dimethyl xanthene; x-phos: 2-dicyclohexylphosphino-2',4',6'-triisopropylbiphenyl):

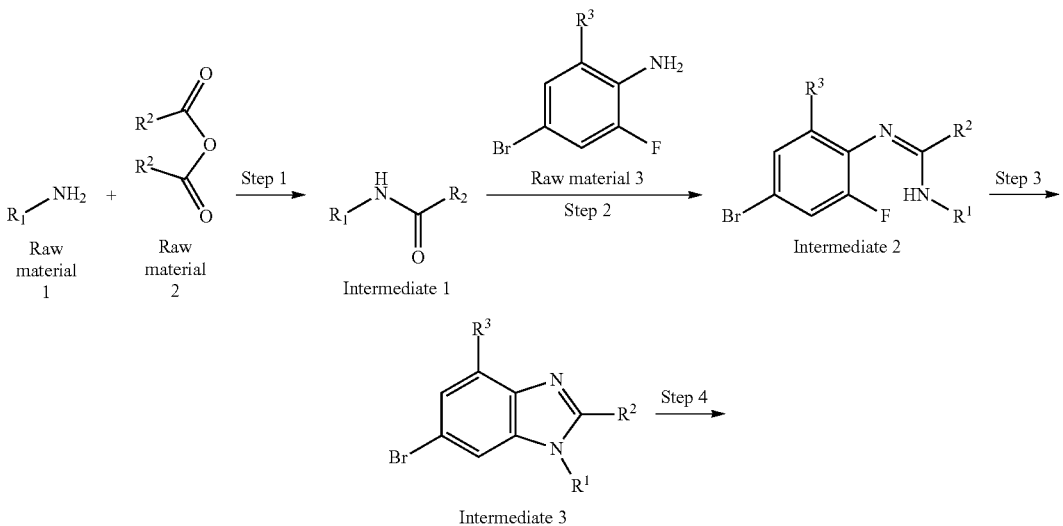

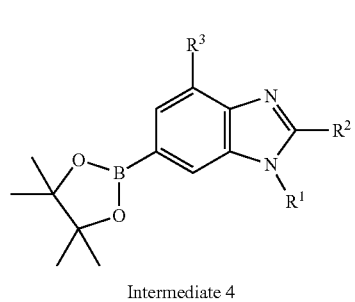
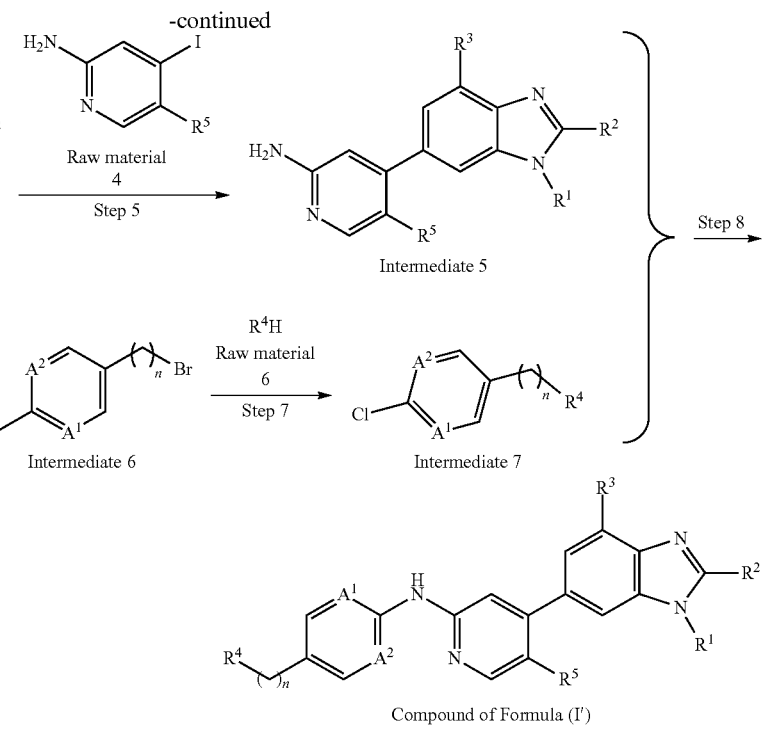

Compound of Formula (I')

wherein, $R^1$, $R^2$, $R^3$, $R^4$, $R^5$, n, $A^1$, $A^2$ have the same meanings as defined above, X represents halogen, selected from F, Cl, Br and I; and halogenating agent is selected from $I_2$ and $Br_2$.

The exemplified steps are as follows:

1. Preparation of Intermediate 1

Raw material 1 and an organic base are dissolved in an organic solvent, and raw material 2 is added dropwisely and slowly at low temperature. The reaction is carried out under stirring. After the reaction, the reaction mixture is extracted; the organic phase is dried and concentrated to obtain Intermediate 1, wherein the organic solvent is preferably DCM or 1,4-dioxane, and the organic base is preferably triethylamine.

2. Preparation of Intermediate 2

Intermediate 1, raw material 3 and an organic base are dissolved in an organic solvent, and phosphorus oxychloride is added dropwisely. After the reaction, a base is added to adjust the pH of the reaction mixture to neutral. The resultant mixture is extracted, and the separated organic phase is dried and concentrated to obtain Intermediate 2, wherein the organic solvent is preferably DCM or 1,2-dichloroethane, and the organic base is preferably triethylamine.

3. Preparation of Intermediate 3

Intermediate 2 is dissolved in an organic solvent, and potassium tert-butoxide is added. The resultant mixture is heated to 100° C. and reacted for 2 h. After the reaction, water is added to quench the reaction. The reaction mixture is extracted, and the organic phase is dried and concentrated. The resultant residue is subjected to column chromatography to obtain Intermediate 3, wherein the organic solvent is preferably DCM.

4. Preparation of Intermediate 4

Intermediate 3 and pinacol borate are dissolved in an organic solvent; and palladium diacetate, phosphorus tricyclohexyl and potassium acetate are added. Under the protection of nitrogen gas, the reaction is carried out under heating. After the reaction, water and an organic solvent are added to extract the reaction mixture. The organic phase is dried, concentrated, and separated by column chromatography to obtain Intermediate 4, wherein the organic solvent is preferably DMF or 1, 4-dioxane.

5. Preparation of Intermediate 5

Raw material 4 and Intermediate 4 are dissolved in an organic solvent, and an inorganic base and tetrakis(triphenylphosphine)palladium are added. Under the protection of nitrogen gas, the reaction is carried out under heating. After the reaction, water is added. The reaction mixture is extracted, and the organic phase is dried and concentrated. The resultant residue is separated by column chromatography to obtain Intermediate 5, wherein the organic solvent is preferably 1,4-dioxane or DMF.

6. Preparation of Intermediate 6

Raw material 5 is dissolved in an organic solvent, and benzoyl peroxide and NBS are added. The reaction is carried out under heating. After the reaction, the reaction mixture is filtrated, and the filtrate is concentrated. The resultant residue is separated by column chromatography to obtain Intermediate 6, wherein the organic solvent is preferably carbon tetrachloride.

7. Preparation of Intermediate 7

Intermediate 6 and raw material 6 are dissolved in an organic solvent, and an inorganic base is added. The reaction is carried out at room temperature. After the reaction, the reaction mixture is filtrated, the filtrate is concentrated, and the residue is separated by column chromatography to obtain Intermediate 7, wherein the organic solvent is preferably acetonitrile.

8. Preparation of Compound of Formula (I')

Intermediate 5 and Intermediate 7 are dissolved in an organic solvent; and tris(dibenzylideneacetone)dipalladiu, 2-dicyclohexylphosphino-2',4',6'-triisopropylbiphenyl, and cesium carbonate are added. Under the protection of nitrogen gas, the reaction is carried out under heating. After the reaction, water is added. The reaction mixture is extracted, and the organic phase is dried and concentrated. The resultant residue is separated by column chromatography to obtain the compound of Formula (I'), wherein the organic solvent is preferably 1,4-oxane or DMF.

Raw material 6 is primary amine or secondary amine, etc.

"A pharmaceutically acceptable salt" of the compound of Formula (I') or Formula (I) according to the invention refers to a salt formed by the reaction of acidic group(s) (e.g., —COOH, —OH, —SO$_3$H etc.) in the compound of Formula (I') or Formula (I) with suitable inorganic or organic cation(s) (base), including a salt formed with alkaline metal or alkaline earth metal, ammonium salt, and a salt formed with a nitrogen-containing organic base; and a salt formed by the reaction of the basic group(s) (e.g., —NH$_2$, etc.) in the compound of Formula (I') or Formula (I) with suitable inorganic or organic anion(s) (acid), including inorganic acid and organic carboxylic acid.

"A ester" of the compound of Formula (I') or Formula (I) according to the invention refers to an ester formed by the esterification reaction of the compound of Formula (I') or Formula (I) with an alcohol when the compound of Formula (I') or Formula (I) has a carboxyl group; or an ester formed by the esterification reaction of the compound of Formula (I') or Formula (I) with an organic acid, inorganic acid, or organic acid salt, etc., when the compound of Formula (I') or Formula (I) has a hydroxyl group. In the presence of acid or base, an ester may be hydrolyzed to produce the corresponding acid or alcohol.

"A solvate" of the compound of Formula (I') or Formula (I) according to the invention refers to a substance formed by its association with solvent molecule (s). The solvent may be an organic solvent (e.g., methanol, ethanol, propanol, acetonitrile, etc.), and water, etc. For example, the compound of Formula (I') or Formula (I) according to the invention may form an alcoholate with ethanol, or form a hydrate with water.

"Stereoisomerism" of the compound according to the invention is divided into conformational isomerism and configurational isomerism, wherein configurational isomerism is further divided into cis-trans isomerism and optical isomerism. Conformational isomerism is a form of stereoisomerism in which rotations or distortions of single C—C bonds result in different spatial arrangements of atoms or atomic groups in an organic molecule with a certain configuration, commonly in alkane and cycloalkane compounds, such as cyclohexane conformations with chair and boat conformers. "Stereoisomers" means that the compounds according to the invention have one or more asymmetry centers, and thus can be racemes and racemic mixtures, single enantiomers, diastereoisomer mixtures, and single diastereoisomers. The compounds according to the invention have asymmetry centers, which each independently lead to two optical isomers. The scope of the invention includes all the possible optical isomers and diastereoisomer mixtures, as well as pure or partially pure compounds. If the compounds according to the invention have alkene carbon-carbon double bond, unless otherwise specified, the compounds according to the invention include cis-isomers and trans-isomers. The compounds according to the invention may be present in form of tautomers, which have different hydrogen connection sites due to one or more double-bond shifts. For example, ketone and its enol form are keto-enol tautomers. Various tautomers and mixtures thereof all are included in the compounds according to the invention. All the enantiomers, diastereoisomers, racemes, cis-trans-isomers, tautomers, geometric isomers, and epimerides of the compound of Formula (I') or Formula (I), and mixtures thereof fall into the scope of the invention.

The invention further provides a pharmaceutical composition comprising the compound of Formula (I') or Formula (I), or a pharmaceutically acceptable salt, ester, or solvate thereof, or their stereoisomers, and optionally one or more pharmaceutically acceptable carriers. The pharmaceutical composition may be prepared in any pharmaceutically acceptable form. The pharmaceutical composition may be administered to a patient or subject in need thereof by any suitable route, such as orally, parenterally, rectally, or intrapulmonarily, etc. When administered orally, the pharmaceutical composition may be prepared into a conventional solid formulation, such as tablet, capsule, pill, and granule; or may be prepared into an oral liquid formulation, such as oral solution, oral suspension, and syrup. When the pharmaceutical composition is prepared as an oral formulation, suitable fillers, binding agents, disintegrating agents, lubricants and the like may be added. When administered parenterally, the pharmaceutical composition may be prepared into an injection, including injectio, sterile powder for injection and concentrated solution for injection. When the pharmaceutical composition is prepared into an injection, conventional methods in pharmaceutical field may be used. When preparing an injection, additives may not be added, or suitable additives are added depending on the properties of drug. When administered rectally, the pharmaceutical composition may be prepared into a suppository, etc. When administered intrapulmonarily, the pharmaceutical composition may be prepared into inhalant, or spraying agent, etc.

In addition to the compound of Formula (I') or Formula (I), or a pharmaceutically acceptable salt, ester, or solvate thereof, or their stereoisomers, the pharmaceutical composition according to the invention may further comprise one or more additional anti-tumor agents and/or immunosuppressors. The anti-tumor agents and/or immunosuppressors include, but are not limited to methotrexate, capecitabine, gemcitabine, doxifluridine, pemetrexed disodium, pazopanib, imatinib, erlotinib, lapatinib, gefitinib, vandetanib, herceptin, bevacizumab, rituximab, trastuzumab, paclitaxel, vinorelbine, docetaxel, doxorubicin, hydroxycamptothecine, mitomycin, epirubicin, pirarubicin, bleomycin, letrozole, tamoxifen, fulvestrant, triptorelin, flutamide, leuprorelin, anastrozole, ifosfamide, busulfan, cyclophosphamide, carmustine, nimustine, semustine, mechlorethamine, melphalan, chlorambucil, carboplatin, cisplatin, oxaliplatin, lobaplatin, topotecan, camptothecin, topotecan, everolimus, sirolimus, temsirolimus, 6-mercaptopurine, 6-thioguanine, azathioprine, actinomycin D, daunorubicin, adriamycin, mitoxantrone, bleomycin, mithramycin and aminoglutethimide.

The invention further provides use of the compound of formula (I') or Formula (I), or a pharmaceutically acceptable salt, ester, or solvate thereof, or their stereoisomers according to the invention, in the manufacture of a medicament for treating and/or preventing a cancer-related disease mediated by CDK4/6 kinase in a subject. In a preferred embodiment, the cancer-related disease is selected from brain tumor, lung cancer, squamous carcinoma, bladder carcinoma, gastric cancer, ovarian cancer, peritoneal carcinoma, pancreatic carcinoma, breast cancer, head and neck cancer, cervical cancer, endometrial cancer, rectal cancer, liver cancer, renal carcinoma, esophageal adenocarcinoma, esophageal squamous cancer, prostatic cancer, female reproductive duct cancer, cancer in situ, lymphoma, neurofibromas, thyroid carcinoma, osteocarcinoma, skin cancer, brain cancer, colon cancer, testiculus cancer, gastrointestinal stromal tumor, prostate neoplasms, mast cell tumor, multiple myeloma, melanoma, glioma, sarcoma, esophageal cancer, acute leukemia, malignant neoplasm of female genital organs, myeloma, teratoma, neuroblastoma, rhabdomyosarcoma, meningioma, colorectal cancer, cholangiocarcinoma, medulloepithelioma, anaplastic astrocytoma, malignant mesothelioma, malignant peripheral nerve sheath tumor, undifferentiated (embryonal) sarcoma, myelofibrosis, liposarcoma, dedifferentiated liposarcoma, soft-tissue sarcoma, ewing sarcoma, angiosarcoma, epithelioid sarcoma, fibrosarcoma, leiomyosarcoma, synovial sarcoma or myxofibrosarcoma; preferably, said malignant neoplasm of female genital organs is selected from ovarian cancer, cervical cancer, endometrial cancer or carcinoma of fallopian tube; preferably, said myeloma is multiple myeloma; preferably, said lung cancer is non-small cell lung cancer; preferably, said acute leukemia is selected from acute myeloid leukemia or acute lymphoblastic leukemia; preferably, said lymphoma is mantle cell lymphoma.

In the invention, the subject or patient may be any animal, preferably mammal, such as bovine, equine, caprid, suidae, canine, feline, rodent, and primate; wherein the particularly preferred subject is human.

The invention further provides a method for treating and/or preventing a cancer-related disease mediated by CDK4/6 kinase, comprising administering to a subject in need thereof a therapeutically and/or prophylactically effective amount of the compound, or a pharmaceutically acceptable salt, ester, or solvate thereof, or their stereoisomers according to the invention or of the pharmaceutical composition according to the invention.

As used herein, the term "an effective amount" refers to an amount that is sufficient to achieve or at least partially achieve a desired effect. For example, an effective amount for preventing a disease (such as a cancer-related disease mediated by CDK4/6 kinase) refers to an amount that is sufficient to prevent, suppress or delay the development of the disease (such as a cancer-related disease mediated by CDK4/6 kinase); a therapeutically effective amount refers to an amount that is sufficient to cure or at least partially suppress a disease and its complications in a patient with the disease. It is completely within the ability of a person skilled in the art to determine such an effective amount. For example, a therapeutically effective amount will depend on the severity of a disease to be treated, the overall state of the immune system in a patient, general conditions of a patient such as age, body weight and gender, administration route of a drug, and other therapy used in combination, and the like.

As described in detail above, the compounds or pharmaceutical compositions of the invention can be administered to a subject in need thereof by any suitable route in any suitable form. For example, the compounds or pharmaceutical composition of the invention may be administered to a subject in need thereof orally, parenterally, rectally, or intrapulmonarily, etc. The compounds or pharmaceutical composition of the invention may be tablets, capsules, pills, granules, solutions, suspensions, syrups, injections (including injectio, sterile powder for injection and concentrated solution for injection), suppositories, inhalants, or spraying agents.

In addition, the method according to the invention can be performed in any subject, preferably mammal, such as bovine, equine, caprid, suidae, canine, feline, rodent, and primate; wherein the particularly preferred subject is human.

In addition, as described in detail above, the method according to the invention is useful for treating and/or preventing various cancer-related diseases mediated by CDK4/6 kinase, including, but not limited to brain tumor, lung cancer, squamous carcinoma, bladder carcinoma, gastric cancer, ovarian cancer, peritoneal carcinoma, pancreatic carcinoma, breast cancer, head and neck cancer, cervical cancer, endometrial cancer, rectal cancer, liver cancer, renal carcinoma, esophageal adenocarcinoma, esophageal squamous cancer, prostatic cancer, female reproductive duct cancer, cancer in situ, lymphoma, neurofibromas, thyroid carcinoma, osteocarcinoma, skin cancer, brain cancer, colon cancer, testiculus cancer, gastrointestinal stromal tumor, prostate neoplasms, mast cell tumor, multiple myeloma, melanoma, glioma, sarcoma, esophageal cancer, acute leukemia, malignant neoplasm of female genital organs, myeloma, teratoma, neuroblastoma, rhabdomyosarcoma, meningioma, colorectal cancer, cholangiocarcinoma, medulloepithelioma, anaplastic astrocytoma, malignant mesothelioma, malignant peripheral nerve sheath tumor, undifferentiated (embryonal) sarcoma, myelofibrosis, liposarcoma, dedifferentiated liposarcoma, soft-tissue sarcoma, ewing sarcoma, angiosarcoma, epithelioid sarcoma, fibrosarcoma, leiomyosarcoma, synovial sarcoma or myxofibrosarcoma; preferably, said malignant neoplasm of female genital organs is selected from ovarian cancer, cervical cancer, endometrial cancer or carcinoma of fallopian tube; preferably, said myeloma is multiple myeloma; preferably, said lung cancer is non-small cell lung cancer; preferably, said acute leukemia is selected from acute myeloid leukemia or acute lymphoblastic leukemia; preferably, said lymphoma is mantle cell lymphoma.

Moreover, in addition to the compound of Formula (I') or Formula (I), or a pharmaceutically acceptable salt, ester, or solvate thereof, or their stereoisomers, the method according to the invention may further comprise administering to the subject one or more additional anti-tumor agents and/or immunosuppressors. In other words, in the method according to the invention, the compound according to the invention may be used in combination with one or more additional anti-tumor agents and/or immunosuppressors.

In one preferred embodiment, the additional anti-tumor agents and/or immunosuppressors are selected from one or more of: methotrexate, capecitabine, gemcitabine, doxifluridine, pemetrexed disodium, pazopanib, imatinib, erlotinib, lapatinib, gefitinib, vandetanib, herceptin, bevacizumab, rituximab, trastuzumab, paclitaxel, vinorelbine, docetaxel, doxorubicin, hydroxycamptothecine, mitomycin, epirubicin, pirarubicin, bleomycin, letrozole, tamoxifen, fulvestrant, triptorelin, flutamide, leuprorelin, anastrozole, ifosfamide, busulfan, cyclophosphamide, carmustine, nimustine, semustine, mechlorethamine, melphalan, chlorambucil, carboplatin, cisplatin, oxaliplatin, lobaplatin, topotecan, camptothecin, topotecan, everolimus, sirolimus, temsirolimus, 6-mercaptopurine, 6-thioguanine, azathioprine, actinomycin D, daunorubicin, adriamycin, mitoxantrone, bleomycin, mithramycin and aminoglutethimide. In a preferred embodiment, the compound according to the invention and the additional anti-tumor agent and/or immunosuppressor may be administered in any order. For example, the additional anti-tumor agent and/or immunosuppressor may be administered to the subject before, at the same time, or after the administration of the compound according to the invention.

The invention further provides use of the compound of formula (I') or Formula (I), or a pharmaceutically acceptable salt, ester, or solvate thereof, or their stereoisomers, in the manufacture of a formulation for reducing or inhibiting CDK4 and/or CDK6 kinase activity in a cell. In a preferred embodiment, the formulation is administered in vivo or in vitro. For example, the formulation is administered to a subject (e.g., mammal, such as bovine, equine, caprid, suidae, canine, feline, rodent, and primate; e.g., human), to reduce or inhibit CDK4 and/or CDK6 kinase activity in a cell of the subject; or the formulation is administered to an in vitro cell (e.g., a cell line or a cell from a subject such as a cancer cell), to reduce or inhibit CDK4 and/or CDK6 kinase activity in the in vitro cell. In a preferred embodiment, the cell is selected from brain tumor cells, lung cancer cells, squamous carcinoma cells, bladder carcinoma cells, gastric cancer cells, ovarian cancer cells, peritoneal carcinoma cells, pancreatic carcinoma cells, breast cancer cells, head and neck cancer cells, cervical cancer cells, endometrial cancer cells, rectal cancer cells, liver cancer cells, renal carcinoma cells, esophageal adenocarcinoma cells, esophageal squamous cancer cells, prostatic cancer cells, female reproductive duct cancer cells, cancer in situ cells, lymphoma cells, neurofibromas cells, thyroid carcinoma cells, osteocarcinoma cells, skin cancer cells, brain cancer cells, colon cancer cells, testiculus cancer cells, gastrointestinal stromal tumor cells, prostate neoplasms cells, mast cell tumor cells, multiple myeloma cells, melanoma cells, glioma cells, sarcoma cells, esophageal cancer cells, acute leukemia cells, malignant neoplasm cells of female genital organs, myeloma cells, teratoma cells, neuroblastoma cells, rhabdomyosarcoma cells, meningioma cells, colorectal cancer cells, cholangiocarcinoma cells, medulloepithelioma cells, anaplastic astrocytoma cells, malignant mesothelioma cells, malignant peripheral nerve sheath tumor cells, undifferentiated (embryonal) sarcoma cells, myelofibrosis cells, liposarcoma cells, dedifferentiated liposarcoma cells, soft-tissue sarcoma cells, ewing sarcoma cells, angiosarcoma cells, epithelioid sarcoma cells, fibrosarcoma cells, eiomyosarcoma cells, synovial sarcoma cells or myxofibrosarcoma cells; preferably, said malignant neoplasm cells of female genital organs are selected from ovarian cancer cells, cervical cancer cells, endometrial cancer cells or carcinoma cells of fallopian tube; preferably, said myeloma cells are multiple myeloma cells; preferably, said lung cancer cells are non-small cell lung cancer cells; preferably, said acute leukemia cells are selected from acute myeloid leukemia cells or acute lymphoblastic leukemia cells; preferably, said lymphoma cells are mantle cell lymphoma cells.

The invention further provides a method for reducing or inhibiting CDK4 and/or CDK6 kinase activity in a cell, comprising administering to the cell an effective amount of the compound, or a pharmaceutically acceptable salt, ester, or solvate thereof, or their stereoisomers according to the invention. In a preferred embodiment, the method is performed in vivo, for example, the cell is a cell in a subject (e.g., mammal, such as bovine, equine, caprid, suidae, canine, feline, rodent, and primate; e.g., human); or the method is performed in vitro, for example, the cell is an in vitro cell (e.g., a cell line or a cell from a subject such as a cancer cell). In a preferred embodiment, the cell is selected from brain tumor cells, lung cancer cells, squamous carcinoma cells, bladder carcinoma cells, gastric cancer cells, ovarian cancer cells, peritoneal carcinoma cells, pancreatic carcinoma cells, breast cancer cells, head and neck cancer cells, cervical cancer cells, endometrial cancer cells, rectal cancer cells, liver cancer cells, renal carcinoma cells, esophageal adenocarcinoma cells, esophageal squamous cancer cells, prostatic cancer cells, female reproductive duct cancer cells, cancer in situ cells, lymphoma cells, neurofibromas cells, thyroid carcinoma cells, osteocarcinoma cells, skin cancer cells, brain cancer cells, colon cancer cells, testiculus cancer cells, gastrointestinal stromal tumor cells, prostate neoplasms cells, mast cell tumor cells, multiple myeloma cells, melanoma cells, glioma cells, sarcoma cells, esophageal cancer cells, acute leukemia cells, malignant neoplasm cells of female genital organs, myeloma cells, teratoma cells, neuroblastoma cells, rhabdomyosarcoma cells, meningioma cells, colorectal cancer cells, cholangiocarcinoma cells, medulloepithelioma cells, anaplastic astrocytoma cells, malignant mesothelioma cells, malignant peripheral nerve sheath tumor cells, undifferentiated (embryonal) sarcoma cells, myelofibrosis cells, liposarcoma cells, dedifferentiated liposarcoma cells, soft-tissue sarcoma cells, ewing sarcoma cells, angiosarcoma cells, epithelioid sarcoma cells, fibrosarcoma cells, leiomyosarcoma cells, synovial sarcoma cells or myxofibrosarcoma cells; preferably, said malignant neoplasm cells of female genital organs are selected from ovarian cancer cells, cervical cancer cells, endometrial cancer cells or carcinoma cells of fallopian tube; preferably, said myeloma cells are multiple myeloma cells; preferably, said lung cancer cells are non-small cell lung cancer cells; preferably, said acute leukemia cells are selected from acute myeloid leukemia cells or acute lymphoblastic leukemia cells; preferably, said lymphoma cells are mantle cell lymphoma cells.

The invention further provides a kit for reducing or inhibiting CDK4 and/or CDK6 kinase activity in a cell, comprising the compound, or a pharmaceutically acceptable salt, ester, or solvate thereof, or their stereoisomers according to the invention, and optionally an instruction.

Beneficial Technical Effects of the Invention

Compared with the prior art, the technical solutions of the invention have the following advantages:

(1) The compound of Formula (I') or Formula (I), or a pharmaceutically acceptable salt, ester, or solvate thereof, or their stereoisomers according to the invention have excellent activity of inhibiting CDK4/6 kinase.

(2) The compound of Formula (I') or Formula (I), or a pharmaceutically acceptable salt, ester, or solvate thereof, or their stereoisomers according to the invention exhibit good biostability, a longer lasting effect, and high bioavailability.

(3) The compound of Formula (I') or Formula (I), or a pharmaceutically acceptable salt, ester, or solvate thereof, or their stereoisomers according to the invention exhibit good blood-brain barrier permeability, which makes CDK inhibitors as therapy of brain cancer possible.

(4) The compound of Formula (I') or Formula (I), or a pharmaceutically acceptable salt, ester, or solvate thereof, or their stereoisomers according to the invention exhibit low toxicity, good drug-resistance, and high safety.

Specific Modes for Carrying Out the Invention

The invention is further described, but is not restricted by the following embodiments. A person skilled in the art, based on the teachings of the invention, can make various modification or improvement without departing from the basic thought and scope of the invention.

EXPERIMENTS

The exemplified experiments are provided for a part of the compounds according to the invention, to show the advantageous activity and beneficial technical effect of the compounds according to the invention. However, it should be understood that the following experiments are provided merely for the purpose of illustration, rather than restricting the scope of the invention. A person skilled in the art, based on the teachings of the description, can make various modification or improvement to the technical solutions of the invention without departing from the spirit and scope of the invention.

Experimental Example 1: Assay on In Vitro Enzyme-Inhibiting Activity of the Compounds According to the Invention Test compounds: compounds 1, 13 and 14 of the invention, the chemical names, structures and preparation methods of which can be found in their preparation examples.

Control agents: LY2835219, the structures of which can be found in the Background Art, prepared by the inventors (please refer to Patent CN102264725A for the preparation methods).

The meanings represented by the abbreviations in the below experiments are described as follows.

| Symbol | Name | Symbol | Name |
|---|---|---|---|
| DMSO | dimethyl sulfoxide | ATP | adenosine triphosphate |
| DTT | dithiothreitol | EDTA | ethylenediaminetetraacetic acid |
| CDK | cyclin-dependent kinase | HEPES | N-2-hydroxyeth-ylpiperazine-N'-2-ethanesulfonic acid |
| FAM | carboxyfluorescein | Triton X-100 | polyethylene glycol octylphenol ether |
| Brij-35 | polyethylene glycol dodecyl ether | CTD | carboxyl-terminal domain |

Experimental Method:

Measurement of activity for inhibiting CDK4/6 kinase by Caliper Mobility Shift method.

1. Preparation of 1-Fold Buffer for Kinase

1) Preparation of 1-Fold Buffer for CDK4 Kinase 800 μL stock solution containing 1000 mM HEPES (pH 7.5), and 40 μL stock solution containing 10% Triton X-100, were added to 39160 μL ultra pure water, and the resultant mixture was mixed homogeneously.

2) Preparation of 1-Fold Buffer for CDK6 Kinase 50 mL stock solution containing 1000 mM HEPES (pH 7.5), and 50 μL stock solution containing 30% Brij-35, were added to 949.95 mL ultra pure water, and the resultant mixture was mixed homogeneously.

2. Preparation of Stop Solution 25 mL stock solution containing 4% Coating Reagent #3 (provided with the 12-sipper chip used in Caliper device), 50 mL stock solution containing 1000 mM HEPES (pH 7.5), 50 mL stock solution containing 0.5 M EDTA, and 0.25 mL stock solution containing 30% Brij-35, were added to 374.75 mL ultra pure water, and the resultant mixture was mixed homogeneously.

3. Preparation of 2.5-Fold Kinase Solution

1) Preparation of 2.5-Fold CDK4/D3 Kinase Solution

7 μL CDK4/D3 enzyme solution, and 9 μL stock solution containing 1M DTT were added to 1784 μL 1-fold CDK4 kinase buffer, and the resultant mixture was mixed homogeneously.

2) Preparation of 2.5-Fold CDK6/D3 Kinase Solution

18 μL CDK6/D3 enzyme solution, and 14 μL stock solution containing 1M DTT were added to 2768 μL 1-fold CDK6 kinase buffer, and the resultant mixture was mixed homogeneously.

4. Preparation of 2.5-Fold Polypeptide Solution

1) Preparation of 2.5-Fold CDK4/D3 Polypeptide Solution

10 μL stock solution containing 100 mM ATP, 45 μL stock solution containing 1M $MgCl_2$, and 45 μL FAM-tagged polypeptide 8, were added to 1700 μL 1-fold CDK4 kinase buffer, and the resultant mixture was mixed homogeneously.

2) Preparation of 2.5-Fold CDK6/D3 Polypeptide Solution

23 μL stock solution containing 100 mM ATP, 75 μL stock solution containing 1M $MgCl_2$, and 75 μL FAM-tagged polypeptide 8, were added to 2827 μL 1-fold CDK6 kinase buffer, and the resultant mixture was mixed homogeneously.

5. Preparation of 5-Fold Test Compound Solution:

DMSO solution containing 10 mM test compound was diluted with DMSO to a solution containing 50 μM test compound (which was used as a stock solution). Said stock solution was subjected to 4-fold stepwise dilution with DMSO to prepare solutions containing 12.5 μM, 3.125 μM, 0.78 μM, 0.195 μM, 0.0488 μM, 12.2 nM, 3 nM, 0.76 nM, and 0.19 nM test compound, respectively, and each of them was 10-fold diluted with 1-fold kinase buffer to prepare a 5-fold compound solution.

6. CDK4/6 Enzymatic Reaction 1) 5 μL 5-fold test compound solution and 10 μL 2.5-fold kinase solution were added to the corresponding wells in a 384-well plate, and incubated at room temperature for 10 min.

2) To the corresponding wells, 10 μL 2.5-fold polypeptide solution was added to start the enzymatic reaction, and incubation was performed at 28° C. for 5 h.

7. Enzymatic Assay

To the corresponding wells, 25 μL stop solution was added to stop the reaction.

8. The data was read by Caliper device, the inhibition rate was calculated by the following formula, and curve fitting was carried out by GraphPad5.0 software to get $IC_{50}$ value.

Inhibition rate=(maximal value−sample value)/(maximal value−minimal value)×100, wherein, maximal value: positive control without addition of test compound; minimal value: negative control without addition of enzyme.

Experimental results are shown in Table 1:

TABLE 1

| In vitro enzyme-inhibiting activity of the compounds according to the invention | | |
|---|---|---|
| Test compound | CDK enzyme-inhibiting activity $IC_{50}$ (nM) | |
| | CDK6/D3 | CDK4/D3 |
| Compound 1 | 16 | 2.7 |
| Compound 13 | 31.3 | 3.0 |
| Compound 14 | 23.1 | 2.6 |
| LY2835219 | 12.3 | 1.8 |

Experimental conclusion: it is shown in Table 1 that the compounds according to the invention have an inhibitory activity on CDK4 and CDK6 kinase, which is comparable to that of the control agent, i.e., show a sufficient inhibitory activity.

Experimental Example 2: Assay on In Vitro Cell-Inhibiting Activity of the Compounds According to the Invention Test compounds: compounds of the invention, the chemical names, formulae and preparation methods of which can be found in their preparation examples.

Control agent: LY2835219, the formula of which can be found in the Background Art, prepared by the inventors (please refer to Patent CN102264725A for the preparation methods).

The meanings represented by the abbreviations in the below experiments are described as follows.

| Symbol | Name | Symbol | Name |
|---|---|---|---|
| MDA-MB-435S | human melanoma cell | MCF-7 | human breast cancer cell |
| U87MG | human glioblastoma cell | L-15 | Leibovitz culture medium |
| MEM | minimum essential medium | DMEM | Dulbecco's modified Eagle's medium |
| DMSO | dimethyl sulfoxide | PBS | phosphate-buffered saline |
| BrdU | bromodeoxyuridine | TMB | tetramethyl benzidine |
| HRP | horseradish peroxidase | IgG | immunoglobulin G |
| FBS | fetal bovine serum | OD | optical density |

Experimental method: cell proliferation assay was carried out by BrdU method (BrdU cell proliferation assay kit, Cell Signaling Technology Company).

1. Preparation of Reagents and Compounds

Preparation of 1-Fold Washing Liquor 20-fold washing liquor as stock solution was diluted with ultra pure water to prepare 1-fold liquor.

Preparation of 1-Fold Detection Antibody Solution:

The 100-fold BrdU detection antibody stock solution was diluted with a detection antibody diluent to prepare 1-fold detection antibody solution.

Preparation of 1-Fold HRP-Labelled Secondary Antibody Solution

The 100-fold stock solution of HRP-labelled anti-mouse IgG antibody was diluted with HRP-labelled antibody diluent to prepare 1-fold HRP-labelled secondary antibody solution.

10-Fold BrdU Solution:

The 1000-fold BrdU stock solution was diluted with the corresponding medium to prepare a 10-fold BrdU solution.

Preparation of Test Compound

Preparation of test compound stock solution: 10 mM stock solution of a test compound was prepared by using 100% DMSO.

Preparation of gradient dilution solutions of test compound: the stock solution containing 10 mM test compound was subjected to 4-fold stepwise dilution with DMSO to prepare solutions containing 2.5 mM, 625 μM, 156 μM, 39 μM, 9.8 μM, and 2.5 μM test compound, respectively. 2 μL DMSO-diluted compound was added to 198 μL culture medium containing 10% FBS to prepare 10-fold test compound, wherein the maximum concentration of the test compound was 100 μM, the concentration of DMSO was 1%, and there were 7 concentration gradients.

Preparation of Culture Medium

MDA-MB-435S medium: L-15+10% FBS+0.01 mg/mL insulin

MCF-7 medium: DMEM+10% FBS+0.01 mg/mL insulin

U87MG medium: MEM+10% FBS

2. Experimental Steps (1) Cells grown to 80% confluence (in exponential growth phase) were digested with pancreatin, and centrifuged to collect the cells. MDA-MB-435S and U87MG cells were re-suspended in FBS-free culture medium, counted, and seeded to a 96-well plate; MDA-MB-435S cells were seeded at 3000 cells/well/81 μL; U87MG cells were seeded at 4000 cells/well/81 MCF-7 cells were resuspended in culture medium containing 1% FBS, and counted and seeded to a 96-well plate, at 4000 cell/well/82 μL. The plates were placed in a cell incubator at 37° C.

(2) After 24 h culture, FBS (9 μL) was added to each of the MDA-MB-435S and U87MG cell wells, and 8 μL FBS was added to each of the MCF-7 cell wells, to reach a final FBS concentration of 10%.

(3) To each well, a different concentration of 10-fold test compound (10 μL) was added, to make the test compound at a final concentration of 10 μM, 2.5 μM, 625 nM, 156 nM, 39 nM, 9.8 nM, and 2.5 nM, respectively, with 3 repeated wells/group, and the cells were cultured for 72 h at 37° C.

Solvent control: 0.1% DMSO

Blank control: culture medium without addition of cells

Normal cell control: normal cells without any treatment (4) To each well, 10-fold BrdU solution (10 μL) was added, and the culture medium was discarded after incubation for 4 h in the incubator.

(5) To each well, fixing/denaturation solution (10 μL) was added, the solution was discarded after incubation for 30 min at room temperature.

(6) To each well, 1-fold detection antibody solution (100 μL) was added, the solution was discarded after incubation for 1 h, and the well was washing with 1-fold washing liquor at 200 μL/well for three times.

(7) To each well, 1-fold HRP-labelled secondary antibody solution (100 μL) was added, the solution was discarded after incubation for 30 min at room temperature, and the well was washing with 1-fold washing liquor at 200 μL/well for three times.

(8) To each well, TMB substrate solution (100 μL) was added, and incubation was carried out at room temperature for 30 min.

(9) To each well, stop solution (100 μL) was added, and OD value at 450 nm was measured by ELISA instrument 3. Data Processing $$\text{Cell survival rate } (\%) = (OD_{test\ compound} - OD_{blank\ control}) / (OD_{normal\ cell\ control} - OD_{blank\ control}) \times 100\%, \quad 1)$$

$OD_{blank\ control}$: blank control value; $OD_{normal\ cell\ control}$: normal cell control value;

2) The data was processed by GraphPad Prism 5 software to get a curve and $IC_{50}$ values.

The experimental results are shown in Table 2:

TABLE 2

| In vitro cell-inhibiting activity of the compounds according to the invention | | | |
|---|---|---|---|
| Test compound | In vitro cell-inhibiting activity ($IC_{50}$, nM) | | |
| | MDA-MB-435S | MCF-7 | U87MG |
| Compound 6-1 | 70 | 83 | 47 |
| LY2835219 | 200 | 176 | 40 |

Experimental conclusion: as shown in Table 2, the compounds according to the invention have high in vitro cell-inhibiting activity, and are superior to LY2835219 obviously.

Experimental Example 3: Assay on Pharmacokinetics of the Compounds According to the Invention in Nude Mouse Test compounds: a part of compounds of the invention, prepared by the inventors; the chemical names, and preparation methods thereof can be found in their preparation examples.

Control agent: LY2835219, prepared by the inventors (please refer to Patent CN102264725A for the preparation methods), the formula thereof can be found in the Background Art.

Test animal: female nude mouse (BALB/c); control agent: 3 mice/administration route at each time point, weight: 22-25 g/mouse; Compound 1: 3 mice/administration route at each time point, weight: 22-25 g/mouse; Compound 6-1: 6 mice/administration route/test compound, weight: 18-26 g/mouse.

Preparation of Test Compound Solutions

Preparation of Blank Solvent 1

MC (methylcellulose) (500 mg) and SDS (sodium dodecylsulfate) (100 mg) were weighed and mixed homogenously, and water (100 mL) was added; the resultant mixture was ground and mixed homogeneously under vortexing to get 0.5% MC+0.1% SDS solution.

Preparation of Blank Solvent 2

Preparation of pH 5.0 buffer: sodium dihydrogen phosphatedihydrate (1.56 g) was weighed and added to purified water to prepare 50 mL solution, which was adjusted to a pH of 5.0 using sodium hydroxide solution.

Preparation of Blank Solvent 3

0.1% Tween 80+2% HPC: HPC (hydroxypropyl cellulose) (20 g) was weighed, and was added slowly to purified water (1000 mL) under stirring; Tween 80 (1 mL) was then added, and the resultant mixture was stirred until a clear solution was obtained.

Control Agent:

① Control agent (12.18 mg) was weighed, and normal saline (9.529 mL) was added; the resultant mixture was dissolved ultrasonically and mixed homogeneously under vortexing to prepare a 1 mg/mL colorless transparent solution 1, which was used as liquid 1 of control agent for IV administration to nude mouse;

② Control agent (13.12 mg) was weighed, and blank solvent 1 (10.265 mL) was added; the resultant mixture was ground and suspended homogeneously to prepare a 1 mg/mL homogenous solution 2, which was used as liquid 2 of control agent for PO administration to nude mouse.

Compound 1:

① Compound 1 (5.79 mg) was weighed, and DMF (N,N-dimethylformamide) (0.556 mL) was added; the resultant mixture was dissolved ultrasonically; normal saline (4.999 mL) was then added, and the resultant mixture was mixed homogeneously under vortexing to obtain a clear solution, which was used as liquid 1 of Compound 1 for IV administration to nude mouse;

② Compound 1 (12.20 mg) was weighed, and blank solvent 1 (11.706 mL) was added; the resultant mixture was ground and suspended homogeneously to prepare a 1 mg/mL homogenous solution, which was used as liquid 2 of compound 1 for PO administration to nude mouse.

③ Compound 1 (84.63 mg) was weighed, and blank solvent 1 (8.120 mL) was added; the resultant mixture was ground and suspended homogeneously to prepare a 10 mg/mL homogenous solution, which was used as liquid 3 of compound 1 for PO administration to nude mouse.

Compound 6-1:

① Compound 6-1 (2.01 mg) was weighed, and blank solvent 2 (3.928 mL) was added; the resultant mixture was dissolved ultrasonically and mixed homogeneously under vortexing to prepare a 0.5 mg/mL homogenous solution, which was used as liquid 1 of compound 6-1 for IV administration to nude mouse;

② Compound 6-1 (5.11 mg) was weighed and blank solvent 3 (4.951 mL) was added; the resultant mixture was ground homogeneously at 1000 r/min in a tissue grinder; the grinding fluid was transferred to a centrifuge tube and was mixed homogeneously under vortexing to prepare a 1 mg/mL homogenous solution, which was used as liquid 2 of compound 6-1 for PO administration to nude mouse at 10 mg/kg;

③ Compound 6-1 (51.10 mg) was weighed and blank solvent 3 (1.496 mL) was added; the resultant mixture was ground homogeneously at 1000 r/min in a tissue grinder; the grinding fluid was transferred to a centrifuge tube, and said solvent (1 mL) was added to wash the tissue grinder; the solvent was transferred to the centrifuge tube after washing; the resultant mixture was mixed homogeneously under vortexing to prepare a 20 mg/mL homogenous solution, which was used as liquid 3 of compound 6-1 for PO administration to nude mouse at 200 mg/kg.

Experimental Method

Administration:

The test compounds are administered by the methods listed in the following table:

| Test compound | Cases of experimental animal | Administration route | Administration dose (mg/kg) | Administration concentration (mg/mL) | Administration volume (mL/kg) |
|---|---|---|---|---|---|
| LY2835219 | 33 | IV | 5 | 1 | 5 |
|  | 30 | PO | 10 | 1 | 10 |
| Compound 1 | 33 | IV | 5 | 1 | 5 |
|  | 30 | PO | 10 | 1 | 10 |
|  | 33 | PO | 100 | 10 | 10 |
| Compound6-1 | 6 | IV | 2.5 | 0.5 | 5 |
|  | 6 | PO | 10 | 1 | 10 |
|  | 6 | PO | 200 | 20 | 10 |

Blood Collection:

Collecting Time Point:

Control agent/Compound 1, IV administration group: before administration, 0.083, 0.25, 0.5, 1, 2, 4, 6, 8, 24, and 30 h after administration; PO administration group (10 mg/kg): before administration, 0.167, 0.5, 1, 2, 4, 6, 8, 24, and 30 h after administration.

Compound 1, PO administration group (100 mg/kg): 0.167, 0.5, 1, 2, 4, 6, 8, 24, 30, and 48 h after administration.

Compound 6-1, IV administration group (2.5 mg/kg) and PO administration group (10 mg/kg): 0.083, 0.25, 0.5, 1, 2, 4, 6, 8 and 24 h after administration; Compound 6-1, PO administration group (100 mg/kg): 0.083, 0.25, 0.5, 1, 2, 4, 6, 8, 24, 30, 48 h after administration.

Control agent/Compound 1: 300 μL whole blood was collected from intraocular canthus at each time point, and was centrifuged at 8000 r/min for 6 min in a high speed centrifuge to separate the plasma; the plasma was stored in a refrigerator at −80° C. Compound 6-1: 60 μL whole blood was collected from intraocular canthus at each time point, and was placed in an anticoagulation tube containing anticoagulant agent $K_2$EDTA; the blood sample was centrifuged at 8000 r/min for 6 min to obtain a plasma sample.

Plasma Sample Analysis

The plasma samples of control agent and compound 1 were analyzed by precipitation of protein: to 50 μL plasma, 200 μL internal standard (acetonitrile solution containing 500 ng/mL Warfarin) was added; the resultant mixture was vortexed for 3 min at 1500 r/min, and centrifuged for 5 min at 13000 r/min; to 100 μL supernatant, 400 μL water was added; the resultant mixture was mixed homogeneously under vortexing and analyzed by LC-MS/MS.

The plasma sample of compound 6-1 was analyzed by precipitation of protein: to a suitable amount of plasma, a given volume of internal standard solution was added; the resultant mixture was vortexed and centrifuged; the supernatant was diluted by adding a given volume of water; the resultant mixture was mixed homogeneously under vortexing and analyzed by LC-MS/MS.

TABLE 3-1

PK evaluation result (IV) in Nude mouse

| Test compound | Dose (mg/kg) | $AUC_{last}$ (h*ng/mL) | CL (L/h/kg) | $V_{ss}$ (L/kg) |
|---|---|---|---|---|
| LY2835219 | 5 | 1587 | 3.01 | 5.79 |
| Compound 1 | 5 | 2084 | 2.29 | 4.61 |
| Compound 6-1 | 2.5 | 985 | 2.41 | 12.5 |

TABLE 3-2

PK evaluation result (PO) in Nude mouse

| Test compound | Dose (mg/kg) | $T_{max}$ | $C_{max}$ | $AUC_{last}$ (h*ng/mL) | F (%) |
|---|---|---|---|---|---|
| LY2835219 | 10 | 0.5 | 368 | 1307 | 41.1 |
| Compound 1 | 10 | 2 | 675 | 2763 | 65.5 |
|  | 100 | 2 | 3078 | 33902 | 77.9 |
| Compound 6-1 | 10 | 2 | 300 | 1407 | 39.3 |
|  | 200 | 2 | 5373 | 90916 | 115 |

$AUC_{last}$ represents area under concentration-time curve during administration 0→t.
CL represents clearance.
$V_{ss}$ represents apparent volume of distributionat steady state.
$T_{max}$ represents time of maximum blood concentration.
$C_{max}$ represents maximum blood concentration.
F % represents absolute bioavailability.

As seen from the experimental results shown in Tables 3-1 and 3-2, compared to the control agent at the same dose, the compounds according to the invention have good pharmacokinetic properties, and are superior to the control agent particularly with respect to exposure dose and bioavailability; and the high-dose group had a bioavailability close to 100%.

Experimental Example 4: Assay on Linear Pharmacokinetics of the Compounds According to the Invention in Rat Test compounds: compound 1 of the invention, prepared by the inventors; the chemical name and preparation method thereof can be found in the preparation example.

Control agent: LY2835219, prepared by the inventors (please refer to Patent CN102264725A for the preparation methods); the formula thereof can be found in the Background Art.

Test animal: male SD rat, 3 rats/administration dose/test compound, weight: 200-240 g/rat.

Preparation of Test Compound Solutions

Preparation of Solvent pH 4.0 buffer: citric acid (21 g) was dissolved in water, and water was added to a final volume of 1000 mL to get solution A, which was stored for further use; disodium hydrogen phosphate (71.63 g) was dissolved in water, and water was added to a final volume of 1000 mL to get solution B, which was stored for further use. Said solution A (614.5 mL) was mixed with said solution B (385.5 mL) homogeneously under shaking to get Solvent pH 4.0 buffer.

Control Agent:

① Solvent pH 4.0 buffer was used as solvent to prepare solution 1 of control agent LY2835219 at a concentration of 1.5 mg/mL;

② Solvent pH 4.0 buffer was used as solvent to prepare solution 2 of control agent LY2835219 at a concentration of 4.5 mg/mL;

③ Solvent pH 4.0 buffer was used as solvent to prepare solution 3 of control agent LY2835219 at a concentration of 13.5 mg/mL;

Said solutions 1-3 were used as liquids for PO administration of control agent LY2835219 at 15 mg/kg, 45 mg/kg and 135 mg/kg.

For Compound 1:

① Solvent pH 4.0 buffer was used as solvent to prepare solution 4 of compound 1 at a concentration of 13.5 mg/mL;

② said homogeneous solution 4 (4 mL) was diluted with solvent pH 4.0 buffer to prepare solution 5 of compound 1 at a concentration of 4.5 mg/mL;

③ said homogeneous solution 4 (1.4 mL) was diluted with solvent pH 4.0 buffer to prepare solution 6 of compound 1 at a concentration of 1.5 mg/mL;

Said solutions 4-6 were used as liquids for PO administration of compound 1 at 15 mg/kg, 45 mg/kg and 135 mg/kg.

Experimental Method

Administration:

The test compounds are administered by the methods listed in the following table:

| Test compound | Cases of experimental animal | Administration route | Administration dose (mg/kg) | Administration concentration (mg/mL) | Administration volume (mL/kg) |
|---|---|---|---|---|---|
| LY2835219 | 3 | PO | 15 | 1.5 | 10 |
|  | 3 | PO | 45 | 4.5 | 10 |
|  | 3 | PO | 135 | 13.5 | 10 |
| Compound 1 | 3 | PO | 15 | 1.5 | 10 |
|  | 3 | PO | 45 | 4.5 | 10 |
|  | 3 | PO | 135 | 13.5 | 10 |

Blood Collection

Control Agent:

Collecting time point: for PO group (15 mg/kg), 0.167, 0.5, 1, 2, 4, 6, 8, 24, 30, and 48 h after administration. For PO group (45 mg/kg), 0.167, 0.5, 1, 2, 4, 6, 8, 24, 30, 48, 56 and 72 h after administration. For PO group (135 mg/kg), 0.167, 0.5, 1, 2, 4, 6, 8, 24, 30, 48, 56, 72, 96 and 102 h after administration.

For Compound 1:

Collecting time point: for PO group (15 mg/kg), 0.167, 0.5, 1, 2, 4, 6, 8, 24, 30, and 48 h after administration. For PO group (45 mg/kg), 0.167, 0.5, 1, 2, 4, 6, 8, 24, 30, and 48 h after administration. For PO group (135 mg/kg), 0.167, 0.5, 1, 2, 4, 6, 8, 24, 30, 48, 56, 72 and 96 h after administration.

100 µL whole blood was collected from caudal vein at each time point, added to an anticoagulation tube containing $K_2EDTA$, and centrifuged at 8000 r/min in a high speed centrifuge for 6 min to separate the plasma; the plasma was stored in a refrigerator at −80° C.

Plasma Sample Analysis

The plasma samples of control agent and compound 1 were analyzed by precipitation of protein: to 30 µL plasma, 200 µL internal standard (acetonitrile solution containing 50 ng/mL PD0332991, the formula of which is

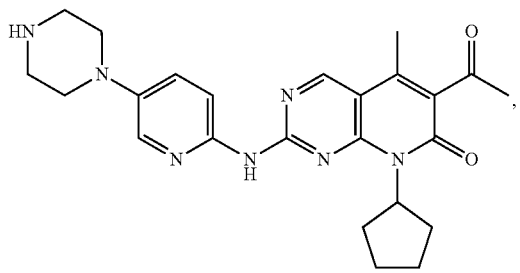 [SMILES: CC(=O)c1c(C)c2cnc(Nc3ccc(N4CCNCC4)cn3)nc2n(C2CCCC2)c1=O]

prepared by referring to the method in Patent CN101001857A) was added; the resultant mixture was vortexed for 10 min at 1500 r/min, and centrifuged for 20 min at 4000 r/min; to 100 µL supernatant, 100 µL water was added; the resultant mixture was mixed homogeneously under vortexing and analyzed by LC-MS/MS.

TABLE 4-1

PK evaluation result of control agent (PO) in Rat

| Test compound | Dose (mg/kg) | $T_{max}$ (h) | $C_{max}$ (ng/mL) | $AUC_{last}$ (h*ng/mL) |
|---|---|---|---|---|
| LY2835219 | 15 | 4 | 504 | 9686 |
|  | 45 | 4 | 860 | 32631 |
|  | 135 | 24 | 1370 | 97593 |

TABLE 4-2

PK evaluation result of Compound 1 (PO) in Rat

| Test Compound | Dose (mg/kg) | $T_{max}$ (h) | $C_{max}$ (ng/mL) | $AUC_{last}$ (h*ng/mL) |
|---|---|---|---|---|
| Compound 1 | 15 | 4 | 941 | 12647 |
|  | 45 | 4 | 1583 | 37655 |
|  | 135 | 24 | 2410 | 136005 |

$T_{max}$ represents time of maximum blood concentration.
$C_{max}$ represents maximum blood concentration.
$AUC_{last}$ represents area under concentration-time curve during administration 0→t.

As seen from the experimental results shown in Tables 4-1 and 4-2, compared with control agent at the same dose, the compounds according to the invention are superior to the control agent with respect to $C_{max}$ and $AUC_{last}$; and with the increase of dose, $AUC_{last}$ increases in a linear manner; compound 1 of the invention has good linear pharmacokinetic properties.

Experimental Example 5: Assess on Pharmacodynamics and Pharmaceutical Safety of the Compounds According to the Invention in Subcutaneous Tumor Model of BALB/c Nude Mouse with Human Colon Cancer Cell Colo-205

Test compounds: compound 1 of the invention, the chemical name, and preparation method of which can be found in the preparation example.

Control agent: LY2835219, the formula of which can be found in the Background Art, prepared by the inventors (please refer to Patent CN102264725A for the preparation methods).

The meanings represented by the abbreviations in the below experiments are described as follows.

| Symbol | Name | Symbol | Name |
|---|---|---|---|
| COLO205 | human colon cancer cell | PBS | phosphate-buffered saline |
| RPMI-1640 | 1640 Medium | QD | once a day |
| RTV | relative tumor volume | TGI | tumor growth inhibition |
| BALB/c | inbred albino mouse | MC | methylcellulose |
| SDS | sodium dodecylsulfate | $CO_2$ | carbon dioxide |

Test animal: female nude mouse (BALB/c), 8 mice/dose group/test compound, weight: 19-27 g/mouse.

Preparation of Test Compound Solutions

Preparation of a blank solvent containing 0.5% MC and 0.1% SDS: MC (2 g) was weighed, and was dissolved by adding ultra pure water (350 mL); SDS (0.4 g) was then added, and the volume was set to 400 mL. After mixing well, the resultant mixture was filtrated by a 0.22 µm filter to remove bacteria, and was subpackaged and stored at 4° C., to obtain the blank solvent.

Control agent (32 mg) was weighed, and solvent (2.5 mL) was added; the resultant mixture was mixed homogeneously under vortexing to get a homogeneous solution 1 containing control agent at a concentration of 10 mg/mL; solvent (1.5 mL) was added to the homogeneous solution 1 (0.5 mL) to get a homogeneous solution 2 containing control agent at a concentration of 2.5 mg/mL.

Compound 1 (6.3 mg) was weighed, and solvent (2.4 mL) was added; the resultant mixture was mixed homogeneously under vortexing to get a homogeneous solution 1 containing compound 1 at a concentration of 2.5 mg/mL; compound 1 (12.6 mg) was weighed, and solvent (2.4 mL) was added; the resultant mixture was mixed homogeneously under vortexing to get a homogeneous solution 2 containing compound 1 at a concentration of 5 mg/mL; compound 1 (25.2 mg) was weighed, and solvent (2.4 mL) was added; the resultant mixture was mixed homogeneously under vortexing to get a homogeneous solution 3 containing compound 1 at a concentration of 10 mg/mL. Said homogeneous solutions of control agent and compound 1 were prepared immediately before administration every day, and were stored in dark.

Experimental Method

Cell Culture:

COLO205 cancer cells were cultured in RPMI-1640 medium containing inactivated 10% fetal bovine serum, 100 U/mL penicillin, 100 μg/mL streptomycin and 2 mM glutamine, in a 37° C., 5% $CO_2$ incubator. The initial concentration of cell culture was $5\times10^5$ cells/mL, and the cells were transferred to other bottles every 3 or 4 days and passaged. Tumor cells in exponential growth phase were used for in vivo tumor seeding.

Cell Seeding and Grouping:

COLO205 tumor cells suspended in PBS were seeded subcutaneously to right lateral thorax of experimental animal at $1\times10^7$ cells/0.1 mL, and the animal was sacrificed when the tumor grew to a volume of 800 $mm^3$ to 1000 $mm^3$; under aseptic conditions, tumors were peeled off, and necrotic tissues were removed; the well-grown tumor tissues were selected; the tumor cells were isolated and subjected to primary culture and proliferation, and then were subcutaneously seeded to animal. The tumor cells were passaged for two generations in mice by this method, and the primary culture cells were seeded subcutaneously to right lateral thorax of experimental animal, at $5\times10^6$ cells/0.1 mL per animal. When tumor grew to a volume of about 100 $mm^3$, the animals were grouped and administered. For oral administration, the administration volume is 0.1 mL/10 g body weight of animal.

Administration:

The test compounds are administered by the methods listed in the following table:

| Test compounds | Cases of experimental animal | route | dose (mg/kg) | Administration concentration (mg/mL) | Administration volume (mL/kg) | Administration period |
|---|---|---|---|---|---|---|
| Solvent control | 8 | PO | 0 | 0 | 10 | QD, 22 days |
| LY2835219 | 8 | PO | 25 | 2.5 | 10 | QD, 22 days |
| LY2835219 | 8 | PO | 100 | 10 | 10 | QD, 22 days |
| Compound 1 | 8 | PO | 25 | 2.5 | 10 | QD, 22 days |
| Compound 1 | 8 | PO | 100 | 10 | 10 | QD, 22 days |

Blood collection: blood was collected from intraocular canthus. After the last administration (22th Day) of control agent and compound 1, blood/tumor was collected at the same time points, wherein 8 nude mice for each dose group were divided into A and B groups A group (No. 1-4): blood was collected at 15 min, 1 h and 2 h, and the mouse was sacrificed after blood collection at 2 h;

B group (No. 5-8): blood was collected at 4 h, 8 h and 24 h, and the mouse was sacrificed after blood collection at 24 h;

100 μL whole blood at each time point was collected and added to an anticoagulation tube containing $K_2EDTA$, and centrifuged at 4500 r/min at 4° C. in a high speed centrifuge for 5 min to separate the plasma; the plasma was stored in a refrigerator at −80° C.

Plasma Sample Analysis

The plasma samples of control agent and compound 1 were analyzed by precipitation of protein: to 50 μL plasma, 150 μL internal standard (acetonitrile solution containing 50 ng/mL dexamethasone) was added; the resultant mixture was vortexed at 1500 r/min for 3 min, and centrifuged at 4000 r/min for 20 min; to 100 μL supernatant, 100 μL water was added; the resultant mixture was mixed homogeneously under vortexing and analyzed by LC-MS/MS.

TABLE 5-1

PK evaluation result of control agent in nude mouse

| Test compound | Dose (mg/kg) | $T_{max}$ | $C_{max}$ | $AUC_{last}$ (h*ng/mL) |
|---|---|---|---|---|
| LY2835219 | 25 | 4.00 | 733 | 9123 |
|  | 100 | 8.00 | 1077 | 22980 |

TABLE 5-2

PK evaluation result of Compound 1 in nude mouse

| Test compound | Dose (mg/kg) | $T_{max}$ | $C_{max}$ | $AUC_{last}$ (h*ng/mL) |
|---|---|---|---|---|
| Compound 1 | 25 | 2.00 | 1145 | 12280 |
|  | 100 | 8.00 | 2425 | 48305 |

$AUC_{last}$ represents area under concentration-time curve during administration 0→t.
$T_{max}$ represents time of maximum blood concentration.
$C_{max}$ represents maximum blood concentration.

As seen from the experimental results shown in Tables 5-1 and 5-2, compared with the control agent, compound 1 according to the invention has good pharmacokinetic properties; compound 1 is superior to the control agent at the same dose with respect to exposure dose $AUC_{last}$ and $C_{max}$.

Experimental Example 6: In Vivo Assay for Assessing Blood Brain Barrier Permeability of the Compounds According to the Invention in Rat Test compounds: compound 1 of the invention, prepared by the inventors; the chemical name, and preparation method thereof can be found in the preparation example.

Control agent: LY2835219, the formula of which can be found in the Background Art, prepared by the inventors (please refer to Patent CN102264725A for the preparation methods).

Test animal: male SD rat, 3 rats/test compound/time point, weight: 250-300 g/rat Preparation of Test Compound Solution Preparation of solvent (0.5% MC (methylcellulose)+0.1% SDS (sodium dodecylsulfate) solution): MC (500 mg) and SDS (100 mg) were mixed homogenously, and water (100 mL) was added; the resultant mixture was ground and mixed homogeneously under vortexing.

Control agent (108.22 mg) was weighed, and solvent (36.07 mL) was added; the resultant mixture was ground and suspended homogeneously to get a homogeneous solution 1. The solution was used as liquid for PO administration of control agent LY2835219 to rat.

Compound 1 (111.52 mg) was weighed, and solvent (35.39 mL) was added; the resultant mixture was ground and suspended homogeneously to get a homogeneous solution 2. The solution was used as liquid for PO administration of compound 1 to rat.

Experimental Method

Administration:

The test compounds are administered by the methods listed in the following table:

| Test compound | Cases of experimental animal | Administration route | Administration dose (mg/kg) | Administration concentration (mg/mL) | Administration volume (mL/kg) |
|---|---|---|---|---|---|
| LY2835219 | 12 | intragastric administration (PO) | 30 | 3 | 10 |
| Compound 1 | 12 | intragastric administration (PO) | 30 | 3 | 10 |

Collection Method:

After separate PO administration of control agent and compound 1, blood was collected by cardiac puncture at 2, 4, 24 and 48 h; about 8 ml whole blood was collected, and placed in a centrifuge tube containing $K_2EDTA$ anticoagulant agent; cerebrospinal fluid and brain tissue were also collected at the same time, 3 rats at each time point. The collected whole blood was centrifuged at 3000 r/min at 4° C. in a high speed centrifuge for 10 min to separate the plasma; and the plasma was stored in a refrigerator at −80° C. After sample collection, the concentrations of control agent and compound 1 in plasma, brain tissue and cerebrospinal fluid were determined, respectively.

Plasma Sample Analysis

The plasma samples of control agent and compound 1 were analyzed by precipitation of protein: the test samples were taken from the refrigerator (−80° C.), thawed at room temperature, and then vortexed for 3 min; to 30 μL plasma, 200 μL internal standard (acetonitrile solution containing 25 ng/mL PD0332991) was added; the resultant mixture was vortexed for 10 min at 1500 r/min, and centrifuged at 4000 r/min for 20 min; to 100 μL supernatant, 100 μL water was added; the resultant mixture was mixed homogeneously under vortexing and analyzed by LC-MS/MS.

Analysis of Brain Tissue and Cerebrospinal Fluid Sample

The brain tissue and cerebrospinal fluid samples for control agent and compound 1 were analyzed by precipitation of protein: the test samples were taken from the refrigerator (−80° C.), thawed at room temperature, and then vortexed for 3 min; to 20 μL homogenated brain tissue sample, 200 μL internal standard (a solution of methanol and water at 1:1 containing 40 ng/mL dextromethorphan and 50 ng/mL dextrorphan) was added; the resultant mixture was vortexed for 3 min at 1500 r/min, and centrifuged at 4° C., 4000 g for 5 min; to 100 μL supernatant, 50 μL 0.1% formic acid-water was added; the resultant mixture was mixed homogeneously under vortexing and analyzed by LC-MS/MS. Cerebrospinal fluid sample was treated by the same way as the homogenated brain tissue sample.

TABLE 6

Experimental results of assessment on blood brain barrier permeability of compound 1 according to the invention in rat

| Compound Name | Administration Dose | Sample type | $T_{max}$ (h) | $C_{max}$ (ng/mL) | $AUC_{last}$ (ng·h/mL) |
|---|---|---|---|---|---|
| Compound 1 | 30 | plasma | 4 | 2606 | 49238 |
| | | brain tissue | 4 | 535 | 12075 |
| | | cerebrospinal fluid | 4 | 106 | 1294 |
| LY2835219 | 30 | plasma | 4 | 1497 | 40455 |
| | | brain tissue | 4 | 673 | 18097 |
| | | cerebrospinal fluid | 4 | 11.8 | 451 |

$AUC_{last}$ represents area under concentration-time curve during administration 0→t.
$T_{max}$ represents time of maximum blood concentration.
$C_{max}$ represents maximum blood concentration.

As seen from the experimental results shown in Table 6, compared with the control agent, the compounds according to the invention can effectively enter brain tissue from plasma via the assay for assessing blood brain barrier permeability, and were superior to the control agent LY2835219 with respect to the exposure dose in cerebrospinal fluid.

Example 7: Assess on Pharmacodynamics and Pharmaceutical Safety of the Compounds According to the Invention in Subcutaeous Tumor Model of BALB/c Nude Mouse with Human Brain Glioma Cell U-87MG Test compounds: the compounds of the invention, prepared by the inventors; the chemical names, and preparation methods thereof can be found in their preparation examples.

Control agent: LY2835219, the formula of which can be found in the Background Art, prepared by the inventors (please refer to Patent CN102264725A for the preparation methods).

The meanings represented by the abbreviations in the below experiments are described as follows.

| Symbol | Name | Symbol | Name |
|---|---|---|---|
| U87MG | human glioblastoma cell | ATCC | American Type Culture Collection |
| MEM | minimum essential medium | EDTA | ethylenediaminetraacetic acid |
| BALB/c | inbred albino mouse | MC | methylcellulose |
| SDS | sodium dodecylsulfate | $CO_2$ | carbon dioxide |
| QD | once a day | PBS | phosphate-buffered saline |

Test animal: female nude mouse (BALB/c), 10 mice/dose group/test compound, weight: 18-22 g/mouse.

Preparation of Test Compound Solutions

Preparation of solvent containing 0.5% MC: a suitable amount of MC was dissolved in a given volume of ultra pure water; the resultant mixture was mixed homogeneously to get solvent 1 containing 0.5% MC.

Preparation of solvent containing 0.5% MC and 0.1% SDS: a suitable amount of MC and a suitable amount of SDS were dissolved in a given volume of ultra pure water; the resultant mixture was mixed homogeneously to get solvent 2 containing 0.5% MC and 0.1% SDS.

Control agent (508.87 mg) and SDS (39.37 mg) were weighed, and diluted with solvent 1 (39.37 mL); the resultant mixture was ground homogeneously to get a homogeneous solution 1 containing control agent at a concentration of 10.1 mg/mL; the homogeneous solution 1 (13.125 mL) containing control agent was taken, and solvent 2 (13.125 mL) was added; the resultant mixture was ground homogeneously to get a homogeneous solution 2 containing control agent at a concentration of 5.0 mg/mL.

Compound 1 (931.77 mg) and SDS (45.9 mg) were weighed, and diluted with solvent 1 (45.9 mL); the resultant mixture was ground homogeneously to get a homogeneous solution 1 containing compound 1 at a concentration of 20.0 mg/mL; the homogeneous solution 1 (19.69 mL) containing compound 1 (20.0 mg/mL) was taken, and solvent 2 (19.69 mL) was added; the resultant mixture was ground homogeneously to get a homogeneous solution 2 containing compound 1 at a concentration of 10.0 mg/mL; the homogeneous solution 2 (13.125 mL) containing compound 1 (10.0 mg/mL) was taken, and solvent 2 (13.125 mL) was added; the resultant mixture was ground homogeneously to get a homogeneous solution 3 containing compound 1 at a concentration of 5.0 mg/mL.

Experimental Method

Cell Culture:

U87MG cells from ATCC were cultured in MEM medium containing 10% fetal bovine serum; the cells were digested with trypsin containing EDTA by conventional methods; the cells were passaged for two generations every week, and were continuously cultured in a 37° C., 5% $CO_2$ incubator.

Cell Seeding and Grouping:

Tumor cells in exponential growth phase were collected; U87MG cells were adjusted with PBS and matrigel at a ratio of 1:1 to a concentration of $5 \times 10^7$/mL; 0.1 mL cell suspension was seeded subcutaneously to right back of each mouse by injection with a 1 mL syringe. Tumor volumes were observed and measured, and the average tumor volume of U87MG reached about 200 mm$^3$ 8 days after seeding; the tumor-bearing mice were grouped and were treated by oral administration of test compounds, at a dose of 0.1 mL/10 g body weight.

Administration:

The test compounds are administered by the methods listed in the following table:

| Test compound | Cases of experimental animal | Administration route | dose (mg/kg) | Administration concentration (mg/mL) | volume (mL/kg) | Administration period |
|---|---|---|---|---|---|---|
| Control agent | 10 | intragastric administration (PO) | 50 | 5.0 | 10 | QD, 3 weeks |
| | 10 | intragastric administration (PO) | 100 | 10.1 | 10 | QD, 3 weeks |
| Compound 1 | 10 | intragastric administration (PO) | 50 | 5.0 | 10 | QD, 3 weeks |
| | 10 | intragastric administration (PO) | 100 | 10.0 | 10 | QD, 3 weeks |
| | 10 | intragastric administration (PO) | 200 | 20.0 | 10 | QD, 3 weeks |

Blood collection: blood was collected from intraocular canthus. After the last administration (Day 22) of control agent and compound 1, blood/tumor was collected at the same time points, wherein as to 10 nude mice for each dose group, one was for standby, and the other 9 mice were divided into three groups, i.e., A, B and C groups.

A group (No. 1-3): blood was collected before administration, and at 1 h and 2 h after administration, and the mouse was sacrificed after blood collection at 2 h;

B group (No. 4-6): blood was collected at 15 min, 4 h and 6 h after administration, and the mouse was sacrificed after blood collection at 6 h;

C group (No. 7-9): blood was collected at 30 min, 10 h and 24 h after administration, and the mouse was sacrificed after blood collection at 24 h;

300 μL whole blood was collected at each time point, added to an anticoagulation tube containing $K_2$EDTA, and centrifuged at 8000 r/min in a high speed centrifuge for 6 min to separate the plasma; the plasma was stored in a refrigerator at −80° C.

Plasma Sample Analysis

The plasma samples of control agent and compound 1 were analyzed by precipitation of protein: 30 μL plasma was added to a 96-deep well plate, and 200 μL internal standard (acetonitrile solution containing 25 ng/mL PD0332991) was added; the resultant mixture was vortexed for 3 min at 1500 r/min, and centrifuged for 20 min at 4000 r/min; to 100 μL supernatant, 100 μL water was added; the resultant mixture was mixed homogeneously under vortexing and analyzed by LC-MS/MS.

TABLE 7-1

PK evaluation result of control agent in nude mouse

| Test compound | Dose (mg/kg) | $T_{max}$ | $C_{max}$ | $AUC_{last}$ (h*ng/mL) |
|---|---|---|---|---|
| LY2835219 | 50 | 1.00 | 1156 | 19356 |
| | 100 | 4.00 | 1533 | 27922 |

TABLE 7-2

PK evaluation result of Compound 1 in nude mouse

| Test compound | Dose (mg/kg) | $T_{max}$ | $C_{max}$ | $AUC_{last}$ (h * ng/mL) |
|---|---|---|---|---|
| Compound 1 | 50 | 2.00 | 1770 | 23453 |
| | 100 | 1.00 | 2183 | 34765 |
| | 200 | 6.00 | 2513 | 49678 |

$AUC_{last}$ represents area under concentration-time curve during administration 0 → t.
$T_{max}$ represents time of maximum blood concentration.
$C_{max}$ represents maximum blood concentration.

As seen from the experimental results shown in Tables 7-1 and 7-2, compared with the control agent, the compounds according to the invention have good pharmacokinetic properties; compound 1 is superior to the positive control agent at the same dose with respect to exposure dose and $C_{max}$.

Experimental Example 8: Assay on In Vitro Enzyme-Inhibiting Activity of the Compounds According to the Invention Test compounds: compounds of the invention, the chemical names and preparation methods of which can be found in their preparation examples.

The meanings represented by the abbreviations in the below experiments are described as follows.

| Symbol | Name | Symbol | Name |
|---|---|---|---|
| DMSO | dimethyl sulfoxide | BrdU-Eu | Eu-labelled bromodeoxyuridine |
| FBS | fetal bovine serum | Flu | Fluorescence value |
| L15 | Leibovitz culture medium | RPMI1640 | Roswell Park Memorial Institute 1640 medium |
| F12K | F12K medium | IMDM | Iscoves modified Dulbecco medium |
| H358 | lung cancer cell | H441 | lung cancer cell |
| PC3 | prostatic cancer cell | MV-4-11 | leukemia cell |
| JeKo-1 | lymphoma cell | SW780 | bladder cancer cell |

Experimental method: cell proliferation assay was carried out by BrdU method (BrdU cell proliferation assay kit, PerkinElme Company).

1. Preparation of Reagents and Compounds (1) Preparation of 1-Fold Washing Liquor:

25-fold washing liquor as stock solution was diluted with ultra-pure water to prepare 1-fold liquor.

(2) Preparation of 1-Fold Detection Antibody Solution:

The 200-fold BrdU-Eu detection antibody stock solution was diluted with a detection antibody diluent to prepare 1-fold detection antibody solution.

(3) 100-Fold BrdU Label Solution:

The 1000-fold BrdU stock solution was diluted with the corresponding medium to prepare a 100-fold BrdU label solution.

(4) Preparation of Test Compound

Preparation of test compound stock solution: 5 mM stock solution of a test compound was prepared by using 100% DMSO.

Preparation of gradient dilution solutions of test compound: the stock solution containing 5 mM test compound was diluted by DMSO to prepare a 2 mM solution, then was subjected to 4-fold stepwise dilution to 9 concentration gradients.

(5) Preparation of Culture Medium

H358 medium: RPMI 1640+10% FBS

PC3 medium: F12K+10% FBS

MV-4-11 medium: IMDM+10% FBS

H441 medium: RPMI1640+10% FBS

JeKo-1 medium: RPMI1640+20% FBS

SW780 medium: L15+10% FBS

2. Experimental Steps (1) Cells grown to exponential growth phase were digested with pancreatin, and centrifuged to collect the cells. The adherent cells were re-suspended in the corresponding culture medium, counted, and seeded to a 96-well plate; H358 cells and SW780 cells were seeded at 4000 cells/well/100 μL; PC3 cells were seeded at 1500 cells/well/100 μL; H441 cells were seeded at 6000 cells/well/100 μL. The plates were placed in a cell incubator at 37° C. After the cells adhered to the wall, the medium was replaced by serum-free medium. The suspended cells MV-4-11 and JeKo-1 were re-suspended with serum-free medium, counted, seeded to a 96-well plate by 10000 cells/well/100 μL and placed in a cell incubator overnight at 37° C. with 5% $CO_2$.

(2) To each well, 99 μL growth medium containing 2×FBS was added, then 1 μL diluted 200× test compound was added to the well. The final concentration of the test compound was 10000, 2500, 625, 156.25, 39.06, 9.77, 2.44, 0.61, 0.15 or 0 nM, and the cells were cultured for 48 h at 37° C.

Solvent control: 0.5% DMSO

Blank control: culture medium without addition of cells (3) To each well, 2 μL 100-fold BrdU labelled solution was added, and the culture medium was sucked by a vacuum pump after incubation in a cell incubator overnight and equilibrated at room temperature for 0.5 h.

(4) To each well, 100 μL fixing solution was added; the solution was discarded after incubation for 30 min at room temperature.

(5) To each well, 100 μL 1-fold BrdU-Eu detection antibody solution was added, the solution was discarded after incubation for 1 h at room temperature, and the well was washed with 1-fold washing liquor at 250 μL/well for 5 times.

(6) To each well, 200 μL of DELFIA Inducer was added and incubated for 15 min at room temperature. Value of fluorescence (Flu) was measured by ELISA instrument 3. Data Processing $$\text{Cell inhibition rate (\%)} = 1 - (\text{Flu}_{test\ compound} - \text{Flu}_{blank\ control})/(\text{Flu}_{solvent\ control} - \text{Flu}_{blank\ control}) \times 100\%, \quad (1)$$

$\text{Flu}_{blank\ control}$: blank control value; $\text{Flu}_{solvent\ control}$: solvent control value;

(2) The data was processed by GraphPad Prism 6 software to get a curve and $IC_{50}$ values.

The experimental results are shown in Table 8:

TABLE 8

In vitro cell-inhibiting activity of the compounds according to the invention

| Test compound | In vitro cell-inhibiting activity ($IC_{50}$, nM) | | | | | |
|---|---|---|---|---|---|---|
| | H358 | H441 | PC3 | MV-4-11 | JeKo-1 | SW780 |
| Compound 1 | 290.9 | 147.8 | 260.5 | 139 | 36.98 | 162.5 |

Experimental conclusion: as shown in Table 8, the compounds according to the invention have high in vitro cell-inhibiting activity.

Experimental Example 9: Assay on In Vivo Pharmacodynamics of the Compounds According to the Invention in Different Cancer Xenograft Models Test compounds: compounds of the invention, the chemical names and preparation methods of which can be found in their preparation examples.

The meanings represented by the abbreviations in the below experiments are described as follows.

| Symbol | Name | Symbol | Name |
|---|---|---|---|
| PDX | patient-derived xenograft | RTV | relative tumor volume |

Experimental Method:

1. Seeding of Tumors and Grouping

Tumor tissues were harvested from tumor-bearing mice of esophageal cancer PDX model, cut into pieces with diameter of 2-4 mm and seeded subcutaneously to right lateral thorax of female BALB/c nude mouse. When the tumors' average volume reached about 150 mm³, the animals were grouped and administered with a drug. Compound 1 was orally administrated once a day at an amount of 150 mg/kg, for 21 days. The volume of the drug for administration is 0.1 mL/10 g according to animal's body weight.

Tumor tissues were harvested from tumor-bearing mice of liver cancer PDX model, cut into pieces with diameter of 10-15 mm and seeded subcutaneously to back of female NU/NU nude mouse. When the tumors' average volume reached 100-300 mm³, the animals were grouped and administered with a drug. Compound 1 was orally administrated once a day at an amount of 200 mg/kg, for 21 days. The volume of the drug for administration is 0.1 mL/10 g according to animal's body weight.

2. Measurement of Tumor and Experimental Index

Tumor volume was measured with vernier calipers twice a week by measuring the major diameter and the minor diameter. The tumor volume is calculated by the following formula: volume=0.5×(major diameter)×(minor diameter)². The relative tumor volume (RTV) and the proliferation ratio (T/C) were calculated according to the result of measurement. $RTV=V_t/V_0$, wherein $V_t$ is the average tumor volume on the t day after grouping, and $V_0$ is the average tumor volume on the day of grouping. T/C (%)=RTV of treatment group/RTV of solvent control group×100%.

3. Statistical Analysis

One-way ANOVA was used for analysing the group statistical analysis of tumor volumes. $p<0.05$ was regarded as having significant difference.

The experimental results are shown in Table 9:

TABLE 9

The tumor inhibition result of the compounds according to the invention on the two xenograft models

| Model | Group | Tumor volume before administration (mm³) [a] | Tumor volume after administration (mm³) [a] | T/C (%) | P [b] |
|---|---|---|---|---|---|
| esophageal cancer PDX model | Group 1: solvent control group | 177.8 ± 25.1 | 880.8 ± 186.3 | — | — |
| | Group 2: Compound 1 (150 mg/kg) | 177.7 ± 28.5 | 221.6 ± 27.2 | 29% | 0.008 |
| Liver cancer PDX model | Group 1: solvent control group | 163.31 ± 10.33 | 621.98 ± 59.53 | — | — |
| | Group 2: Compound 1 (200 mg/kg) | 164.8 ± 10.35 | 199.22 ± 33.76 | 31.74 | <0.05 |

Note:
[a] average ± standard error;
[b] compared with solvent control group

Experimental Conclusion:

As shown in Table 9, Compound 1 according to the invention has significant inhibitory effect on the growth of esophageal cancer cell (the proliferation ratio (T/C) is 29%, and has significant difference compared with solvent control group); Compound 1 has significant inhibitory effect on the growth of liver cancer cell (the relative tumor volume ratio (T/C) is 31.74%, and has significant difference compared with solvent control group).

Experimental Example 10: Assess on In-Vivo Pharmacodynamics of the Compounds According to the Invention in Capan-1 Pancreatic Cancer Xenograft Model Test compounds: compounds of the invention, the chemical names and preparation methods of which can be found in their preparation examples.

1. Method

Cell Culture

Culture medium of Capan-1 pancreatic cancer cell: IMDM culture medium+10% fetal bovine serum+100 U/mL penicillin and 100 μg/mL streptomycin+2 mM glutamine.

2. Seeding and Grouping of Cells

Cells were cultured and passaged. Tumor cells in exponential growth phase were used for in vivo tumor seeding. The cells were seeded subcutaneously to right lateral thorax of female BALB/c nude mouse. When tumor grew to a volume of about 150 mm$^3$, the animals were grouped and administered with a drug. Compound 1 was orally administrated once a day at an amount of 100 mg/kg, for 21 days. The volume of the drug for administration is 0.1 mL/10 g according to animal's body weight.

3. Measurement of Tumor and Experimental Index

Tumor volume was measured with vernier calipers twice a week by measuring the major diameter and the minor diameter. The tumor volume is calculated by the following formula: volume=0.5×(major diameter)×(minor diameter). The relative tumor volume (RTV) and the proliferation ratio (T/C) were calculated according to the result of measurement. RTV=$V_t/V_0$, wherein $V_t$ is the average tumor volume on the t day after grouping, and $V_0$ is the average tumor volume on the day of grouping. T/C=RTV of treatment group/RTV of solvent control group×100%. Inhibition ratio of tumor growth (%, TGI) is calculated according to the following formula: (1−T/C)×100%.

4. Statistical Analysis

SPSS statistical software was used for T test on the 2 groups of independent samples, and for group statistical analysis of tumor volumes. p<0.05 was regarded as having significant difference.

The experimental results are shown in Table 10:

TABLE 10

The tumor inhibition result of the compounds of the application on subcutaneous Capan-1 xenograft model

| Group | Tumor volume before administration (mm$^3$) [a] | Tumor volume after administration (mm$^3$) [a] | T/C (%) | TGI (%) | P [b] |
|---|---|---|---|---|---|
| Group 1: solvent control group | 141 ± 6 | 1,177 ± 71 | — | — | — |
| Group 2: Compound 1 (100 mg/kg) | 150 ± 12 | 368 ± 48 | 31.5 | 68.5 | <0.001 |

Note:
[a] average ± standard error;
[b] compared with solvent control group

Experimental Conclusion:

As shown in Table 10, Compound 1 according to the invention have significant inhibiting activity on Capan-1 human pancreatic cancer cell (inhibition ratio of tumor growth (%, TGI) is 68.5%, p<0.001 compared with solvent control group).

Experimental Example 11: Assay on In Vitro Enzyme-Inhibiting Activity of the Compounds According to the Invention Test compounds: compounds of the invention, the chemical names and preparation methods of which can be found in their preparation examples.

The meanings represented by the abbreviations in the below experiments are described as follows.

| Symbol | Name | Symbol | Name |
|---|---|---|---|
| HGC-27 | gastric cancer cell | DMEM | Dulbecco's modified Eagle's medium |
| DMSO | dimethyl sulfoxide | PBS | phosphate buffer solution |
| BrdU | bromodeoxyuridine | TMB | tetramethyl benzidine |
| HRP | horseradish peroxidase | IgG | Immunoglobulin G |
| FBS | fetal bovine serum | OD | optical density |

Experimental method: cell proliferation assay was carried out by BrdU method (BrdU cell proliferation assay kit, Cell Signaling Technology Company).

1. Preparation of Reagents and Compounds (1) Preparation of 1-Fold Washing Liquor:

20-fold washing liquor as stock solution was diluted with ultra-pure water to prepare 1-fold liquor.

(2) Preparation of 1-Fold Detection Antibody Solution:

The 100-fold BrdU detection antibody stock solution was diluted with a detection antibody diluent to prepare 1-fold detection antibody solution.

(3) Preparation of 1-Fold HRP-Labelled Secondary Antibody Solution

The 100-fold stock solution of HRP-labelled anti-mouse IgG antibody was diluted with HRP-labelled antibody diluent to prepare 1-fold HRP-labelled secondary antibody solution.

(4) 10-Fold BrdU Label Solution:

The 1000-fold BrdU stock solution was diluted with the corresponding medium to prepare a 10-fold BrdU label solution.

(5) Preparation of Test Compound

Preparation of test compound stock solution: 10 mM stock solution of a test compound was prepared by using 100% DMSO.

Preparation of gradient dilution solutions of test compound: the stock solution containing 10 mM test compound was subjected to 4-fold stepwise dilution with DMSO to prepare solutions containing 2.5 mM, 625 µM, 156 µM, 39 µM, 9.8 µM, and 2.5 µM test compound, respectively. 2 µL DMSO-diluted compound was added to 198 µL culture medium containing 10% FBS to prepare 10-fold test compound, wherein the maximum concentration of the test compound was 100 µM, the concentration of DMSO was 1%, and there were 7 concentration gradients.

(6) Preparation of Culture Medium

HGC-27 medium: DMEM+10% FBS

2. Experimental Steps (1) Cells grown to 80% confluence (in exponential growth phase) were digested with pancreatin, and centrifuged to collect the cells. Cells were re-suspended in FBS-free culture medium, counted, and seeded to a 96-well plate at 4000 cells/well/81 µL. The plates were placed in a cell incubator at 37° C.

(2) After 24 h culture, 9 µL FBS was added to each well to reach a final FBS concentration of 10%.

(3) To each well, a different concentration of 10-fold test compound (10 µL) was added, to make the test compound at a final concentration of 10 µM, 2.5 µM, 625 nM, 156 nM, 39 nM, 9.8 nM, and 2.5 nM, respectively, with 3 repeated wells/group, and the cells were cultured for 72 h at 37° C.

Solvent control: 0.1% DMSO

Blank control: culture medium without addition of cells

Normal cell control: normal cells without any treatment (4) To each well, 10 µL 10-fold BrdU solution was added, and the culture medium was discarded after incubation for 4 h in the incubator.

(5) To each well, 10 µL fixing/denaturation solution was added, the solution was discarded after incubation for 30 min at room temperature.

(6) To each well, 100 µL 1-fold detection antibody solution was added, the solution was discarded after incubation for 1 h at room temperature, and the well was washed with 1-fold washing liquor at 200 µL/well for three times.

(7) To each well, 100 µL 1-fold HRP-labelled secondary antibody solution was added, the solution was discarded after incubation for 30 min at room temperature, and the well was washed with 1-fold washing liquor at 200 µL/well for three times.

(8) To each well, 100 µL TMB substrate solution was added, and incubation was carried out at room temperature for 30 min.

(9) To each well, 100 µL stop solution was added, and OD value at 450 nm was measured by ELISA instrument 3. Data processing Cell survival rate (%)=($OD_{test\ compound}$−$OD_{blank\ control}$)/($OD_{solvent\ control}$−$OD_{blank\ control}$)×100%, (1)

$OD_{blank\ control}$: blank control value; $OD_{solvent\ control}$: solvent control value;

(2) The data was processed by GraphPad Prism 5 software to get a curve and $IC_{50}$ values.

The experimental results are shown in Table 11:

TABLE 11

In vitro cell-inhibiting activity of the compounds according to the invention

| Test compound | In vitro cell-inhibiting activity ($IC_{50}$, nM) HGC-27 |
|---|---|
| Compound 1 | 316.4 |

Experimental conclusion: as shown in Table 11, the compounds according to the invention have high in vitro cell-inhibiting activity.

Preparation Schemes

The exemplified preparation schemes are provided for a part of the compounds according to the invention. However, it should be understood that the following experiments are provided merely for the purpose of illustrating the invention, rather than restricting the scope of the invention. A person skilled in the art, based on the teachings contained in the description, can make various modification or improvement to the technical solutions of the invention without departing from the spirit and scope of the invention.

Preparation Example 1: Preparation of 5-(bromomethyl)-2-chloropyrimidine

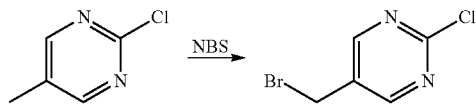

2-chloro-5-methylpyrimidine (12.86 g, 0.1 mol) was dissolved in carbon tetrachloride (300 mL), and N-bromobutanimide (25.72 g, 0.14 mol) and benzoyl peroxide (1.29 g, 5 mmol) were added under stirring. The resultant mixture was heated to reflux by oil bath, and was cooled to room temperature after reacting for 8 h. The mixture was filtrated under suction. The filtrate was concentrated and then subjected to silica gel column chromatography (petroleum ether: acetic ether=1:1) to get the title compound (8.7 g, yield: 42%).

Preparation Example 2: Preparation of 2,5-difluoro-4-iodopyridine

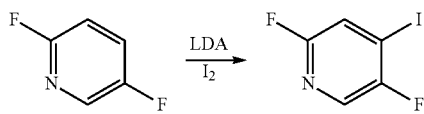

Diisopropylamine (17 mL, 122 mmol) was added to tetrahydrofuran (220 mL), and the mixture was cooled to −20° C. Under the protection of nitrogen, n-butyl lithium (49 mL, 122.5 mmol) was added slowly. After the addition, the mixture was stirred at −20° C. for 0.5 h, and cooled to −78° C. 2,5-difluoropyridine (13.3 g, 115 mmol) in tetrahydrofuran (30 mL) was added slowly and stirred at the temperature for 4 h. Iodine (32 g, 126 mmol) was dissolved in tetrahydrofuran (100 mL), and was slowly added to said reaction solution at −78° C. After the addition, the mixture was stirred for 1 h. After adding water (10 mL) and tetrahydrofuran (30 mL), the temperature was increased to room temperature. Saturated sodium thiosulfite solution was added. The organic phase was separated, and the water phase was extracted with acetic ether (3×100 mL). The organic phases were combined, dried by anhydrous sodium sulfate, filtrated under suction, and the filtrate was concentrated and then subjected to silica gel column chromatography (petroleum ether:acetic ether=50:1) to get the title compound (13.5 g, yield: 48%).

Preparation Example 3: Preparation of 5-fluoro-4-iodopyridin-2-amine

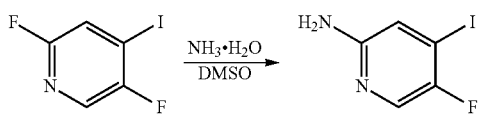

2,5-difluoro-4-iodopyridine (4.82 g, 20 mmol) was dissolved in DMSO (40 mL), and ammonia water (40 mL) was added under stirring. The mixture was stirred for 12 h at 90° C. in a sealed tube. Acetic ether (150 mL) was added to separate the organic phase, and the organic phase was dried by anhydrous sodium sulfate, filtrated under suction. The filtrate was concentrated and then subjected to silica gel column chromatography (dichloromethane:methanol=30:1) to get the title compound (2.38 g, yield: 50%).

Preparation Example 4: Preparation of N-Isopropylacetamide

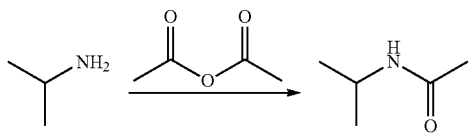

Isopropylamine (5.0 g, 84.7 mmol) and triethylamine (12.8 g, 126.7 mmol) were dissolved in dichloromethane (50 mL), and the temperature was cooled to 0° C. Acetic anhydride (17.3 g, 169.4 mmol) was added slowly. After the addition, the mixture was warmed up to room temperature, and reacted for 12 h. The solvent was removed by reduced pressure distillation. To the residue, acetic ether (100 mL) and potassium carbonate (20 g) were added. After stirring for 6 h, the mixture was filtrated under suction, and the solvent was removed by reduced pressure distillation to get the oil title compound (7.65 g, yield: 89.5%).

Preparation Example 5: Preparation of (Z)—N'-(4-bromo-2,6-difluorophenyl)-N-isopropyl acetamidine

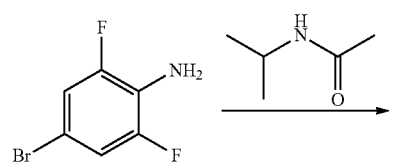

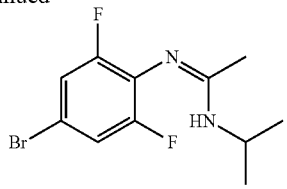

4-bromo-2,6-difluroaniline (7.87 g, 37.9 mmol)), N-isopropylacetamide (7.65 g, 75.7 mmol) and triethylamine (5.7 g, 56.9 mmol) were dissolved in toluene (150 mL), and phosphorus oxychloride (5.8 g, 37.9 mmol) was added slowly. After the addition, the mixture was heated to reflux for 3 h. Then, the reaction mixture was cooled to room temperature, the solvent was removed by reduced pressure distillation, and dichloromethane (200 mL) was added. The resultant mixture was washed with saturated sodium hydrogen carbonate solution (2×100 mL) twice, dried by anhydrous sodium sulfate, filtrated under suction, and distilled under reduced pressure, to get the solid title compound (7.3 g, yield: 66.2%).

Preparation Example 6: Preparation of 6-bromo-4-fluoro-1-isopropyl-2-methyl-1H-benzo[d]imidazole

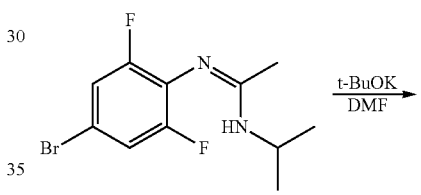

(Z)—N'-(4-bromo-2,6-difluorophenyl)-N-isopropyl acetamidine (7.0 g, 24.1 mmol) was dissolved in N,N-dimethylformamide (50 mL), and potassium tert-butoxide (3.2 g, 28.9 mmol) was added. The resultant mixture was heated up to 100° C. and reacted for 2 h. The reaction mixture was cooled to room temperature, and dichloromethane (100 mL) and saturated NaCl water (50 mL) were added to separate the organic phase. The organic phase was dried by anhydrous sodium sulfate, filtrated, and concentrated to get the crude product. The crude product was purified by silica gel column chromatography (petroleum ether:acetic ether=2:1) to get the solid title compound (4.0 g, yield: 61.3%).

Preparation Example 7: Preparation of 4-fluoro-1-isopropyl-2-methyl-6-(4,4,5,5-tetramethyl-1,3,2-dioxaborolane-2-yl)-1H-benzo

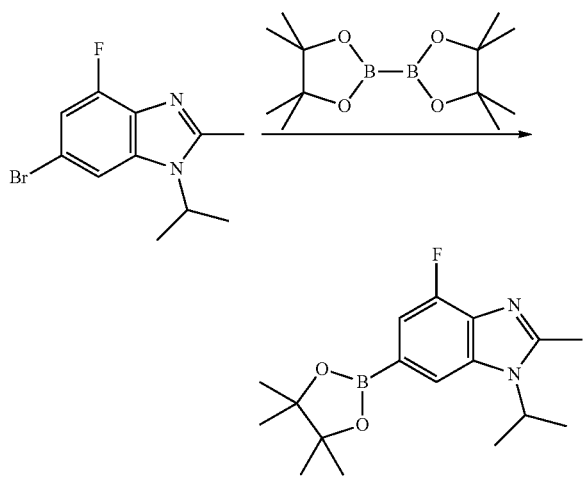

6-bromo-4-fluoro-1-isopropyl-2-methyl-1H-benzo[d]imidazole (9.0 g, 33.2 mmol), bis(pinacolato)diboron (12.65 g, 49.8 mmol), palladium acetate (840 mg, 3.75 mmol), tricyclohexylphosphine (1.63 g, 5.8 mmol) and potassium acetate (9.78 g, 99.8 mmol) were added to DMSO (60 mL). Under the protection of nitrogen, the mixture was heated to 80° C. and reacted for 6 h. Water (200 mL) and acetic ether (200 mL) were added to separate the organic phase from the water phase. The water phase was extracted with acetic ether twice, and the organic phases were combined, and dried by anhydrous sodium sulfate, filtrated under suction. The filtrate was concentrated and then subjected to silica gel column chromatography (petroleum ether:acetic ether=1:2) to get the title compound (6.0 g, yield: 56.8%).

Preparation Example 8: Preparation of 5-fluoro-4-(4-fluoro-1-isopropyl-2-methyl-1H-benzo[d]imidazol-6-yl)pyridin-2-amine

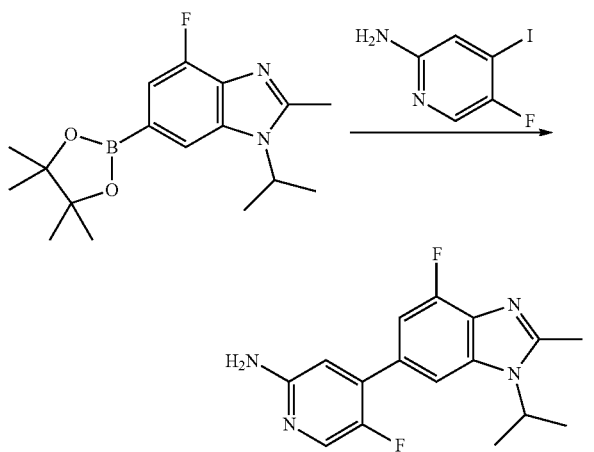

4-fluoro-1-isopropyl-2-methyl-6-(4,4,5,5-tetramethyl-1,3,2-dioxaborolane-2-yl)-1H-benzo[d]imidazole (3.18 g, 10 mmol), 5-fluoro-4-iodopyridin-2-amine (2.38 g, 10 mmol), potassium carbonate (2.76 g, 20 mmol) and tetrakis(triphenylphosphine)palladium(1.15 g, 1 mmol) were added to a 35 mL microwave tube, and 1,4-dioxane (15 mL) and water (3 mL) were added. The mixture was reacted at 120° C. under condition of microwave for 1 h. Water and acetic ether were added to separate the organic phase from the water phase. The organic phase was dried by anhydrous sodium sulfate, and filtrated under suction. The filtrate was concentrated and then subjected to silica gel column chromatography (petroleum ether:acetic ether=1:1) to get the title compound (2.1 g, yield: 69.5%).

Preparation Example 9: Preparation of 4-fluoro-6-(5-fluoro-2-iodopyridin-4-yl)-1-isopropyl-2-methyl-1H-benzo f dl imidazole

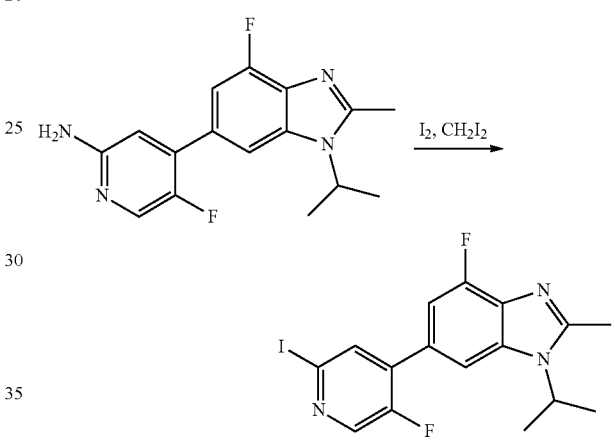

5-Fluoro-4-(4-fluoro-1-isopropyl-2-methyl-1H-benzo[d]imidazol-6-yl)pyridin-2-amine (1.0 g, 3.31 mmol) was dissolved in diiodomethane (30 mL), and CuI (0.63 g, 3.32 mmol), tert-butyl nitrite (0.341 g, 3.31 mmol) and iodine (0.84 g, 3.31 mmol) were added. The mixture was heated to 85° C. and reacted for 15 min. The resultant mixture was cooled and then directly separated by silica gel column chromatography (petroleum ether:acetic ether=200:1~1:1) to get the title compound (700 mg, yield: 51.1%).

Preparation Example 10: Preparation of 5-bromo-2-aminopyrimidine

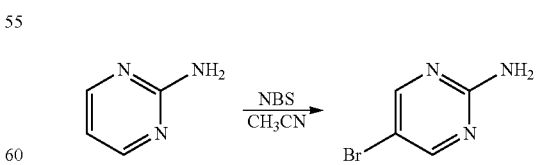

2-aminopyrimidine (20.0 g, 0.21 mol) was dissolved in acetonitrile (500 mL), and N-bromobutanimide (37.0 g, 0.21 mol) was added. The mixture was stirred at 20° C. for 4 h, and filtrated under suction. The filter cake was dried to get the product (33.0 g, yield: 90.2%).

Preparation Example 11: Preparation of 5-bromo-N,N-bis(4-methoxybenzyl)pyrimidin-2-amine

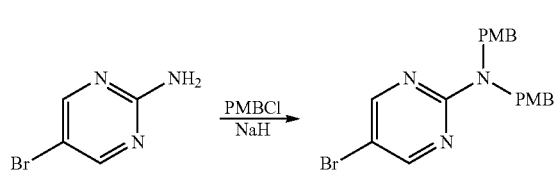

5-Bromo-2-aminopyrimidine (8.9 g, 51.15 mmol) was dissolved in tetrahydrofuran (150 mL), and sodium hydride (4.4 g, 110.0 mmol, 60%) was added slowly under the condition of ice bath. The mixture was warmed up to room temperature and stirred for 30 min. 4-methoxybenzyl chloride (20.0 g, 127.71 mmol) was added, and the mixture was heated to 75° C. and reacted for 8 h. Ice water was added to quench the reaction, and the reaction solution was extracted with acetic ether (200 mL). The water phase was washed with acetic ether (50 mL), and the organic phases were combined, dried, concentrated, and separated by silica gel column chromatography (petroleum ether:acetic ether=20:1) to get the title compound (10.0 g, yield: 47.2%).

Preparation Example 12: Preparation of tert-butyl 4-(2-(bis(4-methoxybenzyl)amino)pyrimidin-5-yl)piperazin-1-carboxylate

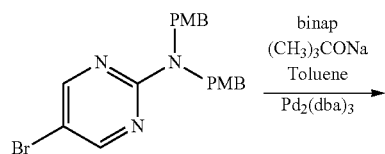

5-bromo-N,N-bis(4-methoxybenzyl)pyrimidin-2-amine (10.0 g, 24.1 mmol), tert-butyl piperazin-1-carboxylate (8.97 g, 48.2 mmol), sodium tert-butoxide (4.63 g, 48.2 mmol), tris(dibenzylideneacetone)dipalladium (200 mg) and racemic-2,2'-bis(diphenylphosphino)-1,1'-binaphthyl (400 mg) were added to toluene (200 mL). Under the protection of nitrogen, the mixture was heated in an 80° C. oil bath for 8 h, and the solvent was removed by distillation under rotation. The residue was purified by silica gel column chromatography (petroleum ether:acetic ether=1:1) to get the title compound (6.2 g, yield: 49.6%).

Preparation Example 13: Preparation of 5-(piperazin-1-yl)pyrimidin-2-amine

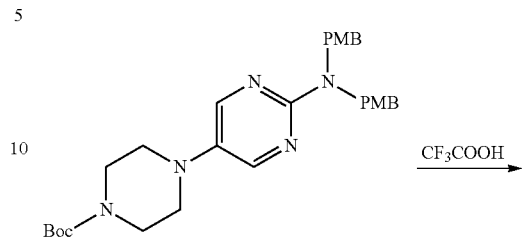

Tert-butyl 4-(2-(bis(4-methoxybenzyl)amino)pyrimidin-5-yl)piperazin-1-carboxylate (6.2 g, 11.9 mmol) was dissolved in a mixed solution of dichloromethane (30 mL) and trifluoroacetic acid (30 mL), and stirred at room temperature for 30 min. The solvent was removed by distillation under rotation. A small amount of dichloromethane was added, and distillation under rotation was performed again to remove the solvent and get the crude product (2.1 g). The product was used in next step without purification.

Preparation Example 14: Preparation of tert-butyl 4-(2-aminopyrimidin-5-yl)piperazin-1-carboxylate

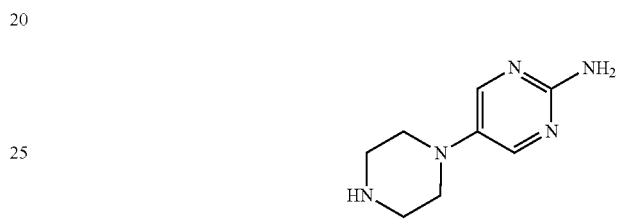

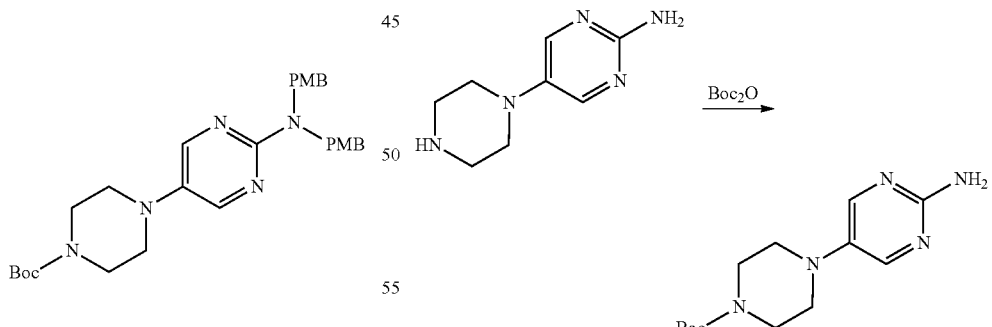

5-(Piperazin-1-yl)pyrimidin-2-amine (2.1 g, 11.7 mmol) was dissolved in dichloromethane (25 mL), and triethylamine (1.77 g, 17.5 mmol) was added. Di-tert-butyl dicarbonate (3.05 g, 14.0 mmol) was added dropwisely. After the addition, the mixture was stirred at room temperature for 1 h. The solvent was removed by distillation under rotation. The residue was purified by silica gel column chromatography (dichloromethane:methanol=10:1) to get the product (1.52 g, two-step yield: 45.8%).

Preparation Example 15: Preparation of tert-butyl 4-(2-(5-fluoro-4-(4-fluoro-1-isopropyl-2-methyl-1H-benzo[d]imidazol-6-yl)pyridin-2-yl)amino)pyrimidin-5-yl)piperazin-1-carboxylate

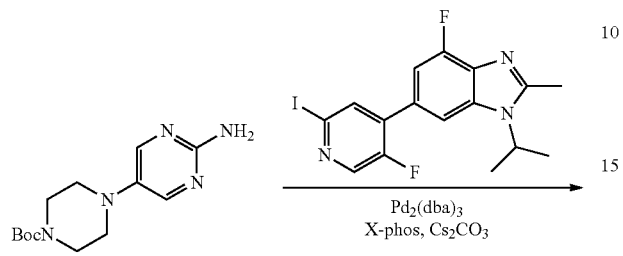

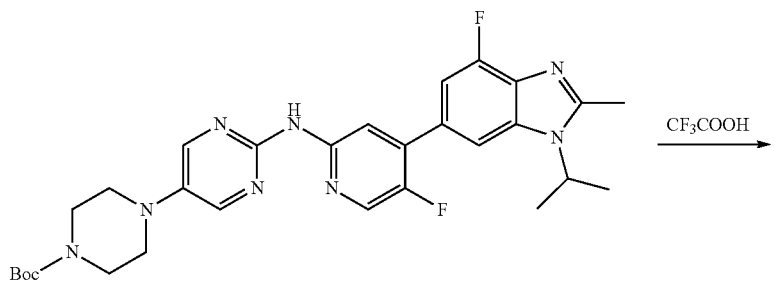

-continued

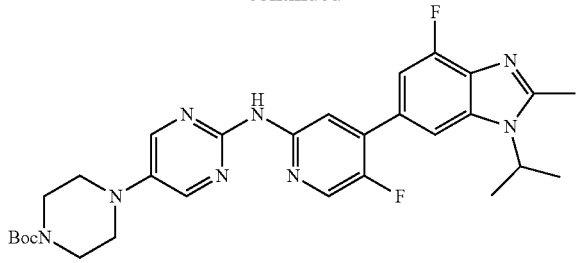

Tert-butyl 4-(2-aminopyrimidin-5-yl)piperazin-1-carboxylate (475 mg, 1.70 mmol) and 4-fluoro-6-(5-fluoro-2-iodopyridin-4-yl)-1-isopropyl-2-methyl-1H-benzo[d]imidazole (350 mg, 0.85 mmol) were dissolved in 1,4-dioxane (20 mL), and cesium carbonate (826 mg, 2.54 mmol), tris(dibenzylideneacetone)dipalladium (78 mg, 0.085 mmol) and 2-dicyclohexylphosphino-2',4',6'-triisopropylbiphenyl (81 mg, 0.17 mmol) were added. Under the protection of nitrogen, the mixture was heated to 110° C. and reacted for 16 h. The reaction solution was filtrated, and the filtrate was concentrated and separated by silica gel column chromatography (petroleum ether:acetic ether=1:1) to get the title compound (250 mg, yield: 52.1%).

Preparation Example 16: Preparation of N-(5-fluoro-4-(4-fluoro-1-isopropyl-2-methyl-1H-benzo[d]imidazol-6-yl)pyridin-2-yl)-5-(piperazin-2-yl)pyrimidin-2-amine Tert-butyl 4-(2-(5-fluoro-4-(4-fluoro-1-isopropyl-2-methyl-1H-benzo[d]imidazol-6-yl)pyridin-2-yl)amino)pyrimidin-5-yl)piperazin-1-carboxylate (250 mg, 0.44 mmol) was dissolved in a mixed solution of dichloromethane (5 mL) and trifluoroacetic acid (5 mL), and the mixture was stirred at 20° C. for 30 min. The solvent was removed by distillation under rotation, and dichloromethane (10 mL) was added. The solvent was removed by distillation under rotation, and the residue was separated by silica gel column chromatography (dichloromethane:methanol=10:1) to get the title compound (180 mg, yield: 88.1%).

Example 1: Preparation of 5-((4-ethylpiperazin-1-yl)methyl)-N-(5-fluoro-4-(4-fluoro-1-isopropyl-2-methyl-1H-benzo[d]imidazol-6-yl)pyridin-2-yl)pyrimidin-2-amine (Compound 1)

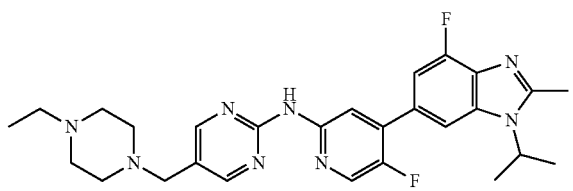 [SMILES: CCN1CCN(Cc2cnc(Nc3cc(-c4cc(F)c5nc(C)n(C(C)C)c5c4)c(F)cn3)nc2)CC1]

(1) Preparation of 2-chloro-5-((4-ethylpiperazin-1-yl)methyl)pyrimidine

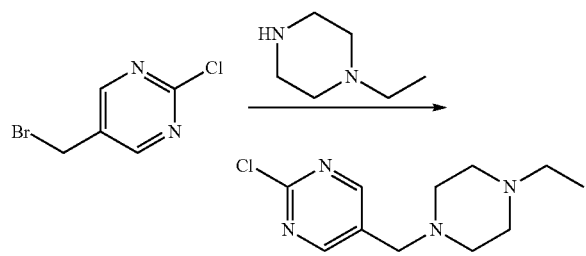

5-(Bromomethyl)-2-chloropyrimidine (4.14 g, 20 mmol) was dissolved in tetrahydrofuran (70 mL), and triethylamine (6.06 g, 60 mmol) and 1-ethylpiperazine (4.56 g, 40 mmol) were added under stirring. The mixture was stirred at room temperature for 4 h. After the raw material disappeared as detected by TLC, the mixture was filtrated under suction. The filtrate was concentrated and then subjected to silica gel column chromatography (dichloromethane:methanol=30:1) to get the title compound (3.4 g, yield: 70.8%).

(2) Preparation of 5-((4-ethylpiperazin-1-yl)methyl)-N-(5-fluoro-4-(4-fluoro-1-isopropyl-2-methyl-1H-benzo[d]imidazol-6-yl)pyridin-2-yl)pyrimidin-2-amine

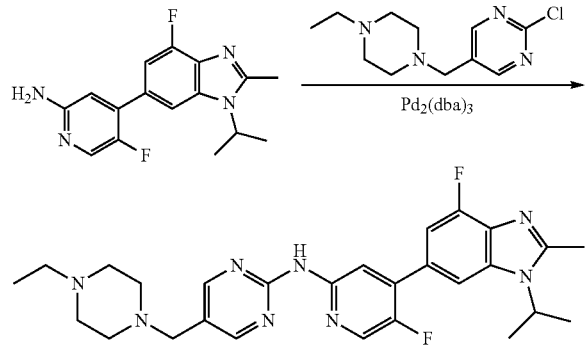

5-fluoro-4-(4-fluoro-1-isopropyl-2-methyl-1H-benzo[d]imidazol-6-yl)pyridin-2-amine (700 mg, 2.32 mmol), 2-chloro-5-((4-ethylpiperazin-1-yl)methyl)pyrimidine (557 mg, 2.32 mmol), 4,5-bis(diphenylphosphino)-9,9-dimethylxanthene (221 mg, 0.38 mmol), cesium carbonate (2.26 g, 6.96 mmol) and tris(dibenzylideneacetone)dipalladium (212 mg, 0.23 mmol) were added to a 100 mL eggplant shaped bottle, and 1,4-dioxane (50 mL) was added. Under the protection of nitrogen, the reaction was carried out at 110° C. for 4 h, and the resultant mixture was filtrated under suction. The filtrate was concentrated and then subjected to silica gel column chromatography (dichloromethane:methanol=15:1) to get the title compound (500 mg, yield: 42.6%).

Molecular formula: $C_{27}H_{32}F_2N_8$ Molecular weight: 506.3
LC-MS (m/z): 507.4 (M+H$^+$)

$^1$H-NMR (400 MHz, MeOD-d$_4$): δ: 8.56 (d, J=6.4 Hz, 1H), 8.49 (s, 2H), 8.26 (d, J=2.4 Hz, 1H), 7.79 (s, 1H), 7.27 (d, J=11.6 Hz, 1H), 3.50 (s, 2H), 2.69 (s, 3H), 2.38-2.64 (m, 10H), 1.70 (d, J=7.2 Hz, 6H), 1.11 (t, J=7.2 Hz, 3H).

Example 2: Preparation of N-(5-fluoro-4-(4-fluoro-1-isopropyl-2-methyl-1H-benzo[d]imidazol-6-yl)pyridin-2-yl)-5-((7-methyl-2,7-diazaspiro[3.5]nonan-2-yl)methyl)pyrimidin-2-amine (Compound 2)

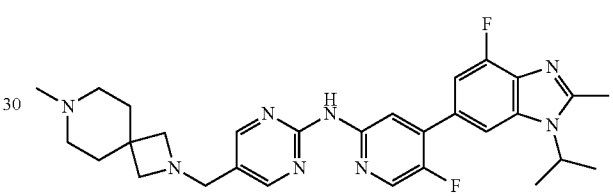

(1) Preparation of tert-butyl 2-(2-chloropyrimidin-5-yl)methyl)-2,7-diazaspiro[3.5]nonan-7-carboxylate

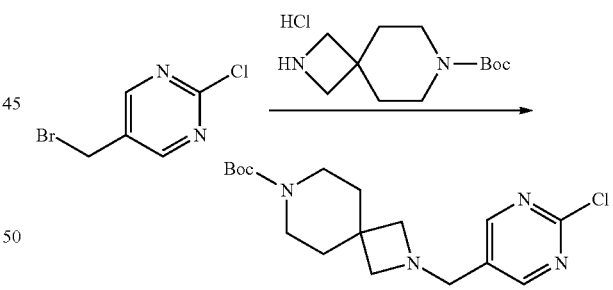

5-Bromomethyl-2-chloropyrimidine (235 mg, 1.14 mmol) was dissolved in tetrahydrofuran (5 mL), and tert-butyl 2,7-diazaspiro[3.5]nonan-7-carboxylate hydrochloride (300 mg, 1.14 mmol) and triethylamine (345 mg, 3.42 mmol) were added. The mixture was stirred at room temperature overnight, and the excessive solvent was removed by reduced pressure distillation. The residue was diluted with water (5 mL), and extracted with acetic ether (3×10 mL). The organic phase was dried by anhydrous sodium sulfate, filtrated, and dried under rotation. The crude product was purified by silica gel column chromatography (dichloromethane:methanol=20:1) to get the title compound (240 mg, yield: 60%).

(2) Preparation of 2-((2-chloropyrimidin-5-yl)methyl)-2,7-diazaspiro[3.5]nonane

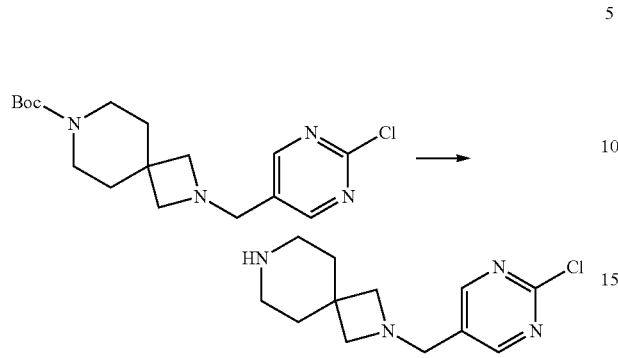

Tert-butyl 2-((2-chloropyrimidin-5-yl)methyl)-2,7-diazaspiro[3.5]nonan-7-carboxylate (240 mg, 0.68 mmol) was dissolved in dichloromethane (2 mL), and trifluoroacetic acid (1 mL) was added. The mixture was stirred at room temperature for 2 h. The excessive solvent was removed by reduced pressure distillation to get the title compound (156 mg, yield: 91%).

(3) Preparation of 2-((2-chloropyrimidin-5-yl)methyl)-7-methyl-2,7-diazaspiro[3.5]nonane

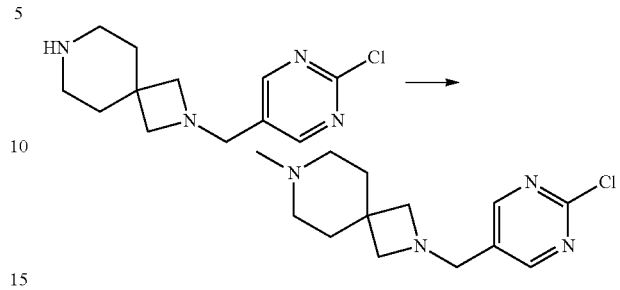

2-((2-Chloropyrimidin-5-yl)methyl)-2,7-diazaspiro[3.5]nonane (156 mg, 0.62 mmol) was dissolved in acetonitrile (5 mL), and 37% aqueous formaldehyde solution (251 mg, 3.1 mmol) and sodium cyanoborohydride (78 mg, 1.24 mmol) were added. The mixture was stirred at room temperature for 2 h. The excessive solvent was removed by reduced pressure distillation, and the crude product was subjected to silica gel column chromatography (dichloromethane:methanol=20:1) to get the title compound (100 mg, yield: 61%).

(4) Preparation of N-(5-fluoro-4-(4-fluoro-1-isopropyl-2-methyl-1H-benzo[d]imidazol-6-yl)pyridin-2-yl)-5-((7-methyl-2,7-diazaspiro[3.5]nonan-2-yl)methyl)pyrimidin-2-amine

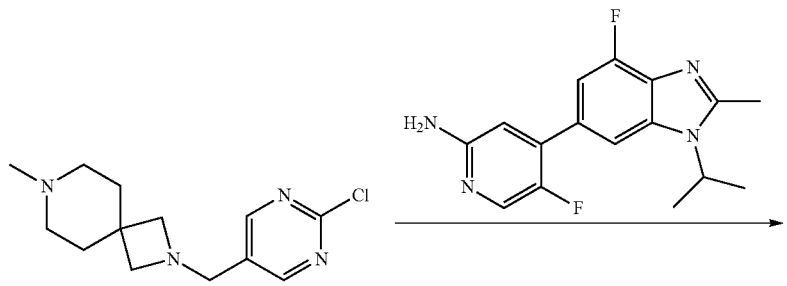

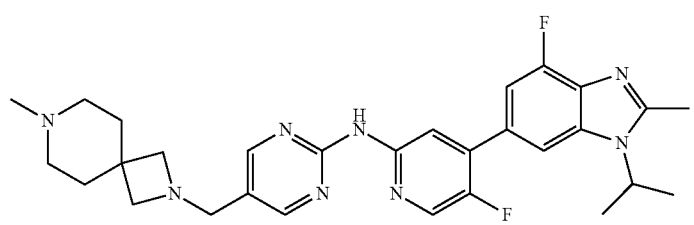

5-fluoro-4-(4-fluoro-1-isopropyl-2-methyl-1H-benzo[d] imidazol-6-yl)pyridin-2-amine (113 mg, 0.37 mmol) and 2-((2-chloropyrimidin-5-yl)methyl)-7-methyl-2,7-diazaspiro[3.5]nonane (100 mg, 0.37 mmol) was dissolved in 1,4-dioxane (5 mL), and tris(dibenzylideneacetone)dipalladium (34 mg, 0.037 mmol), 2-dicyclohexylphosphino-2',4',6'-triisopropylbiphenyl (35 mg, 0.074 mmol) and cesium carbonate (300 mg, 0.93 mmol) were added. Under the protection of nitrogen, the mixture was stirred under reflux overnight, and filtrated. The excessive solvent was removed by reduced pressure distillation. The crude product was subjected to silica gel column chromatography (dichloromethane:methanol=10:1) to get the title compound (17 mg, yield: 8.6%).

Molecular formula: $C_{29}H_{34}F_2N_8$ Molecular weight: 532.6
LC-MS (m/z): 533 (M+H$^+$)

$^1$H-NMR (400 MHz, MeOD-d$_4$) δ: 8.53 (d, J=6.0 Hz, 1H), 8.50 (s, 2H), 8.27 (d, J=2.4 Hz, 1H), 7.79 (s, 1H), 7.27 (d, J=11.2 Hz, 1H), 3.68 (s, 2H), 3.21-3.22 (m, 4H), 2.80-3.00 (m, 4H), 2.69 (s, 3H), 2.63 (s, 3H), 1.90-2.00 (m, 4H), 1.70 (d, J=6.8 Hz, 6H).

Example 3: Preparation of N-(5-fluoro-4-(4-fluoro-1-isopropyl-2-methyl-1H-benzo[d]imidazol-6-yl)pyridin-2-yl)-5-((2-methyl-2,7-diazaspiro[3.5]nonan-7-yl)methyl)pyrimidin-2-amine (Compound 3)

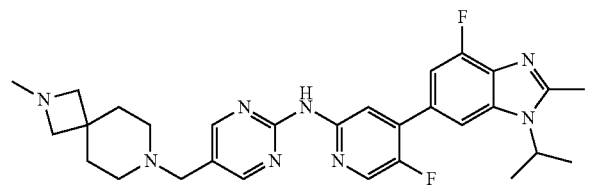

(1) Preparation of tert-butyl 7-(2-chloropyrimidin-5-yl)methyl)-2,7-diazaspiro[3.5]nonan-2-carboxylate

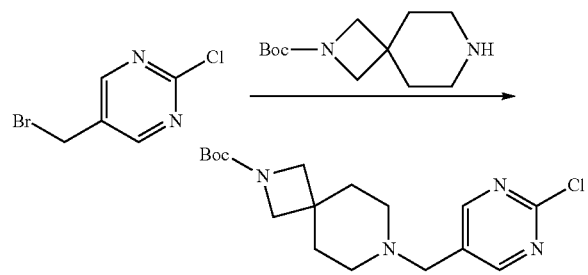

5-(Bromomethyl)-2-chloropyrimidine (220 mg, 1.06 mmol) was dissolved in tetrahydrofuran (5 mL), and tert-butyl 2,7-diazaspiro[3.5]nonan-2-carboxylate (200 mg, 0.88 mmol) and triethylamine (268 mg, 2.65 mmol) were added. The mixture was stirred at room temperature overnight. The solvent was removed by reduced pressure distillation. The residue was diluted with water (5 mL), and extracted with acetic ether (3×10 mL). The organic phase was dried by anhydrous sodium sulfate, filtrated, and dried under rotation. The crude product was purified by silica gel column chromatography (petroleum ether:acetic ether=1:1) to get the title compound (190 mg, yield: 60.5%).

(2) Preparation of 7-((2-chloropyrimidin-5-yl)methyl)-2,7-diazaspiro[3.5]nonane

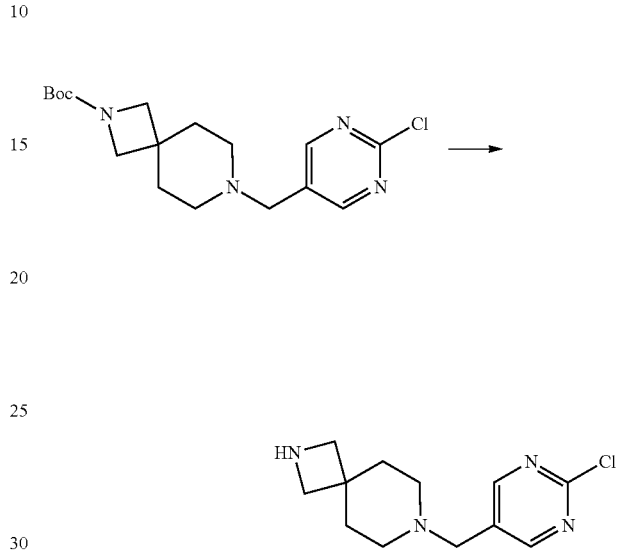

Tert-butyl 7-((2-chloropyrimidin-5-yl)methyl)-2,7-diazaspiro[3.5]nonan-2-carboxylate (190 mg, 0.54 mmol) was dissolved in dichloromethane (2 mL), and trifluoroacetic acid (1 mL) was added. The mixture was stirred at room temperature for 2 h. The solvent was removed by reduced pressure distillation to get the title compound (110 mg, yield: 81%).

(3) Preparation of 7-((2-chloropyrimidin-5-yl)methyl)-2-methyl-2,7-diazaspiro[3.5]nonane

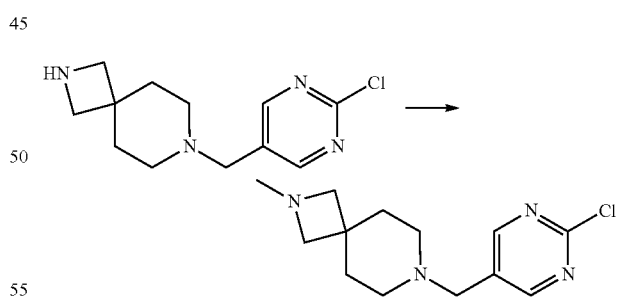

7-((2-Chloropyrimidin-5-yl)methyl)-2,7-diazaspiro[3.5]nonane (110 mg, 0.44 mmol) was dissolved in acetonitrile (5 mL), and 37% aqueous formaldehyde solution (178 mg, 2.2 mmol) and sodium cyanoborohydride (55 mg, 0.88 mmol) were added. The mixture was stirred at room temperature for 2 h. The solvent was removed by reduced pressure distillation, and the crude product was subjected to silica gel column chromatography (dichloromethane:methanol=20:1) to get the title compound (80 mg, yield: 68%).

(4) Preparation of N-(5-fluoro-4-(4-fluoro-1-isopropyl-2-methyl-1H-benzo[d]imidazol-6-yl)pyridin-2-yl)-5-((2-methyl-2,7-diazaspiro[3.5]nonan-7-yl)methyl)pyrimidin-2-amine ¹H-NMR (400 MHz, MeOD-d4) δ: 8.67 (s, 2H), 8.56 (d, J=6.0 Hz, 1H), 8.31 (d, J=2.4 Hz, 1H), 7.77 (s, 1H), 7.23 (d, J=11.6 Hz, 1H), 4.00-4.11 (m, 6H), 3.00-3.19 (m, 4H), 2.96 (s, 3H), 2.69 (s, 3H), 2.11-2.21 (m, 4H), 1.69 (d, J=6.8 Hz, 6H).

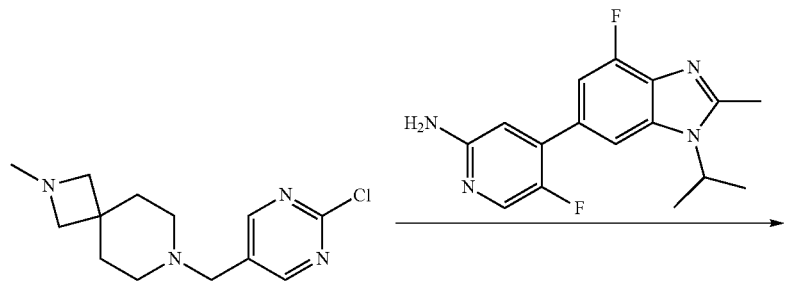

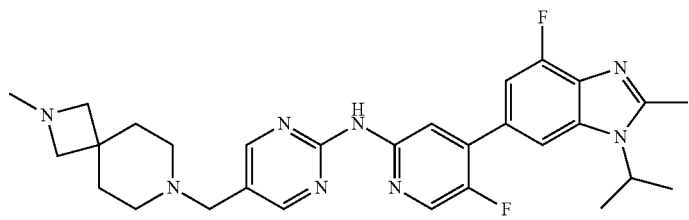

5-fluoro-4-(4-fluoro-1-isopropyl-2-methyl-1H-benzo[d]imidazol-6-yl)pyridin-2-amine (90 mg, 0.3 mmol) and 7-(2-chloropyrimidin-5-yl)methyl)-2-methyl-2,7-diazaspiro[3.5]nonane (80 mg, 0.3 mmol) was dissolved in 1,4-dioxane (5 mL), and tris(dibenzylideneacetone)dipalladium (27 mg, 0.03 mmol), 2-dicyclohexylphosphino-2',4',6'-triisopropylbiphenyl (29 mg, 0.06 mmol) and cesium carbonate (244 mg, 0.75 mmol) were added. Under the protection of nitrogen, the mixture was stirred under reflux overnight, and filtrated. The solvent was removed by reduced pressure distillation. The crude product was subjected to silica gel column chromatography (dichloromethane:methanol=10:1) to get the title compound (8 mg, yield: 5%).

Molecular formula: $C_{29}H_{34}F_2N_8$ Molecular weight: 532.6
LC-MS (m/z): 533 (M+H⁺)

Example 4: Preparation of N-(5-fluoro-4-(4-fluoro-1-isopropyl-2-methyl-1H-benzo[d]imidazol-6-yl)pyridin-2-yl)-5-(((6-methyl-2,6-diazaspiro[3.3]heptan-2-yl)methyl)pyrimidin-2-amine (Compound 4)

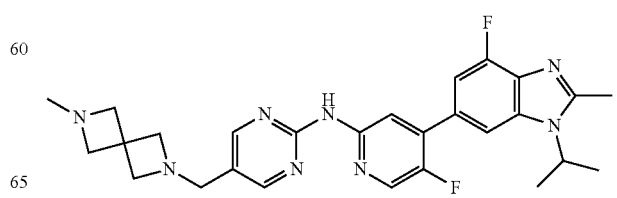

85

(1) Preparation of tert-butyl 6-((2-chloropyrimidin-5-yl)methyl)-2,6-diazaspiro[3.3]heptan-2-carboxylate

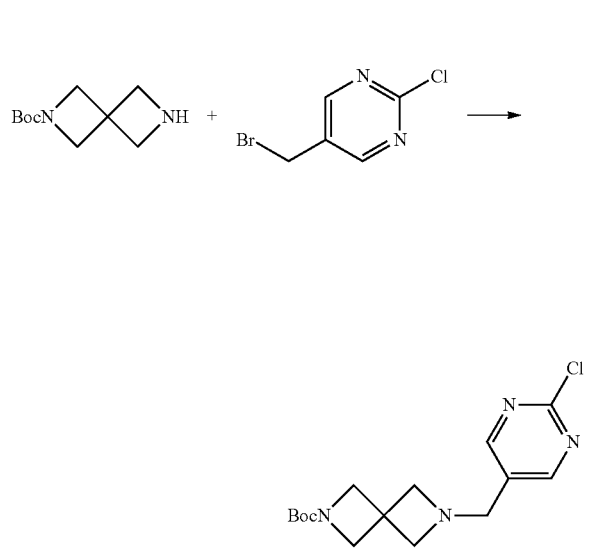

5-(Bromomethyl)-2-chloropyrimidine (326 mg, 1.57 mmol) was dissolved in acetonitrile (10 mL), and potassium carbonate (433 mg, 3.14 mmol) and tert-butyl 2,6-diazaspiro[3.3]heptan-2-carboxylate (310 mg, 1.57 mmol) were added. The reaction was carried out at room temperature for 16 h. The mixture was filtrated under suction. The filtrate was concentrated, and purified by silica gel column chromatography (dichloromethane:methanol=20:1) to get the title compound (330 mg, yield: 65%).

(2) Preparation of 2-((2-chloropyrimidin-5-yl)methyl)-2,6-diazaspiro[3.3]heptane

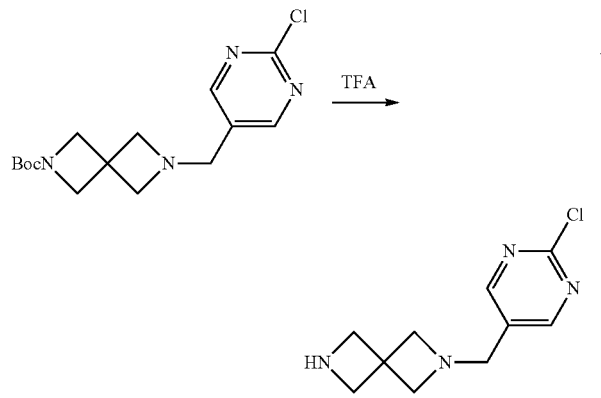

Tert-butyl 6-((2-chloropyrimidin-5-yl)methyl)-2,6-diazaspiro[3.3]heptan-2-carboxylate (330 mg, 1.01 mmol) was dissolved in dichloromethane (10 mL), and trifluoroacetic acid (5 mL) was added. The mixture was stirred at room temperature for 1 h and concentrated to get the oil title compound (210 mg, yield: 93%).

86

(3) Preparation of 2-((2-chloropyrimidin-5-yl)methyl)-6-methyl-2,6-diazaspiro[3.3]heptane

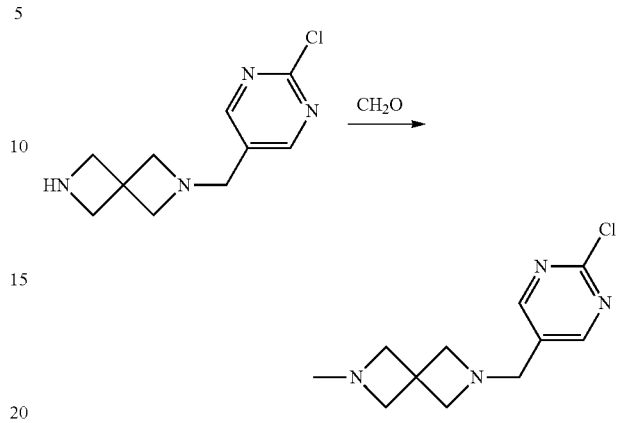

2-((2-Chloropyrimidin-5-yl)methyl)-2,6-diazaspiro[3.3]heptane (210 mg, 0.94 mmol) was dissolved in acetonitrile (5 mL), and formaldehyde solution (0.5 mL) and sodium cyanoborohydride (65 mg, 1.04 mmol) were added. The mixture was stirred at room temperature for 2 h. The solvent was removed by reduced pressure distillation, and the crude product was subjected to silica gel column chromatography (dichloromethane:methanol=10:1) to get the title compound (150 mg, yield: 67%).

(4) Preparation of N-(5-fluoro-4-(4-fluoro-1-isopropyl-2-methyl-1H-benzo[d]imidazol-6-yl)pyridin-2-yl)-5-(((6-methyl-2,6-diazaspiro[3.3]heptan-2-yl)methyl)pyrimidin-2-amine

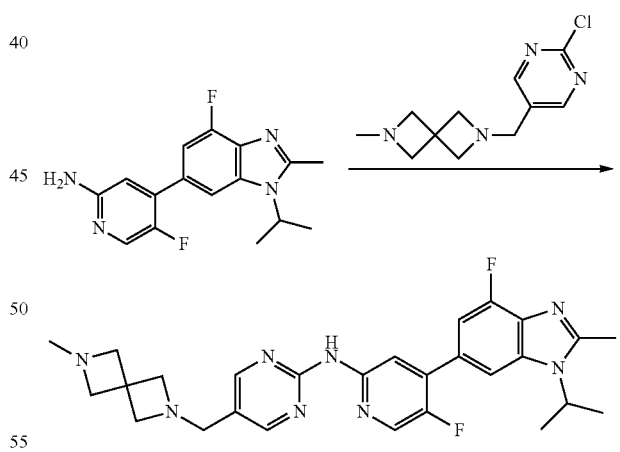

5-fluoro-4-(4-fluoro-1-isopropyl-2-methyl-1H-benzo[d]imidazol-6-yl)pyridin-2-amine (190 mg, 0.63 mmol) and 2-((2-chloropyrimidin-5-yl)methyl)-6-methyl-2,6-diazaspiro[3.3]heptane (150 mg, 0.63 mmol) were dissolved in 1,4-dioxane (10 mL), and 2-dicyclohexylphosphino-2',4',6'-triisopropylbiphenyl (60 mg, 0.13 mmol), cesium carbonate (614 mg, 1.89 mmol) and tris(dibenzylideneacetone)dipalladium(60 mg, 0.06 mmol) were added. Under the protection of nitrogen, the mixture was heated to 110° C. and reacted for 16 h. The resultant mixture was filtrated under suction. The filtrate was concentrated, and purified by silica gel column chromatography (dichloromethane:methanol=5:1) to get solid title compound (23 mg, yield: 7%).

Molecular formula: $C_{27}H_{30}F_2N_8$ Molecular weight: 504.3
LC-MS (m/z): 505.3 (M+H$^+$)
$^1$H-NMR (400 MHz, CD$_3$OD-d$_4$) δ: 8.54 (d, J=6.0 Hz, 1H), 8.46 (s, 2H), 8.26 (d, J=2.4 Hz, 1H), 7.79 (s, 1H), 7.27 (d, J=11.2 Hz, 1H), 4.84-4.85 (m, 1H), 3.54 (s, 6H), 3.39 (s, 4H), 2.69 (s, 3H), 2.41 (s, 3H), 1.69 (d, J=6.8 Hz, 6H).

Example 5: Preparation of N-(5-fluoro-4-(4-fluoro-1-isopropyl-2-methyl-1H-benzo[d]imidazol-6-yl)pyridin-2-yl)-5-((9-methyl-3,9-diazaspiro[5.5]undecan-3-yl)methyl)pyrimidin-2-amine (Compound 5)

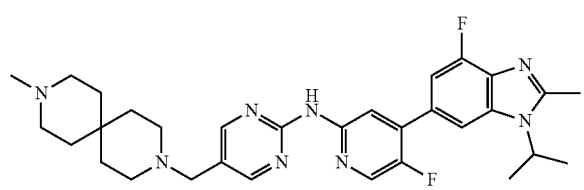

(1) Preparation of tert-butyl 9-((2-chloropyrimidin-5-yl)methyl)-3,9-diazaspiro[5.5]undecan-3-carboxylate

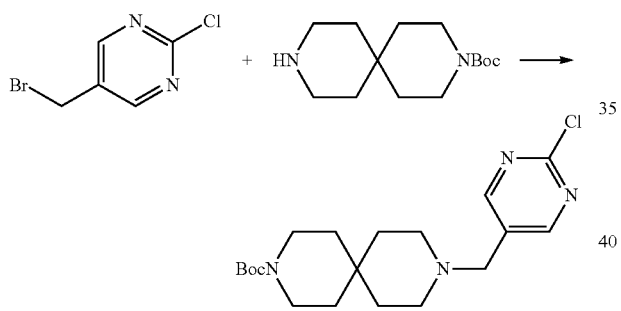

5-(Bromomethyl)-2-chloropyrimidine (326 mg, 1.57 mmol) was dissolved in tetrahydrofuran(10 mL), and triethylamine (158 mg, 1.57 mmol) and tert-butyl 3,9-diazaspiro[5.5]undecan-3-carboxylate (200 mg, 0.79 mmol) were added under stirring. The reaction mixture was stirred at room temperature for 4 h, and filtrated under suction. The filtrate was concentrated, and purified by silica gel column chromatography (dichloromethane:methanol=30:1) to get the title compound (210 mg, yield: 70%).

(2) Preparation of 3-((2-chloropyrimidin-5-yl)methyl)-3,9-diazaspiro[5.5]undecane

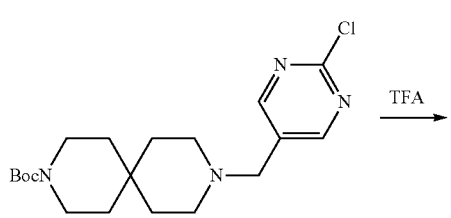

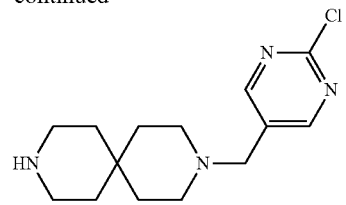

Tert-butyl 9-((2-chloropyrimidin-5-yl)methyl)-3,9-diazaspiro[5.5]undecan-3-carboxylate (210 mg, 0.55 mmol) was added to dichloromethane (10 mL), and trifluoroacetic acid (5 mL) was added. The mixture was stirred at room temperature for 1 h, and concentrated to get the title compound (145 mg, yield: 94%).

(3) Preparation of 3-((2-chloropyrimidin-5-yl)methyl)-9-methyl-3,9-diazaspiro[5.5]undecane

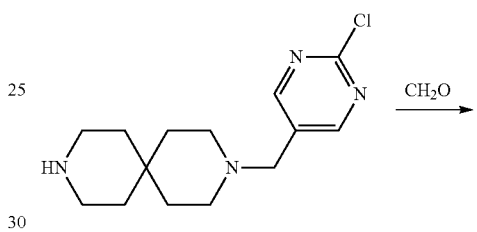

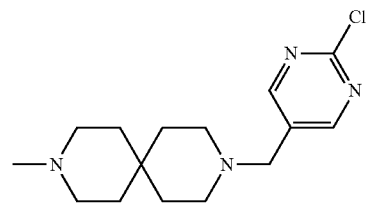

3-((2-Chloropyrimidin-5-yl)methyl)-3,9-diazaspiro[5.5]undecane (145 mg, 0.52 mmol) was dissolved in acetonitrile (5 mL), and 37% aqueous formaldehyde solution (0.5 mL) and sodium cyanoborohydride (65 mg, 1.04 mmol) were added under stirring. After the addition, the mixture was stirred at room temperature for 2 h. The resultant mixture was concentrated and subjected to silica gel column chromatography (dichloromethane:methanol=20:1) to get the title compound (65 mg, yield: 42.7%).

(4) Preparation of N-(5-fluoro-4-(4-fluoro-1-isopropyl-2-methyl-1H-benzo[d]imidazol-6-yl)pyridin-2-yl)-5-((9-methyl-3,9-diazaspiro[5.5]undecan-3-yl)methyl)pyrimidin-2-amine

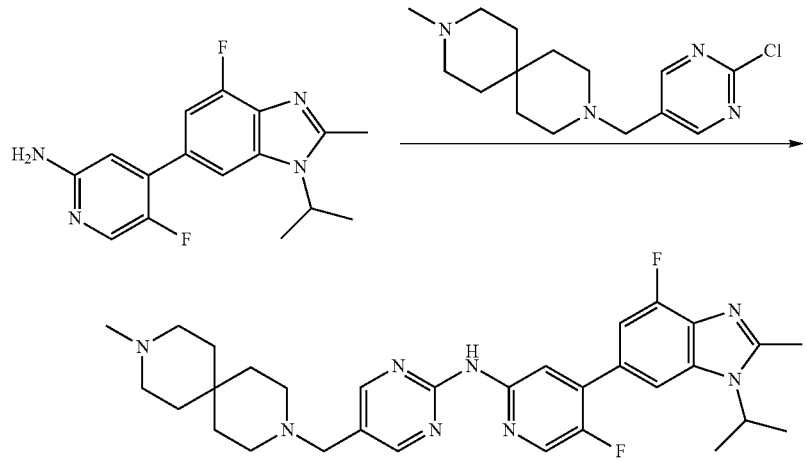

5-fluoro-4-(4-fluoro-1-isopropyl-2-methyl-1H-benzo[d]imidazol-6-yl)pyridin-2-amine (77 mg, 0.26 mmol), 3-(2-chloropyrimidin-5-yl)methyl)-9-methyl-3,9-diazaspiro[5.5]undecane (65 mg, 0.22 mmol), 2-dicyclohexylphosphino-2',4',6'-triisopropylbiphenyl(20 mg, 0.04 mmol), cesium carbonate (205 mg, 0.63 mmol) and tris(dibenzylideneacetone)dipalladium (20 mg, 0.02 mmol) were added to 1,4-dioxane (10 mL). Under the protection of nitrogen, the reaction was carried out at 110° C. for 16 h, and then the reaction mixture was filtrated under suction. The filtrate was concentrated and subjected to silica gel column chromatography (dichloromethane:methanol=10:1) to get the title compound (10 mg, yield: 8%).

Molecular formula: $C_{31}H_{38}F_2N_8$ Molecular weight: 560.7 LC-MS (m/z): 561.4 (M+H$^+$)

$^1$H-NMR (400 MHz, CD$_3$OD-d$_4$) δ: 8.54 (d, J=6.0 Hz, 1H), 8.49 (s, 2H), 8.26 (d, J=2.4 Hz, 1H), 7.79 (s, 1H), 7.28 (d, J=11.6 Hz, 1H), 3.53 (s, 2H), 2.98-3.07 (m, 4H), 2.71-2.68 (m, 6H), 2.50-2.52 (m, 4H), 1.66-1.71 (m, 9H), 1.61-1.65 (m, 5H).

Example 6: Preparation of N-(5-fluoro-4-(4-fluoro-1-isopropyl-2-methyl-1H-benzo[d]imidazol-6-yl)pyridin-2-yl)-5-((5-methylhexahydropyrrolo[3,4-c]pyrrol-2(1H)-yl)methyl)pyrimidin-2-amine (Compound 6)

(1) Preparation of tert-butyl 5-((2-chloropyrimidin-5-yl)methyl)hexahydropyrrolo[3,4-c]pyrrol-2(1H)-carboxylate

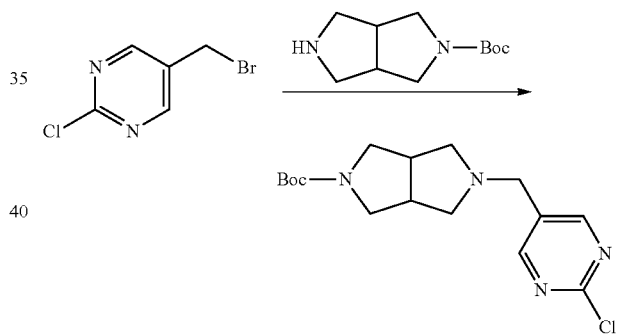

Tert-butyl hexahydropyrrolo[3,4-c]pyrrol-2(1H)-carboxylate (318 mg, 1.5 mmol) and 5-(bromomethyl)-2-chloropyrimidine (310 mg, 1.5 mmol) were dissolved in acetonitrile (50 mL), and potassium carbonate (621 mg, 4.5 mmol) was added. The mixture was reacted at room temperature for 8 h. The mixture was filtrated. The filtrate was concentrated, and purified by silica gel column chromatography (the eluent was dichloromethane:methanol=50:1) to get the title compound (430 mg, yield: 85%).

(2) Preparation of 2-((2-chloropyrimidin-5-yl)methyl)octahydropyrrolo[3,4-c]pyrrole

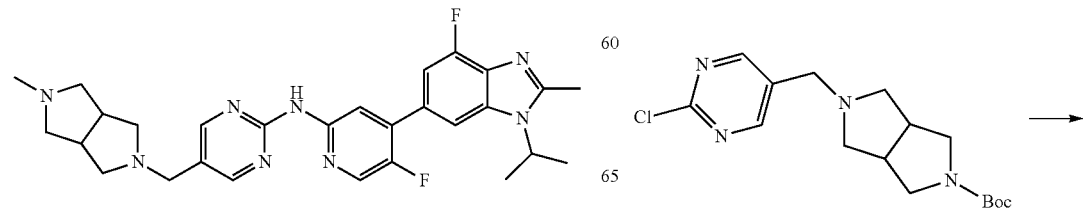

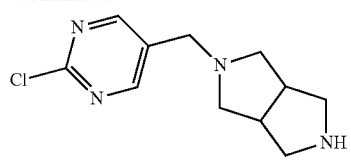 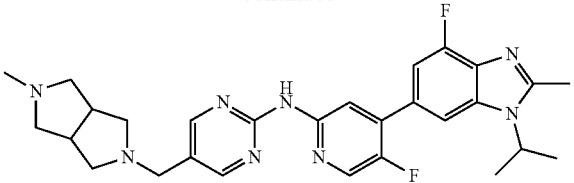

Tert-butyl 5-((2-chloropyrimidin-5-yl)methyl)hexahydropyrrolo[3,4-c]pyrrol-2(1H)-carboxylate (430 mg, 1.27 mmol) was dissolved in dichloromethane (10 mL), and trifluoroacetic acid (5 mL) was added. The mixture was stirred at room temperature for 3 h. The solvent was removed by reduced pressure distillation to get the yellow oil title compound (302 mg crude), which was directly used in the next step without purification.

(3) Preparation of 2-((2-chloropyrimidin-5-yl)methyl)-5-methyloctahydropyrrolo[3,4-c]pyrrole

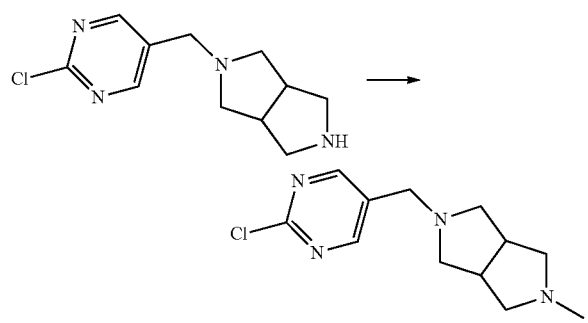

2-((2-Chloropyrimidin-5-yl)methyl)hexahydropyrrolo[3,4-c]pyrrole (302 mg crude product) was dissolved in methanol (50 mL). Aqueous formaldehyde solution (37%, 1 g, 12.3 mmol) was added at room temperature, the reaction was carried out for 2 h. Sodium cyanoborohydride (0.8 g, 12.7 mmol) was added, and the mixture was stirred at room temperature for 12 h. After the reaction, the reaction solution was concentrated and purified by silica gel column chromatography (dichloromethane:methanol=20:1) to get the title compound (260 mg, two step yield: 81%).

(4) Preparation of N-(5-fluoro-4-(4-fluoro-1-isopropyl-2-methyl-1H-benzo[d]imidazol-6-yl)pyridin-2-yl)-5-((5-methyl hexahydropyrrolo[3,4-c]pyrrol-2(1H)-yl)methyl)pyrimidin-2-amine 5-Fluoro-4-(4-fluoro-1-isopropyl-2-methyl-1H-benzo[d]imidazol-6-yl)pyridin-2-amine (302 mg, 1.0 mmol) and 2-((2-chloropyrimidin-5-yl)methyl)-5-methyl octahydropyrrolo[3,4-c]pyrrole (252 mg, 1.0 mmol) were dissolved in 1,4-dioxane (50 mL), and tris(dibenzylideneacetone)dipalladium (92 mg, 0.1 mmol), 2-dicyclohexylphosphino-2',4',6'-triisopropylbiphenyl (95 mg, 0.2 mmol) and cesium carbonate (975 mg, 3.0 mmol) were added. Under the protection of nitrogen, the mixture was heated to 110° C. and reacted for 8 h. The mixture was cooled to room temperature, and concentrated. Water (100 mL) and acetic ether (150 mL) were added to separate the organic phase from the water phase. The water phase was extracted with acetic ether (150 mL×2), and the organic phases were combined and washed with saturated NaCl solution, dried by anhydrous sodium sulfate, and concentrated. The crude product was purified by silica gel column chromatography (the eluent was dichloromethane:methanol=20:1) to get the title compound (223 mg, yield: 43%).

Molecular formula: $C_{28}H_{32}F_2N_8$ Molecular weight: 518.6
LC-MS (m/z): 519.3 (M+H$^+$)
$^1$H-NMR (400 MHz, DMSO-d$_6$) δ: 10.03 (s, 1H), 8.45 (s, 2H), 8.43 (d, J=6.4 Hz, 1H), 8.36 (s, 1H), 7.75 (s, 1H), 7.23 (d, J=11.6 Hz, 1H), 4.80-4.83 (m, 1H), 3.34-3.49 (m, 6H), 2.66 (brs., 4H), 2.61 (s, 3H), 2.35 (brs., 5H), 1.57 (d, J=6.8 Hz, 6H).

Example 6-1: Preparation of N-(5-fluoro-4-(4-fluoro-1-isopropyl-2-methyl-1H-benzo[d]imidazol-6-yl)pyridin-2-yl)-5-(((cis)-5-methylhexahydropyrrolo[3,4-c]pyrrol-2(1H)-yl)methyl)pyrimidin-2-amine (Compound 6-1)

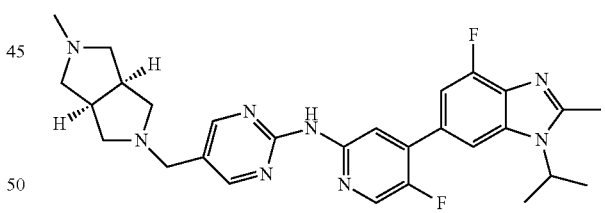

(1) Preparation of tert-butyl 5-(2-chloropyrimidin-5-yl)methyl)-(cis)-hexahydropyrrolo[3,4-c]pyrrol-2(1H)-carboxylate

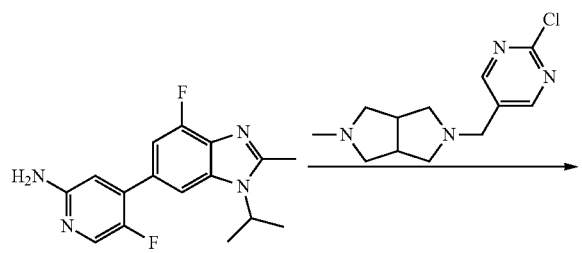 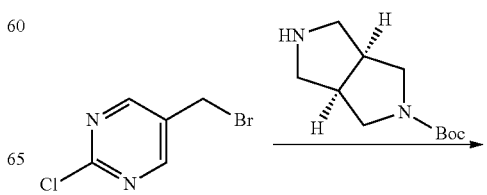

-continued

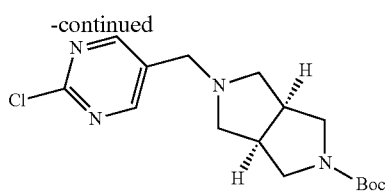

Tert-butyl (cis)-hexahydropyrrolo[3,4-c]pyrrol-2(1H)-carboxylate (300 mg, 1.41 mmol) and 5-(bromomethyl)-2-chloropyrimidine (292.5 mg, 1.41 mmol) were dissolved in acetonitrile (50 mL), and potassium carbonate (585 mg, 4.23 mmol) was added. The reaction was carried out at room temperature for 4 h. The mixture was filtrated. The filtrate was dried by distillation, and purified by silica gel column chromatography (the eluent was dichloromethane:methanol=50:1) to get the title compound (402 mg, yield: 82%).

(2) Preparation of 2-((2-chloropyrimidin-5-yl)methyl)-(cis)-octahydropyrrolo[3,4-c]pyrrole

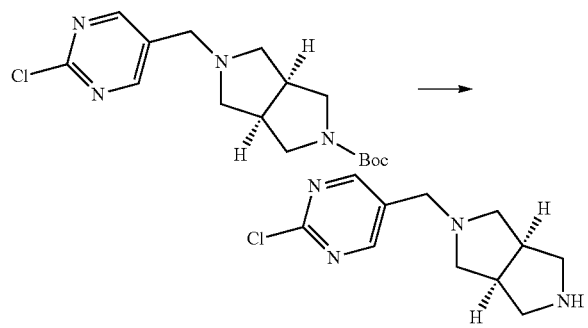

Tert-butyl 5-((2-chloropyrimidin-5-yl)methyl)-(cis)-hexahydropyrrolo[3,4-c]pyrrol-2(1H)-carboxylate (400 mg, 1.18 mmol) was dissolved in dichloromethane (10 mL), and trifluoroacetic acid (5 mL) was added. The mixture was stirred at room temperature for 3 h. The solvent was removed by reduced pressure distillation to get the title compound (300 mg crude product), which was used directly in the next step without purification.

(3) Preparation of 2-((2-chloropyrimidin-5-yl)methyl)-5-methyl-(cis)-octahydropyrrolo [3,4-c]pyrrole

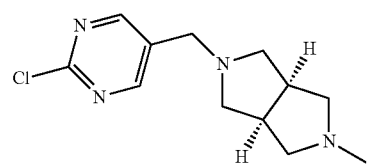

2-((2-chloropyrimidin-5-yl)methyl)-(cis)-octahydropyrrolo[3,4-c]pyrrole (300 mg) crude product was dissolved in methanol (50 mL). Aqueous formaldehyde solution (37%, 0.96 g, 11.8 mmol) was added at room temperature, the reaction was carried out for 2 h. Sodium cyanoborohydride (0.74 g, 11.8 mmol) was added, and the mixture was stirred at room temperature for 12 h. After the reaction, the solvent was dried by distillation, and the residue was subjected to silica gel column chromatography (dichloromethane:methanol=20:1) to get the title compound (175 mg, two step yield: 58%).

(4) Preparation of N-(5-fluoro-4-(4-fluoro-1-isopropyl-2-methyl-1H-benzo[d]imidazol-6-yl)pyridin-2-yl)-5-(((cis)-5-methyl hexahydropyrrolo[3,4-c]pyrrol-2(1H)-yl)methyl)pyrimidin-2-amine

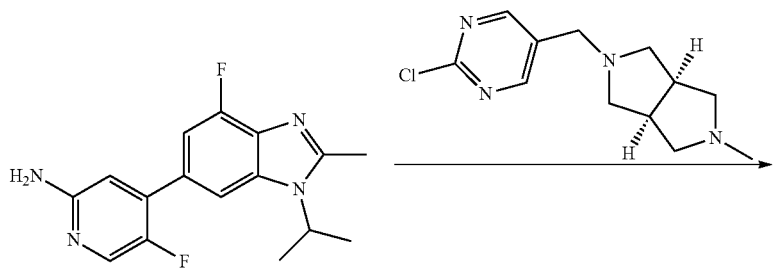

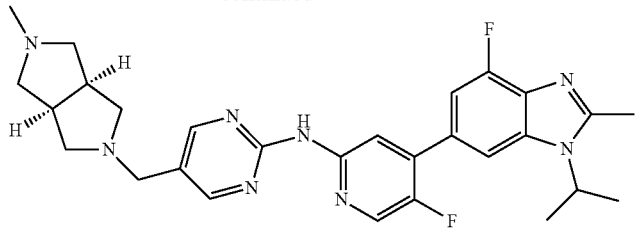

5-Fluoro-4-(4-fluoro-1-isopropyl-2-methyl-1H-benzo[d] imidazol-6-yl)pyridin-2-amine (302 mg, 1.0 mmol) and 2-((2-chloropyrimidin-5-yl)methyl)-5-methyl-(cis)-octahydropyrrolo[3,4-c] pyrrole (252 mg, 1.0 mmol) were dissolved in 1,4-dioxane (50 mL), and tris(dibenzylideneacetone)dipalladium (92 mg, 0.1 mmol), 2-dicyclohexylphosphino-2',4',6'-triisopropylbiphenyl (95 mg, 0.2 mmol) and cesium carbonate (975 mg, 3.0 mmol) were added. Under the protection of nitrogen, the mixture was heated to 110° C. and reacted for 8 h. The mixture was cooled to room temperature, and concentrated. Water (100 mL) and acetic ether (150 mL) were added to separate the organic phase from the water phase. The water phase was extracted with acetic ether (150 mL×2), and the organic phases were combined and washed with saturated NaCl solution, dried by anhydrous sodium sulfate, and concentrated. The crude product was purified by silica gel column chromatography (the eluent was dichloromethane:methanol=20:1) to get the title compound (207 mg, yield: 40%).

Molecular formula: $C_{28}H_{32}F_2N_8$ Molecular weight: 518.60 LC-MS (m/z): 519.3 (M+H$^+$)

$^1$H-NMR (400 MHz, CDCl$_3$) δ: 8.64 (d, J=6.0 Hz, 1H), 8.48-8.47 (m, 3H), 8.29 (d, J=2.4 Hz, 1H), 7.64 (t, J=1.2 Hz, 1H), 7.25 (d, J=9.6 Hz, 1H), 4.70-4.74 (m, 1H), 3.57 (s, 2H), 3.40 (brs, 2H), 3.07 (s, 2H), 2.64-2.69 (m, 10H), 2.40-2.48 (m, 2H), 1.69 (d, J=6.8 Hz, 6H).

Example 6-2: Preparation of 5-(((cis)-5-ethylhexahydropyrrolo[3,4-c]pyrrol-2(1H)-yl)methyl)-N-(5-fluoro-4-(4-fluoro-1-isopropyl-2-methyl-1H-benzo[d]imidazol-6-yl)pyridin-2-yl)pyrimidin-2-amine (Compound 6-2)

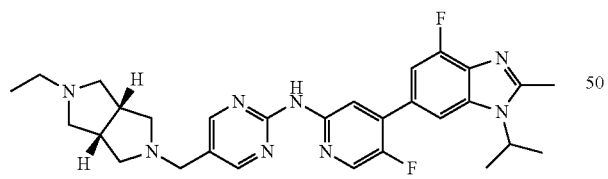

(1) Preparation of tert-butyl (cis)-5-ethylhexahydropyrrolo[3,4-c]pyrrol-2(1H)-carboxylate

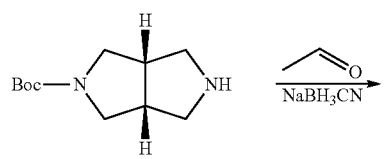

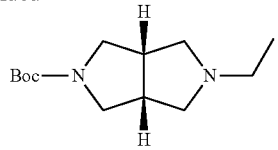

Tert-butyl (cis)-hexahydropyrrolo[3,4-c]pyrrol-2(1H)-carboxylate (424 mg, 2.0 mmol) was dissolved in methanol (10 mL), and aqueous acetaldehyde solution (40%, 2.2 mL, 20 mmol) was added dropwisely. The mixture was stirred at room temperature for 2 h. Sodium cyanoborohydride (1.26 g, 20 mmol) was added slowly. After the addition, the mixture was further stirred at room temperature for 30 min. The solvent was removed by evaporation under rotation, and the residue was separated by silica gel column chromatography (dichloromethane:methanol=10:1) to get the product (317 mg, yield: 66.0%).

(2) Preparation of (cis)-2-ethyloctahydropyrrolo[3,4-c]pyrrole

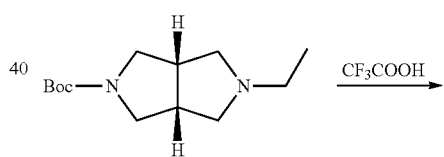

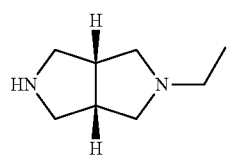

Tert-butyl (cis)-5-ethyl hexahydropyrrolo[3,4-c]pyrrol-2(1H)-carboxylate (317 mg, 1.32 mmol) was dissolved in a mixed solution of dichloromethane (3 mL) and trifluoroacetic acid (3 mL), and stirred at room temperature for 30 min. The solvent was removed by distillation under rotation. A small amount of dichloromethane was added, and the solvent was removed by distillation under rotation to get the crude product (181 mg). The product was used in the next step without purification.

(3) Preparation of (cis)-2-((2-chloropyrimidin-5-yl)methyl)-5-ethyloctahydropyrrolo[3,4-c] pyrrole

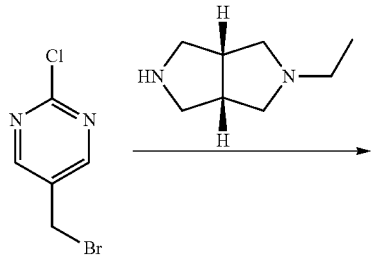

To acetonitrile (15 mL) were added (cis)-2-ethyl octahydropyrrolo[3,4-c]pyrrole (181 mg, 1.29 mmol), 5-(bromomethyl)-2-chloropyrimidine (267 mg, 1.29 mmol) and potassium carbonate (178 mg, 1.29 mmol), and the mixture was heated in an oil bath at 60° C. for 1 h. The solvent was removed by distillation under rotation, and the residue was separated by silica gel column chromatography (dichloromethane:methanol=10:1) to get the product (300 mg, yield: 87.0%).

(4) Preparation of 5-(((cis)-5-ethylhexahydropyrrolo[3,4-c]pyrrol-2(1H)-yl)methyl)-N-(5-fluoro-4-(4-fluoro-1-isopropyl-2-methyl-1H-benzo[d]imidazol-6-yl)pyridin-2-yl)pyrimidin-2-amine

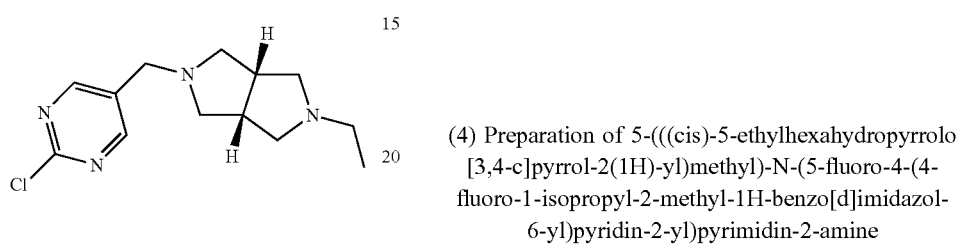

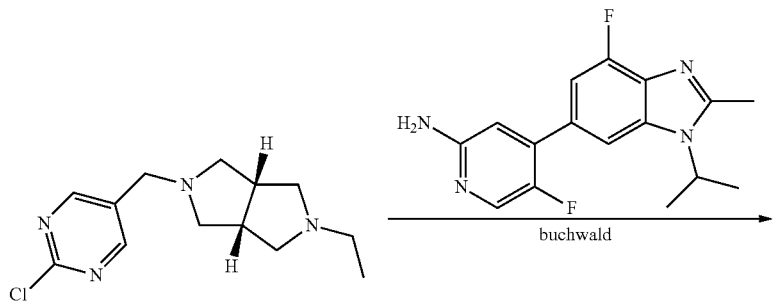

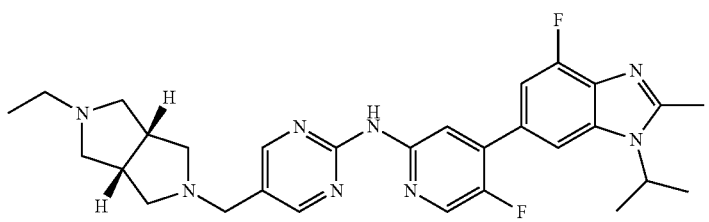 [SMILES: CCN1C[C@@H]2CN(Cc3cnc(Nc4cc(-c5cc(F)c6nc(C)n(C(C)C)c6c5)c(F)cn4)nc3)C[C@@H]2C1]

(cis)-2-((2-chloropyrimidin-5-yl)methyl)-5-ethyloctahydropyrrolo[3,4-c]pyrrole (300 mg, 1.12 mmol), 5-fluoro-4-(4-fluoro-1-isopropyl-2-methyl-1H-benzo[d]imidazol-6-yl)pyridin-2-amine (338 mg, 1.12 mmol), cesium carbonate (730 mg, 2.24 mmol), tris(dibenzylideneacetone)dipalladium (30 mg) and 2-dicyclohexylphosphino-2',4',6'-triisopropylbiphenyl(60 mg) were added to 1,4-dioxane (20 mL). Under the protection of nitrogen, the mixture was heated in an 110° C. oil bath for 8 h. The solvent was removed by distillation under rotation. Reversion phase column chromatography (water:methanol=10:1-1:1) was performed to get the title compound (176 mg, yield: 29.5%).

Molecular formula: $C_{29}H_{34}F_2N_8$ Molecular weight: 532.6
LC-MS (m/z): 533.3 (M+H$^+$)

$^1$H-NMR (400 MHz, CDCl$_3$) δ: 8.64 (d, J=5.6 Hz, 2H), 8.44 (s, 2H), 8.29 (d, J=2.0 Hz, 1H), 8.24 (s, 1H), 8.06 (s, 1H), 7.63 (s, 1H), 7.24-7.26 (m, 1H), 4.70-4.73 (m, 1H), 3.55 (s, 2H), 2.90-3.05 (m, 2H), 2.80-2.87 (m, 2H), 2.69 (s, 3H), 2.45-2.60 (m, 6H), 2.25-2.35 (m, 2H), 1.68 (d, J=8.4 Hz, 6H), 1.15-1.18 (m, 3H).

Example 7: Preparation of N-(5-fluoro-4-(4-fluoro-1-isopropyl-2-methyl-1H-benzo[d]imidazol-6-yl)pyridin-2-yl)-5-(((cis)-hexahydropyrrolo[3,4-b][1,4]oxazin-6(2H)-yl) methyl)pyrimidin-2-amine (Compound 7)

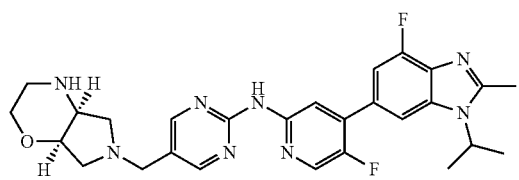 [SMILES: Cc1nc2c(F)cc(-c3cc(Nc4ncc(CN5C[C@@H]6NCCO[C@@H]6C5)cn4)ncc3F)cc2n1C(C)C]

(1) Preparation of 4-benzyl-6-tert-butyl (cis)-hexahydropyrrolo[3,4-b][1,4]oxazin-4,6-dicarboxylate

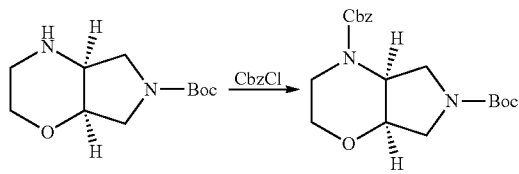 [SMILES: "CbzCl" ; CC(C)(C)OC(=O)N1C[C@@H]2NCCO[C@@H]2C1 ; CC(C)(C)OC(=O)N1C[C@H]2OCCN(C(=O)OCc3ccccc3)[C@H]2C1]

Tert-butyl (cis)-hexahydropyrrolo[3,4-b][1,4]oxazin-6(2H)-carboxylate (342 mg, 1.5 mmol) and N,N-diisopropylethylamine (581 mg, 4.5 mmol) were dissolved in dichloromethane (30 mL), and benzyl chloroformate (358 mg, 2.1 mmol) was added dropwisely under the condition of ice bath. After the addition, the reaction was carried out at room temperature for 4 h. Water (30 mL) was added to separate the organic phase from the water phase. The water phase was extracted with dichloromethane (50 mL×2). The organic phases were combined, washed with saturated NaCl solution, dried by anhydrous sodium sulfate and purified by silica gel column chromatography (the eluent was petroleum ether:acetic ether of 5:1) to get the title compound (473 mg, yield: 87%).

(2) Preparation of benzyl (cis)-hexahydropyrrolo[3,4-b][1,4]oxazin-4(4aH)-carboxylate

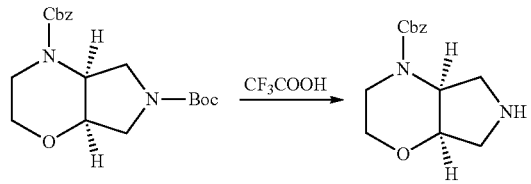 [SMILES: CC(C)(C)OC(=O)N1C[C@H]2OCCN(C(=O)OCc3ccccc3)[C@H]2C1 ; "CF3COOH" ; O=C(OCc1ccccc1)N1CCO[C@@H]2CNC[C@@H]21]

4-Benzyl-6-tert-butyl (cis)-hexahydropyrrolo[3,4-b][1,4]oxazin-4,6-dicarboxylate (473 mg, 1.3 mmol) was dissolved in dichloromethane (10 mL), and trifluoroacetic acid (5 mL) was added. The mixture was stirred at room temperature for 3 h. The solvent was removed by reduced pressure distillation to get the title compound (400 mg crude product), which was used directly in the next step without purification.

(3) Preparation of benzyl (cis)-6-((2-chloropyrimidin-5-yl)methyl)hexahydropyrrolo[3,4-b][1,4]oxazin-4(4aH)-carboxylate

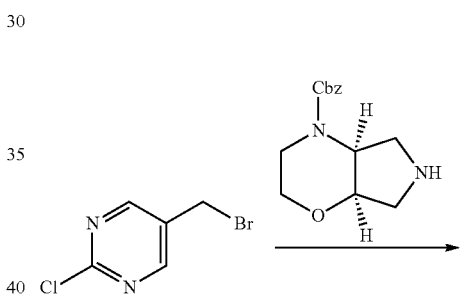

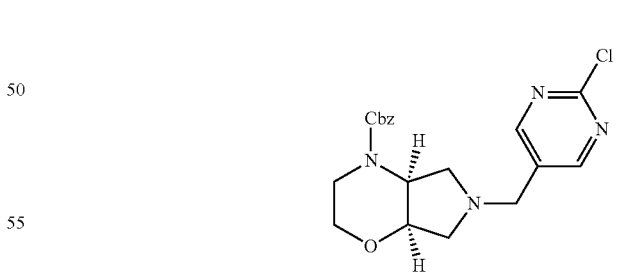

Benzyl (cis)-hexahydropyrrolo[3,4-b][1,4]oxazin-4(4aH)-carboxylate (400 mg, crude product) and 5-(bromomethyl)-2-chloropyrimidine (269 mg, 1.3 mmol) were dissolved in acetonitrile (50 mL), and potassium carbonate (538 mg, 3.9 mmol) was added. The reaction was carried out at room temperature for 8 h. The mixture was filtrated. The filtrate was concentrated, and purified by silica gel column chromatography (the eluent was dichloromethane:methanol=50:1) to get the title compound (409 mg, yield: 81%).

(4) Preparation of benzyl (cis)-6-((2-((5-fluoro-4-(4-fluoro-1-isopropyl-2-methyl-1H-benzo[d]imidazol-6-yl)pyridin-2-yl)amino)pyrimidin-5-yl)methyl)hexahydropyrrolo[3,4-b][1,4]oxazin-4(4aH)-carboxylate

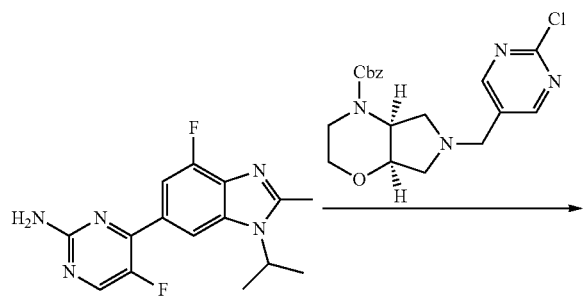

5-Fluoro-4-(4-fluoro-1-isopropyl-2-methyl-1H-benzo[d]imidazol-6-yl)pyridin-2-amine (302 mg, 1.0 mmol) and benzyl 6-((2-chloropyrimidin-5-yl)methyl)(cis)hexahydropyrrolo[3,4-b] [1,4]oxazin-4(4aH)-carboxylate (389 mg, 1.0 mmol) were dissolved in 1,4-dioxane (50 mL), and tris(dibenzylideneacetone)dipalladium (92 mg, 0.1 mmol), 2-dicyclohexylphosphino-2',4',6'-triisopropylbiphenyl(95 mg, 0.2 mmol) and cesium carbonate (975 mg, 3.0 mmol) were added. Under the protection of nitrogen, the mixture was heated to 110° C. and reacted for 8 h. The mixture was cooled to room temperature, and concentrated. Water (100 mL) and acetic ether (150 mL) were added to separate the organic phase from the water phase. The water phase was extracted with acetic ether (150 mL×2), and the organic phases were combined, washed with saturated NaCl solution, dried by anhydrous sodium sulfate, and concentrated. The crude product was purified by silica gel column chromatography (the eluent was dichloromethane:methanol=20:1) to get the title compound (288 mg, yield: 44%).

(5) Preparation of N-(5-fluoro-4-(4-fluoro-1-isopropyl-2-methyl-1H-benzo[d]imidazol-6-yl)pyridin-2-yl)-5-(((cis)-hexahydropyrrolo[3,4-b][1,4]oxazin-6(2H)-yl)methyl)pyrimidin-2-amine

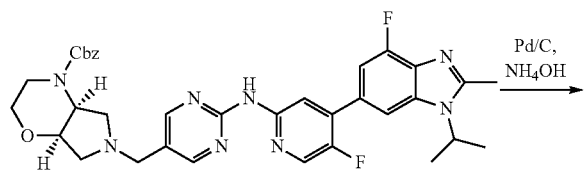

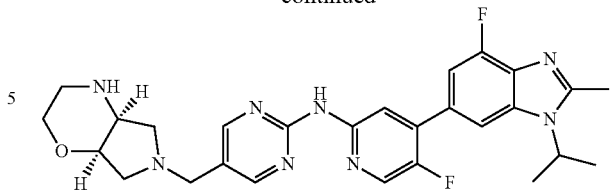

Benzyl 6-((2-((5-fluoro-4-(4-fluoro-1-isopropyl-2-methyl-1H-benzo[d]imidazol-6-yl)pyridin-2-yl)amino)pyrimidin-5-yl)methyl)(cis)hexahydropyrrolo[3,4-b][1,4]oxazin-4(4aH)-carboxylate (280 mg, 0.43 mmol) and palladium-carbon (30 mg) were suspended in methanol (40 mL) and ammonia water (6 mL). The system was vacuumed, and hydrogen was introduced. The reaction was carried out at room temperature for 16 h. The mixture was filtrated by celite, the filtrate was concentrated, and the crude product was purified by silica gel column chromatography (methanol:dichloromethane=1:20, with the addition of 0.2% triethylamine) to get the white solid title compound (178 mg, yield: 80%).

Molecular formula: $C_{27}H_{30}F_2N_8O$ Molecular weight: 520.6 LC-MS (m/z): 521.3 (M+H$^+$)

$^1$H-NMR (400 MHz, DMSO-d$_6$) δ: 10.02 (s, 1H), 8.44-8.42 (m, 3H), 8.35 (s, 1H), 7.75 (s, 1H), 7.23 (d, J=11.6 Hz, 1H), 4.79-4.83 (m, 1H), 3.79 (s, 1H), 3.16-3.60 (m, 6H), 3.15 (m, 1H), 2.91-2.95 (m, 1H), 2.80-2.85 (m, 1H), 2.73-2.69 (m, 1H), 2.54-2.65 (m, 5H), 1.57 (d, J=6.8 Hz, 6H).

Example 8: Preparation of (exo)-3-((2-((5-fluoro-4-(4-fluoro-1-isopropyl-2-methyl-1H-benzo[d]imidazol-6-yl)pyridin-2-yl)amino)pyrimidin-5-yl)methyl)-3-diazabicyclo[3.1.0]hexan-6-amine (Compound 8)

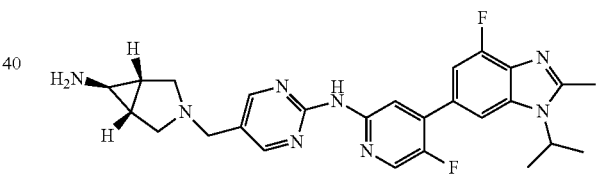

(1) Preparation of tert-butyl (exo)-6-((carbobenzoxy)amino)-3-azabicyclo[3.1.0]hexan-3-carboxylate

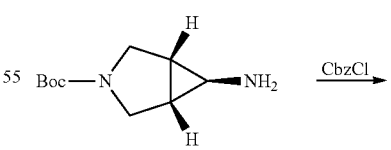

Tert-butyl (exo)-6-amino-3-azabicyclo[3.1.0]hexan-3-carboxylate (396 mg, 2.0 mmol) and N,N-diisopropylethylamine (774 mg, 6.0 mmol) were dissolved in dichloromethane (30 mL), and benzyl chloroformate (409 mg, 2.4 mmol) was added dropwisely under the condition of ice bath. After the addition, the reaction was carried out at room temperature for 4 h. The reaction solution was concentrated and purified by silica gel column chromatography (the eluent was petroleum ether:acetic ether=10:1) to get the title compound (578 mg, yield: 87%).

(2) Preparation of benzyl ((exo)-3-azabicyclo[3.1.0]hexan-6-yl)carbamate

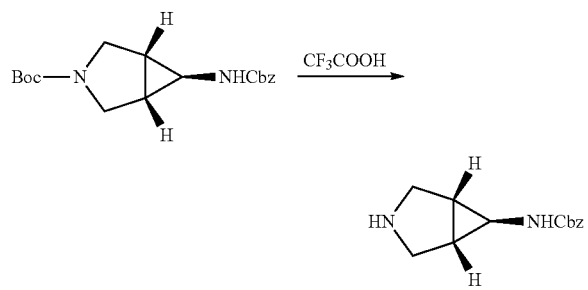

Tert-butyl (exo)-6-((carbobenzoxy)amino)-3-azabicyclo[3.1.0]hexan-3-carboxylate (578 mg, 1.74 mmol) was dissolved in dichloromethane (10 mL), and trifluoroacetic acid (5 mL) was added. The mixture was stirred at room temperature for 3 h. The solvent was removed by reduced pressure distillation to get the title compound (450 mg crude product), which was used directly in the next step without purification.

(3) Preparation of benzyl ((exo)-3-((2-chloropyrimidin-5-yl)methyl)-3-diazabicyclo[3.1.0] hexan-6-yl)carbamate

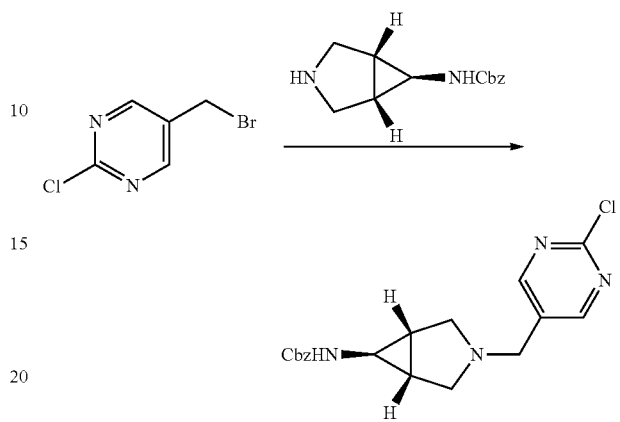

Benzyl ((exo)-3-azabicyclo[3.1.0]hexan-6-yl)carbamate (450 mg crude product) and 5-(bromomethyl)-2-chloropyrimidine (415 mg, 2.0 mmol) were dissolved in acetonitrile (50 mL), and potassium carbonate (828 mg, 6.0 mmol) was added. The reaction was carried out at room temperature for 4 h. The reaction solution was filtrated. The filtrated was concentrated and subjected to silica gel column chromatography (the eluent was dichloromethane:methanol=50:1) to get the title compound (487 mg, two step yield: 78%).

(4) Preparation of benzyl (exo)-3-((2-(5-fluoro-4-(4-fluoro-1-isopropyl-2-methyl-1H-benzo[d] imidazol-6-yl)pyridin-2-yl)amino)pyrimidin-5-yl)methyl)-3-diazabicyclo[3.1.0]hexan-6-carbamate

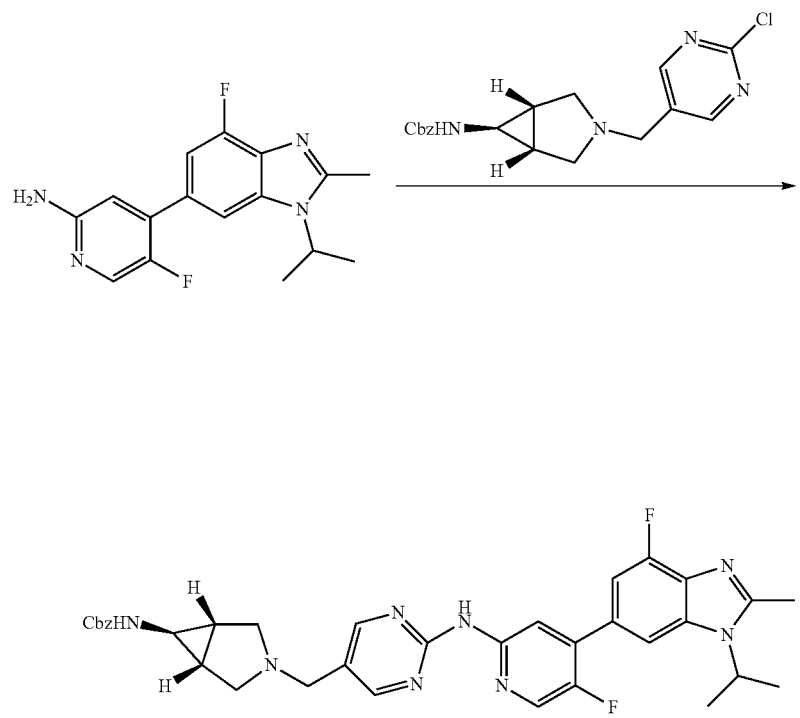

Benzyl ((exo)-3-((2-chloropyrimidin-5-yl)methyl)-3-diazabicyclo[3.1.0]hexan-6-yl)carbamate (480 mg, 1.34 mmol) and 5-fluoro-4-(4-fluoro-1-isopropyl-2-methyl-1H-benzo[d]imidazol-6-yl)pyridin-2-amine (405 mg, 1.34 mmol) were dissolved in 1,4-dioxane (50 mL), and tris(dibenzylideneacetone)dipalladium (119 mg, 0.13 mmol), 2-dicyclohexylphosphino-2',4',6'-triisopropylbiphenyl (124 mg, 0.26 mmol) and cesium carbonate (1.3 g, 4.02 mmol) were added. Under the protection of nitrogen, the mixture was heated to 110° C. and reacted for 8 h. The mixture was cooled to room temperature, and concentrated. Water (100 mL) and acetic ether (150 mL) were added to separate the organic phase from the water phase. The water phase was extracted with acetic ether (150 mL×2). The organic phases were combined, washed with saturated NaCl solution, dried by anhydrous sodium sulfate, and concentrated. The crude product was purified by silica gel column chromatography (the eluent was dichloromethane:methanol=20:1) to get the title compound (527 mg, yield: 63%).

(5) Preparation of (exo)-3-((2-(5-fluoro-4-(4-fluoro-1-isopropyl-2-methyl-1H-benzo[d] imidazol-6-yl)pyridin-2-yl)amino)pyrimidin-5-yl)methyl)-3-diazabicyclo[3.1.0]hexan-6-amine

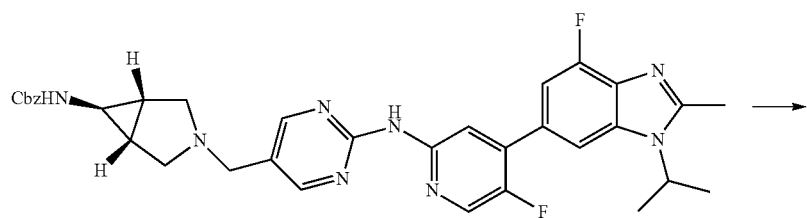

Benzyl (exo)-3-((2-((5-fluoro-4-(4-fluoro-1-isopropyl-2-methyl-1H-benzo[d]imidazol-6-yl) pyridin-2-yl)amino)pyrimidin-5-yl)methyl)-3-azabicyclo[3.1.0]hexan-6-yl)carbamate (500 mg, 0.80 mmol) and palladium-carbon (50 mg) were suspended in methanol (40 mL), and ammonia water (6 mL) was added dropwisely. The system was vacuumed, and hydrogen was introduced. After reacting at room temperature for 16 h, the reaction mixture was filtrated. The filtrate was concentrated, and purified by silica gel column chromatography (the eluent was dichloromethane:methanol=10:1) to get the title compound (192 mg, yield: 49%).

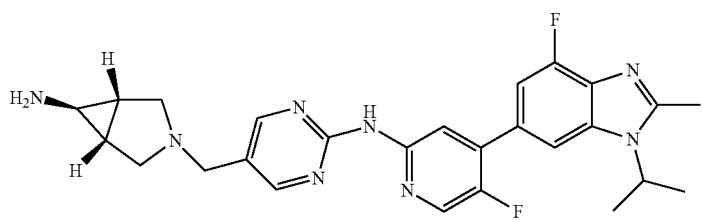

Molecular formula: $C_{26}H_{28}F_2N_8$ Molecular weight: 490.6
LC-MS (m/z): 491.3 (M+H$^+$)
$^1$H-NMR (400 MHz, DMSO-d$_6$) δ: 10.04 (s, 1H), 8.43 (d, J=6.0 Hz, 1H), 8.39 (s, 2H), 8.35 (d, J=2.0 Hz, 1H), 7.75 (s, 1H), 7.23 (d, J=11.6 Hz, 1H), 4.78-4.85 (m, 1H), 3.46 (s, 2H), 2.87 (d, J=8.8 Hz, 2H), 2.62 (s, 3H), 2.55 (s, 1H), 2.33 (d, J=8.4 Hz, 2H), 1.57-1.60 (m, 8H).

Example 9: Preparation of N-(5-fluoro-4-(4-fluoro-1-isopropyl-2-methyl-1H-benzo[d] imidazol-6-yl)pyridin-2-yl)-5-(((exo)-octahydro-6H-pyrido[3,4-b][1,4]oxazin-6-yl)methyl) pyrimidin-2-amine (Compound 9)

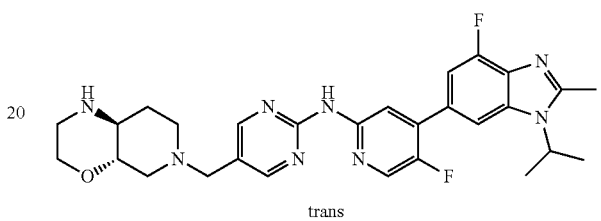

(1) Preparation of 1-benzyl 6-tert-butyl (trans)-hexahydro-1H-pyrido[3,4-b][1,4]oxazin-1,6(5H)-dicarboxylate

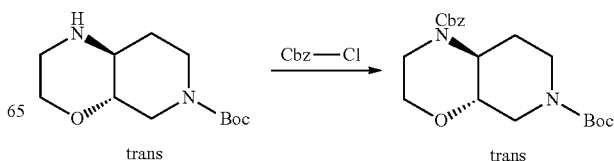

Tert-butyl (trans)-octahydro-6H-pyrido[3,4-b][1,4]oxazin-6-carboxylate (242 mg, 1.0 mmol) and triethylamine (120 mg, 1.2 mmol) were added to dichloromethane (5 mL). Benzyl chloroformate (188 mg, 1.1 mmol) was added dropwisely and slowly under the condition of ice bath. After the addition, the mixture was warmed up to room temperature and stirred for 30 min. The solvent was distilled under rotation to get the crude product (300 mg crude product), which was used in the next step without purification.

(2) Preparation of benzyl (trans)-octahydro-1H-pyrido[3,4-b][1,4]oxazin-1-carboxylate

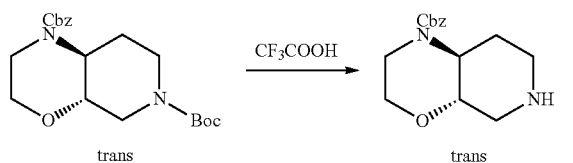 [SMILES: CC(C)(C)OC(=O)N1CC[C@H]2[C@H](C1)OCCN2C(=O)OCc1ccccc1 ; "CF3COOH" ; O=C(OCc1ccccc1)N1CCO[C@H]2CNCC[C@@H]21]

1-benzyl 6-tert-butyl (trans)-hexahydro-1H-pyrido[3,4-b][1,4]oxazin-1,6(5H)-dicarboxylate was dissolved in a mixed solution of dichloromethane (3 mL) and trifluoroacetic acid (3 mL). The mixture was stirred at room temperature for 30 min. The solvent was distilled under rotation, and a small amount of dichloromethane was added. The solvent was distilled under rotation again to get the crude product (260 mg), which was used in the next step without purification.

(3) Preparation of benzyl (trans)-6-((2-chloropyrimidin-5-yl)methyl)octahydro-1H-pyrido[3,4-b][1,4]oxazin-1-carboxylate

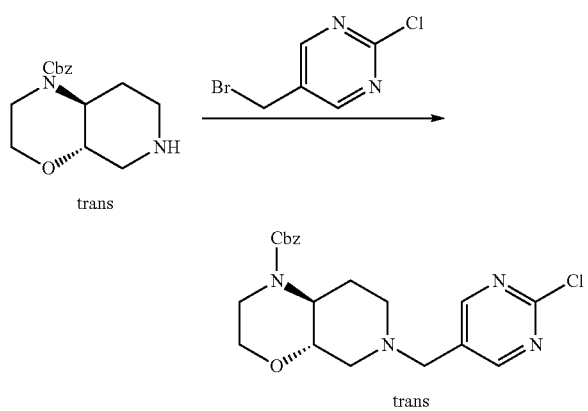

Benzyl (trans)-octahydro-1H-pyrido[3,4-b][1,4]oxazin-1-carboxylate (260 mg, 0.94 mmol), 5-(bromomethyl)-2-chloropyrimidine (393 mg, 1.9 mmol) and potassium carbonate (786 mg, 5.7 mmol) were added to acetonitrile (15 mL), and the mixture was heated in an oil bath at 60° C. for 1 h. The solution was distilled under rotation, and was separated by preparative chromatography (the eluent was water:acetonitrile=10:1-1:1) to get the product (300 mg, three-step yield: 75%).

(4) Preparation of benzyl (trans)-6-((2-((5-fluoro-4-(4-fluoro-1-isopropyl-2-methyl-1H-benzo[d]imidazol-6-yl)pyridin-2-yl)amino)pyrimidin-5-yl)methyl)octahydro-1H-pyrido[3,4-b][1,4]oxazin-1-carboxylate

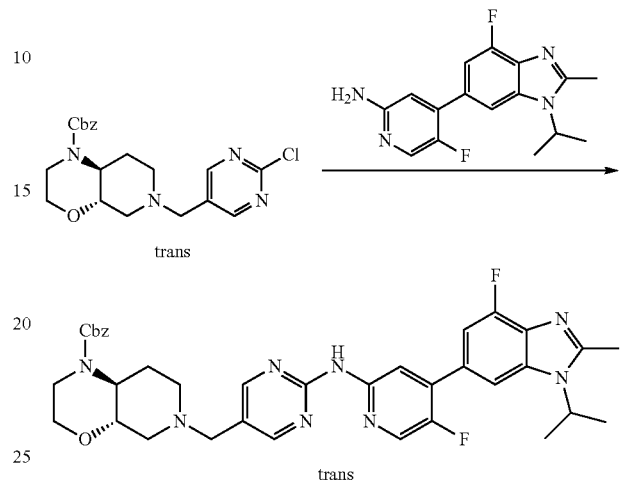

Benzyl (trans)-6-((2-chloropyrimidin-5-yl)methyl)octahydro-1H-pyrido[3,4-b][1,4]oxazin-1-carboxylate (300 mg, 0.75 mmol), 5-fluoro-4-(4-fluoro-1-isopropyl-2-methyl-1H-benzo[d]imidazol-6-yl)pyridin-2-amine (449 mg, 1.5 mmol), potassium carbonate (317 mg, 2.3 mmol), tris(dibenzylideneacetone)dipalladium (30 mg), and 2-dicyclohexylphosphino-2',4',6'-triisopropylbiphenyl (60 mg, 0.13 mmol) were added to 20 mL 1,4-dioxane. Under the protection of nitrogen, the mixture was heated in an 110° C. oil bath for 8 h, and the solvent was removed by distillation under rotation. The residue was purified by preparative chromatography (the eluent was water:acetonitrile of 10:1-1:1) to get the title compound (113 mg, yield: 23%).

(5) Preparation of N-(5-fluoro-4-(4-fluoro-1-isopropyl-2-methyl-1H-benzo[d]imidazol-6-yl)pyridin-2-yl)-5-(((trans)-octahydro-6H-pyrido[3,4-b][1,4]oxazin-6-yl)methyl)pyrimidin-2-amine

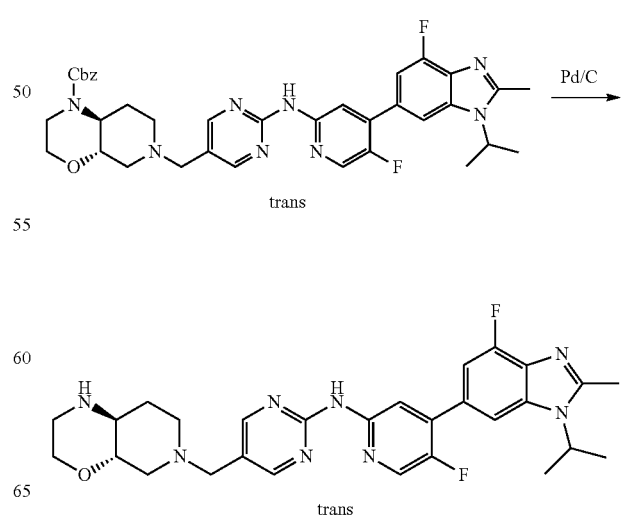

Benzyl (trans)-6-((2-((5-fluoro-4-(4-fluoro-1-isopropyl-2-methyl-1H-benzo[d]imidazol-6-yl) pyridin-2-yl)amino)pyrimidin-5-yl)methyl)octahydro-1H-pyrido[3,4-b][1,4]oxazin-1-carboxylate (113 mg, 0.17 mmol) was dissolved in methanol (5 mL) and ammonia water (0.50 mL). Palladium-carbon catalyst (30 mg) was added, and hydrogen was introduced to carry out the reduction reaction for 2 h. The mixture was filtrated under suction, and the solution was distilled under rotation. The residue was separated by preparative chromatography (the eluent was water:acetonitrile=10:1-1:1) to get the product (30 mg, yield: 33%).

Molecular formula: $C_{28}H_{32}F_2N_8O$ Molecular weight: 534.6 LC-MS (m/z): 535.3 (M+H$^+$)

$^1$H-NMR (400 MHz, CDCl$_3$) δ: 8.63-8.66 (m, 2H), 8.44 (s, 2H), 8.29 (d, J=2.0 Hz, 1H), 7.62 (s, 1H), 7.26 (d, J=8.0 Hz, 1H), 4.70-4.73 (m, 1H), 3.84 (dd, J$_1$=2.8 Hz, J$_2$=11.2 Hz, 1H), 3.62-3.63 (m, 1H), 3.47-3.48 (m, 2H), 3.20-3.21 (m, 1H), 2.86-3.02 (m, 4H), 2.68 (s, 3H), 2.35-2.40 (m, 1H), 2.11-2.12 (m, 1H), 1.94-2.01 (m, 1H), 1.68 (d, J=10.8 Hz, 6H), 1.66-1.63 (m, 1H), 1.55-1.45 (m, 1H).

Example 10: Preparation of 5-((4-(8-oxa-3-diazabicyclo[3.2.1]octan-3-yl)piperidin-1-yl) methyl)-N-(5-fluoro-4-(4-fluoro-1-isopropyl-2-methyl-1H-benzo[d]imidazol-6-yl)pyridin-2-yl)pyrimidin-2-amine (Compound 10)

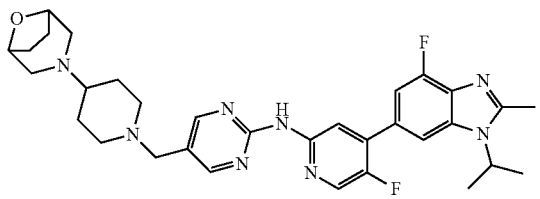 [SMILES: Cc1nc2c(F)cc(-c3cc(Nc4ncc(CN5CCC(N6CC7CCC(C6)O7)CC5)cn4)ncc3F)cc2n1C(C)C]

(1) Preparation of 1-((2-chloropyrimidin-5-yl)methyl)piperidin-4-ol

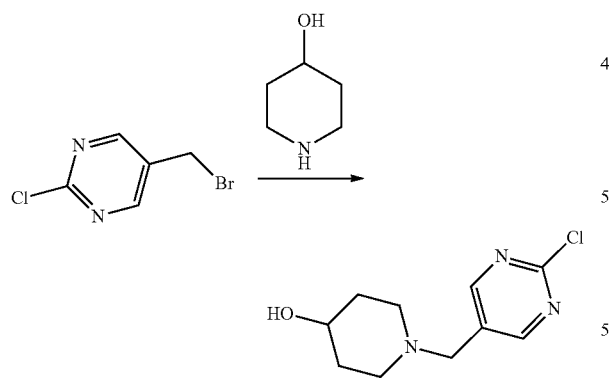

4-Hydroxypiperidine (202 mg, 2 mmol) and 5-(bromomethyl)-2-chloropyrimidine (414 mg, 2.0 mmol) were dissolved in acetonitrile (50 mL), and potassium carbonate (828 mg, 6.0 mmol) was added. The mixture was reacted at room temperature for 4 h. The mixture was filtrated, and the solvent was removed by distillation. The product was purified by silica gel column chromatography (the eluent was dichloromethane:methanol=50:1) to get the title compound (378 mg, yield: 83%).

(2) Preparation of 1-((2-((5-fluoro-4-(4-fluoro-1-isopropyl-2-methyl-1H-benzo[d]imidazol-6-yl)pyridin-2-yl)amino)pyrimidin-5-yl)methyl)piperidin-4-ol

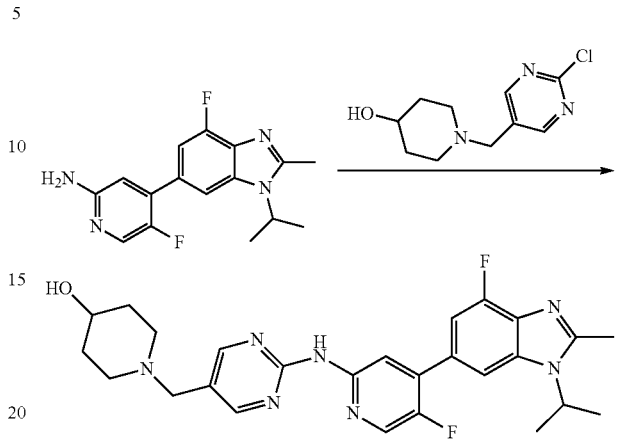

1-((2-Chloropyrimidin-5-yl)methyl)piperidin-4-ol (342 mg, 1.5 mmol) and 5-fluoro-4-(4-fluoro-1-isopropyl-2-methyl-1H-benzo[d]imidazol-6-yl)pyridin-2-amine (453 mg, 1.5 mmol) were dissolved in 1,4-dioxane (50 mL), and tris(dibenzylideneacetone)dipalladium (137 mg, 0.15 mmol), 2-dicyclohexylphosphino-2',4',6'-triisopropylbiphenyl (143 mg, 0.3 mmol) and cesium carbonate (1.47 g, 4.5 mmol) were added. Under the protection of nitrogen, the mixture was heated to 110° C. and reacted for 8 h. The mixture was cooled to room temperature, and concentrated. Water (100 mL) and acetic ether (150 mL) were added to separate the organic phase from the water phase. The water phase was extracted with acetic ether (150 mL×2). The organic phases were combined, washed with saturated NaCl solution, dried by anhydrous sodium sulfate, and concentrated. The crude product was purified by silica gel column chromatography (the eluent was dichloromethane:methanol=20:1) to get the title compound (489 mg, yield: 66%).

(3) Preparation of 1-((2-((5-fluoro-4-(4-fluoro-1-isopropyl-2-methyl-1H-benzo[d]imidazol-6-yl)pyridin-2-yl)amino)pyrimidin-5-yl)methyl)piperidin-4-one

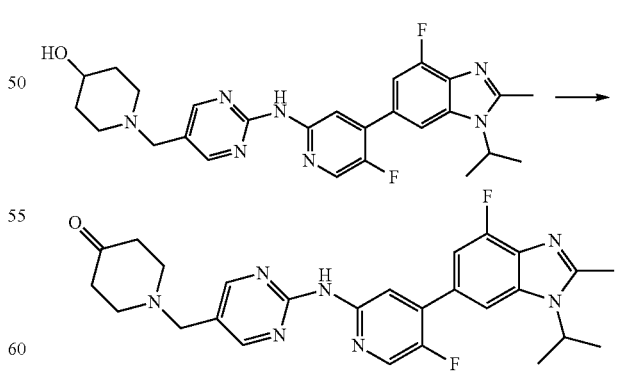

1-((2-((5-Fluoro-4-(4-fluoro-1-isopropyl-2-methyl-1H-benzo[d]imidazol-6-yl)pyridin-2-yl)amino)pyrimidin-5-yl)methyl)piperidin-4-ol (450 mg, 0.91 mmol) was dissolved in DMSO (6 mL) and triethylamine (4 mL), and pyridine sulfur trioxide (723 mg, 4.55 mmol) was added under stirring.

After the addition, the reaction was carried out under stirring at room temperature for 2 h. Water (100 mL) was added. The water phase was extracted with acetic ether (50 mL×3). The organic phases were combined, washed with saturated NaCl solution, dried by anhydrous sodium sulfate, and concentrated. The crude product was purified by silica gel column chromatography (the eluent was dichloromethane:methanol=20:1) to get the title compound (363 mg, yield: 81%).

(4) Preparation of 5((4-(8-oxa-3-azabicyclo[3.2.1]octan-3-yl)piperidin-1-yl)methyl)-N-(5-fluoro-4-(4-fluoro-1-isopropyl-2-methyl-1H-benzo[d]imidazol-6-yl)pyridin-2-yl)pyrimidin-2-amine to silica gel column chromatography (dichloromethane:methanol=10:1) to get the title compound (133 mg, yield: 37%).

Molecular formula: $C_{32}H_{38}F_2N_8O$ Molecular weight: 588.7 LC-MS (m/z): 589.4 (M+H$^+$)

$^1$H-NMR (400 MHz, DMSO-d$_6$) δ: 10.01 (s, 1H), 8.43-8.42 (m, 3H), 8.35 (d, J=2.0 Hz, 1H), 7.75 (s, 1H), 7.23 (d, J=11.6 Hz, 1H), 4.79-4.83 (m, 1H), 4.10-4.17 (m, 2H), 3.44-3.49 (m, 2H), 2.81-2.87 (m, 2H), 2.65 (s, 3H), 2.22-2.24 (m, 2H), 1.99-2.06 (m, 3H), 1.74-1.76 (m, 2H), 1.67-1.73 (m, 5H), 1.56-1.58 (m, 6H), 1.36-1.38 (m, 2H).

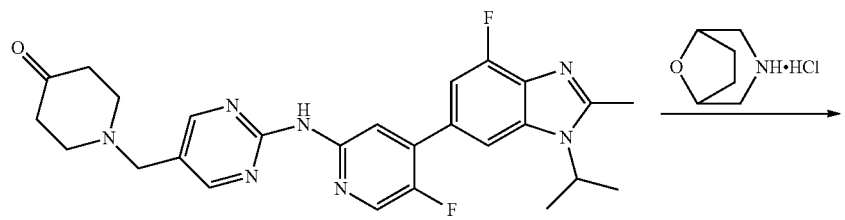

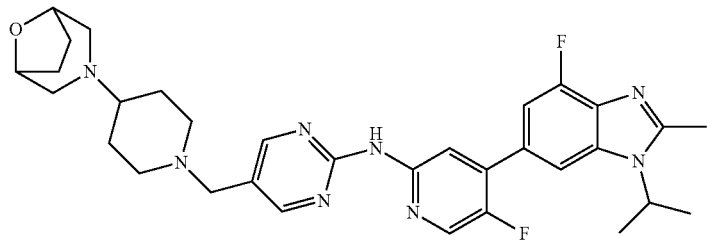

1-((2-((5-Fluoro-4-(4-fluoro-1-isopropyl-2-methyl-1H-benzo[d]imidazol-6-yl)pyridin-2-yl)amino)pyrimidin-5-yl)methyl)piperidin-4-one (300 mg, 0.61 mmol) and 8-oxa-3-azabicyclo[3.2.1]octane hydrochloride (91.3 mg, 0.61 mmol) were dissolved in DMF (5 mL), and Indium trichloride (270 mg, 1.22 mmol) was added. The mixture was stirred at room temperature for 12 h. Sodium cyanoborohydride (77 mg, 1.22 mmol) was added, and the mixture was further stirred at room temperature for 2 h. Water (20 mL) and acetic ether (20 mL×5) were added for extraction. The organic phases were combined, concentrated and dried by anhydrous sodium sulfate. The crude product was subjected Example 11: Preparation of N-(5-fluoro-4-(4-fluoro-1-isopropyl-2-methyl-1H-benzo[d] imidazol-6-yl)pyridin-2-yl)-5-((8-morpholino-3-azabicyclo[3.2.1]octan-3-yl)methyl)pyrimidin-2-amine (Compound 11)

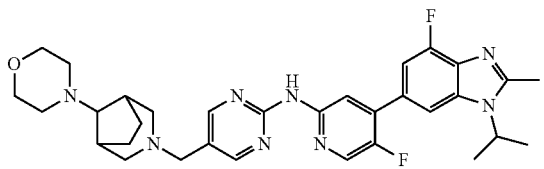 [SMILES: Cc1nc2c(F)cc(-c3cc(Nc4ncc(CN5CC6CCC(C5)C6N5CCOCC5)cn4)ncc3F)cc2n1C(C)C]

(1) Preparation of tert-butyl 8-morpholino-3-azabicyclo[3.2.1]octan-3-carboxylate

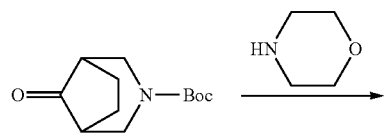

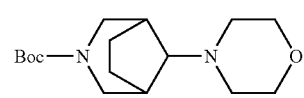

Tert-butyl 8-oxo-3-azabicyclo[3.2.1]octan-3-carboxylate (226 mg, 1.0 mmol) and morpholine (870 mg, 10 mmol) were dissolved in tetrahydrofuran (5 mL). A catalytic amount of acetic acid (20 mg) was added. The mixture was stirred at room temperature for 30 min. Sodium cyanoborohydride (95 mg, 1.5 mmol) was added, and the mixture was stirred at room temperature for 2 h. Acetic ether (100 mL) was added. The mixture was washed. The organic phase was dried, and distilled under rotation to get the crude product (300 mg), which was used in the next step without purification.

(2) Preparation of 4-(3-((2-chloropyrimidin-5-yl)methyl)-3-azabicyclo[3.2.1]octan-8-yl) morpholine

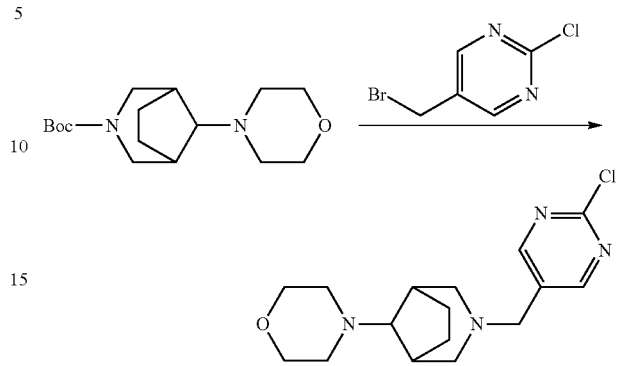

Tert-butyl 8-morpholino-3-azabicyclo[3.2.1]octan-3-carboxylate (300 mg, 1.0 mmol) was dissolved in a mixed solution of dichloromethane (5 mL) and trifluoroacetic acid (5 mL). The mixture was stirred at room temperature for 30 min. The solvent was distilled under rotation. Potassium carbonate (276 mg, 2.0 mmol), 5-bromomethyl-2-chloropyrimidine (310 mg, 1.5 mmol), and acetonitrile (10 mL) were added. The mixture was heated in a 60° C. oil bath for 1 h. The solvent was removed by distillation under rotation, and the residue was separated by silica gel column chromatography (dichloromethane:methanol=20:1) to get the product (236 mg, two-step yield: 73%).

(3) Preparation of N-(5-fluoro-4-(4-fluoro-1-isopropyl-2-methyl-1H-benzo[d]imidazol-6-yl) pyridin-2-yl)-5-((8-morpholino-3-azabicyclo[3.2.1]octan-3-yl)methyl)pyrimidin-2-amine

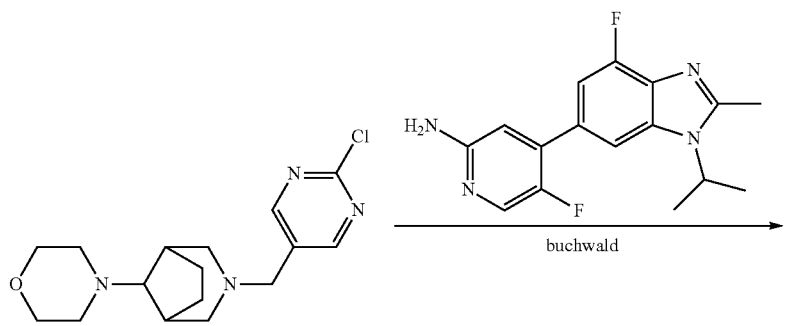

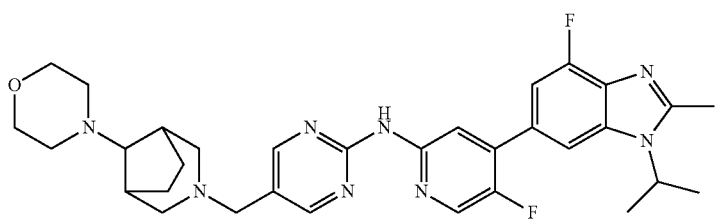

4-(3-((2-chloropyrimidin-5-yl)methyl)-3-azabicyclo [3.2.1]octan-8-yl)morpholine (236 mg, 0.73 mmol), 5-fluoro-4-(4-fluoro-1-isopropyl-2-methyl-1H-benzo[d] imidazol-6-yl)pyridin-2-amine (332 mg, 1.1 mmol), potassium carbonate (202 mg, 1.5 mmol), tris(dibenzylideneacetone)dipalladium (24 mg), and 2-dicyclohexylphosphino-2',4',6'-triisopropylbiphenyl (48 mg) were added to 1,4-dioxane (10 mL). Under the protection of nitrogen, the mixture was heated in an 110° C. oil bath for 8 h. The solvent was distilled under rotation, and the residue was separated by preparative chromatography (the eluent was water:acetonitrile=10:1-1:1) to get the product (41 mg, yield: 10%).

Molecular formula: $C_{32}H_{38}F_2N_8O$ Molecular weight: 588.7 LC-MS (m/z): 589.3 (M+H$^+$)

$^1$H-NMR (400 MHz, CDCl$_3$) δ: 8.66 (d, J=6.0 Hz, 1H), 8.36-8.52 (m, 3H), 8.28 (s, 1H), 7.64 (s, 1H), 7.27 (d, J=8.0 Hz, 1H), 4.70-4.74 (m, 1H), 3.71 (s, 4H), 2.69 (s, 5H), 2.34-2.42 (m, 6H), 2.10-2.15 (m, 3H), 1.68-1.79 (m, 8H), 1.05-1.30 (m, 4H).

Example 12: Preparation of N-(5-fluoro-4-(4-fluoro-1-isopropyl-2-methyl-1H-benzo[d] imidazol-6-yl)pyridin-2-yl)-5-((3-morpholino-8-azabicyclo [3.2.1]octan-8-yl)methyl)pyrimidin-2-amine (Compound 12)

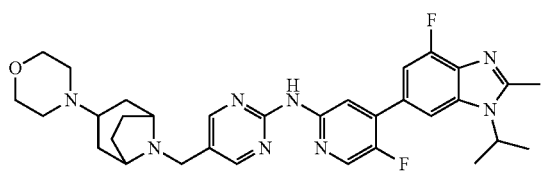 [SMILES: Cc1nc2c(F)cc(-c3cc(Nc4ncc(CN5C6CCC5CC(N5CCOCC5)C6)cn4)ncc3F)cc2n1C(C)C]

(1) Preparation of 8-((2-chloropyrimidin-5-yl) methyl)-8-diazaspiro[3.2.1]octan-3-one

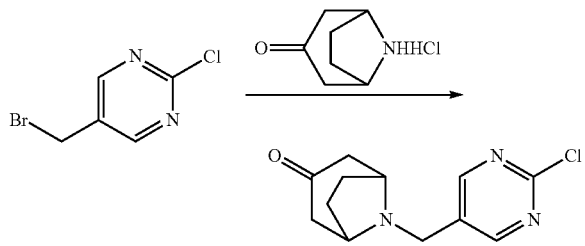

To 20 mL acetonitrile were added 5-bromomethyl-2-chloropyrimidine (621 mg, 3.0 mmol), 3-oxo-8-azabicyclo [3.2.1]octane hydrochloride (324 mg, 2.0 mmol) and potassium carbonate (552 mg, 4.0 mmol). The mixture was heated to reflux for 1 h. The solvent was distilled under rotation, and the residue was separated by silica gel column chromatography (petroleum ether: acetic ether=5:1) to get the product (387 mg, yield: 77%).

(2) Preparation of 8-((2-((5-fluoro-4-(4-fluoro-1-isopropyl-2-methyl-1H-benzo[d]imidazol-6-yl)pyridin-2-yl)amino)pyrimidin-5-yl)methyl)-8-azabicyclo [3.2.1]octan-3-one

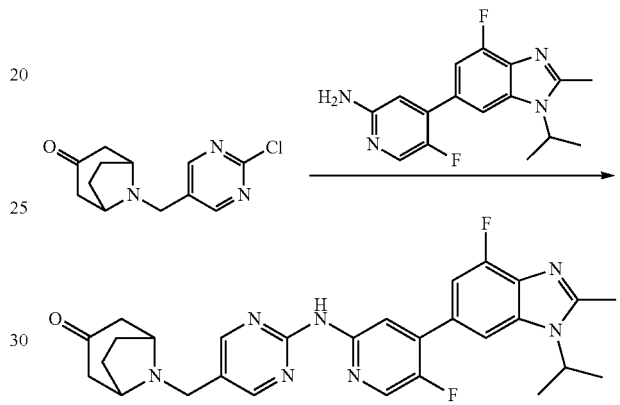

8-((2-chloropyrimidin-5-yl)methyl)-8-azabicyclo[3.2.1] octan-3-one (387 mg, 1.54 mmol), 5-fluoro-4-(4-fluoro-1-isopropyl-2-methyl-1H-benzo[d]imidazol-6-yl)pyridin-2-amine (930 mg, 3.08 mmol), potassium carbonate (638 mg, 4.62 mmol), tris(dibenzylideneacetone)dipalladium (39 mg), and 2-dicyclohexylphosphino-2',4',6'-triisopropylbiphenyl(78 mg) were added to 1,4-dioxane (20 mL). Under the protection of nitrogen, the mixture was heated in an 110° C. oil bath for 8 h. The solvent was distilled under rotation, and the residue was separated by preparative chromatography (the eluent was water:acetonitrile=10:1-1:1) to get the title compound (133 mg, yield: 17%).

(3) Preparation of N-(5-fluoro-4-(4-fluoro-1-isopropyl-2-methyl-1H-benzo[d]imidazol-6-yl) pyridin-2-yl)-5-((3-morpholino-8-azabicyclo[3.2.1]octan-8-yl) methyl)pyrimidin-2-amine

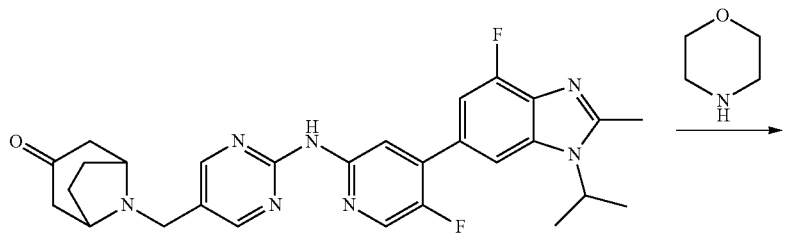

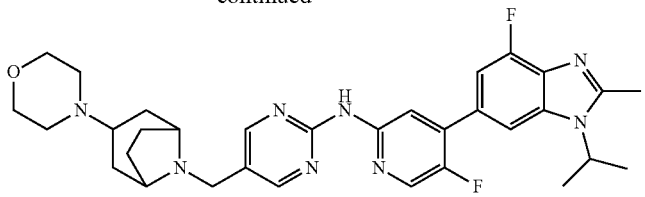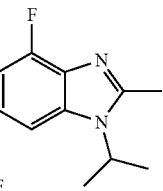

8-((2-((5-Fluoro-(4-fluoro-1-isopropyl-2-methyl-1H-benzo[d] imidazol-6-yl)pyridin-2-yl)amino)pyrimidin-5-yl)methyl)-8-azabicyclo[3.2.1]octan-3-one (133 mg, 0.257 mmol) was dissolved in a mixed solvent of tetrahydrofuran (1 mL) and methanol (1 mL), and morpholine (223 mg, 2.57 mmol) and acetic acid (20 mg) were added. The mixture was stirred at room temperature for 3 h. Sodium cyanoborohydride (25 mg, 0.386 mmol) was added, and the mixture was stirred at room temperature for 1 h. Acetic ether (20 mL) was added to separate the organic phase from the water phase. The organic phase was washed with saturated NaCl water, dried, distilled under rotation, and subjected to preparative chromatography (the eluent was water:acetonitrile=10:1-1:1) to separate the product (40 mg, yield: 33%).

Molecular formula: $C_{32}H_{38}F_2N_8O$ Molecular weight: 588.7 LC-MS (m/z): 589.3 (M+H$^+$)

$^1$H-NMR (400 MHz, CDCl$_3$) δ: 9.48 (brs., 1H), 8.67 (d, J=6.0 Hz, 1H), 8.62 (s, 2H), 8.38 (d, J=2.4 Hz, 1H), 7.62 (s, 1H), 7.25 (d, J=13.2 Hz, 1H), 4.67-4.74 (m, 1H), 3.72 (s, 4H), 3.60 (s, 2H), 3.36 (s, 2H), 2.66 (s, 3H), 2.55 (brs, 5H), 2.05-2.07 (m, 2H), 1.84-1.82 (m, 2H), 1.67-1.68 (m, 10H).

Example 13: Preparation of 5-((3-ethyl-3,8-diazabicyclo[3.2.1]octan-8-yl)methyl)-N-(5-fluoro-4-(4-fluoro-1-isopropyl-2-methyl-1H-benzo[d]imidazol-6-yl)pyridin-2-yl)pyrimidin-2-amine (Compound 13)

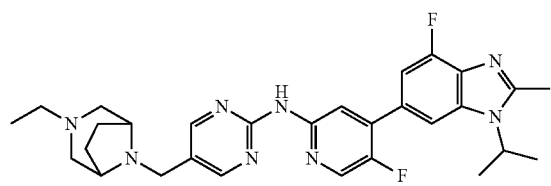 [SMILES: CCN1CC2CCC(C1)N2Cc1cnc(Nc2cc(-c3cc(F)c4nc(C)n(C(C)C)c4c3)c(F)cn2)nc1]

(1) Preparation of tert-butyl 8-((2-chloropyrimidin-5-yl)methyl)-3,8-diazabicyclo[3.2.1]octan-3-carboxylate

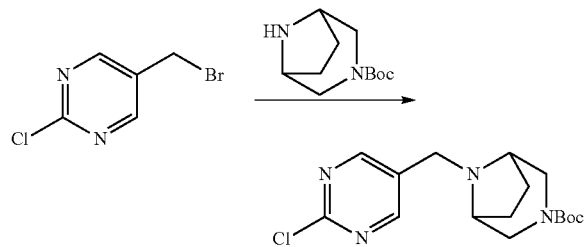

5-(Bromomethyl)-2-chloropyrimidine (412 mg, 2 mmol) was dissolved in tetrahydrofuran (30 mL), and triethylamine (606 mg, 6 mmol) and tert-butyl 3,8-diazabicyclo[3.2.1]octan-3-carboxylate (509 mg, 2.4 mmol) were added under stirring. The reaction was carried out under stirring at room temperature for 4 h. After the raw material disappeared as detected by TLC, the resultant mixture was filtrated under suction, and the filtrate was concentrated. The crude product was purified by silica gel column chromatography (petroleum ether:acetic ether=1:1) to get the title compound (600 mg, yield: 88.8%).

(2) Preparation of 8-((2-chloropyrimidin-5-yl)methyl)-3,8-diazabicyclo[3.2.1]octane

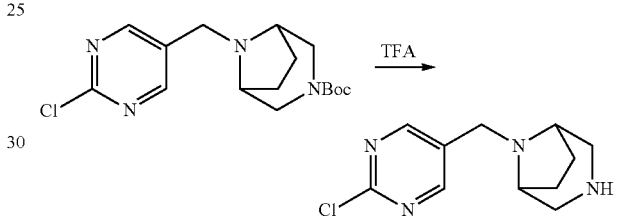

Tert-butyl 8-((2-chloropyrimidin-5-yl)methyl)-3,8-diazabicyclo[3.2.1]octan-3-carboxylate (600 mg, 1.78 mmol) was dissolved in dichloromethane (10 mL), and trifluoroacetic acid (5 mL) was added under stirring. The mixture was stirred at room temperature for 4 h. After the raw material disappeared as detected by TLC, the mixture was filtrated under suction. The filtrate was concentrated and then the crude product was subjected to silica gel column chromatography (dichloromethane:methanol=30:1) to get the title compound (400 mg, yield: 94.6%).

(3) Preparation of 8-((2-chloropyrimidin-5-yl)methyl)-3-ethyl-3,8-diazabicyclo[3.2.1]octane

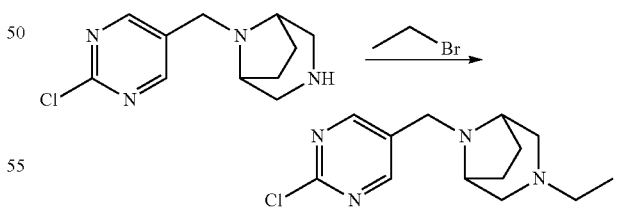

8-((2-Chloropyrimidin-5-yl)methyl)-3,8-diazabicyclo[3.2.1]octane (400 mg, 1.68 mmol) was dissolved in acetonitrile (20 mL), and ethyl bromide (363 mg, 3.36 mmol) and potassium carbonate (695.5 mg, 5.04 mmol) were added under stirring. The mixture was stirred at 40° C. overnight. After the raw material disappeared as detected by TLC, the mixture was filtrated under suction. The filtrate was concentrated and then subjected to silica gel column chromatography (dichloromethane:methanol=20:1) to get the title compound (380 mg, yield: 85.2%).

(4) Preparation of 5-((3-ethyl-3,8-diazabicyclo[3.2.1]octan-8-yl)methyl)-N-(5-fluoro-4-(4-fluoro-1-isopropyl-2-methyl-1H-benzo[d]imidazol-6-yl)pyridin-2-yl)pyrimidin-2-amine

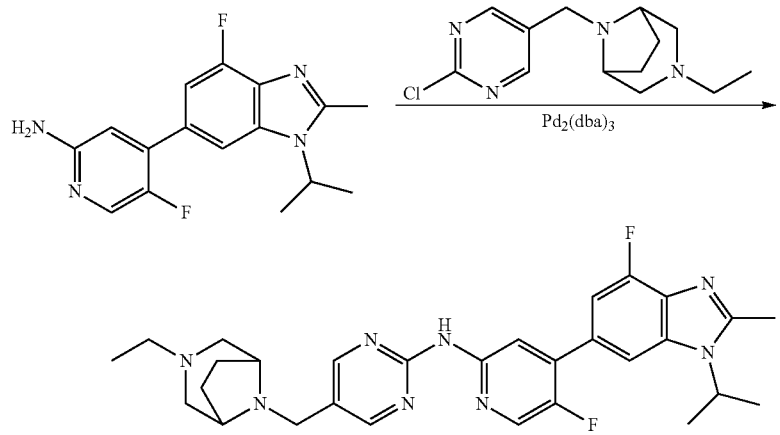

5-fluoro-4-(4-fluoro-1-isopropyl-2-methyl-1H-benzo[d]imidazol-6-yl)pyridin-2-amine (200 mg, 0.66 mmol), 8-((2-chloropyrimidin-5-yl)methyl)-3-ethyl-3,8-diazabicyclo[3.2.1]octane (175.6 mg, 0.66 mmol), 2-dicyclohexylphosphino-2',4',6'-triisopropylbiphenyl (63 mg, 0.13 mmol), cesium carbonate (643.5 mg, 1.98 mmol) and tris(dibenzylideneacetone)dipalladium (60 mg, 0.066 mmol) were added in an eggplant-shaped bottle, and 1,4-dioxane (20 mL) was added. Under the protection of nitrogen, the reaction was carried out at 110° C. for 4 h. The reaction mixture was filtrated under suction. The filtrate was subjected to silica gel column chromatography (dichloromethane:methanol=15:1) to get the title compound (100 mg, yield: 28.5%).

Molecular formula: $C_{29}H_{34}F_2N_8$ Molecular weight: 532.3 LC-MS (m/z): 533.3 (M+H$^+$)

$^1$H-NMR (400 MHz, MeOD-d$_4$) δ: 8.54-8.58 (m, 3H), 8.27 (d, J=2.0 Hz, 1H), 7.80 (s, 1H), 7.26 (d, J=11.6 Hz, 1H), 4.84-4.88 (m, 1H), 3.37-3.60 (m, 3H), 3.00-3.21 (m, 4H), 2.69 (s, 3H), 2.25-2.35 (m, 2H), 1.85-2.05 (m, 2H), 1.67-1.71 (m, 6H), 1.22-1.35 (m, 2H), 1.16-1.20 (m, 4H).

Example 14: Preparation of 5-((8-ethyl-3,8-diazabicyclo[3.2.1]octan-3-yl)methyl)-N-(5-fluoro-4-(4-fluoro-1-isopropyl-2-methyl-1H-benzo[d]imidazol-6-yl)pyridin-2-yl)pyrimidin-2-amine (Compound 14)

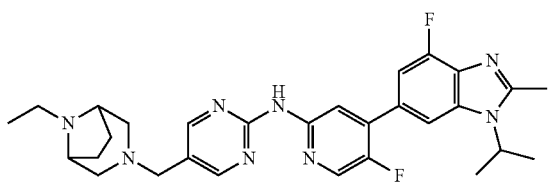 [SMILES: CCN1C2CCC1CN(Cc1cnc(Nc3cc(-c4cc(F)c5nc(C)n(C(C)C)c5c4)c(F)cn3)nc1)C2]

(1) Preparation of tert-butyl 8-ethyl-3,8-diazabicyclo[3.2.1]octan-3-carboxylate

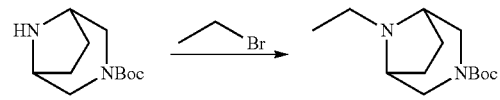

Tert-butyl 3,8-diazabicyclo[3.2.1]octan-3-carboxylate (212 mg, 1 mmol) was dissolved in acetonitrile (20 mL), and ethyl bromide (129.6 mg, 1.2 mmol) and potassium carbonate (414 mg, 3 mmol) were added under stirring. The mixture was stirred overnight at 40° C. After the raw material disappeared as detected by TLC, the mixture was filtrated under suction. The filtrate was distilled under reduced pressure to get the title compound (200 mg, yield: 83.3%).

(2) Preparation of 8-ethyl-3,8-diazabicyclo[3.2.1]octane

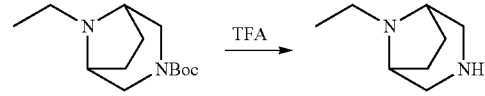

Tert-butyl 8-ethyl-3,8-diazabicyclo[3.2.1]octan-3-carboxylate (200 mg, 0.83 mmol) was dissolved in dichloromethane (5 mL), and trifluoroacetic acid (3 mL) was added under stirring. The mixture was stirred at room temperature for 1 h. After the raw material disappeared as detected by TLC, the mixture was distilled under reduced pressure to get the title compound (100 mg, yield: 85.8%).

(3) Preparation of 3-((2-chloropyrimidin-5-yl)methyl)-8-ethyl-3,8-diazabicyclo[3.2.1]octane

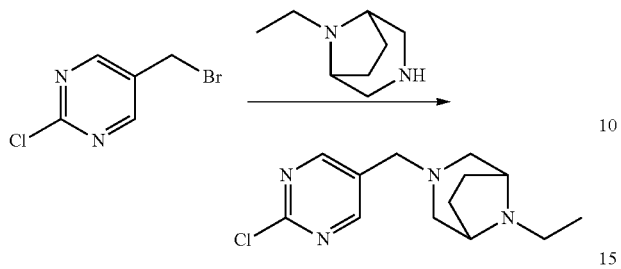

5-(Bromomethyl)-2-chloropyrimidine (146 mg, 0.71 mmol) was dissolved in tetrahydrofuran (30 mL), and potassium carbonate (294 mg, 2.13 mmol) and 8-ethyl-3,8-diazabicyclo[3.2.1]octane (100 mg, 0.71 mmol) were added under stirring. The mixture was stirred at room temperature for 4 h. After the raw material disappeared as detected by TLC, the mixture was filtrated under suction. The filtrate was concentrated and then subjected to silica gel column chromatography (dichloromethane:methanol=30:1) to get the title compound (150 mg, yield: 79.4%).

(4) Preparation of 5-((8-ethyl-3,8-diazabicyclo[3.2.1]octan-3-yl)methyl)-N-(5-fluoro-4-(4-fluoro-1-isopropyl-2-methyl-1H-benzo[d]imidazol-6-yl)pyridin-2-yl)pyrimidin-2-amine

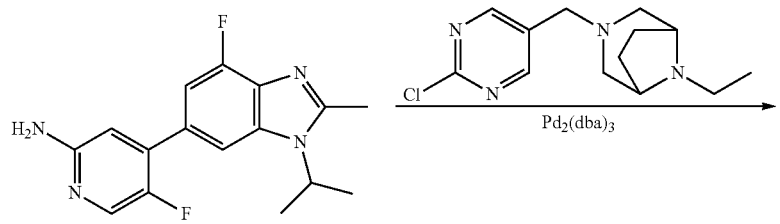

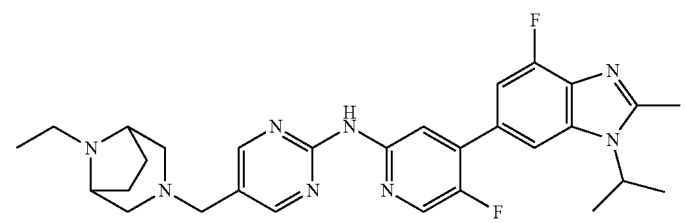

5-fluoro-4-(4-fluoro-1-isopropyl-2-methyl-1H-benzo[d]imidazol-6-yl)pyridin-2-amine (170 mg, 0.564 mmol), 3-((2-chloropyrimidin-5-yl)methyl)-8-ethyl-3,8-diazabicyclo[3.2.1]octane (150 mg, 0.564 mmol), 2-dicyclohexylphosphino-2',4',6'-triisopropylbiphenyl (54 mg, 0.11 mmol), cesium carbonate (550 mg, 1.69 mmol) and tris(dibenzylideneacetone)dipalladium (52 mg, 0.057 mmol) were added to a 100 mL eggplant-shaped bottle, and 1,4-dioxane (20 mL) was added. Under the protection of nitrogen, the reaction was carried out at 110° C. for 4 h, and the mixture was filtrated under suction. The filtrate was concentrated and subjected to silica gel column chromatography (dichloromethane:methanol=15:1) to get the title compound (120 mg, yield: 40%).

Molecular formula: $C_{29}H_{34}F_2N_8$ Molecular weight: 532.3
LC-MS (m/z): 533.3 (M+H$^+$)
$^1$H-NMR (400 MHz, MeOD-d$_4$) δ: 8.53 (d, J=6.0 Hz, 1H), 8.50 (s, 2H), 8.27 (d, J=2.4 Hz, 1H), 7.79 (s, 1H), 7.26 (d, J=11.2 Hz, 1H), 4.60 (s, 1H), 3.95-4.02 (m, 2H), 3.59 (s, 2H), 3.00-3.12 (m, 2H), 2.92 (d, J=12.8 Hz, 2H), 2.69 (s, 3H), 2.59 (d, J=12.8 Hz, 2H), 2.11-2.16 (m, 4H), 1.69 (d, J=6.8 Hz, 6H), 1.31-1.35 (m, 3H).

Example 15: Preparation of N-(5-fluoro-4-(4-fluoro-1-isopropyl-2-methyl-1H-benzo[d]imidazol-6-yl)pyridin-2-yl)-5-(piperazin-1-ylmethyl)pyrimidin-2-amine (Compound 15)

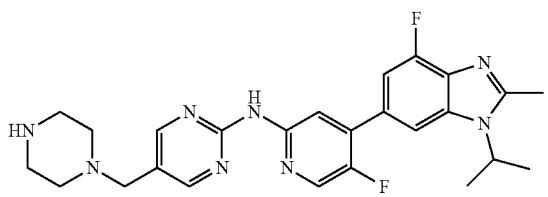 [SMILES: Cc1nc2c(F)cc(-c3cc(Nc4ncc(CN5CCNCC5)cn4)ncc3F)cc2n1C(C)C]

(1) Preparation of tert-butyl 4-(2-chloropyrimidin-5-yl)piperazin-1-carboxylate

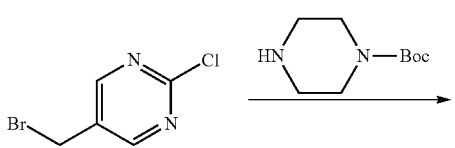

-continued

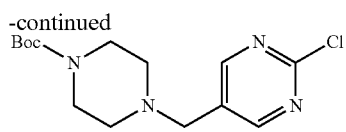

5-(Bromomethyl)-2-chloropyrimidine (500 mg, 2.42 mmol) was dissolved in tetrahydrofuran (15 mL), and tert-butyl piperazin-1-carboxylate (372 mg, 2 mmol) and triethylamine (404 mg, 4 mmol) were added. The mixture was stirred at room temperature for over night. After the reaction, the mixture was concentrated under reduced pressure, diluted with water (15 mL), and extracted with acetic ether (20 mL×3). Phases were separated. The organic phase was dried by anhydrous sodium sulfate, filtrated, and concentrated. The crude product was purified by silica gel column chromatography (petroleum ether:acetic ether=1:1) to get the title compound (520 mg, yield: 83%).

(2) Preparation of tert-butyl 4-((2-((5-fluoro-4-(4-fluoro-1-isopropyl-2-methyl-1H-benzo[d] imidazol-6-yl)pyridin-2-yl)amino)pyrimidin-5-yl)methyl)piperazin-1-carboxylate

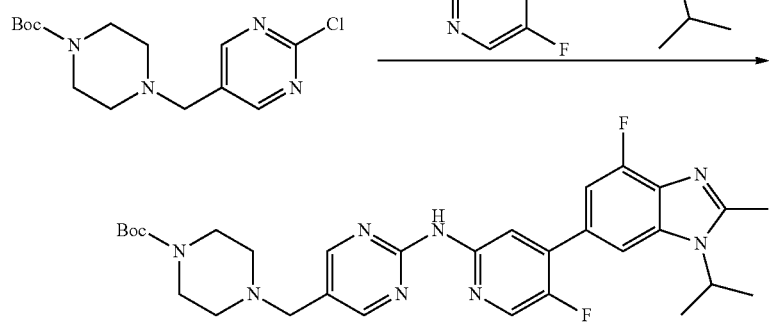

5-Fluoro-4-(4-fluoro-1-isopropyl-2-methyl-1H-benzo[d]imidazol-6-yl)pyridin-2-amine (302 mg, 1 mmol) and 4-((2-chloropyrimidin-5-yl)methyl)piperazin-1-carboxylate (312 mg, 1 mmol) were dissolved in 1,4-dioxane (15 mL), and tris(dibenzylideneacetone)dipalladium (92 mg, 0.1 mmol), 2-dicyclohexylphosphino-2',4',6'-triisopropylbiphenyl (95 mg, 0.2 mmol) and cesium carbonate (815 mg, 2.5 mmol) were added. Under the protection of nitrogen, the mixture was stirred under reflux overnight, and filtrated. The filtrate was concentrated by reduced pressure. The crude product was subjected to silica gel column chromatography (dichloromethane:methanol=30:1) to get the title compound (350 mg, yield: 60%).

(3) Preparation of N-(5-fluoro-4-(4-fluoro-1-isopropyl-2-methyl-1H-benzo[d]imidazol-6-yl) pyridin-2-yl)-5-(piperazin-1-ylmethyl)pyrimidin-2-amine

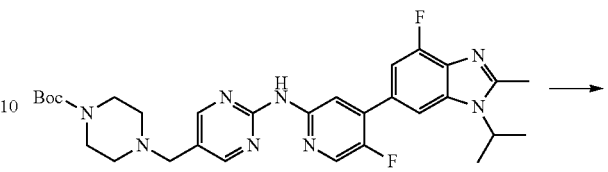

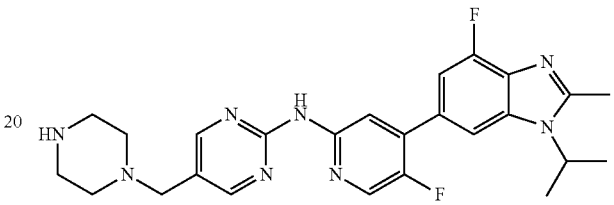

Tert-butyl 4-((2-((5-fluoro-4-(4-fluoro-1-isopropyl-2-methyl-1H-benzo[d]imidazol-6-yl) pyridin-2-yl)amino)pyrimidin-5-yl)methyl)piperazin-1-carboxylate (200 mg, 0.346 mmol) was dissolved in dichloromethane (5 mL), and trifluoroacetic acid (2 mL) was added. The mixture was stirred at room temperature for 2 h, and concentrated under reduced pressure. Dichloromethane and saturated sodium hydrogen carbonate solution were added. The phases were separated. The organi phase was dried, filtrated, and concentrated in vacuum. The crude product was purified by silica gel column chromatography (methanol:dichloromethane=0-1:20, with the addition of 0.5% triethylamine) to get the white solid title compound (110 mg, yield: 67%).

Molecular formula: $C_{25}H_{28}F_2N_8$ Molecular weight: 478.5 LC-MS (m/z): 479.3 (M+H$^+$)

$^1$H-NMR (400 MHz, DMSO-d$_6$) δ: 10.03 (s, 1H), 8.42-8.47 (m, 3H), 8.35 (d, J=2.0 Hz, 1H), 7.75 (s, 1H), 7.23 (d, J=11.6 Hz, 1H), 4.78-4.85 (m, 1H), 3.34 (s, 2H), 2.62-2.66 (m, 7H), 2.20-2.31 (m, 5H), 1.58 (d, J=6.8 Hz, 6H).

Example 16: Preparation of N-(5-fluoro-4-(4-fluoro-1-isopropyl-2-methyl-1H-benzo[d] imidazol-6-yl)pyridin-2-yl)-5-(piperazin-1-yl)pyrimidin-2-amine (Compound 16)

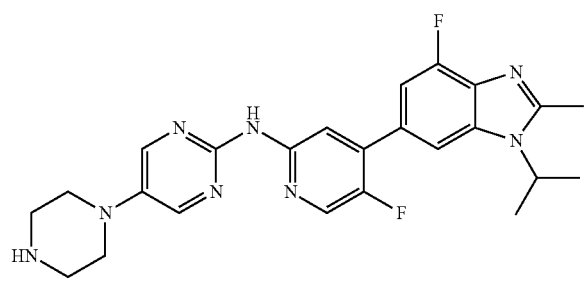 [SMILES: Cc1nc2c(F)cc(-c3cc(Nc4ncc(N5CCNCC5)cn4)ncc3F)cc2n1C(C)C]

(1) Preparation of tert-butyl 4-(pyrimidin-5-yl)piperazin-1-carboxylate

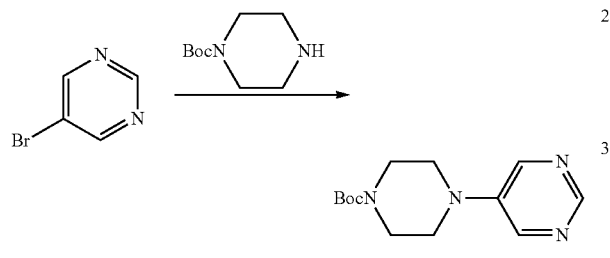

To a 100 mL eggplant-shaped bottle were added 5-bromopyrimidine (3.16 g, 20 mmol), tert-butyl piperazin-1-carboxylate (3.72 g, 20 mmol), 2,2'-bis(diphenylphosphino)-1,1'-binaphthyl (2.49 g, 4 mmol), cesium carbonate (13.0 g, 40 mmol) and tris(dibenzylideneacetone)dipalladium (1.83 g, 2 mmol); and toluene (80 mL) was added. The reaction was carried out at 90° C. under the protection of nitrogen for 12 h. The mixture was filtrated under suction, the filtrate was concentrated, and the crude product was purified by silica gel column chromatography (dichloromethane:methanol=50:1) to get the title compound (3.1 g, yield: 58.7%).

(2) Preparation of tert-butyl 4-(2-bromopyrimidin-5-yl)piperazin-1-carboxylate

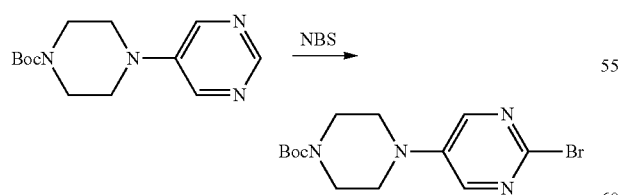

Tert-butyl 4-(pyrimidin-5-yl)piperazin-1-carboxylate (2.64 g, 10 mmol) was weighed and added to acetonitrile (125 mL). N-bromobutanimide (1.78 g, 10 mmol) was added under stirring, and the mixture was stirred at 25° C. for 16 h. The reaction solution was concentrated. Acetic ether (100 mL) and water (100 mL) were added to separate the phases. The organic phase was concentrated and then subjected to silica gel column chromatography (dichloromethane:methanol=30:1) to get the title compound (40 mg, yield: 1.17%).

(3) Preparation of tert-butyl 4-(2-((5-fluoro-4-(4-fluoro-1-isopropyl-2-methyl-1H-benzo[d] imidazol-6-yl)-pyridin-2-yl)amino)pyrimidin-5-yl)piperazin-1-carboxylate

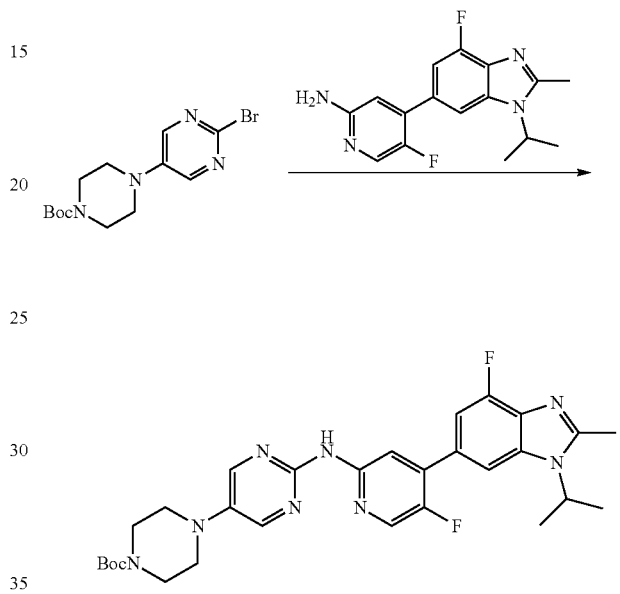

5-fluoro-4-(4-fluoro-1-isopropyl-2-methyl-1H-benzo[d]imidazol-6-yl)pyridin-2-amine (36 mg, 0.12 mmol), tert-butyl 4-(2-bromopyrimidin-5-yl)piperazin-1-carboxylate (40 mg, 0.12 mmol), 2-dicyclohexylphosphino-2',4',6'-triisopropylbiphenyl (11.4 mg, 0.024 mmol), cesium carbonate (97.7 mg, 0.3 mmol) and tris(dibenzylideneacetone)dipalladium (11 mg, 0.012 mmol) were added to a 25 mL eggplant shaped bottle, and 1,4-dioxane (10 mL) was added. Under the protection of nitrogen, the reaction was carried out at 110° C. for 2 h, and the resultant mixture was filtrated under suction. The filtrate was concentrated and then subjected to silica gel column chromatography (dichloromethane:methanol=20:1) to get the title compound (15 mg, yield: 22.2%).

(4) Preparation of N-(5-fluoro-4-(4-fluoro-1-isopropyl-2-methyl-1H-benzo[d]imidazol-6-yl) pyridin-2-yl)-5-(piperazin-1-yl)pyrimidin-2-amine

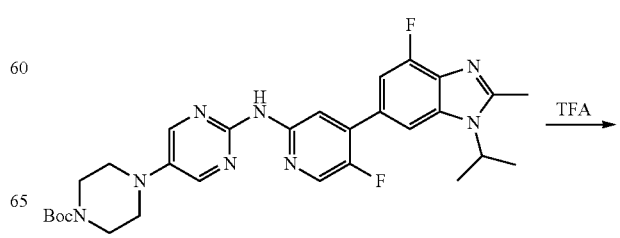

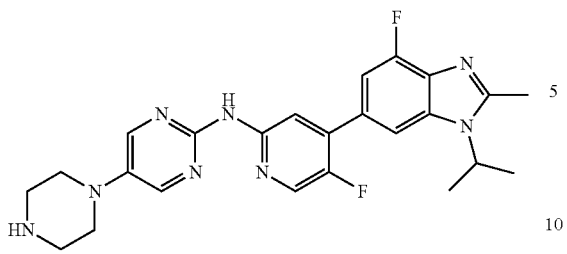

Tert-butyl 4-(2-((5-fluoro-4-(4-fluoro-1-isopropyl-2-methyl-1H-benzo[d]imidazol-6-yl) pyridin-2-yl)amino)pyrimidin-5-yl)piperazin-1-carboxylate (15 mg, 0.027 mmol) was dissolved in dichloromethane (2 mL). Trifluoroacetic acid (2 mL) was added under stirring. The mixture was stirred at 25° C. for 0.5 h. The reaction solution was concentrated, and the residue was diluted with acetic ether (10 mL). Ammonia gas was introduced until the solution was alkaline. The solution was concentrated, and subjected to silica gel column chromatography (dichloromethane:methanol=20:1) to get the title compound (7 mg, yield: 56.0%).

Molecular formula: $C_{24}H_{26}F_2N_8$ Molecular weight: 464.5
LC-MS (m/z): 465.4 (M+H$^+$)

$^1$H-NMR (400 MHz, MeOD-d$_4$) δ: 8.77 (d, J=6.0 Hz, 1H), 8.53 (s, 1H), 8.31 (d, J=2.8 Hz, 1H), 8.27 (s, 1H), 7.81 (s, 1H), 7.30 (d, J=11.2 Hz, 1H), 4.86-4.93 (m, 1H), 3.16-3.18 (m, 4H), 3.04-3.06 (m, 4H), 2.69 (s, 3H), 1.70 (d, J=6.8 Hz, 6H).

Example 17: Preparation of N-(5-fluoro-4-(4-fluoro-1-isopropyl-2-methyl-1H-benzo[d] imidazol-6-yl)pyridin-2-yl)-5-(4-methylpiperazin-1-yl)pyrimidin-2-amine (Compound 17)

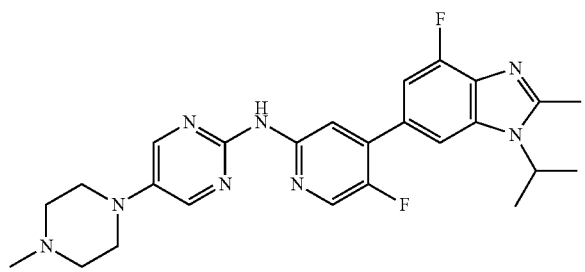

(1) Preparation of N,N-bis(4-methoxybenzyl)-5-(4-methylpiperazin-1-yl)pyrimidin-2-amine

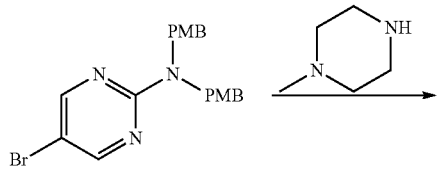

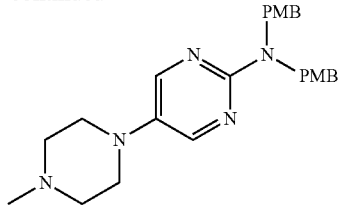

5-Bromo-N,N-bis(4-methoxybenzyl)pyrimidin-2-amine (2.0 g, 4.83 mmol) was dissolved in toluene (20 mL), and N-methylpiperazine (483 mg, 4.83 mmol), tris(dibenzylideneacetone)dipalladium (221 mg, 0.24 mmol), 2,2'-bis(diphenylphosphino)-1,1'-binaphthyl (301 mg, 0.48 mmol) and sodium tert-butoxide (930 mg, 9.7 mmol) were added. Nitrogen was introduced to replace the air in the system, and the reaction was carried out under stirring at 80° C. for 18 h. the mixture was cooled to room temperature, and filtrated. The filtrate was concentrated, and subjected to silica gel column chromatography (dichloromethane:methanol=30:1) to get the title compound (859 mg, 41%)

(2) Preparation of 5-(4-methylpiperazin-1-yl)pyrimidin-2-amine

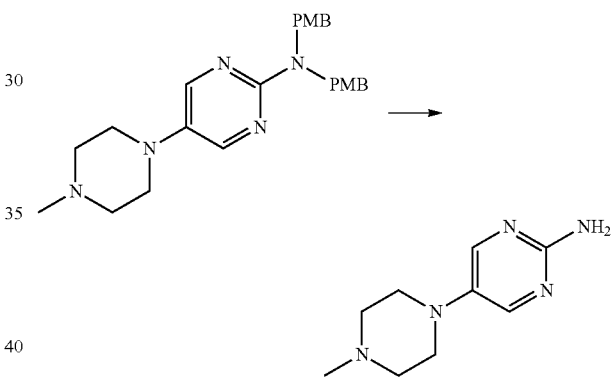

N,N-bis(4-methoxybenzyl)-5-(4-methylpiperazin-1-yl)pyrimidin-2-amine (800 mg, 1.8 mmol) was dissolved in a mixed solution of trifluoroacetic acid (10 mL) and dichloromethane (10 mL). The mixture was heated to 40° C., and reacted for 18 h. The reaction solution was concentrated under reduced pressure and purified by silica gel column chromatography (dichloromethane:methanol=10:1) to get the title compound (285 mg, 82%).

(3) Preparation of N-(5-fluoro-4-(4-fluoro-1-isopropyl-2-methyl-1H-benzo[d]imidazol-6-yl) pyridin-2-yl)-5-(4-methylpiperazin-1-yl)pyrimidin-2-amine

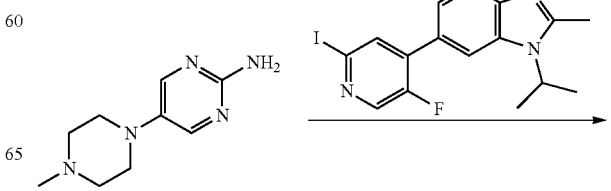

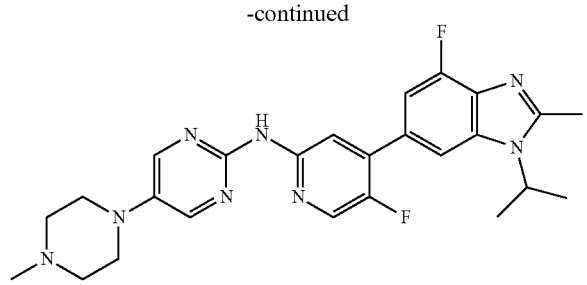

5-(4-(dimethylamino)piperidin-1-yl)pyrimidin-2-amine (193 mg, 1.0 mmol), 4-fluoro-6-(5-fluoro-2-iodopyridin-4-yl)1-isopropyl-2-methyl-1H-benzo[d]imidazole (413 mg, 1.0 mmol), 2-dicyclohexylphosphino-2',4',6'-triisopropylbiphenyl (47.7 mg, 0.10 mmol), cesium carbonate (815 mg, 2.5 mmol) and tris(dibenzylideneacetone)dipalladium (45.8 mg, 0.05 mmol) were dissolved in 1,4-dioxane (20 mL). Nitrogen was introduced to replace the air in the reaction system. The mixture was heated up to 120° C., reacted for 8 h, and filtrated. The filtrate was concentrated and subjected to silica gel column chromatography (dichloromethane:methanol=10:1) to get the title compound (52.6 mg, yield: 11%).

Molecular formula: $C_{25}H_{28}F_2N_8$ Molecular weight: 478.6
LC-MS (m/z): 479.0 (M+H$^+$)
$^1$H-NMR (400 MHz, DMSO-d$_6$) δ: 9.66 (s, 1H), 8.36 (d, J=6 Hz, 1H), 8.29-8.31 (m, 3H), 7.73 (s, 1H), 7.20 (d, J=11.6 Hz, 1H), 4.79-4.83 (m, 1H), 3.07-3.10 (m, 4H), 2.61 (s, 3H), 2.43-2.46 (m, 4H), 2.20 (s, 3H), 1.57 (d, J=6.8 Hz, 6H).

Example 18: Preparation of 5-(4-ethylpiperazin-1-yl)-N-(5-fluoro-4-(4-fluoro-1-isopropyl-2-methyl-1H-benzo[d]imidazol-6-yl)pyridin-2-yl)pyrimidin-2-amine (Compound 18)

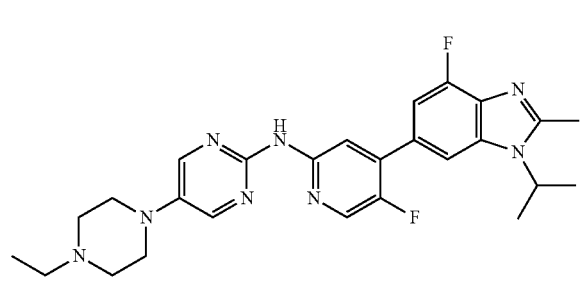 [SMILES: CCN1CCN(c2cnc(Nc3cc(-c4cc(F)c5nc(C)n(C(C)C)c5c4)c(F)cn3)nc2)CC1]

(1) Preparation of 5-(4-ethylpiperazin-1-yl)-N,N-bis(4-methoxybenzyl)pyrimidin-2-amine

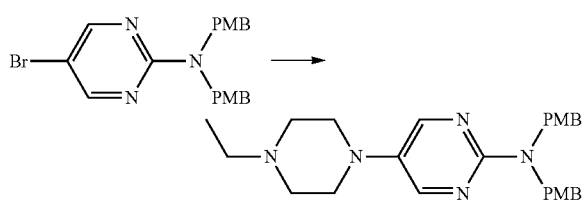

5-Bromo-N,N-bis(4-methoxybenzyl)pyrimidin-2-amine (800 mg, 1.94 mmol) was dissolved in toluene (20 mL), and N-ethylpiperazine (330 mg, 2.89 mmol), tris(dibenzylideneacetone)dipalladium (89 mg, 0.097 mmol), 2,2'-bis(diphenylphosphino)-1,1'-binaphthyl (121 mg, 0.194 mmol) and sodium tert-butoxide (372 mg, 3.88 mmol) were added. The mixture was stirred at 80° C. under the protection of nitrogen for 18 h. The mixture was cooled to room temperature, and filtrated. The filtrate was concentrated, and the crude product was purified by silica gel column chromatography (methanol:dichloromethane=0-1:30) to get the title product (440 mg, yield: 51%).

(2) Preparation of 5-(4-ethylpiperazin-1-yl)pyrimidin-2-amine

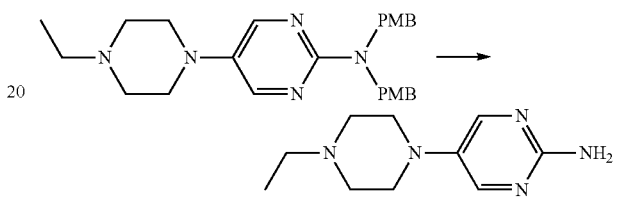

5-(4-Ethylpiperazin-1-yl)-N,N-bis(4-methoxybenzyl)pyrimidin-2-amine (440 mg, 0.98 mmol) was dissolved in trifluoroacetic acid (5 mL). The mixture was heated to 40° C. and reacted for 18 h. The solvent was removed under reduced pressure to get the title compound (180 mg, yield: 89%), which was directly used in the next step.

(3) Preparation of 5-(4-ethylpiperazin-1-yl)-N-(5-fluoro-4-(4-fluoro-1-isopropyl-2-methyl-1H-benzo[d]imidazol-6-yl)pyridin-2-yl)pyrimidin-2-amine

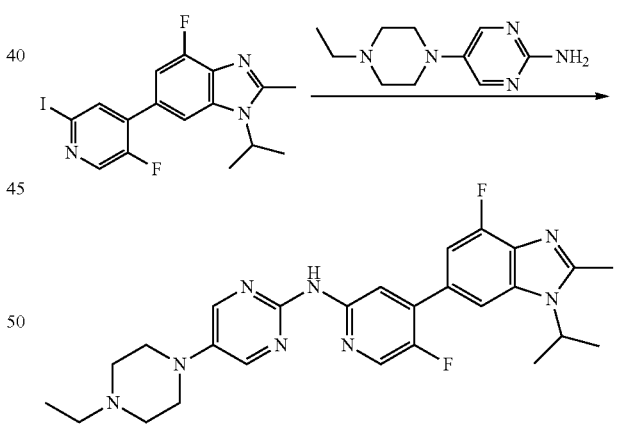

4-Fluoro-6-(5-fluoro-2-iodopyridin-4-yl)1-isopropyl-2-methyl-1H-benzo[d]imidazole (359 mg, 0.87 mmol) and 5-(4-ethylpiperazin-1-yl)pyrimidin-2-amine (180 mg, 0.87 mmol) were dissolved in toluene (10 mL). Tris(dibenzylideneacetone)dipalladium(80 mg, 0.087 mmol), 4,5-bis(diphenylphosphino)-9,9-dimethylxanthene (50 mg, 0.087 mmol) and sodium tert-butoxide (209 mg, 2.18 mmol) were added. Under the protection of nitrogen, the mixture was heated to 100° C. and reacted for 16 h. The mixture was cooled to room temperature, and methanol (5 mL) was added. The mixture was filtrated through celite. The filtrate was concentrated in vacuum, and the crude product was purified by silica gel column chromatography (methanol:dichloromethane=0-1:10, with the addition of 0.5% aqueous ammonia) to get the white solid title compound (18 mg, yield: 4.2%).

Molecular formula: $C_{26}H_{30}F_2N_8$ Molecular weight: 492.6
LC-MS (m/z): 493 (M+H$^+$)

$^1$H-NMR (400 MHz, MeOD-d$_4$) δ: 8.46 (d, J=5.2 Hz, 1H), 8.34 (s, 2H), 8.22 (s, 1H), 7.78 (s, 1H), 7.25 (d, J=11.2 Hz, 1H), 4.55-4.62 (m, 1H), 3.20-3.28 (m, 4H), 2.80-2.91 (m, 4H), 2.72-2.75 (m, 2H), 2.68 (s, 3H), 1.69 (d, J=6.8 Hz, 6H), 1.22 (t, J=7.2 Hz, 3H).

Example 19: Preparation of N-(5-fluoro-4-(4-fluoro-1-isopropyl-2-methyl-1H-benzo[d] imidazol-6-yl)pyridin-2-yl)-5-(4-(oxacyclobutan-3-yl)piperazin-1-yl)pyrimidin-2-amine (Compound 20)

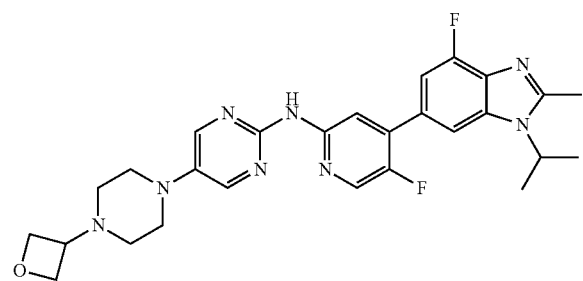 [SMILES: Cc1nc2c(F)cc(-c3cc(Nc4ncc(N5CCN(C6COC6)CC5)cn4)ncc3F)cc2n1C(C)C]

(1) Preparation of 6-(2-bromo-5-fluoropyridin-4-yl)-4-fluoro-1-isopropyl-2-methyl-1H-benzo[d]imidazole

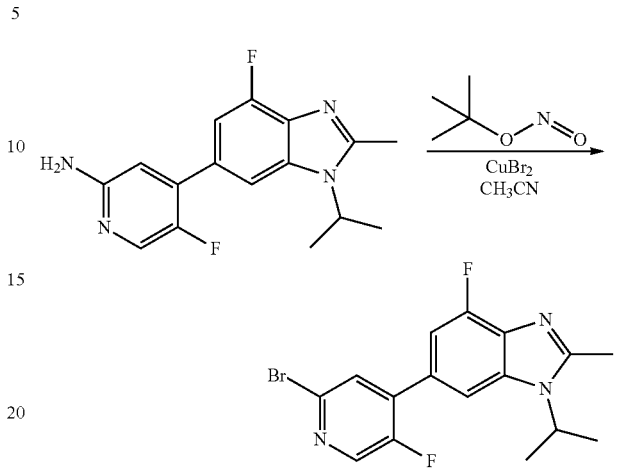

5-Fluoro-4-(4-fluoro-1-isopropyl-2-methyl-1H-benzo[d] imidazol-6-yl)pyridin-2-amine (906 mg, 3.0 mmol) was dissolved in acetonitrile (30 mL), and tert-butyl nitrite (340 mg, 3.3 m mol) was added slowly. After the addition, the mixture was stirred at room temperature for 30 min, and CuBr$_2$ (1.00 g, 4.5 mmol) was added. The resultant mixture was stirred at room temperature for 2 h, and filtrated under suction. The solvent was removed by distillation under rotation, and the crude product was purified by silica gel column chromatography (petroleum ether:acetic ether=1:1) to get the product (498 mg, yield: 45.4%).

(2) Preparation of tert-butyl 4-(2-((5-fluoro-4-(4-fluoro-1-isopropyl-2-methyl-1H-benzo[d] imidazol-6-yl)pyridin-2-yl)amino)pyrimidin-5-yl)piperazin1-carboxylate

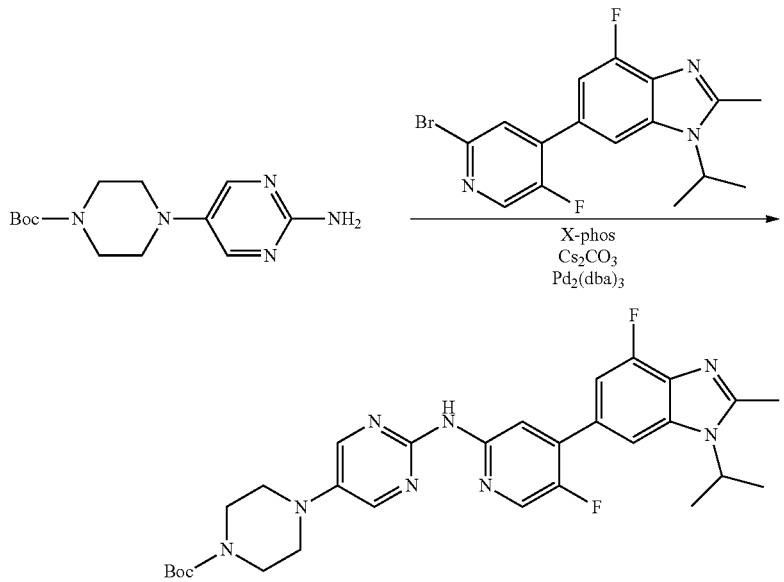

Tert-butyl 4-(2-aminopyrimidin-5-yl)piperazin-1-carboxylate (380 mg, 1.36 mmol), 6-(2-bromo-5-fluoropyridin-4-yl)-4-fluoro-1-isopropyl-2-methyl-1H-benzo[d]imidazole (498 mg, 1.36 mmol), cesium carbonate (447 mg, 1.36 mmol), tris(dibenzylideneacetone)dipalladium (38 mg) and 2-dicyclohexylphosphino-2',4',6'-triisopropylbiphenyl (76 mg) were added to 1,4-dioxane (20 mL). Under the protection of nitrogen, the mixture was heated in an 110° C. oil bath for 8 h, and the solvent was removed by distillation under rotation. The residue was purified by silica gel column chromatography (petroleum ether:acetic ether=10:1-1:1) to get the title compound (256 mg, yield: 33.3%).

(3) Preparation of N-(5-fluoro-4-(4-fluoro-1-isopropyl-2-methyl-1H-benzo[d]imidazol-6-yl) pyridin-2-yl)-5-(4-(oxacyclobutan-3-yl)piperazin-1-yl)pyrimidin-2-amine

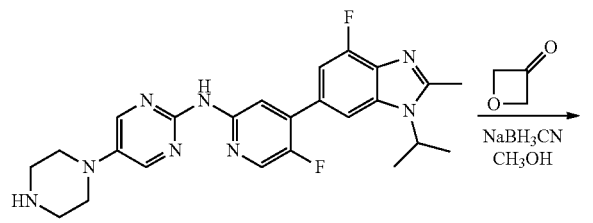

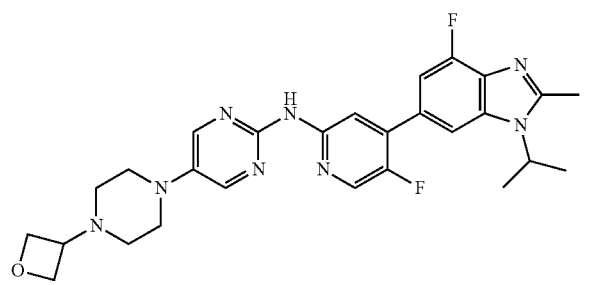

N-(5-fluoro-4-(4-fluoro-1-isopropyl-2-methyl-1H-benzo[d]imidazol-6-yl)pyridin-2-yl)-5-(piperazin-1-yl)pyrimidin-2-amine (170 mg, 0.366 mmol) was dissolved in methanol (5 mL), and 3-oxetanone (39.5 mg, 0.549 mmol) was added dropwisely. The mixture was stirred at room temperature for 2 h, and sodium cyanoborohydride (34.6 mg, 0.549 mmol) was added slowly. The mixture was further stirred at room temperature for 30 min. The solvent was removed by distillation under rotation, and the residue was purified by silica gel column chromatography (dichloromethane:methanol=10:1) to get the product (82 mg, yield: 42.1%).

Molecular formula: $C_{27}H_{30}F_2N_8O$ Molecular weight: 520.6 LC-MS (m/z): 521.3 (M+H$^+$)

$^1$H-NMR (400 MHz, MeOD) δ: 8.47 (m, J=6.4 Hz, 1H), 8.30 (s, 2H), 8.20 (d, J=2.4 Hz, 1H), 7.77 (s, 1H), 7.26 (d, J=8.0 Hz, 1H), 4.72 (t, J=6.4 Hz, 2H), 4.59-4.64 (m, 3H), 3.50-3.55 (m, 1H), 3.19 (t, J=4.8 Hz, 4H), 2.68 (s, 3H), 2.52 (t, J=4.8 Hz, 4H), 1.68 (d, J=6.8 Hz, 6H).

Example 20: Preparation of 5-(4-(dimethylamino)piperidin-1-yl)-N-(5-fluoro-4-(4-fluoro-1-isopropyl-2-methyl-1H-benzo[d]imidazol-6-yl)pyridin-2-yl)pyrimidin-2-amine (Compound 21)

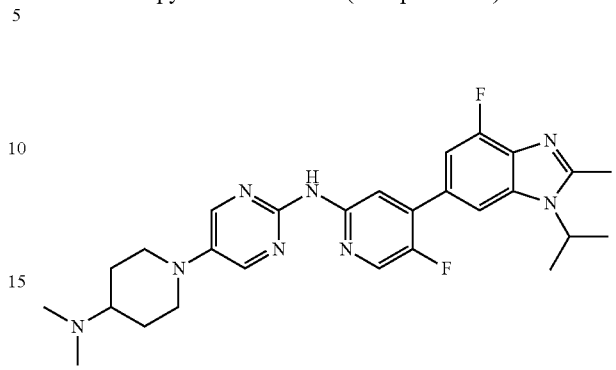

(1) Preparation of 5-(4-(dimethylamino)piperidin-1-yl)-N,N-bis(4-methoxybenzyl)pyrimidin-2-amine

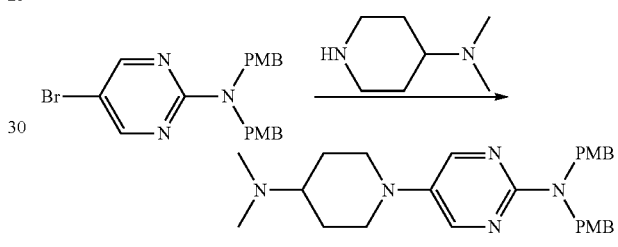

Under the protection of nitrogen, to toluene (50 mL) in the reaction bottle were added 5-bromo-N,N-bis(4-methoxybenzyl)-pyrimidin-2-amine (2.0 g, 4.84 mmol), N,N-dimethylpiperidin-4-amine (620 mg, 4.84 mmol), tris(dibenzylideneacetone)dipalladium (221 mg, 0.24 mmol), 2,2'-bis(diphenylphosphino)-1,1'-binaphthyl (301 mg, 0.48 mmol) and sodium tert-butoxide (930 mg, 9.7 mmol). The mixture was heated to 80° C., and reacted for 16 h. After the reaction, the mixture was cooled to room temperature and filtrated, and the filtrate was concentrated and separated by silica gel column chromatography (petroleum ether:acetic ether=5:1) to get the title compound (758 mg, 34%).

(2) Preparation of 5-(4-(dimethylamino)piperidin-1-yl)pyrimidin-2-amine

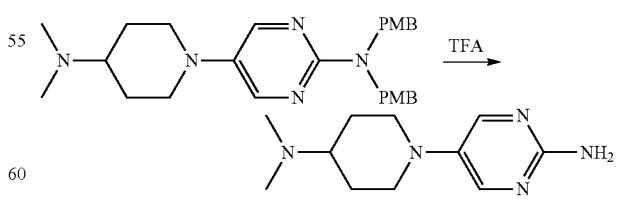

To a solution of 5-(4-(dimethylamino)piperidin-1-yl)-N,N-bis(4-methoxybenzyl)pyrimidin-2-amine (758 mg, 1.64 mmol) in dichloromethane (20 mL), trifluoroacetic acid (10 mL) was added. The mixture was heated to 40° C. and reacted for 16 h. After the reaction, the reaction solution was cooled to room temperature, concentrated and purified by silica gel column chromatography (dichloromethane:methanol=20:1) to get the title compound (282 mg, 78%).

(3) Preparation of 5-(4-(dimethylamino)piperidin-1-yl)-N-(5-fluoro-4-(4-fluoro-1-isopropyl-2-methyl-1H-benzo[d]imidazol-6-yl)pyridin-2-yl)pyrimidin-2-amine

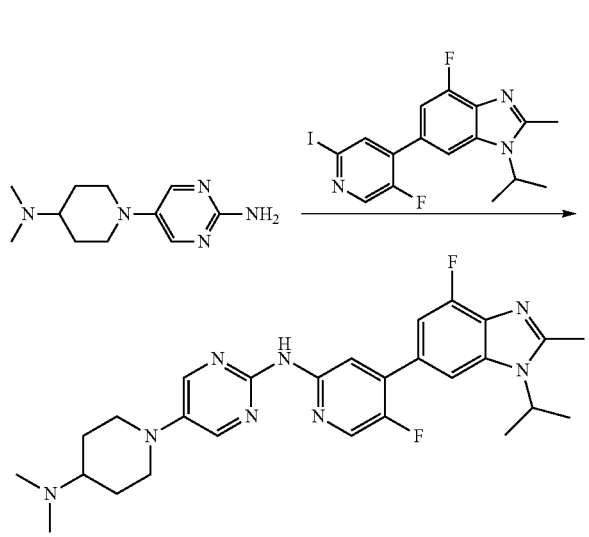

5-(4-(dimethylamino)pyrimidin-2-amine (282 mg, 1.28 mmol), 4-fluoro-6-(5-fluoro-2-iodopyridin-4-yl)-1-isopropyl-2-methyl-1H-benzo[d]imidazole (528 mg, 1.28 mmol), 2-dicyclohexylphosphino-2',4',6'-triisopropyl-biphenyl (61 mg, 0.13 mmol), cesium carbonate (1.2 g, 3.7 mmol) and tris(dibenzylideneacetone)dipalladium (58 mg, 0.06 mmol) were added to 1,4-dioxane (20 mL). Under the protection of nitrogen, the reaction was carried out at 120° C. for 2 h, and filtrated under suction. The filtrate was concentrated and subjected to silica gel column chromatography (dichloromethane:methanol=10:1) to get the title compound (40 mg, yield: 6%).

Molecular formula: $C_{27}H_{32}F_2N_8$ Molecular weight: 506.6 LC-MS (m/z): 507.1 (M+H$^+$)

$^1$H-NMR (400 MHz, MeOD) δ: 8.46 (d, J=6.0 Hz, 1H), 8.34 (s, 2H), 8.21 (d, J=2.4 Hz, 1H), 7.77 (s, 1H), 7.25 (d, J=11.6 Hz, 1H), 4.57 (s, 1H), 3.71-3.76 (m, 2H), 2.96-3.11 (m, 1H), 2.77-2.83 (m, 2H), 2.72 (s, 6H), 2.68 (s, 3H), 2.11-2.14 (m, 2H), 1.78-1.82 (m, 2H), 1.69 (d, J=6.8 Hz, 6H).

Example 21: Preparation of 5-(4-(cyclopropylmethyl)piperazin-1-yl)-N-(5-fluoro-4-(4-fluoro-1-isopropyl-2-methyl-1H-benzo[d]imidazol-6-yl)pyridin-2-yl)pyrimidin-2-amine (Compound 22)

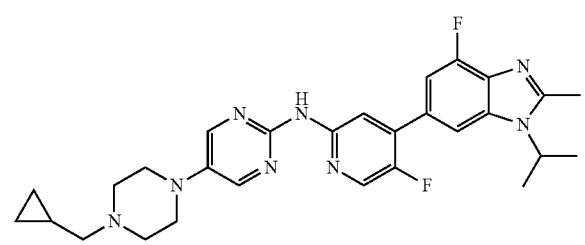 [SMILES: Cc1nc2c(F)cc(-c3cc(Nc4ncc(N5CCN(CC6CC6)CC5)cn4)ncc3F)cc2n1C(C)C]

(1) Preparation of 5-(4-(cyclopropylmethyl)piperazin-1-yl)-N-(5-fluoro-4-(4-fluoro-1-isopropyl-2-methyl-1H-benzo[d]imidazol-6-yl)pyridin-2-yl)pyrimidin-2-amine

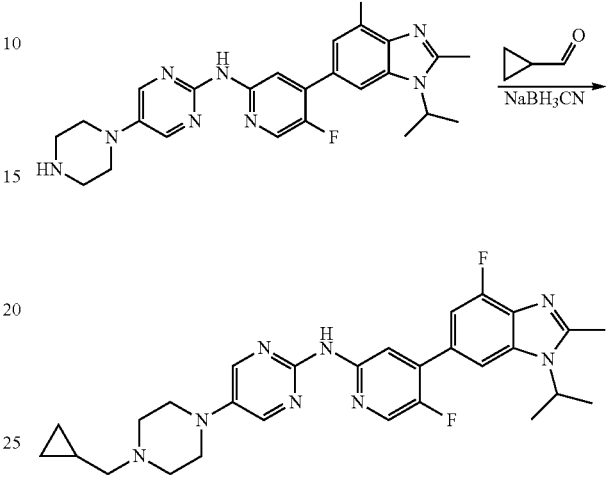

N-(5-fluoro-4-(4-fluoro-1-isopropyl-2-methyl-1H-benzo[d]imidazol-6-yl)pyridin-2-yl)-5-(piperazin-1-yl)pyrimidin-2-amine (90 mg, 0.194 mmol) was dissolved in methanol (5 mL), and cyclopropanecarboxaldehyde (68 mg, 0.97 mmol) was added. The mixture was stirred at 20° C. for 30 min. Sodium cyanoborohydride (122 mg, 1.94 mmol) was added. After the addition, the mixture was stirred at 20° C. for 16 h. Water (10 mL) and acetic ether (20 mL) were added to separate the phases. The organic phase was concentrated, and separated by silica gel column chromatography (dichloromethane:methanol=10:1) to get the title compound (19 mg, yield: 18.9%).

Molecular formula: $C_{28}H_{32}F_2N_8$ Molecular weight: 518.6 LC-MS (m/z): 519.2 (M+H$^+$)

$^1$H-NMR (400 MHz, MeOD) δ: 8.41 (s, 1H), 8.09-8.20 (m, 3H), 7.74 (s, 1H), 7.17-7.19 (m, 1H), 4.89-4.91 (m, 1H), 2.95-3.15 (m, 4H), 2.68 (s, 3H), 2.52-2.68 (m, 4H), 2.26-2.29 (m, 2H), 1.67 (d, J=6.8 Hz, 6H), 1.29-1.31 (m, 1H), 0.55-0.57 (m, 2H), 0.21-0.29 (m, 2H).

Example 22: Preparation of N-(5-fluoro-4-(4-fluoro-1-isopropyl-2-methyl-1H-benzo[d] imidazol-6-yl)pyridin-2-yl)-5-(((cis)-hexahydropyrrolo[3,4-b]pyrrol-5(1H)-yl)methyl)pyrimidin-2-amine (Compound 23)

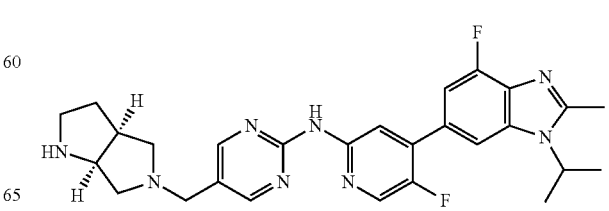

(1) Preparation of tert-butyl (cis)-5-((2-chloropyrimidin-5-yl)methyl)hexahydropyrrolo[3,4-b] pyrrol-1(2H)-carboxylate

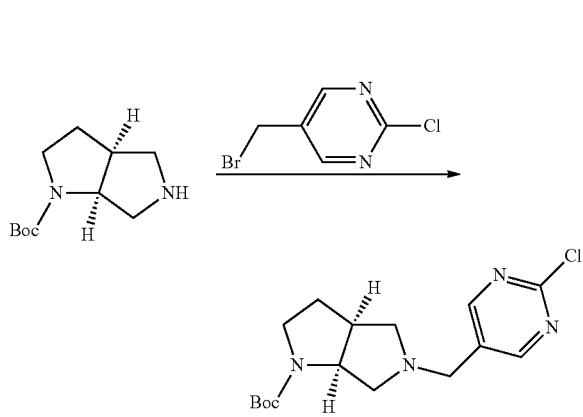

Tert-butyl (cis)-hexahydropyrrolo[3,4-b]pyrrole-1(2H)-carboxylate (250 mg, 1.18 mmol) and 5-(bromomethyl)-2-chloropyrimidine (490 mg, 2.37 mmol) were weighed and added to tetrahydrofuran (10 mL), and triethaylamine (238 mg, 2.36 mmol) was added. The mixture was stirred at room temperature for 16 h. The resultant mixture was concentrated directly. The crude product was purified by silica gel column chromatography (petroleum ether:acetic ether=3:1) to get the title compound (300 mg, yield: 75.2%).

(2) Preparation of tert-butyl (cis)-5-((2-((5-fluoro-4-(4-fluoro-1-isopropyl-2-methyl-1H-benzo[d]imidazol-6-yl)pyridin-2-yl)amino)pyrimidin-5-yl)methyl) hexahydropyrrolo[3,4-b]pyrrol-1(2H)-carboxylate

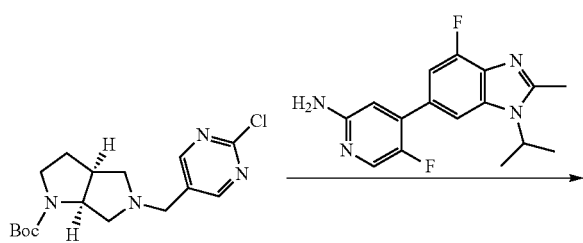

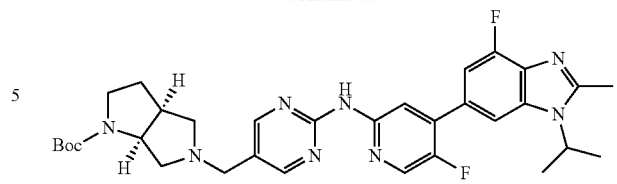

Tert-butyl (cis)-5-((2-chloropyrimidin-5-yl)methyl)hexahydropyrrolo[3,4-b]pyrrol-1(2H)-carboxylate (300 mg, 0.89 mmol), 5-fluoro-4-(4-fluoro-1-isopropyl-2-methyl-1H-benzo[d] imidazol-6-yl)pyridin-2-amine (269 mg, 0.89 mmol), 2-dicyclohexylphosphino-2',4',6'-triisopropylbiphenyl (87 mg, 0.18 mmol), tris(dibenzylideneacetone)dipalladium(82 mg, 0.09 mmol) and cesium carbonate (587 mg, 1.8 mmol) were weighed and added to 1,4-dioxane (5 mL). Under the protection of nitrogen, the mixture was heated up to 110° C. and reacted for 16 h. The mixture was filtrated under suction, the filtrate was concentrated, and the crude product was purified by silica gel column chromatography (dichloromethane:methanol=30:1) to get the title compound (370 mg, yield: 68.7%).

(3) Preparation of N-(5-fluoro-4-(4-fluoro-1-isopropyl-2-methyl-1H-benzo[d]imidazol-6-yl) pyridin-2-yl)-5-(((cis)-hexahydropyrrolo[3,4-b]pyrrol-5(1H)-yl)methyl)pyrimidin-2-amine

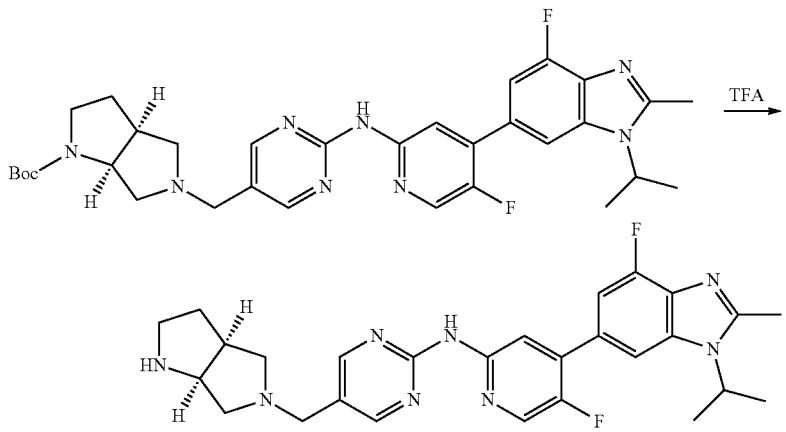

Tert-butyl (cis)-5-((2-((5-fluoro-4-(4-fluoro-1-isopropyl-2-methyl-1H-benzo[d]imidazol-6-yl) pyridin-2-yl)amino)pyrimidin-5-yl)methyl)hexahydropyrrolo[3,4-b]pyrrole-1 (2H)-carboxylate (370 mg, 0.61 mmol) was weighed and dissolved in dichloromethane (8 mL). Trifluoroacetic acid (1 mL) was added under the condition of ice bath. The mixture was then warmed up to room temperature and stirred for 2 h. The reaction solution was distilled under rotation, dissolved in dichloromethane (10 mL), neutralized with sodium hydrogen carbonate and concentrated. The crude product was purified by silica gel column chromatography (dichloromethane:methanol=15:1) to get the title compound (250 mg, yield: 81.2%).

Molecular formula: $C_{27}H_{30}F_2N_8$ Molecular weight: 504.6
LC-MS (m/z): 505.3 (M+H$^+$)
$^1$H-NMR (400 MHz, MeOD-d$_4$) δ: 8.51-8.54 (m, 3H), 8.28 (d, J=2.4 Hz, 1H), 7.80 (s, 1H), 7.27 (d, J=11.2 Hz, 1H), 4.85-4.95 (m, 1H), 4.12-4.18 (m, 1H), 3.58 (s, 2H), 3.35-3.42 (m, 1H), 3.16-3.27 (m, 1H), 3.08-3.15 (m, 1H), 2.96-3.05 (m, 1H), 2.77-2.83 (m, 1H), 2.69 (s, 3H), 2.40-2.55 (m, 2H), 2.15-2.28 (m, 1H), 1.85-1.95 (m, 1H), 1.69 (d, J=7.2 Hz, 6H).

Example 23: Preparation of N-(5-fluoro-4-(4-fluoro-1-isopropyl-2-methyl-1H-benzo[d] imidazol-6-yl)pyridin-2-yl)-5-(((cis)-octahydro-6H-pyrrolo[3,4-b]pyridin-6-yl)methyl)pyrimidine-2-amine (Compound 24)

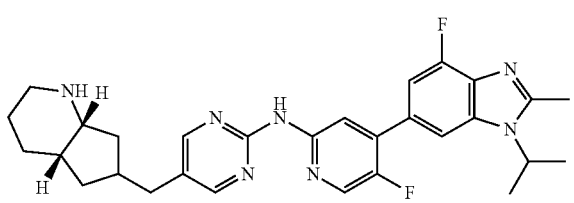 [SMILES: Cc1nc2c(F)cc(-c3cc(Nc4ncc(CC5C[C@@H]6CCCN[C@@H]6C5)cn4)ncc3F)cc2n1C(C)C]

(1) Preparation of tert-butyl (cis)-6-((2-chloropyrimidin-5-yl)methyl)octahydro-1H-pyrrolo [3,4-b]pyridin-1-carboxylate

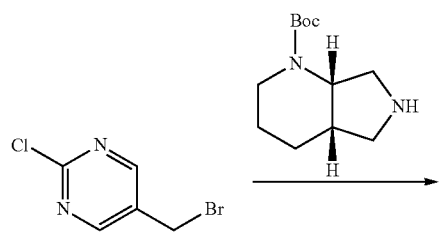

5-(Bromomethyl)-2-chloropyrimidine (183.4 mg, 0.884 mmol) was dissolved in tetrahydrofuran (10 mL), and triethylamine (134.3 mg, 1.33 mmol) and tert-butyl (cis)-octahydro-1H-pyrrolo[3,4-b]pyridin-1-carboxylate (100 mg, 0.442 mmol) were added under stirring. The mixture was stirred at room temperature for 4 h and filtrated under suction. The filtrate was concentrated, and the crude product was purified by silica gel column chromatography (dichloromethane:methanol=100:1) to get the title compound (102 mg, yield: 65.4%).

(2) Preparation of tert-butyl (cis)-6-((2-(5-fluoro-4-(4-fluoro-1-isopropyl-2-methyl-1H-benzo [d]imidazol-6-yl)pyridin-2-yl)amino)pyrimidin-5-yl)methyl)octahydro-1H-pyrrolo[3,4-b]pyridin-1-carboxylate

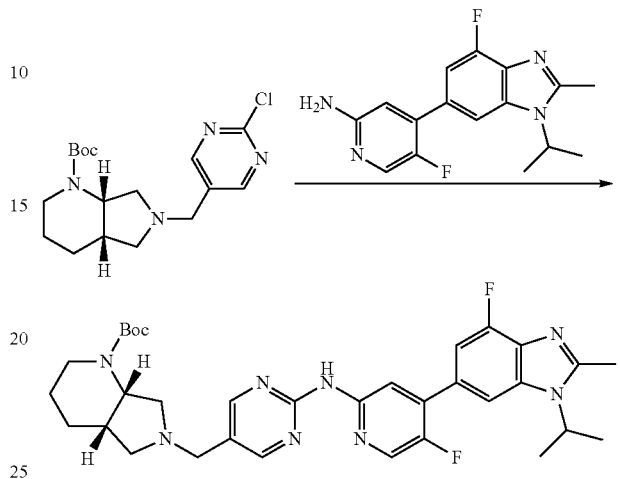

5-fluoro-4-(4-fluoro-1-isopropyl-2-methyl-1H-benzo[d]imidazol-6-yl)pyridin-2-amine (85.6 mg, 0.283 mmol), tert-butyl (cis)-6-((2-chloropyrimidin-5-yl)methyl)octahydro-1H-pyrrolo[3,4-b] pyridin-1-carboxylate (100 mg, 0.283 mmol), 2-dicyclohexylphosphino-2',4',6'-triisopropylbiphenyl (27 mg, 0.0566 mmol), cesium carbonate (276.6 mg, 0.849 mmol) and tris(dibenzylideneacetone)dipalladium (25.9 mg, 0.0283 mmol) were added to 1,4-dioxane (10 mL). Under the protection of nitrogen, the reaction was carried out at 110° C. for 6 h, and the mixture was filtrated under suction. The filtrate was concentrated, and the crude product was purified by silica gel column chromatography (dichloromethane:methanol=50:1) to get the title compound (80 mg, yield: 45.6%).

(3) Preparation of N-(5-fluoro-4-(4-fluoro-1-isopropyl-2-methyl-1H-benzo[d]imidazol-6-yl) pyridin-2-yl)-5-(((cis)-octahydro-6H-pyrrolo[3,4-b]pyridin-6-yl)methyl)pyrimidin-2-amine

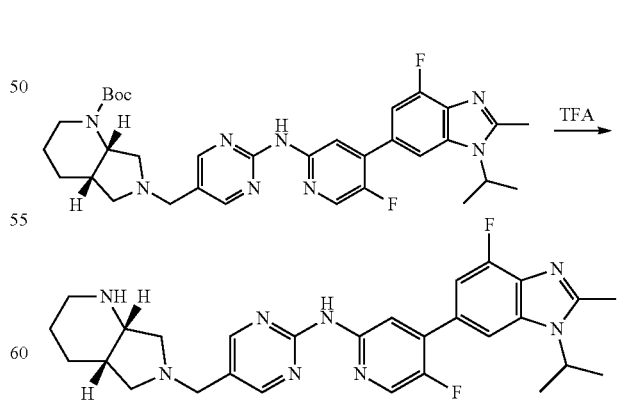

Tert-butyl (cis)-6-((2-((5-fluoro-4-(4-fluoro-1-isopropyl-2-methyl-1H-benzo[d]imidazol-6-yl) pyridin-2-yl)amino)pyrimidin-5-yl)methyl)octahydro-1H-pyrrolo[3,4-b]pyridine-1-carboxylate (80 mg, 0.129 mmol) was dissolved in dichloromethane (5 mL). Trifluoroacetic acid (1 mL) was added. The mixture was stirred at room temperature for 2 h. After the reaction, the mixture was washed with saturated sodium hydrogen carbonate solution and separated into organic phase and water phase. The organic phase was dried by anhydrous sodium sulfate and concentrated. The crude product was separated by silica gel column chromatography (dichloromethane:methanol=20:1) to get the white solid title compound (30 mg, yield: 44.8%).

Molecular formula: $C_{28}H_{32}F_2N_8$ Molecular weight: 518.6
LC-MS (m/z): 519.3 (M+H$^+$)

$^1$H-NMR (400 MHz, CDCl$_3$) δ: 9.31 (s, 1H), 8.66 (d, J=6.0 Hz, 1H), 8.55 (s, 2H), 8.37 (d, J=2.0 Hz, 1H), 7.63 (s, 1H), 7.24-7.26 (m, 1H), 4.65-4.75 (m, 1H), 3.71 (s, 2H), 3.22-3.25 (m, 1H), 2.84-2.94 (m, 3H), 2.68-2.72 (m, 6H), 2.39-2.48 (m, 1H), 1.58-1.73 (m, 11H).

Example 24: Preparation of N-(5-fluoro-4-(4-fluoro-1-isopropyl-2-methyl-1H-benzo[d] imidazol-6-yl)pyridin-2-yl)-5-(((cis)-octahydro-1H-pyrrolo[3,4-b]pyridin-1-yl)methyl)pyrimidin-2-amine (Compound 25)

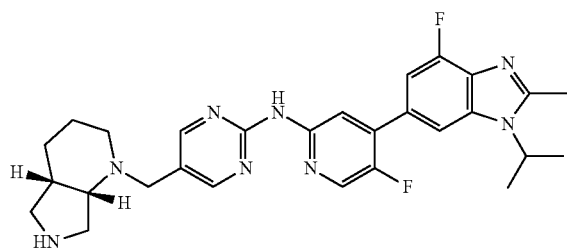 [SMILES: Cc1nc2c(F)cc(-c3cc(Nc4ncc(CN5CCC[C@H]6CNC[C@H]65)cn4)ncc3F)cc2n1C(C)C]

(1) Preparation of tert-butyl (cis)-1-((2-chloropyrimidin-5-yl)methyl)octahydro-6H-pyrrolo [3,4-b] pyridine-6-carboxylate

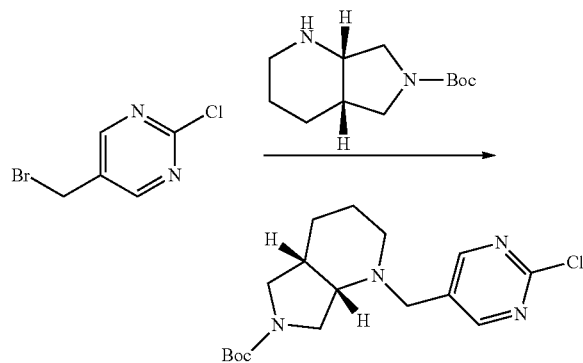

5-(Bromomethyl)-2-chloropyrimidine (183.4 mg, 0.884 mmol) was dissolved in tetrahydrofuran (10 mL), and triethylamine (134.3 mg, 1.33 mmol) and tert-butyl (cis)-octahydro-6H-pyrrolo[3,4-b]pyridine-6-carboxylate (100 mg, 0.442 mmol) were added under stirring. The mixture was stirred at room temperature for 4 h. The mixture was filtrated under suction, the filtrate was concentrated, and the crude product was purified by silica gel column chromatography (dichloromethane:methanol=100:1) to get the title compound (125 mg, yield: 80.1%).

(2) Preparation of tert-butyl (cis)-1-((2-(5-fluoro-4-(4-fluoro-1-isopropyl-2-methyl-1H-benzo [d]imidazol-6-yl)pyridin-2-yl)amino)pyrimidin-5-yl)methyl) octahydro-6H-pyrrolo[3,4-b]pyridine-6-carboxylate

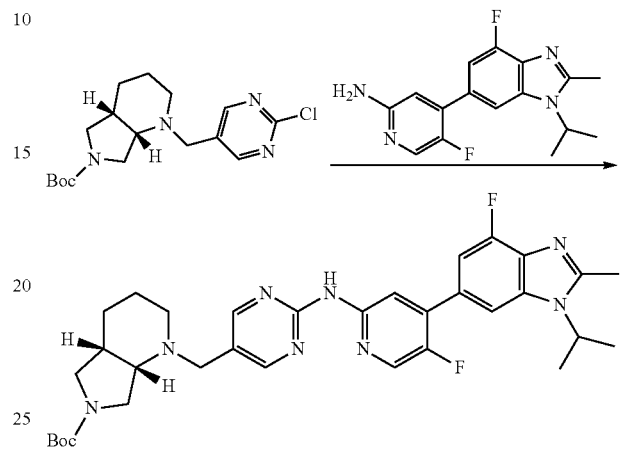

5-fluoro-4-(4-fluoro-1-isopropyl-2-methyl-1H-benzo[d] imidazol-6-yl)pyridin-2-amine (85.6 mg, 0.283 mmol), tert-butyl (cis)-1-((2-chloropyrimidin-5-yl)methyl)octahydro-6H-pyrrolo[3,4-b] pyridine-6-carboxylate (100 mg, 0.283 mmol), 2-dicyclohexylphosphino-2',4',6'-triisopropylbiphenyl (27 mg, 0.0566 mmol), cesium carbonate (276.6 mg, 0.849 mmol) and tris(dibenzylideneacetone)dipalladium (25.9 mg, 0.0283 mmol) were added to 1,4-dioxane (10 mL). Under the protection of nitrogen, the reaction was carried out at 110° C. for 6 h. The mixture was filtrated under suction, the filtrate was concentrated, and the crude product was purified by silica gel column chromatography (dichloromethane:methanol=50:1) to get the title compound (95 mg, yield: 54.2%).

(3) Preparation of N-(5-fluoro-4-(4-fluoro-1-isopropyl-2-methyl-1H-benzo[d]imidazol-6-yl) pyridin-2-yl)-5-(((cis)-octahydro-1H-pyrrolo[3,4-b]pyridin-1-yl)methyl)pyrimidin-2-amine

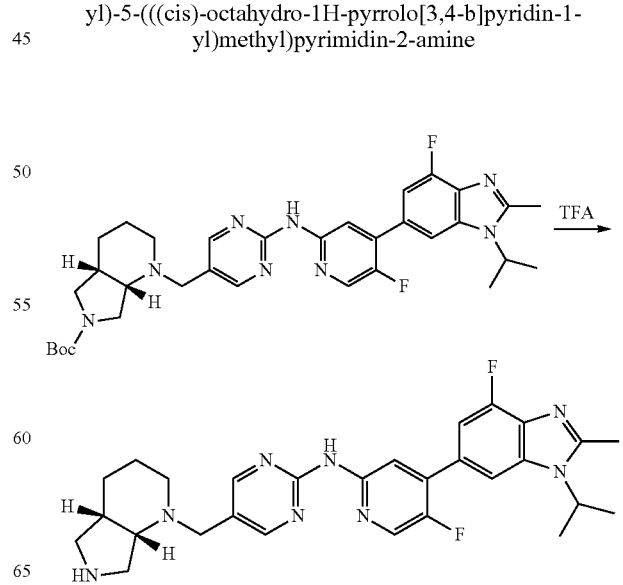

Tert-butyl (cis)-1-((2-((5-fluoro-4-(4-fluoro-1-isopropyl-2-methyl-1H-benzo[d]imidazol-6-yl) pyridin-2-yl)amino)pyrimidin-5-yl)methyl)octahydro-6H-pyrrolo[3,4-b]pyridine-6-carboxylate (95 mg, 0.154 mmol) was dissolved in dichloromethane (5 mL). Trifluoroacetic acid (1 mL) was added. The mixture was stirred at room temperature for 2 h. After the reaction, the mixture was washed with saturated sodium hydrogen carbonate solution. The organic phase was dried by anhydrous sodium sulfate, and concentrated. The crude product was separated by silica gel column chromatography (dichloromethane:methanol=10:1) to get the white solid title compound (40 mg, yield: 50.3%).

Molecular formula: $C_{28}H_{32}F_2N_8$ Molecular weight: 518.6 LC-MS (m/z): 519.3 (M+H$^+$)

$^1$H-NMR (400 MHz, CDCl$_3$) δ: 10.30 (s, 1H), 8.69 (d, J=6.0 Hz, 1H), 8.62 (s, 2H), 8.49 (d, J=2.4 Hz, 1H), 7.64 (s, 1H), 7.25 (d, J=10.8 Hz, 1H), 4.68-4.75 (m, 1H), 3.81-3.92 (m, 2H), 3.27-3.41 (m, 3H), 3.09 (d, J=13.6 Hz, 1H), 2.92 (s, 1H), 2.84 (d, J=10.8 Hz, 1H), 2.68 (s, 3H), 2.48-2.55 (m, 1H), 1.95-2.01 (m, 1H), 1.48-1.72 (m, 10H).

Example 25: Preparation of 5-(((1S,6R)-3,8-diazabicyclo[4.2.0]octan-8-yl)methyl)-N-(5-fluoro-4-(4-fluoro-1-isopropyl-2-methyl-1H-benzo[d]imidazol-6-yl)pyridin-2-yl)pyrimidin-2-amine (Compound 26)

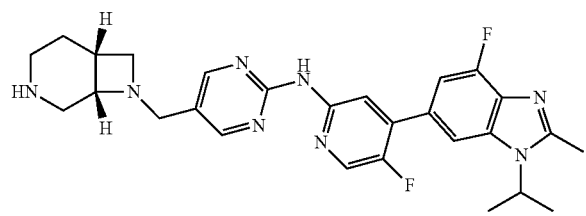 [SMILES: Cc1nc2c(F)cc(-c3cc(Nc4ncc(CN5C[C@H]6CCNC[C@H]65)cn4)ncc3F)cc2n1C(C)C]

(1) Preparation of tert-butyl (1S,6R)-8-((2-chloropyrimidin-5-yl)methyl)-3,8-diazabicyclo [4.2.0]octan-3-carboxylate

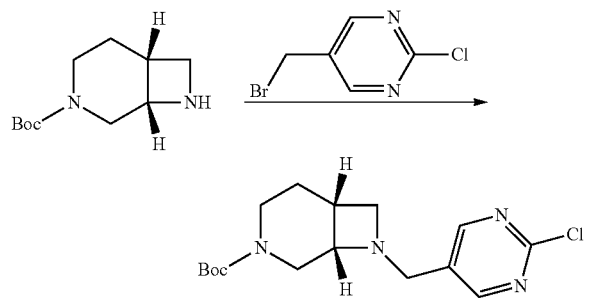

Tert-butyl (1S,6R)-3,8-diazabicyclo[4.2.0]octan-3-carboxylate (240 mg, 1.13 mmol) and 5-(bromomethyl)-2-chloropyrimidine (352 mg, 1.70 mmol) were added to tetrahydrofuran (20 mL), and triethylamine (228 mg, 2.26 mmol) was added. The mixture was stirred at room temperature for 16 h. The mixture was concentrated directly, and the crude product was purified by silica gel column chromatography (dichloromethane:methanol=50:1) to get the title compound (310 mg, yield: 81.0%).

(2) Preparation of tert-butyl (1S,6R)-8-((2-(5-fluoro-4-(4-fluoro-isopropyl-2-methyl-1H-benzo[d]imidazol-6-yl)pyridin-2-yl)amino)pyrimidin-5-yl)methyl)-3,8-diazabicyclo[4.2.0]octan-3-carboxylate

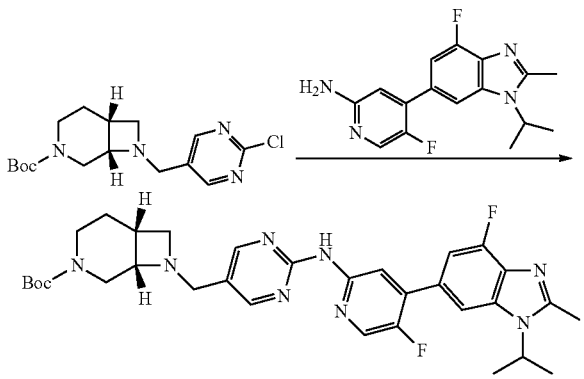

Tert-butyl (1S,6R)-8-((2-chloropyrimidin-5-yl)methyl)-3,8-diazabicyclo[4.2.0]octan-3-carboxylate (310 mg, 0.91 mmol), 5-fluoro-4-(4-fluoro-1-isopropyl-2-methyl-1H-benzo[d]imidazol-6-yl)pyridin-2-amine (275 mg, 0.91 mmol), 2-dicyclohexylphosphino-2',4',6'-triisopropylbiphenyl (86 mg, 0.18 mmol), tris(dibenzylideneacetone)dipalladium (82 mg, 0.09 mmol) and cesium carbonate (743 mg, 2.28 mmol) were weighed and added to 1,4-dioxane (40 mL). Under the protection of nitrogen, the mixture was heated up to 110° C. and reacted for 16 h. The mixture was filtrated under suction, the filtrate was concentrated, and the crude product was purified by silica gel column chromatography (dichloromethane:methanol=30:1) to get the title compound (340 mg, yield: 61.8%).

(3) Preparation of 5-(((1S,6R)-3,8-diazabicyclo[4.2.0]octan-8-yl)methyl)-N-(5-fluoro-4-(4-fluoro-1-isopropyl-2-methyl-1H-benzo[d]imidazol-6-yl)pyridin-2-yl)pyrimidin-2-amine

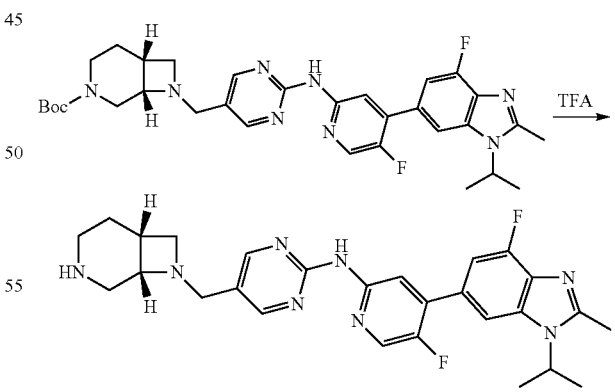

Tert-butyl (1S,6R)-8-((2-(5-fluoro-4-(4-fluoro-1-isopropyl-2-methyl-1H-benzo[d]imidazol-6-yl)pyridin-2-yl)amino)pyrimidin-5-yl)methyl)-3,8-diazabicyclo[4.2.0]octan-3-carboxylate (340 mg, 0.56 mmol) was weighed, and added to dichloromethane (8 mL). Trifluoroacetic acid (6 mL) was added under the condition of ice bath. After the addition, the mixture was warmed up to room temperature and stirred for 2 h. The reaction solution was concentrated, dissolved in dichloromethane (10 mL), neutralized with sodium hydrogen carbonate and concentrated. The crude product was separated by silica gel column chromatography (dichloromethane:methanol=10:1) to get the title compound (260 mg, yield: 92.1%).

Molecular formula: $C_{27}H_{30}F_2N_8$ Molecular weight: 504.6
LC-MS (m/z): 505.3 (M+H$^+$)

$^1$H-NMR (400 MHz, MeOD-d$_4$) δ: 8.54 (d, J=6.4 Hz, 1H), 8.52 (s, 2H), 8.27 (d, J=2.4 Hz, 1H), 7.78 (s, 1H), 7.24 (d, J=11.2 Hz, 1H), 4.87-4.92 (m, 1H), 3.76 (d, J=13.2 Hz, 1H), 3.38-3.47 (m, 3H), 3.35 (s, 3H), 3.18 (d, J=14.0 Hz, 1H), 2.91-3.07 (m, 3H), 2.84-2.88 (m, 1H), 2.48-2.52 (m, 1H), 2.17-2.21 (m, 1H), 2.01-2.07 (m, 1H), 1.69 (d, J=6.8 Hz, 6H).

Example 26: Preparation of N-(5-fluoro-4-(4-fluoro-1-isopropyl-2-methyl-1H-benzo[d] imidazol-6-yl)pyridin-2-yl)-5-(((1S,6R)-3-methyl-3,8-diazabicyclo[4.2.0]octan-8-yl)methyl)pyrimidin-2-amine (Compound 27)

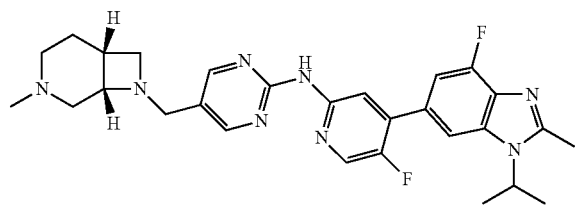

Preparation of N-(5-fluoro-4-(4-fluoro-1-isopropyl-2-methyl-1H-benzo[d]imidazol-6-yl) pyridin-2-yl)-5-(((1S,6R)-3-methyl-3,8-diazabicyclo[4.2.0]octan-8-yl)methyl)pyrimidin-2-amine

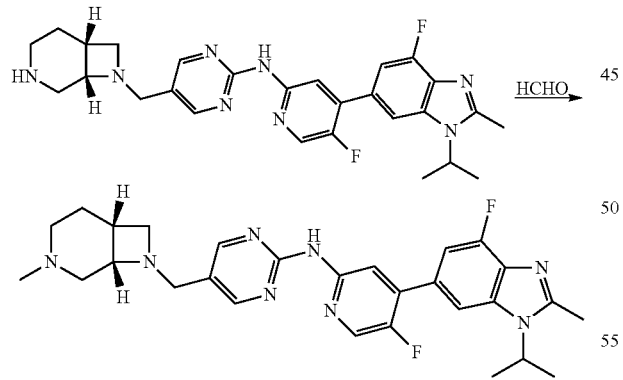

5-(((1S,6R)-3,8-diazabicyclo[4.2.0]octan-8-yl)methyl)-N-(5-fluoro-4-(4-fluoro-1-isopropyl-2-methyl-1H-benzo[d]imidazol-6-yl)pyridin-2-yl)pyrimidin-2-amine (100 mg, 0.20 mmol) was added to methanol (4 mL). Under the condition of ice bath, aqueous formaldehyde solution (0.5 mL, 37%) and sodium cyanoborohydride (100 mg, 1.6 mmol) were added. After the addition, the mixture was warmed up to the room temperature and stirred for 1 h. The reaction solution was subjected to preparative thin-layer chromatography (dichloromethane:methanol=10:1) to get the title compound (70 mg, yield: 68.1%).

Molecular formula: $C_{28}H_{32}F_2N_8$ Molecular weight: 518.6
LC-MS (m/z): 519.3 (M+H$^+$)

$^1$H-NMR (400 MHz, MeOD-d$_4$) δ: 8.55 (d, J=6.4 Hz, 1H), 8.52 (s, 2H), 8.25 (d, J=2.4 Hz, 1H), 7.79 (s, 1H), 7.27 (d, J=11.6 Hz, 1H), 4.85-4.89 (m, 1H), 3.68 (d, J=12.8 Hz, 1H), 3.39 (d, J=13.2 Hz, 1H), 3.23-3.28 (m, 1H), 2.91-2.93 (m, 2H), 2.78 (d, J=12.4 Hz, 2H), 2.69 (s, 3H), 2.27 (s, 3H), 2.17-2.25 (m, 1H), 1.96-2.02 (m, 3H), 1.88-1.95 (m, 1H), 1.69 (d, J=7.2 Hz, 6H).

Example 27: Preparation of 5-(((1R,6S)-3,8-diazabicyclo[4.2.0]octan-8-yl)methyl)-N-(5-fluoro-4-(4-fluoro-1-isopropyl-2-methyl-1H-benzo[d]imidazol-6-yl)pyridin-2-yl)pyrimidin-2-amine (Compound 28)

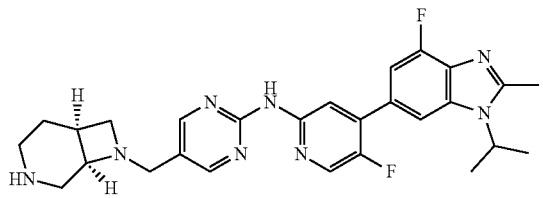 [SMILES: Cc1nc2c(F)cc(-c3cc(Nc4ncc(CN5C[C@@H]6CCNC[C@@H]65)cn4)ncc3F)cc2n1C(C)C]

(1) Preparation of tert-butyl (1R,6S)-8-((2-chloropyrimidin-5-yl)methyl)-3,8-diazabicyclo [4.2.0]octan-3-carboxylate

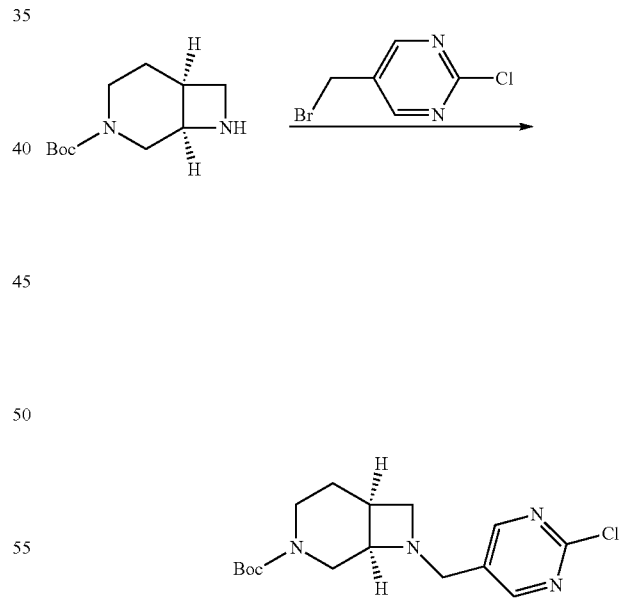

Tert-butyl (1R,6S)-3,8-diazabicyclo[4.2.0]octan-3-carboxylate (200 mg, 0.94 mmol) and 5-(bromomethyl)-2-chloropyrimidine (390 mg, 1.88 mmol) were added to tetrahydrofuran (10 mL), and triethylamine (285 mg, 2.82 mmol) was added. The mixture was stirred at room temperature for 16 h, and concentrated directly. The crude product was purified by silica gel column chromatography (petroleum ether:acetic ether=3:1) to get the title compound (195 mg, yield: 61.7%).

(2) Preparation of tert-butyl (1R,6S)-8-((2-((5-fluoro-4-(4-fluoro-1-isopropyl-2-methyl-1H-benzo[d]imidazol-6-yl)pyridin-2-yl)amino)pyrimidin-5-yl)methyl)-3,8-diazabicyclo[4.2.0]octan-3-carboxylate

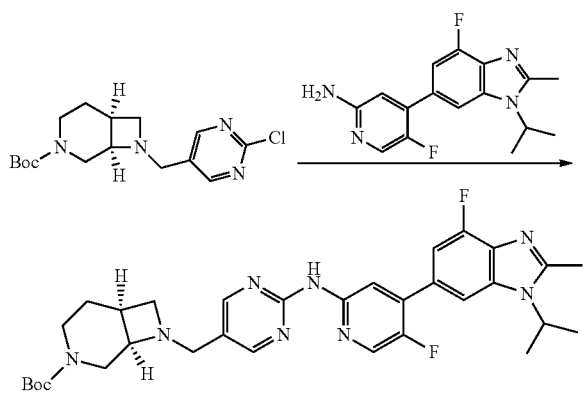

Tert-butyl (1R,6S)-8-((2-chloropyrimidin-5-yl)methyl)-3,8-diazabicyclo[4.2.0]octan-3-carboxylate (100 mg, 0.30 mmol), 5-fluoro-4-(4-fluoro-1-isopropyl-2-methyl-1H-benzo[d]imidazol-6-yl)pyridin-2-amine (90 mg, 0.30 mmol), 2-dicyclohexylphosphino-2',4',6'-triisopropylbiphenyl (30 mg, 0.06 mmol), tris(dibenzylideneacetone)dipalladium (28 mg, 0.03 mmol) and cesium carbonate (295 mg, 0.91 mmol) were weighed and added to 1,4-dioxane (5 mL). Under the protection of nitrogen, the mixture was heated up to 110° C. and reacted for 16 h. The mixture was filtrated under suction, the filtrate was concentrated, and the crude product was purified by silica gel column chromatography (dichloromethane:methanol=30:1) to get the title compound (104 mg, yield: 56.7%).

(3) Preparation of 5-(((1R,6S)-3,8-diazabicyclo[4.2.0]octan-8-yl)methyl)-N-(5-fluoro-4-(4-fluoro-1-isopropyl-2-methyl-1H-benzo[d]imidazol-6-yl)pyridin-2-yl)pyrimidin-2-amine

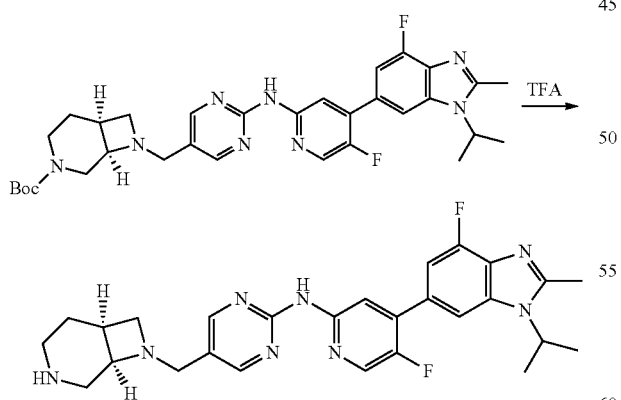

Tert-butyl (1R,6S)-8-((2-(5-fluoro-4-(4-fluoro-1-isopropyl-2-methyl-1H-benzo[d]imidazol-6-yl) pyridin-2-yl)amino)pyrimidin-5-yl)methyl)-3,8-diazabicyclo[4.2.0]octan-3-carboxylate (104 mg, 0.17 mmol) was weighed, and added to dichloromethane (8 mL). Trifluoroacetic acid (1 mL) was added under the condition of ice bath. After the addition, the mixture was warmed up to room temperature and stirred for 2 h. The reaction solution was distilled under rotation, dissolved in dichloromethane (10 mL), neutralized with sodium hydrogen carbonate and concentrated. The crude product was separated by silica gel column chromatography (dichloromethane:methanol=15:1) to get the title compound (44 mg, yield: 52.9%).

Molecular formula: $C_{27}H_{30}F_2N_8$ Molecular weight: 504.6
LC-MS (m/z): 505.3 (M+H$^+$)
$^1$H-NMR (400 MHz, CDCl$_3$) δ: 8.64 (d, J=6.0 Hz, 1H), 8.44 (s, 2H), 8.23 (d, J=2.4 Hz, 1H), 7.96 (s, 1H), 7.63 (s, 1H), 7.26-7.29 (m, 1H), 4.68-4.83 (m, 1H), 3.60-3.63 (m, 1H), 3.31-3.40 (m, 1H), 2.95-3.09 (m, 3H), 2.83-2.93 (m, 1H), 2.75-2.80 (m, 1H), 2.69 (s, 3H), 2.60-2.65 (m, 1H), 2.20-2.40 (m, 2H), 1.85-2.05 (m, 2H), 1.69 (d, J=6.8 Hz, 6H).

Example 28: Preparation of N-(5-fluoro-4-(4-fluoro-1-isopropyl-2-methyl-1H-benzo[d]imidazol-6-yl)pyridin-2-yl)-5-(((1R,6S)-3-methyl-3,8-diazabicyclo[4.2.0]octan-8-yl)methyl)pyrimidin-2-amine (Compound 29)

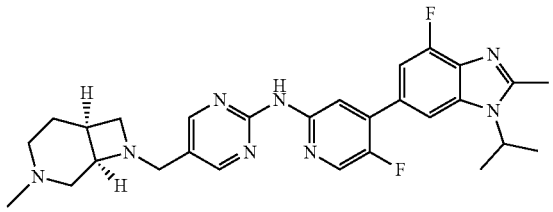

(1) Preparation of tert-butyl (1R,6S)-8-(2-chloropyrimidin-5-yl)methyl)-3,8-diazabicyclo[4.2.0]octan-3-carboxylate

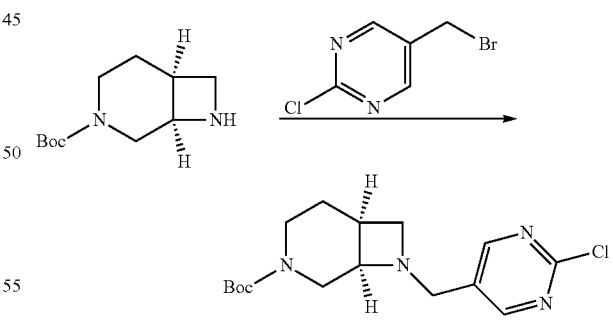

Tert-butyl (1R,6S)-3,8-diazabicyclo[4.2.0]octan-3-carboxylate (100 mg, 0.47 mmol) and 5-(bromomethyl)-2-chloropyrimidine (97.5 mg, 0.47 mmol) were dissolved in anhydrous tetrahydrofuran (10 mL), and triethylamine (71.2 mg, 0.71 mmol) was added dropwisely. The reaction was carried out at room temperature for 4 h. The reaction mixture was concentrated, and purified by silica gel column chromatography (the eluent was dichloromethane:methanol=30:1) to get the title compound (97.3 mg, yield: 61%).

(2) Preparation of tert-butyl (1R,6S)-8-((2-(5-fluoro-4-(4-fluoro-1-isopropyl-2-methyl-1H-benzo[d]imidazol-6-yl)pyridin-2-yl)amino)pyrimidin-5-yl)methyl)-3,8-diazabicyclo[4.2.0]octan-3-carboxylate

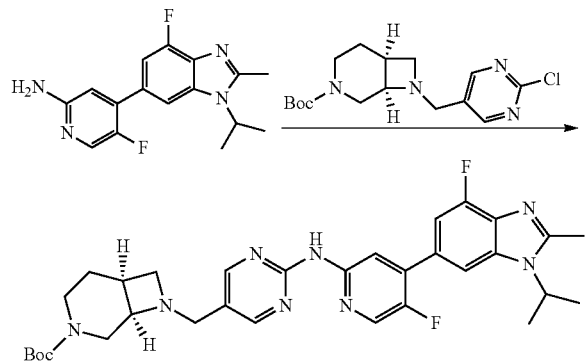

5-Fluoro-4-(4-fluoro-1-isopropyl-2-methyl-1H-benzo[d]imidazol-6-yl)pyridin-2-amine (84.6 mg, 0.28 mmol) and tert-butyl (1R,6S)-8-((2-chloropyrimidin-5-yl)methyl)-3,8-diazabicyclo[4.2.0]octan-3-carboxylate (95 mg, 0.28 mmol) were dissolved in 1,4-dioxane (15 mL), and tris(dibenzylideneacetone)dipalladium (25.6 mg, 0.028 mmol), 2-dicyclohexylphosphino-2',4',6'-triisopropylbiphenyl (26.7 mg, 0.056 mmol) and cesium carbonate (273.7 mg, 0.84 mmol) were added. Under the protection of nitrogen, the mixture was heated to 110° C. and reacted for 8 h. The mixture was cooled to room temperature, and concentrated. Water (30 mL) and acetic ether (50 mL) were added to separate the organic phase from the water phase. The water phase was extracted with acetic ether (50 mL×2), and the organic phases were combined and washed with saturated NaCl solution, dried by anhydrous sodium sulfate, and concentrated. The crude product was purified by silica gel column chromatography (the eluent was dichloromethane:methanol=20:1) to get the title compound (88.2 mg, yield: 52%).

(3) Preparation of 5-(1R,6S)-3,8-diazabicyclo[4.2.0]octan-8-yl)methyl)-N-(5-fluoro-4-(4-fluoro-1-isopropyl-2-methyl-1H-benzo[d]imidazol-6-yl)pyridin-2-yl)pyrimidin-2-amine

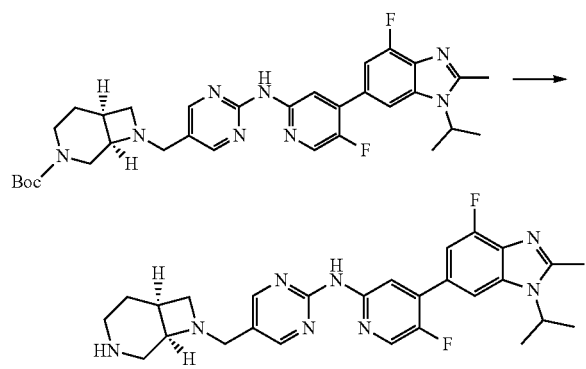

Tert-butyl (1R,6S)-8-((2-((5-fluoro-4-(4-fluoro-1-isopropyl-2-methyl-1H-benzo[d]imidazol-6-yl)pyridin-2-yl)amino)pyrimidin-5-yl)methyl)-3,8-diazabicyclo[4.2.0]octan-3-carboxylate (88 mg, 0.146 mmol) was added to dichloromethane (5 mL). Trifluoroacetic acid (1 mL) was added. The mixture was stirred at room temperature for 3 h. The solvent was removed by reduced pressure distillation. The residue was adjusted by saturated sodium hydrogen carbonate solution to pH=8, and extracted with a mixed solution of dichloromethane:methanol (10:1) (20 mL×3). The organic phases were combined, dried by anhydrous sodium sulfate, and concentrated to get the title compound (100 mg crude product), which was directly used in the next step without purification.

(4) Preparation of N-(5-fluoro-4-(4-fluoro-1-isopropyl-2-methyl-1H-benzo[d]imidazol-6-yl) pyridin-2-yl)-5-(((1R,6S)-3-methyl-3,8-diazabicyclo[4.2.0]octan-8-yl)methyl)pyrimidin-2-amine

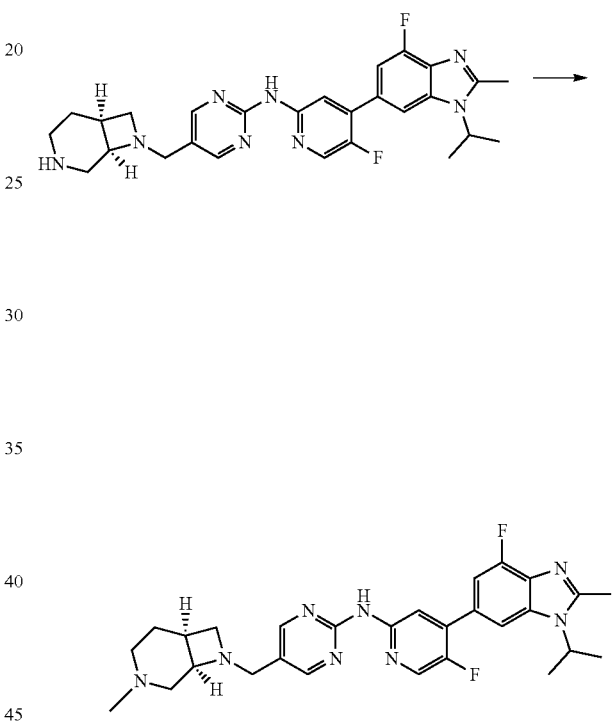

5-(((1R,6S)-3,8-diazabicyclo[4.2.0]octan-8-yl)methyl)-N-(5-fluoro-4-(4-fluoro-1-isopropyl-2-methyl-1H-benzo[d]imidazol-6-yl)pyridin-2-yl)pyrimidin-2-amine (100 mg crude product) was dissolved in methanol (5 mL), and aqueous formaldehyde solution (37%, 118 mg, 1.46 mmol) was added at room temperature. The reaction was carried out for 2 h, and sodium cyanoborohydride (91.7 g, 1.46 mmol) was added to the solution and further stirred at room temperature for 1 h. After the reaction, petroleum ether (50 mL) was added to the reaction solution, and the solution was purified by silica gel column chromatography (dichloromethane:methanol=10:1) to get the title compound (20 mg, two-step yield: 26.4%).

Molecular formula: $C_{28}H_{32}F_2N_8$ Molecular weight: 518.6
LC-MS (m/z): 519.3 (M+H$^+$)
$^1$H-NMR (400 MHz, MeOD-d$_4$) δ: 8.55 (d, J=6.0 Hz, 1H), 8.52 (s, 2H), 8.27 (d, J=2.4 Hz, 1H), 7.78 (s, 1H), 7.25 (d, J=11.2 Hz, 1H), 4.86-4.92 (m, 1H), 3.68 (d, J=13.2 Hz, 1H), 3.37 (d, J=13.2 Hz, 1H), 3.27-3.31 (m, 1H), 2.89-2.95 (m, 2H), 2.85 (d, J=11.6 Hz, 2H), 2.68 (s, 3H), 2.33 (s, 3H), 2.23-2.25 (m, 1H), 2.01-2.07 (m, 5H), 1.69 (d, J=6.8 Hz, 6H).

Example 29: Preparation of N-(5-fluoro-4-(4-fluoro-1-isopropyl-2-methyl-1H-benzo[d] imidazol-6-yl)pyridin-2-yl)-5-(((cis)-6-methyl-3,8-diazabicyclo[4.2.0]octan-8-yl)methyl)pyrimidin-2-amine (Compound 30)

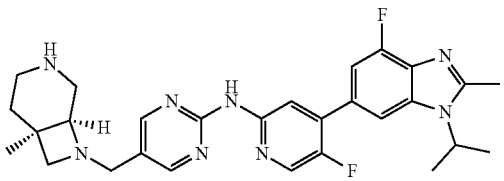

(1) Preparation of tert-butyl (cis)-8-((2-chloropyrimidin-5-yl)methyl)-6-methyl-3,8-diazabicyclo[4.2.0]octan-3-carboxylate

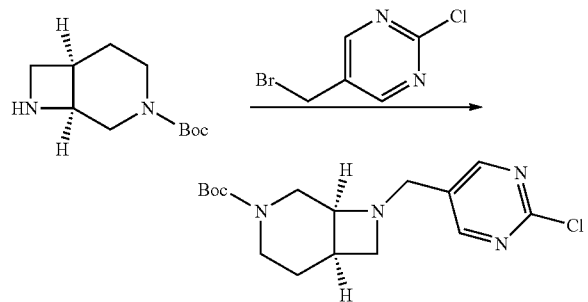

Triethylamine (336 mg, 3.33 mmol) was added to a solution of tert-butyl (cis)-6-methyl-3,8-diazabicyclo[4.2.0]octan-3-carboxylate (250 mg, 1.11 mmol) and 5-(bromomethyl)-2-chloropyrimidine (660 mg, 3.19 mmol) in tetrahydrofuran (20 mL), and the mixture was stirred at 20° C. for 5 h. After the reaction, the mixture was concentrated under reduced pressure. The residue was separated by column chromatography (petroleum ether:acetic ether=2:1) to get the product (200 mg, yield: 51.2%).

(2) Preparation of tert-butyl (cis)-8-((2-((5-fluoro-4-(4-fluoro-1-isopropyl-2-methyl-1H-benzo [d]imidazol-6-yl)pyridin-2-yl)amino)pyrimidin-5-yl)methyl)-6-methyl-3,8-diazabicyclo[4.2.0]octan-3-carboxylate

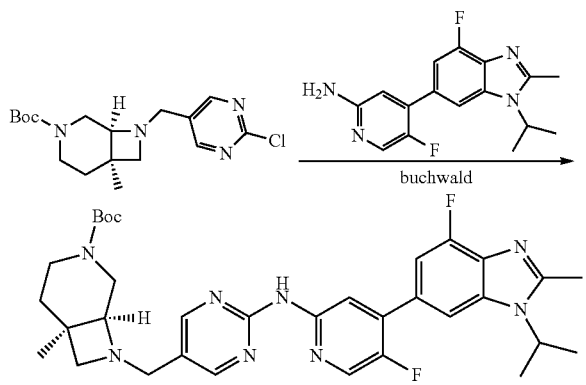

Tert-butyl (cis)-8-((2-chloropyrimidin-5-yl)methyl)-6-methyl-3,8-diazabicyclo[4.2.0]octan-3-carboxylatye (200 mg, 0.57 mmol), 5-fluoro-4-(4-fluoro-1-isopropyl-2-methyl-1H-benzo[d] imidazol-6-yl)pyridin-2-amine (206 mg, 0.68 mmol), cesium carbonate (370 mg, 1.14 mmol), tris(dibenzylideneacetone)dipalladium (26 mg, 0.029 mmol) and 2-dicyclohexylphosphino-2',4',6'-triisopropylbiphenyl (27 mg, 0.057 mmol) were added to 1,4-dioxane (5 mL). Under the protection of nitrogen, the mixture was heated in an 110° C. oil bath for 8 h. After the reaction, the reaction solution was concentrated and purified by silica gel column chromatography (dichloromethane:methanol=10:1) to get the product (50 mg, yield: 14.2%).

(3) Preparation of N-(5-fluoro-4-(4-fluoro-1-isopropyl-2-methyl-1H-benzo[d]imidazol-6-yl) pyridin-2-yl)-5-(((cis)-6-methyl-3,8-diazabicyclo[4.2.0]octan-8-yl)methyl)pyrimidin-2-amine

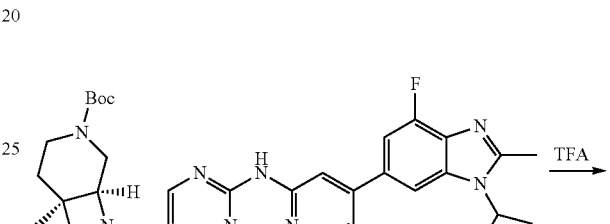

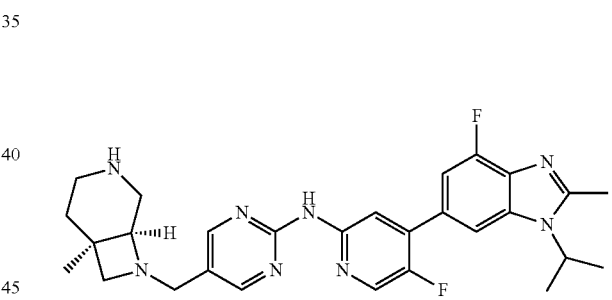

Tert-butyl (cis)-8-((2-((5-fluoro-4-(4-fluoro-1-isopropyl-2-methyl-1H-benzo[d]imidazol-6-yl) pyridin-2-yl)amino) pyrimidin-5-yl)methyl)-6-methyl-3,8-diazabicyclo[4.2.0]octan-3-carboxylate (50 mg, 0.08 mmol) was added to dichloromethane (5 mL). Trifluoroacetic acid (3 mL) was added dropwisely to the reaction system. The mixture was stirred at 20° C. for 5 h. After the reaction, the reaction solution was concentrated under reduced pressure, the residue was dissolved in dichloromethane, and triethaylamine (2 mL) was added dropwisely. After further concentration by reduced pressure distillation, the residue was separated by column chromatography (dichloromethane:methanol=5:1) to get the product (12 mg, yield: 28.6%).

Molecular formula: $C_{28}H_{32}F_2N_8$ Molecular weight: 518.6 LC-MS (m/z): 519.3 (M+H$^+$)

$^1$H-NMR (400 MHz, MeOD) δ: 8.52 (brs, 3H), 8.27 (brs, 1H), 7.79 (brs, 1H), 7.27 (brs, 1H), 4.60-4.68 (m, 1H), 3.73-3.81 (m, 1H), 3.43-3.46 (m, 1H), 3.06-3.14 (m, 3H), 2.90-3.03 (m, 2H), 2.68-2.73 (m, 4H), 2.19 (m, 1H), 1.82-1.85 (m, 1H), 1.69 (s, 6H), 0.80-0.90 (m, 2H).

Example 30: Preparation of N-(5-fluoro-4-(4-fluoro-1-isopropyl-2-methyl-1H-benzo[d] imidazol-6-yl)pyridin-2-yl)-5-(((cis)-1-methyl-3,7-diazabicyclo[4.2.0]octan-7-yl)methyl)pyrimidin-2-amine (Compound 31)

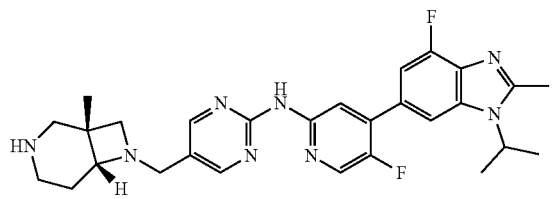 [SMILES: Cc1nc2c(F)cc(-c3cc(Nc4ncc(CN5C[C@@]6(C)CNCC[C@@H]56)cn4)ncc3F)cc2n1C(C)C]

(1) Preparation of tert-butyl (cis)-7-((2-chloropyrimidin-5-yl)methyl)-1-methyl-3,7-diazabicyclo[4.2.0]octan-3-carboxylate

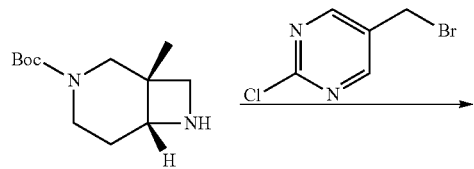

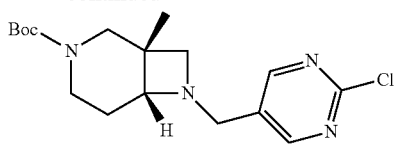

Tert-butyl (cis)-1-methyl-3,7-diazabicyclo[4.2.0]octan-3-carboxylate (0.12 g, 0.53 mmol) and triethylamine (0.11 g, 1.09 mmol) were dissolved in tetrahydrofuran (5 mL), and 5-(bromomethyl)-2-chloropyrimidine (0.13 g, 0.63 mmol) was added. The reaction was carried out under stirring at 25° C. for 18 h. The reaction solution was concentrated, and purified by silica gel column chromatography (petroleum ether:acetic ether=5:1) to get the yellow solid title compound (0.15 g, yield: 80.2%).

(2) Preparation of tert-butyl (cis)-7-((2-((5-fluoro-4-(4-fluoro-isopropyl-2-methyl-1H-benzo [d]imidazol-6-yl)pyridin-2-yl)amino)pyrimidin-5-yl)methyl)-1-methyl-3,7-diazabicyclo[4.2.0]octan-3-carboxylate

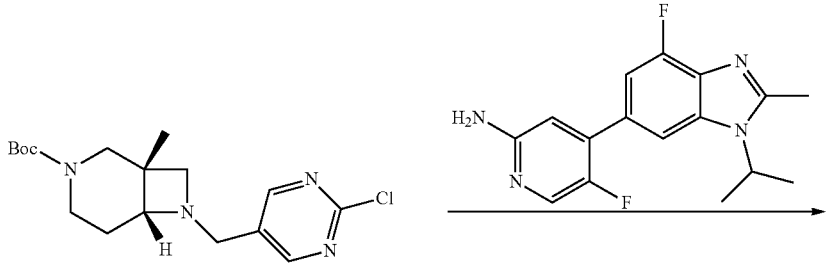

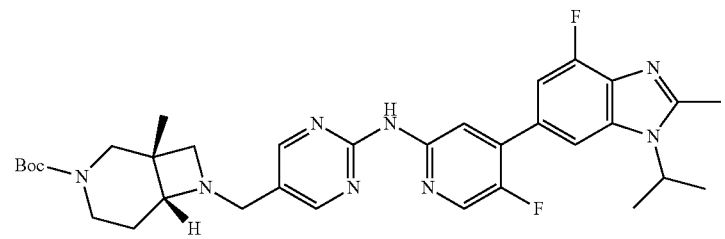

5-Fluoro-4-(4-fluoro-1-isopropyl-2-methyl-1H-benzo[d] imidazol-6-yl)pyridin-2-amine (0.1 g, 0.33 mmol) and tert-butyl (cis)-7-((2-chloropyrimidin-5-yl)methyl)-1-methyl-3, 7-diazabicyclo [4.2.0]octan-3-carboxylate (0.11 g, 0.31 mmol) were dissolved in 1,4-dioxane (10 mL), and tris (dibenzylideneacetone)dipalladium (0.03 g, 0.03 mmol), 2-dicyclohexylphosphino-2',4',6'-triisopropylbiphenyl(0.02 g, 0.04 mmol) and cesium carbonate (0.2 g, 0.61 mmol) were added. Under the protection of nitrogen, the mixture was heated to 100° C. and reacted under stirring for 6 h. The reaction solution was concentrated and purified by silica gel column chromatography (dichloromethane:methanol=50:1) to get the yellow solid title compound (0.12 g, yield: 62.2%).

(3) Preparation of N-(5-fluoro-4-(4-fluoro-1-isopropyl-2-methyl-1H-benzo[d]imidazol-6-yl) pyridin-2-yl)-5-(((cis)-1-methyl-3,7-diazabicyclo[4.2.0]octan-7-yl)methyl)pyrimidin-2-amine Example 31: Preparation of ((((1S,5S)-3,6-diazabicyclo[3.2.0]heptan-3-yl)methyl)-N-(5-fluoro-4-(4-fluoro-1-isopropyl-2-methyl-1H-benzo[d]imidazol-6-yl)pyridin-2-yl)pyrimidin-2-amine (Compound 32)

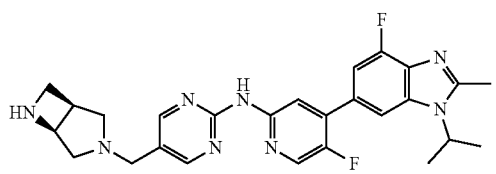 [SMILES: Cc1nc2c(F)cc(-c3cc(Nc4ncc(CN5C[C@@H]6CN[C@@H]6C5)cn4)ncc3F)cc2n1C(C)C]

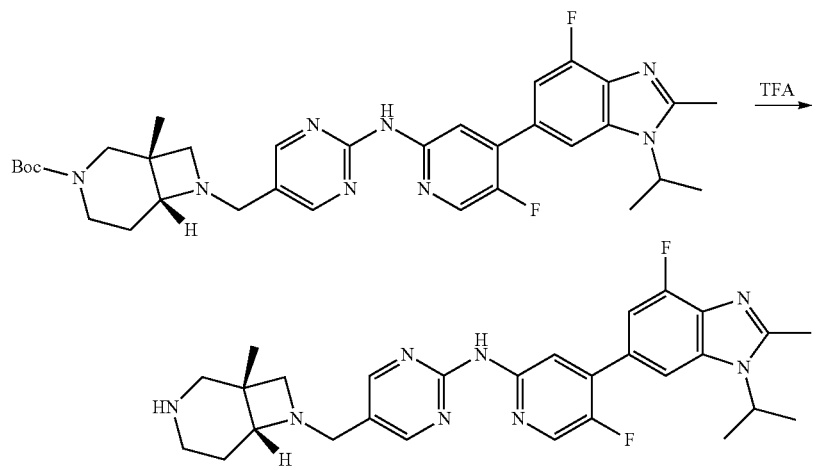

Tert-butyl (cis)-7-((2-((5-fluoro-4-(4-fluoro-1-isopropyl-2-methyl-1H-benzo[d]imidazol-6-yl) pyridin-2-yl)amino) pyrimidin-5-yl)methyl)-1-methyl-3,7-diazabicyclo[4.2.0] octan-3-carboxylate (0.12 g, 0.19 mmol) was dissolved in dichloromethane (5 mL). Trifluoroacetic acid (3 mL) was added. The mixture was reacted at room temperature under stirring for 3 h. The reaction solution was concentrated. Acetic ether (30 mL) was added. Saturated sodium hydrogen carbonate aqueous solution (10 mL×2) was used for washing. The organic phase was dried by anhydrous sodium sulfate, and filtrated. The filtrate was concentrated and then subjected to silica gel column chromatography (dichloromethane:methanol=20:1) to get the yellow solid title compound (58 mg, yield: 47.2%).

Molecular formula: $C_{28}H_{32}F_2N_8$ Molecular weight: 518.62 LC-MS (m/z): 519.3 (M+H$^+$)

$^1$H-NMR (400 MHz, DMSO-d$_6$) δ: 10.07 (s, 1H), 9.08 (brs, 1H), 8.46 (s, 2H), 8.42 (d, J=6.0 Hz, 1H), 8.35 (d, J=1.6 Hz, 1H), 7.75 (s, 1H), 7.23 (d, J=11.6 Hz, 1H), 4.77-4.85 (m, 1H), 3.62 (d, J=12.8 Hz, 1H), 3.14 (d, J=5.2 Hz, 1H), 2.93-3.08 (m, 6H), 2.62 (s, 3H), 2.54 (d, J=6.4 Hz, 1H), 1.72-1.79 (m, 1H), 1.57 (d, J=7.2 Hz, 6H), 1.47-1.56 (m, 1H), 1.15-1.29 (m, 4H).

(1) Preparation of tert-butyl (1R,5S)-3-((2-chloropyrimidin-5-yl)methyl)-3,6-diazabicyclo [3.2.0]heptan-6-carboxylate

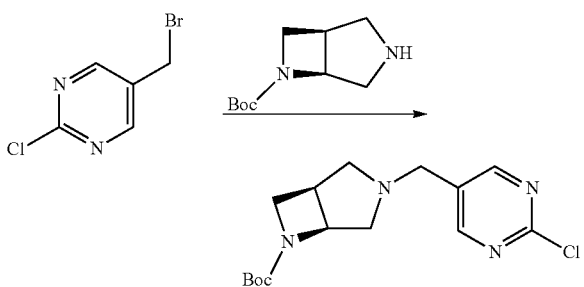

Tert-butyl (1R,5S)-3,6-diazabicyclo[3.2.0]heptan-6-carboxylate (350.0 mg, 1.77 mmol) was dissolved in tetrahydrofuran (15 mL), and triethylamine (715.0 mg, 7.08 mmol) and 5-(bromomethyl)-2-chloropyrimidine (734.0 mg, 3.54 mmol) were added. The mixture was further stirred for 2 h. After the reaction was completed, the reaction solution was concentrated, and acetic ether (50 mL) and water (30 mL) were added to separate the phases. The water phase was extracted with acetic ether (30 mL), and the organic phases were combined, concentrated, and the residues was separated by silica gel column chromatography (petroleum ether:acetic ether=1:1) to get the title compound (500 mg, yield: 87.0%).

(2) Preparation of tert-butyl (1R,5S)-3-((2-((5-fluoro-4-(4-fluoro-1-isopropyl-2-methyl-1H-benzo[d]imidazol-6-yl)pyridin-2-yl)amino)pyrimidin-5-yl)methyl)-3,6-diazabicyclo[3.2.0]octan-6-carboxylate

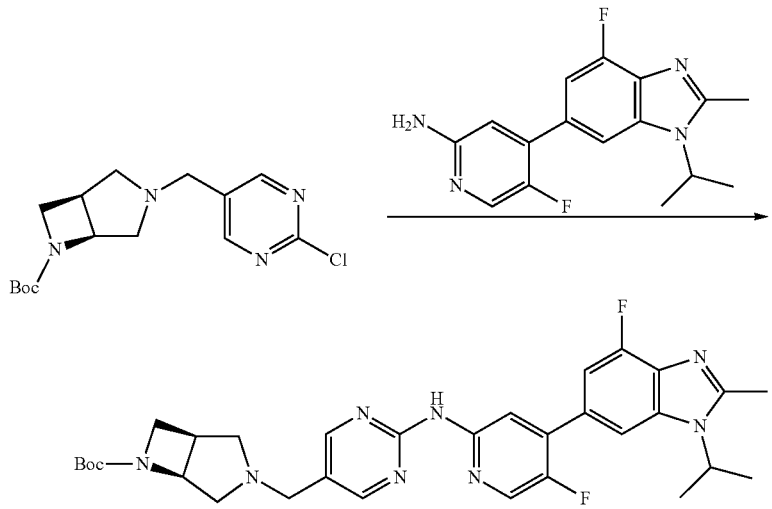

Tert-butyl (1R,5S)-3-((2-chloropyrimidin-5-yl)methyl)-3,6-diazabicyclo[3.2.0]heptan-6-carboxylate (500.0 mg, 1.54 mmol), and 5-fluoro-4-(4-fluoro-1-isopropyl-2-methyl-1H-benzo[d] imidazol-6-yl)pyridine-2-amine (465.5 mg, 1.54 mmol) were dissolved in 1,4-dioxane (15 mL), and cesium carbonate (1.0 g, 3.08 mmol), tris(dibenzylideneacetone)dipalladium (141.0 mg, 0.154 mmol) and 2-dicyclohexylphosphino-2',4',6'-triisopropylbiphenyl (147.0 mg, 0.308 mmol) were added. Under the protection of nitrogen, the mixture was heated to 110° C. and reacted for 16 h. The reaction solution was filtrated. The filtrate was concentrated, and the residue was separated by silica gel column chromatography (dichloromethane:methanol=10:1) to get the title compound (400 mg, yield: 44.0%).

(3) Preparation of (((1S,5S)-3,6-diazabicyclo[3.2.0]heptan-3-yl)methyl)-N-(5-fluoro-4-(4-fluoro-1-isopropyl-2-methyl-1H-benzo[d]imidazol-6-yl)pyridin-2-yl)pyrimidin-2-amine

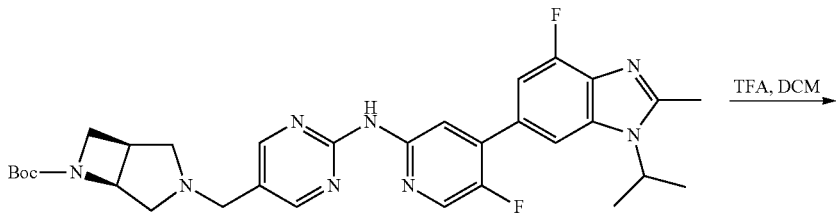

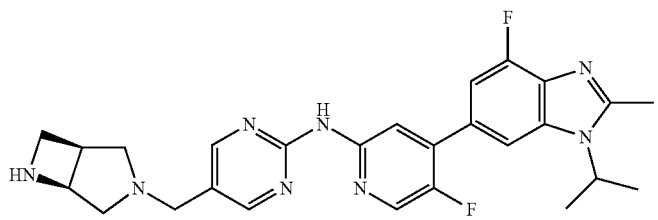

Tert-butyl (1R,5S)-3-((2-((5-fluoro-4-(4-fluoro-1-isopropyl-2-methyl-1H-benzo[d]imidazol-6-yl)pyridin-2-yl)amino)pyrimidin-5-yl)methyl)-3,6-diazabicyclo[3.2.0]octan-6-carboxylate (300 mg, 0.508 mmol) was dissolved in the mixed solution of dichloromethane (5 mL) and trifluoroacetic acid (2 mL). The mixture was stirred at 20° C. for 30 min. The mixture was concentrated, and dichloromethane (10 mL) was added. After further concentration, the residue was separated by silica gel column chromatography (dichloromethane:methanol=10:1) to get the title compound (160 mg, yield: 64.2%).

Molecular formula: $C_{26}H_{28}F_2N_8$ Molecular weight: 490.6
LC-MS (m/z): 491.3 (M+H$^+$)
$^1$H-NMR (400 MHz, DMSO-d$_6$) δ: 10.04 (s, 1H), 8.58 (s, 2H), 8.44 (d, J=6.0 Hz, 1H), 8.36 (d, J=2.4 Hz, 1H), 7.75 (s, 1H), 7.22 (d, J=11.2 Hz, 1H), 4.81-4.86 (m, 1H), 4.62-4.67 (m, 1H), 3.87-3.92 (m, 1H), 3.74 (d, J=14.0 Hz, 1H), 3.63 (d, J=13.6 Hz, 1H), 3.49-3.55 (m, 2H), 3.18-3.21 (m, 1H), 3.05-3.11 (m, 1H), 2.96 (d, J=8.0 Hz, 1H), 2.62 (s, 3H), 2.11-2.19 (m, 2H), 1.57 (d, J=7.2 Hz, 6H).

Example 32: Preparation of N-(5-fluoro-4-(4-fluoro-1-isopropyl-2-methyl-1H-benzo [d]imidazol-6-yl)pyridin-2-yl)-5-(((1R,5S)-6-methyl-3,6-diazabicyclo[3.2.0]heptan-3-yl)methyl)pyrimidin-2-amine (Compound 33)

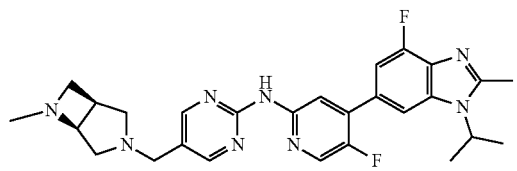

(1) Preparation of N-(5-fluoro-4-(4-fluoro-1-isopropyl-2-methyl-1H-benzo[d]imidazol-6-yl) pyridin-2-yl)-5-(((1R,5S)-6-methyl-3,6-diazabicyclo[3.2.0]heptan-3-yl)methyl)pyrimidin-2-amine

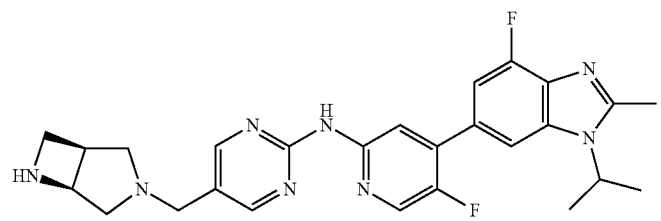

5-(((1S,5S)-3,6-diazabicyclo[3.2.0]heptan-3-yl)methyl)-N-(5-fluoro-4-(4-fluoro-1-isopropyl-2-methyl-1H-benzo[d]imidazol-6-yl)pyridin-2-yl)pyrimidin-2-amine (100 mg, 0.204 mmol) was dissolved in methanol (5 mL), and aqueous formaldehyde solution (0.5 mL) was added. The mixture was stirred for 0.5 h, and sodium cyanoborohydride (64.0 mg, 1.01 mmol) was added to the solution and further stirred for 0.5 h. The sample was separated directly by silica gel column chromatography (dichloromethane:methanol=5:1) to get the title compound (20 mg, yield: 19.4%).

Molecular formula: $C_{27}H_{30}F_2N_8$ Molecular weight: 504.6
LC-MS (m/z): 505.2 (M+H$^+$)
$^1$H-NMR (400 MHz, MeOD) δ: 8.60 (s, 2H), 8.55 (d, J=6.0 Hz, 1H), 8.26 (d, J=2.4 Hz, 1H), 7.79 (s, 1H), 7.26 (d, J=11.2 Hz, 1H), 4.90-4.93 (m, 1H), 4.62-4.71 (m, 1H), 3.91-3.98 (m, 1H), 3.82 (d, J=13.6 Hz, 1H), 3.63 (d, J=13.6 Hz, 1H), 3.23-3.25 (m, 1H), 3.04-3.06 (m, 1H), 2.88 (brs, 3H), 2.69 (s, 3H), 2.35-2.38 (m, 1H), 2.18-2.26 (m, 2H), 2.02-2.04 (m, 1H), 1.69 (d, J=7.2 Hz, 6H).

Example 33: Preparation of 5-(((1R,5R)-3,6-diazabicyclo[3.2.0]heptan-3-yl)methyl)-N-(5-fluoro-4-(4-fluoro-1-isopropyl-2-methyl-1H-benzo[d]imidazol-6-yl)pyridin-2-yl)pyrimidin-2-amine (Compound 34)

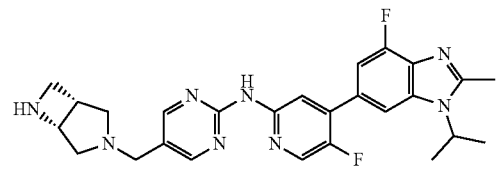 [SMILES: Cc1nc2c(F)cc(-c3cc(Nc4ncc(CN5C[C@H]6CN[C@H]6C5)cn4)ncc3F)cc2n1C(C)C]

(1) Preparation of tert-butyl (1S,5R)-3-((2-chloropyrimidin-5-yl)methyl)-3,6-diazabicyclo [3.2.0]heptan-6-carbonxylate

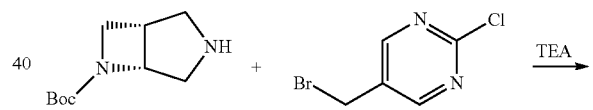

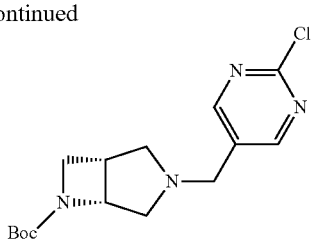

Triethylamine (0.77 g, 7.57 mmol) was added to a solution of tert-butyl (1S,5R)-3,6-diazabicyclo[3.2.0]heptan-6-carboxylate (500 mg, 2.52 mmol) and 5-bromomethyl-2-chloropyrimidine (784 mg, 3.78 mmol) in tetrahydrofuran (20 mL). The mixture was stirred at room temperature for 5 h. After the reaction, the solution was concentrated under reduced pressure, and was separated by column chromatography (petroleum ether:acetic ether=2:1) to get the product (750 mg, yield: 91.6%).

(2) Preparation of tert-butyl (1S,5R)-3-((2-((5-fluoro-4-(4-fluoro-1-isopropyl-2-methyl-1H-benzo[d]imidazol-6-yl)pyridin-2-yl)amino)pyrimidin-5-yl)methyl)-3,6-diazabicyclo[3.2.0]heptan-6-carboxylate

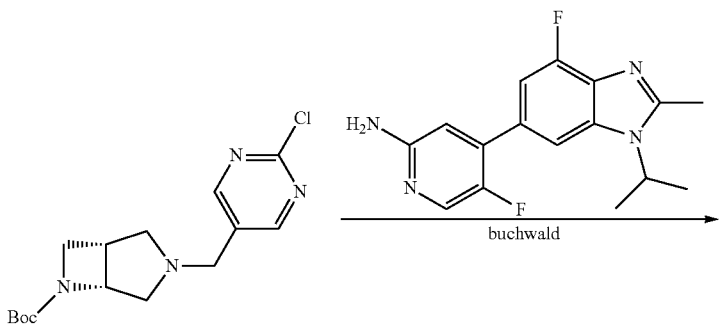

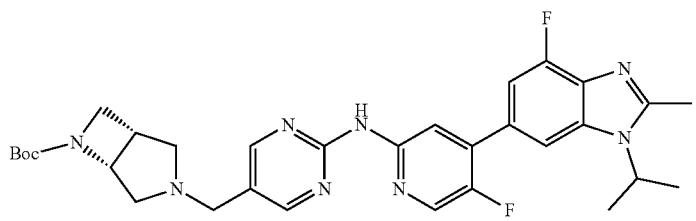

Tert-butyl (1S,5R)-3-((2-chloropyrimidinyl-5-yl)methyl)-3,6-diazabicyclo[3.2.0]heptan-6-carboxylate (200 mg, 0.62 mmol), 5-fluoro-4-(4-fluoro-1-isopropyl-2-methyl-1H-benzo[d]imidazol-6-yl)pyridin-2-amine (223 mg, 0.78 mmol), cesium carbonate (401 mg, 1.23 mmol), Pd$_2$(dba)$_3$ (11 mg, 0.012 mmol), and X-Phos (11 mg, 0.024 mmol) were added to 1, 4-dioxane (5 mL). Under the protection of nitrogen, the mixture was reacted at 110° C. for 8 h. After the reaction, the mixture was concentrated under reduced pressure, and separated by column chromatography (dichloromethane:methanol=10:1) to get the product (210 mg, yield: 57.7%).

(3) Preparation of 5-(((1R,5R)-3,6-diazabicyclo [3.2.0]heptan-3-yl)methyl)-N-(5-fluoro-4-(4-fluoro-1-isopropyl-2-methyl-1H-benzo[d]imidazol-6-yl) pyridin-2-yl)pyrimidin-2-amine

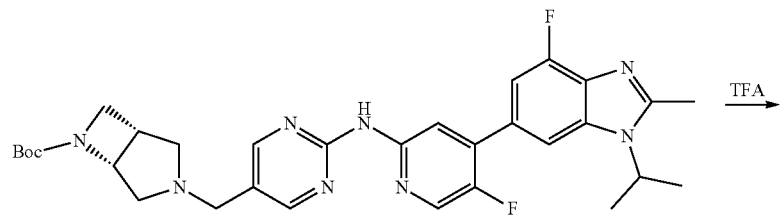

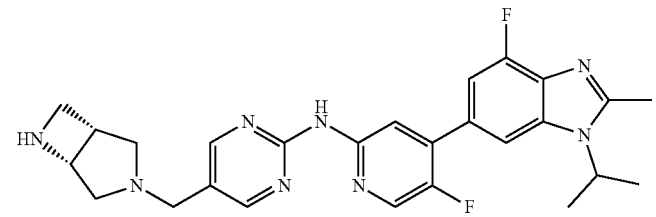

Tert-butyl (1S,5R)-3-((2-((5-fluoro-4-(4-fluoro-1-isopropyl-2-methyl-1H-benzo[d]imidazol-6-yl)pyridin-2-yl) amino)pyrimidin-5-yl)methyl)-3,6-diazabicyclo[3.2.0]heptan-6-carboxylate (210 mg, 0.36 mmol) was added to dichloromethane (10 mL). Trifluoroacetic acid (3 mL) was added dropwisely. The mixture was stirred at room temperature for 5 h. After the reaction, the reaction solution was concentrated under reduced pressure. The residue was dissolved in dichloromethane, and triethylamine (2 mL) was added dropwisely. After further concentration under reduced pressure, the residue was separated by column chromatography (dichloromethane:methanol=5:1) to get the product (120 mg, yield: 68.8%).

Molecular formula: $C_{26}H_{28}F_2N_8$ Molecular weight: 490.6
LC-MS (m/z): 491.3 (M+H$^+$)
$^1$H-NMR (400 MHz, CDCl$_3$) δ: 8.60 (s, 2H), 8.55 (d, J=6.0 Hz, 1H), 8.27 (d, J=2.0 Hz, 1H), 7.79 (s, 1H), 7.27 (d, J=11.2 Hz, 1H), 4.56-4.61 (m, 1H), 3.91 (t, J=9.6 Hz, 1H), 3.75 (q, J=12.4 Hz, 2H), 3.52-3.62 (m, 1H), 3.12-3.26 (m, 2H), 3.01 (d, J=10.0 Hz, 1H), 2.68 (s, 3H), 2.22-2.35 (m, 1H), 2.15-2.22 (m, 1H), 1.89 (s, 1H), 1.69 (d, J=10.0 Hz, 6H).

Example 34: Preparation of N-(5-fluoro-4-(4-fluoro-1-isopropyl-2-methyl-1H-benzo [d]imidazol-6-yl)pyridin-2-yl)-5-(((1S,5R)-6-methyl-3,6-diazabicyclo[3.2.0]heptan-3-yl)methyl)pyrimidin-2-amine (Compound 35)

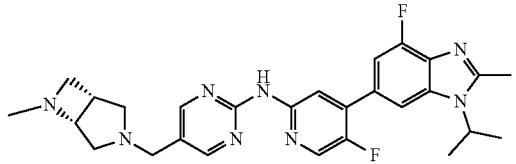

(1) Preparation of tert-butyl (1S,5R)-3-((2-chloropyrimidin-5-yl)methyl)-3,6-diazabicyclo [3.2.0]heptan-6-carboxylate

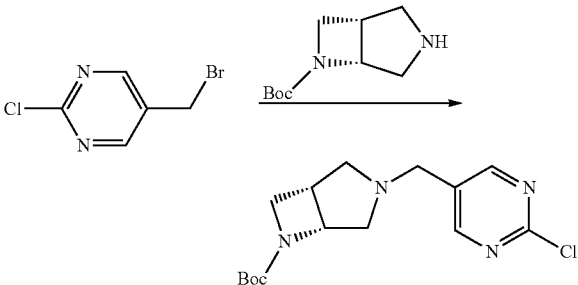

Tert-butyl (1S,5R)-3,6-diazabicyclo[3.2.0]heptan-6-carboxylate (256 mg, 1.29 mmol), 5-(bromomethyl)-2-chloropyrimidine (267 mg, 1.29 mmol) and potassium carbonate (178 mg, 1.29 mmol) were added to acetonitrile (15 mL), and the mixture was heated at 60° C. for 1 h. The reaction solution was concentrated and purified by silica gel column chromatography (dichloromethane:methanol=10:1) to separate the product (300 mg, yield: 71.6%).

(2) Preparation of (1R,5R)-3-((2-chloropyrimidin-5-yl)methyl)-3,6-diazabicyclo[3.2.0]heptane

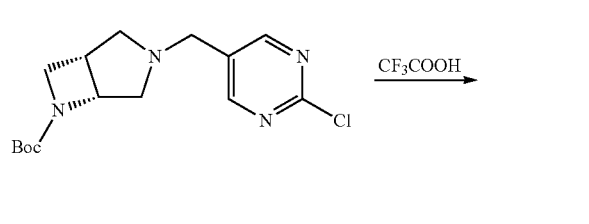

Tert-butyl (1S,5R)-3-((2-chloropyrimidin-5-yl)methyl)-3,6-diazabicyclo[3.2.0]heptan-6-carboxylate (300 mg, 0.92 mmol) was dissolved in a mixed solution of dichloromethane (3 mL) and trifluoroacetic acid (3 mL), and stirred at room temperature for 30 min. The reaction solution was concentrated, and a small amount of dichloromethane was added. The mixture was concentrated again to obtain the crude product (201 mg). The product was used in the next step without purification.

(3) Preparation of (1S,5R)-3-((2-chloropyrimidin-5-yl)methyl)-6-methyl-3,6-diazabicyclo [3.2.0]heptane

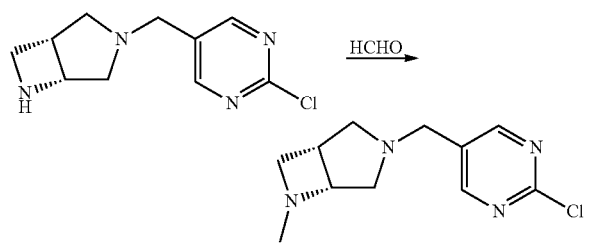

(1R,5R)-3-((2-chloropyrimidin-5-yl)methyl)-3,6-diazabicyclo[3.2.0]heptane (201 mg, 0.89 mmol) was dissolved in methanol (10 mL), and aqueous formaldehyde solution (40%, 0.67 mL, 8.9 mmol) was added dropwisely. The mixture was stirred at room temperature for 2 h. Sodium cyanoborohydride (561 mg, 8.9 mmol) was added slowly. After the addition, the mixture was further stirred at room temperature for 30 min. The reaction solution was concentrated and purified by silica gel column chromatography (dichloromethane:methanol=10:1) to get the product (124 mg, two-step yield: 56.2%).

(4) Preparation of N-(5-fluoro-4-(4-fluoro-1-isopropyl-2-methyl-1H-benzo[d]imidazol-6-yl) pyridin-2-yl)-5-(((1S,5R)-6-methyl-3,6-diazabicyclo[3.2.0]heptan-3-yl)methyl)pyrimidin-2-amine

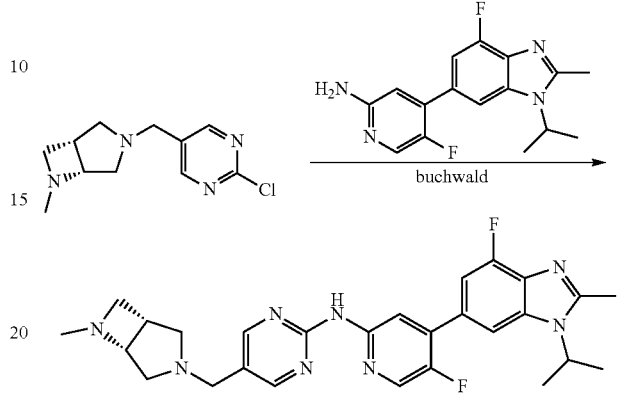

(1S,5R)-3-((2-chloropyrimidin-5-yl)methyl)-6-methyl-3,6-diazabicyclo[3.2.0]heptane (124 mg, 0.52 mmol), 5-fluoro-4-(4-fluoro-1-isopropyl-2-methyl-1H-benzo[d]imidazol-6-yl)pyridin-2-amine (157 mg, 0.52 mmol), cesium carbonate (338 mg, 1.04 mmol), tris(dibenzylideneacetone)dipalladium (30 mg) and 2-dicyclohexylphosphino-2',4',6'-triisopropylbiphenyl (60 mg) were added to 1,4-dioxane (10 mL). Under the protection of nitrogen, the mixture was heated at 110° C. for 8 h. The reaction solution was concentrated, and separated by the reverse phase preparative chromatography (water:methanol=10:1-1:1) to get the title compound (26 mg, yield: 10.0%).

Molecular formula: $C_{27}H_{30}F_2N_8$ Molecular weight: 504.6
LC-MS (m/z): 505.3 (M+H$^+$)
$^1$H-NMR (400 MHz, MeOD) δ: 8.59 (s, 2H), 8.56 (d, J=6.0 Hz, 2H), 8.28 (d, J=2.4 Hz, 1H), 7.77 (s, 1H), 7.23 (d, J=11.6 Hz, 1H), 4.25-4.27 (m, 1H), 3.71-3.74 (m, 3H), 3.64-3.69 (m, 1H), 3.23-3.30 (m, 2H), 3.06-3.15 (m, 1H), 2.93-2.98 (m, 1H), 2.68 (s, 3H), 2.56 (s, 3H), 2.13-2.19 (m, 2H), 1.68 (d, J=8.4 Hz, 6H).

The invention claimed is:

1. A method for treating a cancer-related disease mediated by CDK4/6 kinase, comprising the step of administering to a subject in need thereof a therapeutically effective amount of the compound of Formula (I'), or a pharmaceutically acceptable salt, ester, or solvate thereof, or their stereoisomers,

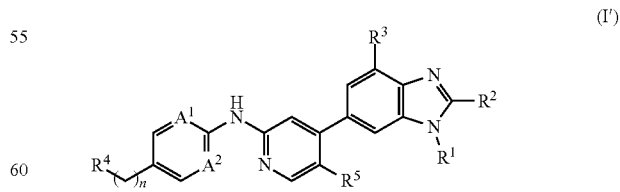

wherein:
each of $A^1$ and $A^2$ is nitrogen;
$R^1$ is selected from $C_{1-6}$alkyl, $C_{1-6}$alkoxy, or 3-8 membered cycloalkyl optionally substituted by $Q^1$, wherein $Q^1$ is selected from $C_{1-6}$ alkyl or $C_{1-6}$alkoxy;

$R^2$ is selected from $C_{1-6}$ alkyl, $C_{1-6}$alkoxy, cyano, carbamoyl or $C_{1-6}$ alkylcarbonylamino;

$R^3$ and $R^5$ are independently selected from halogen or hydrogen, and at least one of $R^3$ and $R^5$ is halogen;

$R^4$ is selected from 3-8 membered heterocyclyl, 6-14 membered fused heterocyclyl, 5-8 membered heteroaryl, 6-14 membered fused heteroaryl, phenyl, naphthyl, 6-12 membered bridged heterocyclyl or 6-12 membered spiroheterocyclyl, each of which is optionally substituted by $Q^2$;

$Q^2$ is selected from amino, hydroxyl, halogen, trifluoromethyl, cyano, $C_{1-6}$ alkoxy, $C_{1-6}$alkylsulfonyl, $C_{1-6}$alkylsulfonylamino, or di-$C_{1-6}$alkylamino; or $C_{1-6}$alkyl, 3-8 membered cycloalkyl, 3-8 membered heterocyclyl or 6-9 membered bridged heterocyclyl, each of which is optionally substituted by a substituent, wherein the substituent is selected from amino, hydroxyl, halogen, trifluoromethyl, cyano, $C_{1-6}$alkyl, $C_{1-6}$alkoxy, $C_{1-6}$alkylamino, di-$C_{1-6}$alkylamino, $C_{1-6}$alkylsulfonyl, 3-8 membered heterocyclyl or 3-8 membered cycloalkyl;

n is selected from 0, 1, 2, 3, 4 or 5; and wherein the cancer-related disease is selected from lung cancer, prostate cancer, lymphoma, leukemia, bladder carcinoma, esophageal cancer, liver cancer, pancreatic carcinoma and gastric cancer.

2. The method of claim 1, wherein each of $A^1$ and $A^2$ is nitrogen;

le is selected from $C_{1-4}$ alkyl or $C_{1-4}$ alkoxy;

$R^2$ is selected from $C_{1-4}$ alkyl, $C_{1-4}$ alkoxy, cyano, carbamoyl or $C_{1-4}$ alkylcarbonylamino;

each of $R^3$ and $R^5$ is halogen;

$R^4$ is selected from a nitrogen-containing 5-6 membered heterocyclyl optionally substituted by $Q^2$;

$Q^2$ is selected from amino, hydroxyl, halogen, trifluoromethyl, cyano, $C_{1-4}$ alkoxy, or di-$C_{1-4}$ alkylamino; or $C_{1-4}$ alkyl, 3-6 membered cycloalkyl or 3-6 membered heterocyclyl, each of which is optionally substituted by a substituent, wherein the substituent is selected from amino, hydroxyl, halogen, trifluoromethyl, $C_{1-4}$ alkyl, $C_{1-4}$ alkoxy, $C_{1-4}$ alkylamino, di-$C_{1-4}$ alkylamino, or 3-6 membered cycloalkyl; and n is 0.

3. The method of claim 2 wherein the nitrogen-containing 5-6 membered heterocyclyl is a nitrogen-containing 6 membered heterocyclyl.

4. The method of claim 1, wherein the compound has the structure of Formula (I),

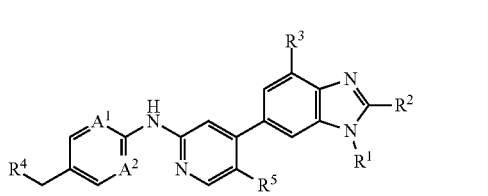

wherein:
each of $A^1$ and $A^2$ is nitrogen;
$R^1$ is selected from $C_{1-6}$alkyl, $C_{1-6}$alkoxy, or 3-8 membered cycloalkyl optionally substituted by $Q^1$, wherein $Q^1$ is selected from $C_{1-6}$alkyl or $C_{1-6}$alkoxy;
$R^2$ is selected from $C_{1-6}$alkyl, $C_{1-6}$alkoxy, cyano, carbamoyl or $C_{1-6}$alkylcarbonylamino;

$R^3$ and $R^5$ are independently selected from halogen or hydrogen, and at least one of $R^3$ and $R^5$ is halogen; and $R^4$ is selected from 3-8 membered heterocyclyl, 6-14 membered fused heterocyclyl, 5-8 membered heteroaryl, 6-14 membered fused heteroaryl, phenyl, naphthyl, 6-12 membered bridged heterocyclyl or 6-12 membered spiroheterocyclyl, each of which is optionally substituted by $Q^2$; wherein $Q^2$ is selected from amino, hydroxyl, halogen, trifluoromethyl, cyano, $C_{1-6}$ alkyl, $C_{1-6}$ alkoxy, 3-8 membered heterocyclyl or 6-9 membered bridged heterocyclyl.

5. The method of claim 4, wherein each of $A^1$ and $A^2$ is nitrogen;

$R^1$ is selected from $C_{1-4}$ alkyl or $C_{1-4}$ alkoxy;

$R^2$ is selected from $C_{1-4}$ alkyl, $C_{1-4}$ alkoxy, cyano, carbamoyl or $C_{1-4}$ alkylcarbonylamino;

each of $R^3$ and $R^5$ is halogen; and $R^4$ is selected from 5-7 membered heterocyclyl, 6-11 membered fused heterocyclyl, 6-11 membered bridged heterocyclyl or 6-11 membered spiroheterocyclyl, each of which is optionally substituted by $Q^2$; wherein $Q^2$ is selected from amino, hydroxyl, trifluoromethyl, cyano, $C_{1-4}$ alkyl, $C_{1-4}$ alkoxy, 5-6 membered heterocyclyl or 7-9 membered bridged heterocyclyl.

6. The method of claim 5, wherein each of $A^1$ and $A^2$ is nitrogen;

$R^1$ is isopropyl;

$R^2$ is selected from methyl, methoxy, cyano, carbamoyl, or acetylamino;

each of $R^3$ and $R^5$ is F; and $R^4$ is selected from 5-6 membered heterocyclyl optionally substituted by $Q^2$; wherein $Q^2$ is selected from amino, hydroxyl, trifluoromethyl, cyano, $C_{1-4}$ alkyl, $C_{1-4}$ alkoxy, 6 membered heterocyclyl or 8 membered bridged heterocyclyl.

7. The method of claim 6, wherein $R^2$ is methyl; and $R^4$ is selected from a nitrogen-containing 5-6 membered heterocyclyl optionally substituted by $Q^2$; wherein the nitrogen-containing 5-6 membered heterocyclyl is linked to the methylene of Formula (I) via a nitrogen atom, wherein $Q^2$ is selected from amino, hydroxyl, trifluoromethyl, cyano, $C_{1-4}$ alkyl, $C_{1-4}$ alkoxy, or a nitrogen-containing 8 membered bridged heterocyclyl.

8. The method of claim 7 wherein the nitrogen-containing 5-6 membered heterocyclyl is a nitrogen-containing 5-6 membered heterocyclyl containing 1 to 2 nitrogen atoms.

9. The method of claim 7, wherein $R^4$ is selected from

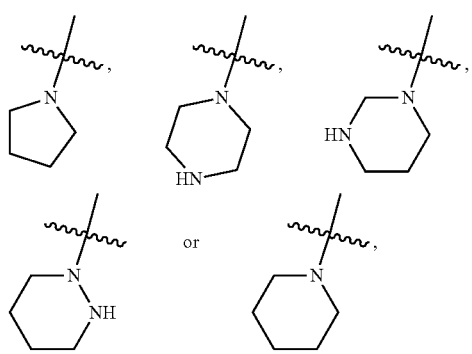

each of which is optionally substituted by $Q^2$, wherein $Q^2$ is selected from $C_{1-4}$ alkyl or a nitrogen-containing 8 membered bridged heterocyclyl.

10. The method of claim 5, wherein
each of $A^1$ and $A^2$ is nitrogen;
$R^1$ is isopropyl;
$R^2$ is selected from methyl, methoxy, cyano, carbamoyl, or acetylamino;
each of $R^3$ and $R^5$ is F; and
$R^4$ is selected from 7-9 membered bridged heterocyclyl optionally substituted by $Q^2$; wherein $Q^2$ is selected from amino, hydroxyl, trifluoromethyl, cyano, $C_{1-4}$ alkyl, 6 membered heterocyclyl or 8 membered bridged heterocyclyl.

11. The method of claim 10, wherein
$R^2$ is methyl; and
$R^4$ is selected from a nitrogen-containing 7-9 membered bridged heterocyclyl optionally substituted by $Q^2$; wherein the nitrogen-containing 7-9 membered bridged heterocyclyl is linked to the methylene of Formula (I) via a nitrogen atom, wherein $Q^2$ is selected from amino, hydroxyl, trifluoromethyl, cyano, $C_{1-4}$ alkyl, or a nitrogen-containing 6 membered heterocyclyl.

12. The method of claim 11 wherein the nitrogen-containing 7-9 membered bridged heterocyclyl is a nitrogen-containing 7-9 membered bridged heterocyclyl containing 1 to 2 nitrogen atoms.

13. The method of claim 11, wherein
$R^4$ is selected from

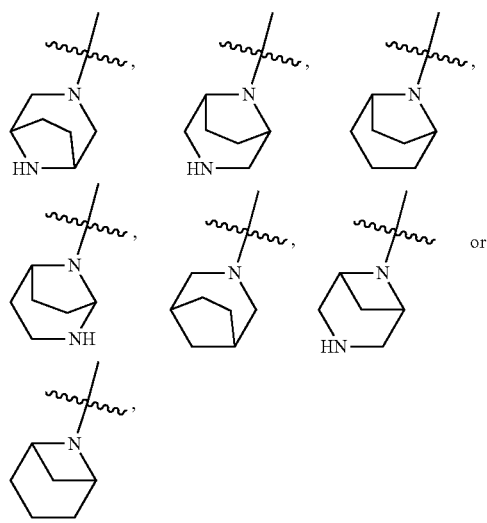

each of which is optionally substituted by $Q^2$, wherein $Q^2$ is selected from $C_{1-4}$ alkyl or a nitrogen-containing 6 membered heterocyclyl.

14. The method of claim 5, wherein
each of $A^1$ and $A^2$ is nitrogen;
$R^1$ is isopropyl;
$R^2$ is selected from methyl, methoxy, cyano, carbamoyl, or acetylamino;
each of $R^3$ and $R^5$ is F; and
$R^4$ is selected from 6-10 membered fused heterocyclyl optionally substituted by $Q^2$; wherein $Q^2$ is selected from amino, hydroxyl, trifluoromethyl, cyano, $C_{1-4}$ alkyl, 6 membered heterocyclyl or 8 membered bridged heterocyclyl.

15. The method of claim 14, wherein
$R^2$ is methyl; and
$R^4$ is selected from a 6-10 membered fused heterocyclyl that contains 1, 2 or 3 identical or different heteroatoms and is optionally substituted by $Q^2$.

16. The method of claim 15 wherein the heteroatoms are selected from nitrogen atom and oxygen atom, and contain at least one nitrogen atom, and the 6-10 membered fused heterocyclyl is linked to the methylene of Formula (I) via a nitrogen atom, wherein $Q^2$ is selected from amino, hydroxyl, trifluoromethyl, cyano, or $C_{1-4}$ alkyl.

17. The method of claim 15, wherein
$R^4$ is selected from

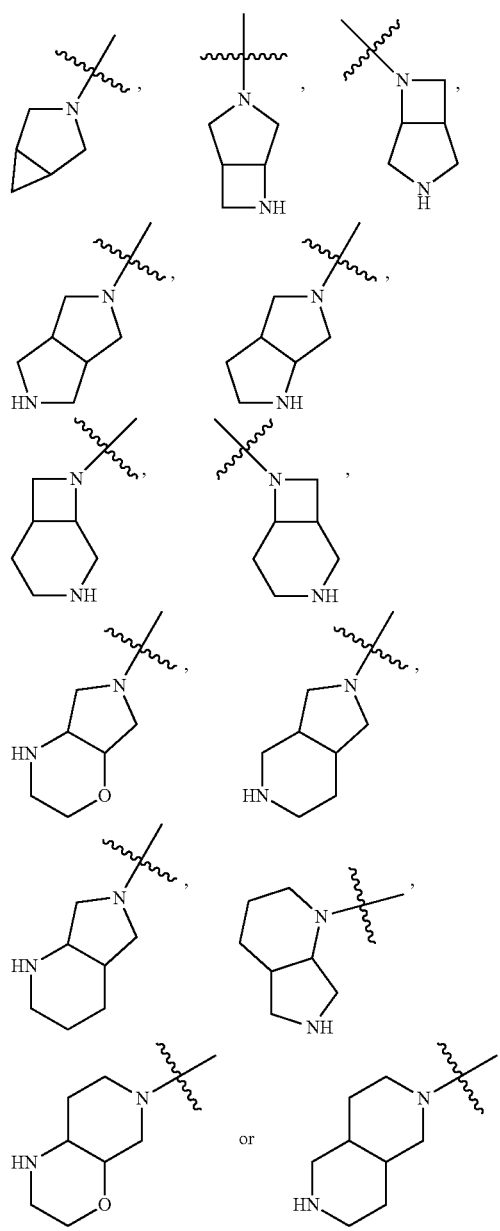

each of which is optionally substituted by $Q^2$, wherein $Q^2$ is selected from amino or $C_{1-4}$ alkyl.

18. The method of claim 5, wherein
each of $A^1$ and $A^2$ is nitrogen;
$R^1$ is isopropyl;
$R^2$ is selected from methyl, methoxy, cyano, carbamoyl, or acetylamino;
each of $R^3$ and $R^5$ is F; and
$R^4$ is selected from 7-11 membered spiroheterocyclyl optionally substituted by $Q^2$; wherein $Q^2$ is selected from amino, hydroxyl, trifluoromethyl, cyano, $C_{1-4}$ alkyl, 6 membered heterocyclyl or 8 membered bridged heterocyclyl.

19. The method of claim 18, wherein
$R^2$ is methyl; and
$R^4$ is selected from a nitrogen-containing 7-11 membered spiroheterocyclyl optionally substituted by $Q^2$; wherein the nitrogen-containing 7-11 membered spiroheterocyclyl is linked to the methylene of Formula (I) via a nitrogen atom, wherein $Q^2$ is selected from amino, hydroxyl, trifluoromethyl, cyano, or $C_{1-4}$ alkyl.

20. The method of claim 19 wherein the nitrogen-containing 7-11 membered spiroheterocyclyl is a nitrogen-containing 7-11 membered spiroheterocyclyl containing 1 to 2 nitrogen atoms.

21. The method of claim 19, wherein
$R^4$ is selected from

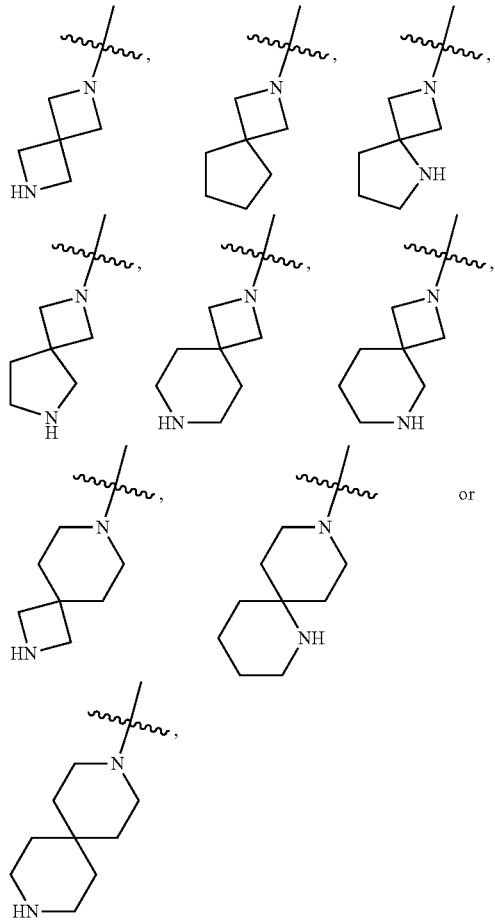

each of which is optionally substituted by $Q^2$, wherein $Q^2$ is selected from $C_{1-4}$ alkyl.

22. The method of claim 1, wherein the compound is selected from:

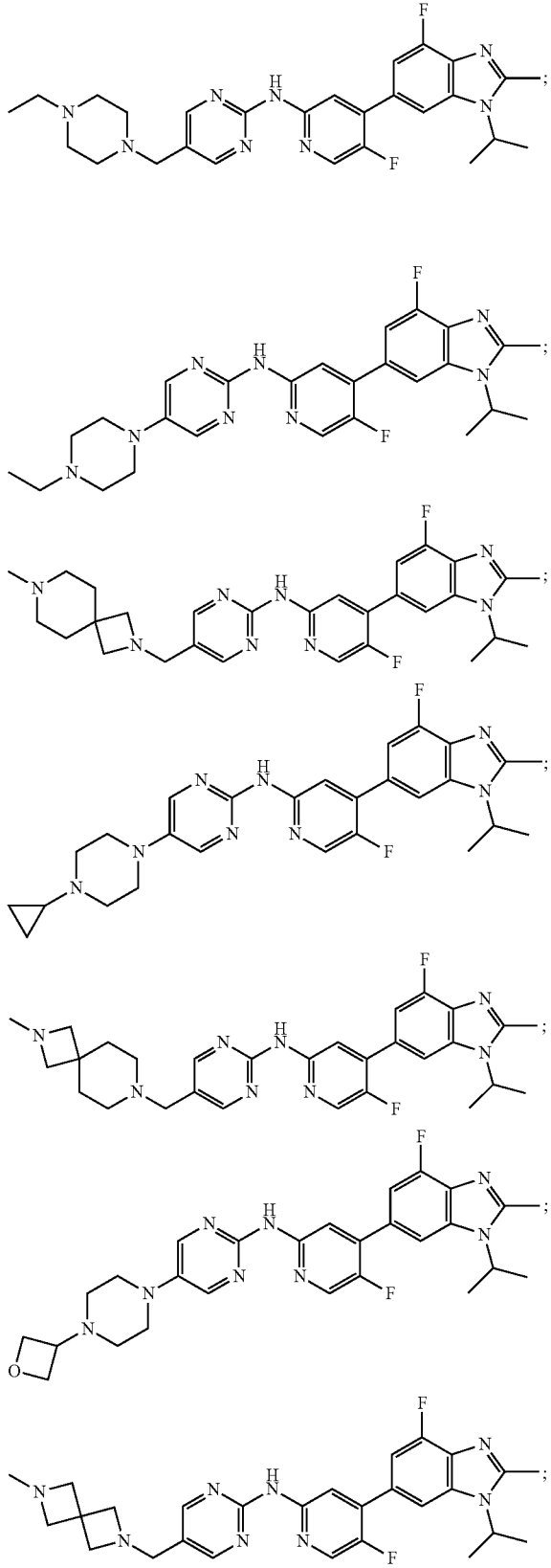

173
-continued
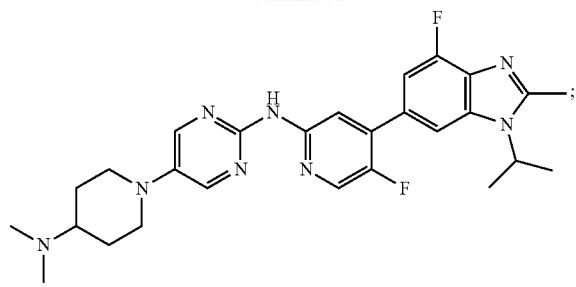
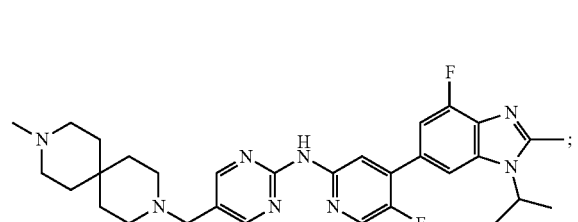
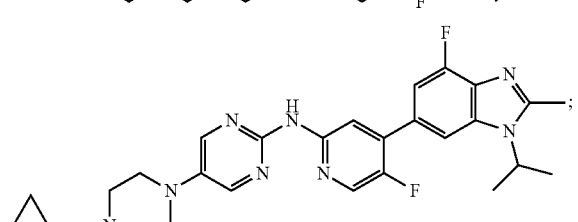
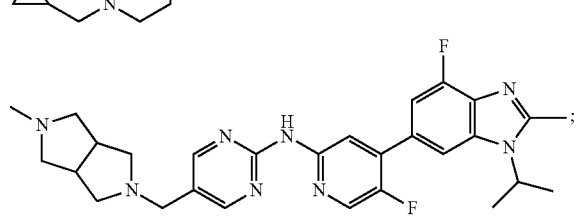
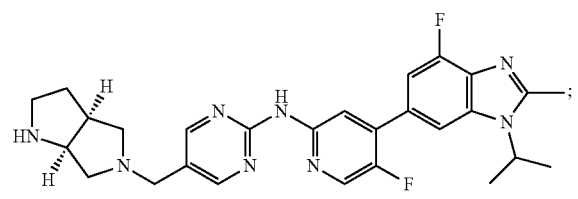
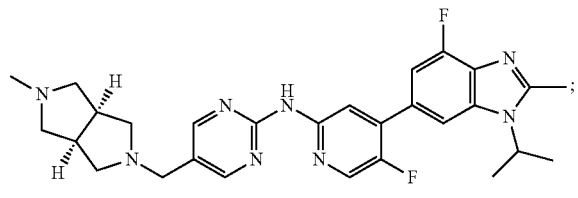
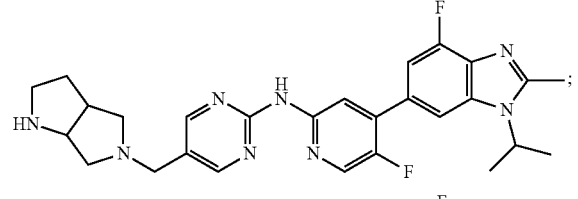
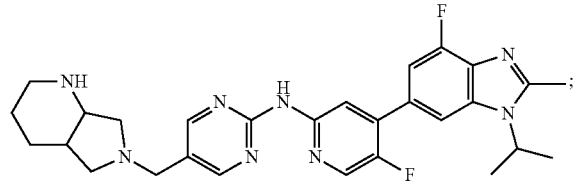
174
-continued
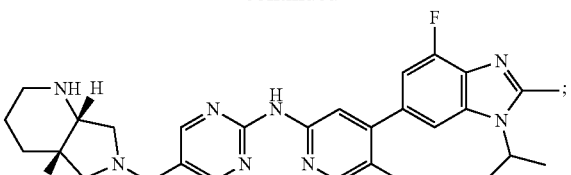
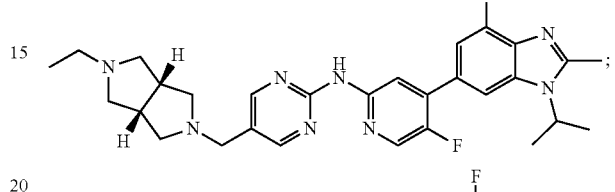
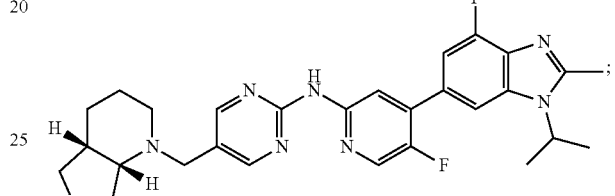
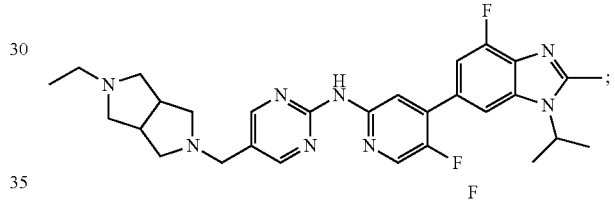
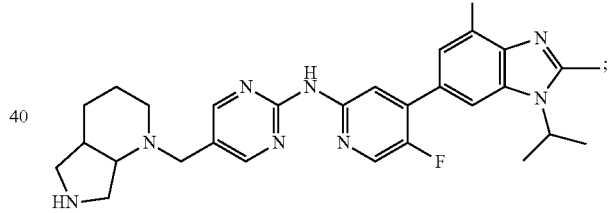
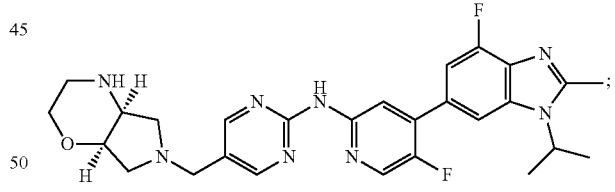
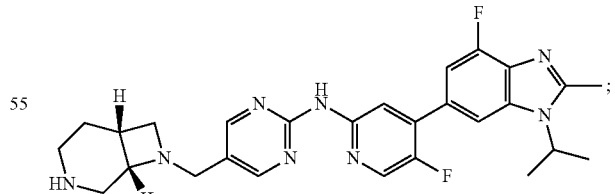
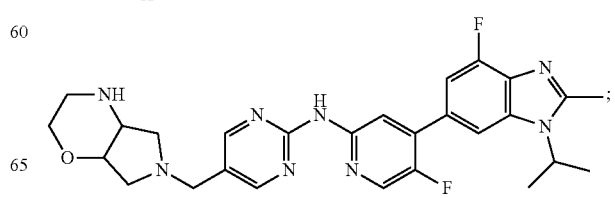

175
-continued
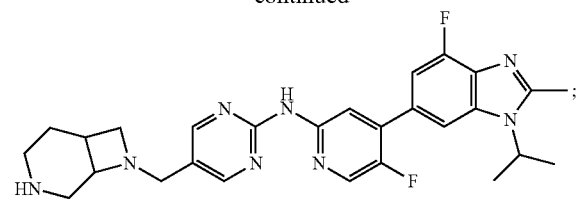
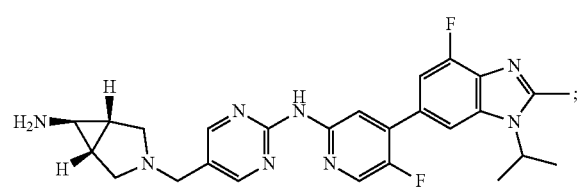
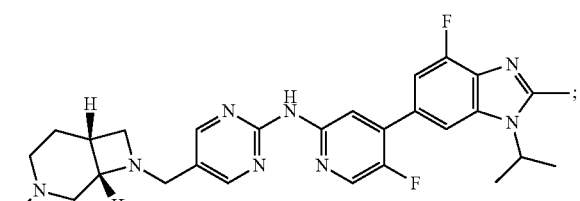
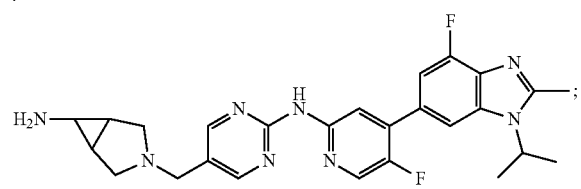
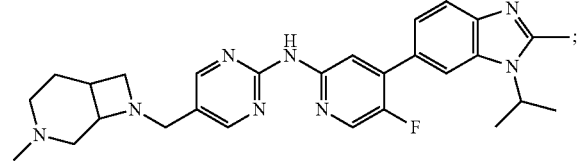
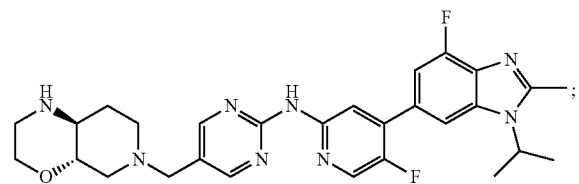
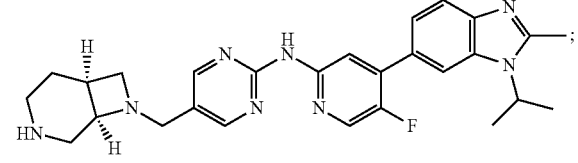
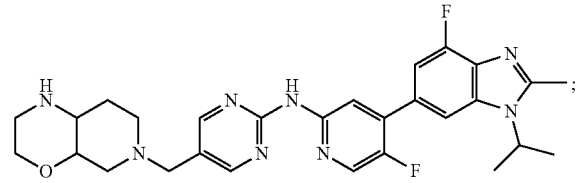
176
-continued
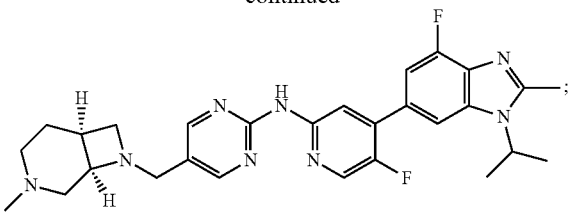
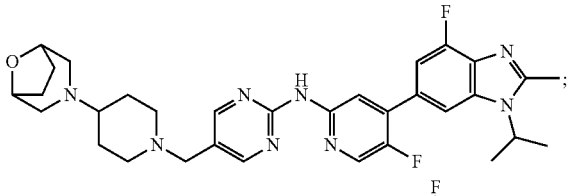
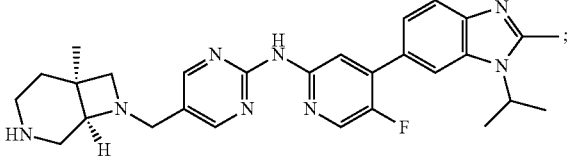
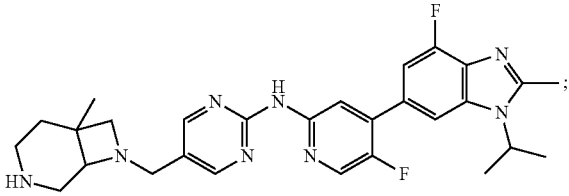
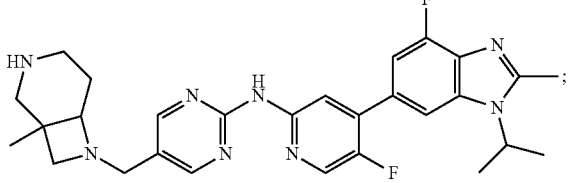
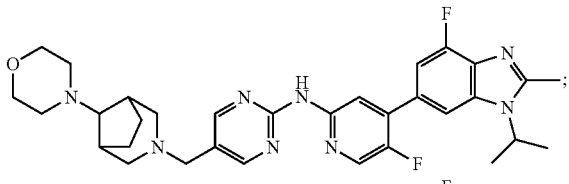
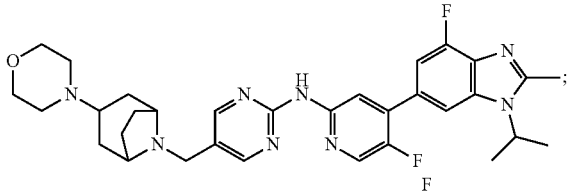
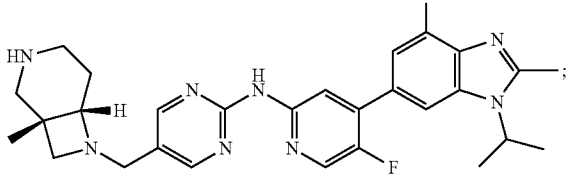
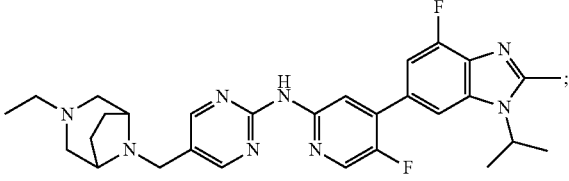

177
-continued
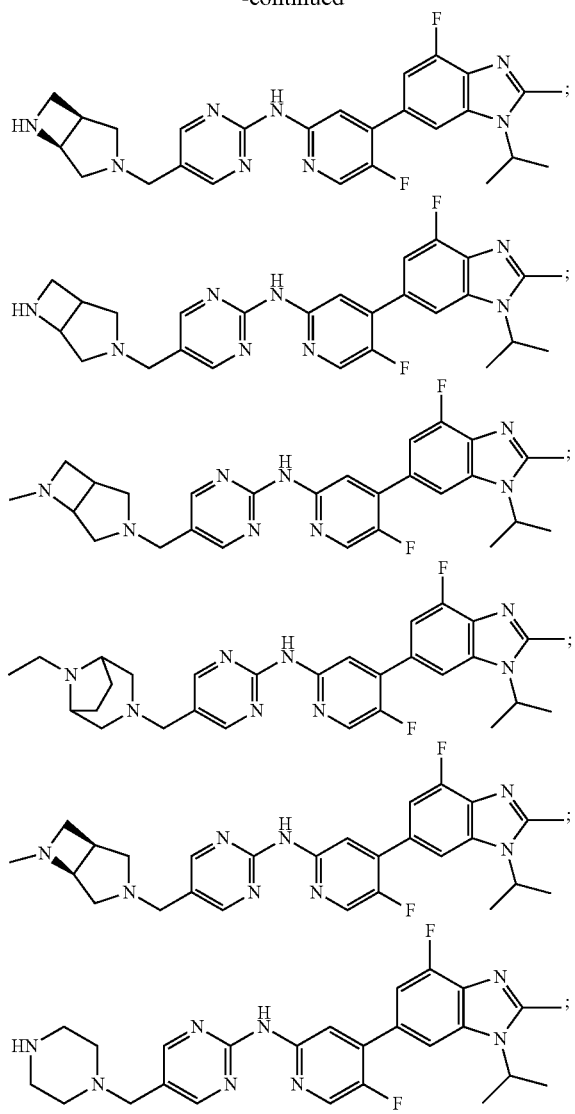
178
-continued
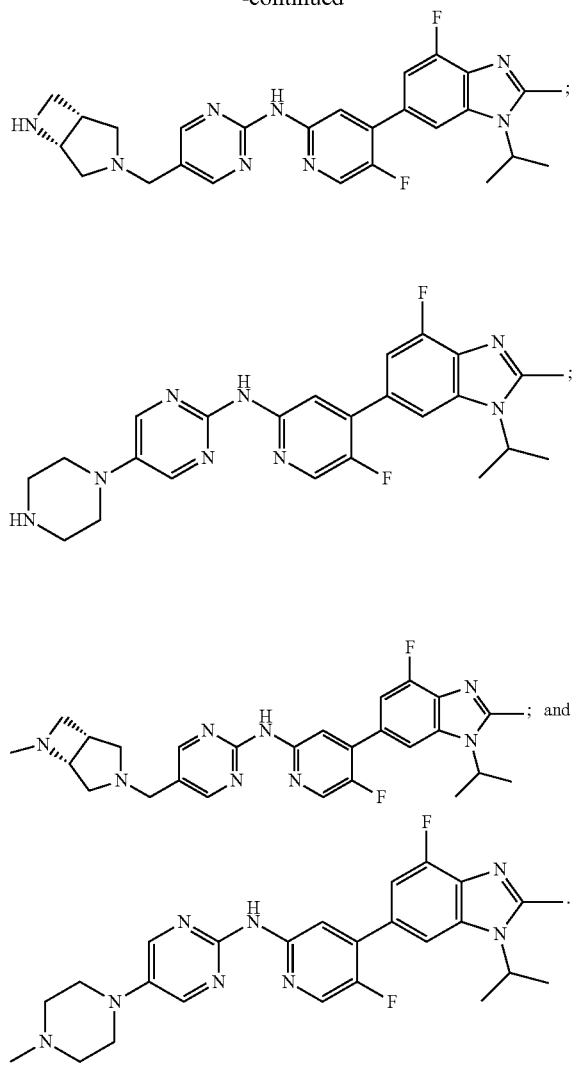
* * * * *

UNITED STATES PATENT AND TRADEMARK OFFICE
CERTIFICATE OF CORRECTION

PATENT NO. : 9,949,976 B2
APPLICATION NO. : 15/704542
DATED : April 24, 2018
INVENTOR(S) : Frank Wu et al.

Page 1 of 1

It is certified that error appears in the above-identified patent and that said Letters Patent is hereby corrected as shown below:

In the Claims

Column 167, Line 30, Claim 2: please delete "1e" and replace with -- $R^1$ --

Signed and Sealed this
Tenth Day of July, 2018

Andrei Iancu
*Director of the United States Patent and Trademark Office*